(12) United States Patent
Gray et al.

(10) Patent No.: US 10,550,121 B2
(45) Date of Patent: Feb. 4, 2020

(54) INHIBITORS OF CYCLIN-DEPENDENT KINASES

(71) Applicant: Dana-Farber Cancer Institute, Inc., Boston, MA (US)

(72) Inventors: Nathanael S. Gray, Boston, MA (US); Tinghu Zhang, Brookline, MA (US); Nicholas Paul Kwiatkowski, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/561,729

(22) PCT Filed: Mar. 25, 2016

(86) PCT No.: PCT/US2016/024345
§ 371 (c)(1),
(2) Date: Sep. 26, 2017

(87) PCT Pub. No.: WO2016/160617
PCT Pub. Date: Oct. 6, 2016

(65) Prior Publication Data
US 2018/0319801 A1    Nov. 8, 2018
US 2019/0315747 A9    Oct. 17, 2019

Related U.S. Application Data

(60) Provisional application No. 62/139,352, filed on Mar. 27, 2015.

(51) Int. Cl.
| | | |
|---|---|---|
| C07D 473/16 | (2006.01) |
| C07D 473/34 | (2006.01) |
| C07D 487/04 | (2006.01) |
| C07K 14/47 | (2006.01) |
| A61P 43/00 | (2006.01) |
| A61K 45/06 | (2006.01) |

(52) U.S. Cl.
CPC ............ *C07D 473/16* (2013.01); *A61K 45/06* (2013.01); *A61P 43/00* (2018.01); *C07D 473/34* (2013.01); *C07D 487/04* (2013.01); *C07K 14/4738* (2013.01)

(58) Field of Classification Search
CPC ....... A61K 45/06; A61P 43/00; C07D 473/16; C07D 473/34; C07D 487/04; C07K 14/4738
See application file for complete search history.

(56) References Cited

U.S. PATENT DOCUMENTS

| | | |
|---|---|---|
| 4,231,938 A | 11/1980 | Monaghan et al. |
| 4,270,537 A | 6/1981 | Romaine et al. |
| 4,596,556 A | 6/1986 | Morrow et al. |
| 4,782,084 A | 11/1988 | Vyas et al. |
| 4,790,824 A | 12/1988 | Morrow et al. |
| 4,885,314 A | 12/1989 | Vyas et al. |
| 4,886,499 A | 12/1989 | Cirelli et al. |
| 4,940,460 A | 7/1990 | Casey et al. |
| 4,941,880 A | 7/1990 | Burns et al. |
| 5,015,235 A | 5/1991 | Crossman et al. |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby et al. |
| 5,334,144 A | 8/1994 | Alchas et al. |
| 5,339,163 A | 8/1994 | Homma et al. |
| 5,383,851 A | 1/1995 | McKinnon et al. |
| 5,417,662 A | 5/1995 | Hjertman et al. |
| 5,420,245 A | 5/1995 | Brown et al. |

(Continued)

FOREIGN PATENT DOCUMENTS

| | | |
|---|---|---|
| CA | 2486101 A1 | 11/2003 |
| CA | 2503646 A1 | 5/2004 |

(Continued)

OTHER PUBLICATIONS

U.S. Appl. No. 14/358,606, filed May 15, 2014, Gray et al.
U.S. Appl. No. 15/188,545, filed Jun. 21, 2016, Gray et al.
U.S. Appl. No. 14/436,496, filed Apr. 17, 2015, Gray et al.
U.S. Appl. No. 14/436,387, filed Apr. 16, 2015, Gray et al.
U.S. Appl. No. 14/436,657, filed Apr. 17, 2015, Gray et al.
U.S. Appl. No. 15/699,948, filed Sep. 8, 2017, Gray et al.
U.S. Appl. No. 15/305,801, filed Oct. 21, 2016, Gray et al.
U.S. Appl. No. 15/305,845, filed Oct. 21, 2016, Gray et al.
U.S. Appl. No. 13/376,539, filed Dec. 6, 2011, Choi et al.
U.S. Appl. No. 14/321,242, filed Jul. 1, 2014, Gray et al.
U.S. Appl. No. 13/519,826, filed Nov. 1, 2012, Gray et al.
U.S. Appl. No. 14/552,229, filed Nov. 24, 2014, Gray et al.

(Continued)

*Primary Examiner* — Erich A Leeser
(74) *Attorney, Agent, or Firm* — Wolf, Greenfield & Sacks, P.C.

(57) ABSTRACT

The present invention provides novel compounds of Formula (I), (II), or (III), and pharmaceutically acceptable salts, solvates, hydrates, polymorphs, co-crystals, tautomers, stereoisomers, isotopically labeled derivatives, prodrugs, and compositions thereof. Also provided are methods and kits involving the inventive compounds or compositions for treating and/or preventing proliferative diseases (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, ovarian cancer, neuroblastoma, lung cancer, colorectal cancer), benign neoplasms, diseases associated with angiogenesis, inflammatory diseases, autoinflammatory diseases, and autoimmune diseases) in a subject. Treatment of a subject with a proliferative disease using a compound or composition of the invention may inhibit the aberrant activity of a kinase, such as a cyclin-dependent kinase (CDK) (e.g., CDK7, CDK12, or CDK13), and therefore, induce cellular apoptosis and/or inhibit transcription in the subject.

10 Claims, 25 Drawing Sheets

Specification includes a Sequence Listing.

(56) References Cited

U.S. PATENT DOCUMENTS

| | | | |
|---|---|---|---|
| 5,466,220 A | 11/1995 | Brenneman et al. |
| 5,480,381 A | 1/1996 | Weston et al. |
| 5,484,596 A | 1/1996 | Hanna et al. |
| 5,503,627 A | 4/1996 | McKinnon et al. |
| 5,510,510 A | 4/1996 | Patel et al. |
| 5,520,639 A | 5/1996 | Peterson et al. |
| 5,523,430 A | 6/1996 | Patel et al. |
| 5,527,288 A | 6/1996 | Gross et al. |
| 5,532,359 A | 7/1996 | Marsters et al. |
| 5,569,189 A | 10/1996 | Parsons et al. |
| 5,571,792 A | 11/1996 | Bolton et al. |
| 5,589,485 A | 12/1996 | Hocolowski et al. |
| 5,599,302 A | 2/1997 | Lilley et al. |
| 5,602,098 A | 2/1997 | Sebti et al. |
| 5,643,958 A | 7/1997 | Iwasawa et al. |
| 5,649,912 A | 7/1997 | Peterson et al. |
| 5,661,152 A | 8/1997 | Bishop et al. |
| 5,704,911 A | 1/1998 | Parsons et al. |
| 5,750,567 A | 5/1998 | Baudoin et al. |
| 5,856,439 A | 1/1999 | Clerc et al. |
| 5,889,053 A | 3/1999 | Baudoin et al. |
| 5,893,397 A | 4/1999 | Peterson et al. |
| 5,925,641 A | 7/1999 | Kanda et al. |
| 5,936,097 A | 8/1999 | Commercon et al. |
| 5,993,412 A | 11/1999 | Deily et al. |
| 6,069,134 A | 5/2000 | Roth et al. |
| 6,214,852 B1 | 4/2001 | Kim et al. |
| 6,921,763 B2 | 7/2005 | Hirst et al. |
| 6,939,874 B2 | 9/2005 | Harmange et al. |
| 7,115,617 B2 | 10/2006 | Buchanan et al. |
| 7,312,225 B2 | 12/2007 | Luecking et al. |
| 7,884,117 B2 | 2/2011 | Zhang et al. |
| 7,928,140 B2 | 4/2011 | Booker et al. |
| 8,273,765 B2 | 9/2012 | Fancelli et al. |
| 8,394,818 B2 | 3/2013 | Gray et al. |
| 8,765,747 B2 | 7/2014 | Choi et al. |
| 8,889,706 B2 | 11/2014 | Gray et al. |
| 8,987,275 B2 | 3/2015 | Gray et al. |
| 9,180,127 B2 | 11/2015 | Gray et al. |
| 9,358,231 B2 | 6/2016 | Gray et al. |
| 9,382,239 B2 | 7/2016 | Gray et al. |
| 9,505,784 B2 | 11/2016 | Choi et al. |
| 9,670,165 B2 | 6/2017 | Cohen et al. |
| 9,758,522 B2 | 9/2017 | Gray et al. |
| 9,862,688 B2 | 1/2018 | Gray et al. |
| 10,000,483 B2 | 6/2018 | Gray et al. |
| 10,017,477 B2 | 7/2018 | Gray et al. |
| 10,112,927 B2 | 10/2018 | Gray et al. |
| 10,144,730 B2 | 12/2018 | Gray et al. |
| 2003/0139416 A1 | 7/2003 | Buchanan et al. |
| 2004/0106634 A1 | 6/2004 | Satoh et al. |
| 2004/0209878 A1* | 10/2004 | Guzi ............... C07D 487/04 514/234.5 |
| 2005/0026914 A1 | 2/2005 | Buchanan et al. |
| 2005/0250837 A1 | 11/2005 | D'Mello et al. |
| 2006/0106083 A1 | 5/2006 | Martina et al. |
| 2006/0189627 A1 | 8/2006 | Laird et al. |
| 2007/0093537 A1 | 4/2007 | Hynes et al. |
| 2007/0185171 A1 | 8/2007 | Germain et al. |
| 2007/0225286 A1 | 9/2007 | Ren et al. |
| 2007/0275963 A1 | 11/2007 | Guzi et al. |
| 2007/0281907 A1 | 12/2007 | Watkins |
| 2008/0039629 A1 | 2/2008 | Ramesh et al. |
| 2008/0090849 A1 | 4/2008 | Bordon-Pallier et al. |
| 2008/0103167 A1 | 5/2008 | Bebernitz et al. |
| 2008/0214501 A1 | 9/2008 | Pan et al. |
| 2008/0249079 A1 | 10/2008 | Chen et al. |
| 2008/0300267 A1 | 12/2008 | Okram et al. |
| 2009/0054392 A1 | 2/2009 | Pelletier et al. |
| 2009/0054405 A1 | 2/2009 | Booker et al. |
| 2009/0082346 A1 | 3/2009 | Brasca et al. |
| 2009/0105250 A1 | 4/2009 | Sim et al. |
| 2010/0056524 A1 | 3/2010 | Mciver et al. |
| 2010/0197688 A1 | 8/2010 | Nantermet et al. |
| 2010/0254905 A1 | 10/2010 | Honigberg et al. |
| 2011/0086858 A1 | 4/2011 | Wang et al. |
| 2011/0098280 A1 | 4/2011 | Garcia-Echeverria et al. |
| 2011/0178070 A1 | 7/2011 | Gong et al. |
| 2011/0207711 A1 | 8/2011 | Katz et al. |
| 2011/0212053 A1 | 9/2011 | Qian et al. |
| 2012/0088766 A1 | 4/2012 | Choi et al. |
| 2012/0094999 A1 | 4/2012 | Gray et al. |
| 2012/0165309 A1 | 6/2012 | Takahashi et al. |
| 2012/0202809 A1 | 8/2012 | Li et al. |
| 2012/0277248 A1 | 11/2012 | Caruso et al. |
| 2012/0329771 A1 | 12/2012 | Treu et al. |
| 2013/0040949 A1 | 2/2013 | Gray et al. |
| 2013/0184264 A1 | 7/2013 | Bradner et al. |
| 2014/0303112 A1 | 10/2014 | Chen et al. |
| 2014/0309249 A1 | 10/2014 | Gray et al. |
| 2015/0094315 A1 | 4/2015 | Choi et al. |
| 2015/0157629 A1 | 6/2015 | Gray et al. |
| 2015/0166532 A1 | 6/2015 | Gray et al. |
| 2015/0246913 A1 | 9/2015 | Gray et al. |
| 2015/0274728 A1 | 10/2015 | Gray et al. |
| 2016/0046636 A1 | 2/2016 | Gray et al. |
| 2016/0122323 A1 | 5/2016 | Gray et al. |
| 2016/0368910 A1 | 12/2016 | Gray et al. |
| 2017/0044111 A1 | 2/2017 | Gray et al. |
| 2017/0044112 A1 | 2/2017 | Gray et al. |
| 2018/0093990 A1 | 4/2018 | Gray et al. |
| 2018/0169097 A1 | 6/2018 | Hammerman et al. |
| 2018/0362483 A1 | 12/2018 | Gray et al. |
| 2019/0055248 A1 | 2/2019 | Gray et al. |
| 2019/0100511 A1 | 4/2019 | Gray et al. |
| 2019/0112305 A1 | 4/2019 | Gray et al. |

FOREIGN PATENT DOCUMENTS

| | | |
|---|---|---|
| CA | 2526430 A1 | 12/2004 |
| CA | 2550128 A1 | 6/2005 |
| CA | 2563212 A1 | 10/2005 |
| EP | 0604181 A1 | 12/1993 |
| EP | 0618221 A2 | 3/1994 |
| EP | 0675112 A1 | 3/1995 |
| EP | 0696593 A2 | 8/1995 |
| EP | 1 935 890 A1 | 6/2008 |
| EP | 2 311 842 A2 | 4/2011 |
| GB | 796524 A | 6/1958 |
| JP | 2003-503481 A | 1/2003 |
| JP | 2004-529140 A | 9/2004 |
| JP | 2005-501860 A | 1/2005 |
| JP | 2005-505535 A | 2/2005 |
| JP | 2005-530711 A | 10/2005 |
| JP | 2005-534635 A | 11/2005 |
| JP | 2005-538100 A | 12/2005 |
| JP | 2006-521394 A | 9/2006 |
| JP | 2007-500226 A | 1/2007 |
| JP | 2007-500725 A | 1/2007 |
| JP | 2008-500320 A | 1/2008 |
| JP | 2008-501669 A | 1/2008 |
| JP | 2008-502610 A | 1/2008 |
| JP | 2009-510110 A | 3/2009 |
| JP | 2010-511655 A | 4/2010 |
| JP | 2010-521487 A | 6/2010 |
| JP | 2011-516533 A | 5/2011 |
| JP | 2012-530071 A | 11/2012 |
| JP | 2016-533379 A | 10/2016 |
| JP | 2017-504651 A | 2/2017 |
| MX | 2016-009974 A | 10/2016 |
| MX | 2016-009975 A | 10/2016 |
| MX | 2016-009976 A | 11/2016 |
| WO | WO 84/02131 A1 | 6/1984 |
| WO | WO 94/19357 A1 | 9/1994 |
| WO | WO 95/08542 A1 | 3/1995 |
| WO | WO 95/10514 A1 | 4/1995 |
| WO | WO 95/10515 A1 | 4/1995 |
| WO | WO 95/10516 A1 | 4/1995 |
| WO | WO 95/11917 A1 | 5/1995 |
| WO | WO 95/12572 A1 | 5/1995 |
| WO | WO 95/12612 A1 | 5/1995 |
| WO | WO 95/24612 A1 | 9/1995 |
| WO | WO 95/25086 A1 | 9/1995 |
| WO | WO 95/26412 A1 | 10/1995 |

(56) References Cited

FOREIGN PATENT DOCUMENTS

| | | |
|---|---|---|
| WO | WO 95/32987 A1 | 12/1995 |
| WO | WO 95/34535 A1 | 12/1995 |
| WO | WO 96/00736 A1 | 1/1996 |
| WO | WO 96/05168 A1 | 2/1996 |
| WO | WO 96/05169 A1 | 2/1996 |
| WO | WO 96/05529 A1 | 2/1996 |
| WO | WO 96/06138 A1 | 2/1996 |
| WO | WO 96/06193 A1 | 2/1996 |
| WO | WO 96/16443 A1 | 5/1996 |
| WO | WO 96/17861 A1 | 6/1996 |
| WO | WO 96/21456 A1 | 7/1996 |
| WO | WO 96/21701 A2 | 7/1996 |
| WO | WO 96/22278 A1 | 7/1996 |
| WO | WO 96/24611 A1 | 8/1996 |
| WO | WO 96/24612 A1 | 8/1996 |
| WO | WO 96/30017 A1 | 10/1996 |
| WO | WO 96/30018 A1 | 10/1996 |
| WO | WO 96/30343 A1 | 10/1996 |
| WO | WO 96/30362 A1 | 10/1996 |
| WO | WO 96/30363 A1 | 10/1996 |
| WO | WO 96/31111 A1 | 10/1996 |
| WO | WO 96/31477 A1 | 10/1996 |
| WO | WO 96/31478 A1 | 10/1996 |
| WO | WO 96/31501 A1 | 10/1996 |
| WO | WO 96/33159 A1 | 10/1996 |
| WO | WO 96/34850 A1 | 11/1996 |
| WO | WO 96/34851 A1 | 11/1996 |
| WO | WO 97/00252 A1 | 1/1997 |
| WO | WO 97/02920 A1 | 1/1997 |
| WO | WO 97/03047 A1 | 1/1997 |
| WO | WO 97/03050 A1 | 1/1997 |
| WO | WO 97/04785 A1 | 2/1997 |
| WO | WO 1997/13537 A1 | 4/1997 |
| WO | WO 97/17070 A1 | 5/1997 |
| WO | WO 97/18813 A1 | 5/1997 |
| WO | WO 97/21701 A1 | 6/1997 |
| WO | WO 97/23478 A1 | 7/1997 |
| WO | WO 97/26246 A1 | 7/1997 |
| WO | WO 97/30053 A1 | 8/1997 |
| WO | WO 97/37705 A1 | 10/1997 |
| WO | WO 97/38665 A2 | 10/1997 |
| WO | WO 97/44350 A1 | 11/1997 |
| WO | WO 98/02436 A1 | 1/1998 |
| WO | WO 98/28980 A1 | 7/1998 |
| WO | WO 98/29119 A1 | 7/1998 |
| WO | WO 99/34850 A1 | 7/1999 |
| WO | WO 00/44777 A1 | 8/2000 |
| WO | WO 2000/50032 A1 | 8/2000 |
| WO | WO 00/61186 A1 | 10/2000 |
| WO | WO 2001/02369 A2 | 1/2001 |
| WO | WO 2001/019829 A2 | 3/2001 |
| WO | WO 02/076986 A1 | 10/2002 |
| WO | WO 02/079197 A1 | 10/2002 |
| WO | WO 02/080926 A1 | 10/2002 |
| WO | WO 02/083653 A1 | 10/2002 |
| WO | WO 02/096905 A1 | 12/2002 |
| WO | WO 02/102800 A1 | 12/2002 |
| WO | WO 2003/018021 A1 | 3/2003 |
| WO | WO 2003/018022 A1 | 3/2003 |
| WO | WO 03/026664 A1 | 4/2003 |
| WO | WO 2003/051847 A1 | 6/2003 |
| WO | WO 2003/078403 A2 | 9/2003 |
| WO | WO 2003/097610 A1 | 11/2003 |
| WO | WO 2004/005283 A1 | 1/2004 |
| WO | WO 2004/009601 A1 | 1/2004 |
| WO | WO 2004/010995 A1 | 2/2004 |
| WO | WO 2004/022561 * | 3/2004 ........... C07D 487/04 |
| WO | WO 2004/022561 A1 | 3/2004 |
| WO | WO 2004/026229 A2 | 4/2004 |
| WO | WO 2004/039796 A1 | 5/2004 |
| WO | WO 2004/074283 A1 | 9/2004 |
| WO | WO 2004/076458 A1 | 9/2004 |
| WO | WO 2004/078757 A2 | 9/2004 |
| WO | WO 2004/081013 A1 | 9/2004 |
| WO | WO 2004/087699 A2 | 10/2004 |
| WO | WO 2004/087707 A1 | 10/2004 |
| WO | WO 2004/100868 A2 | 11/2004 |
| WO | WO 2004/113303 A1 | 12/2004 |
| WO | WO 2004/113304 A1 | 12/2004 |
| WO | WO 2005/011597 A2 | 2/2005 |
| WO | WO 2005/058891 A1 | 6/2005 |
| WO | WO 2005/097790 A1 | 10/2005 |
| WO | WO 2005/108397 A1 | 11/2005 |
| WO | WO 2005/116025 A2 | 12/2005 |
| WO | WO 2006/003276 A1 | 1/2006 |
| WO | WO 2006/024834 A1 | 3/2006 |
| WO | WO 2006/031806 A2 | 3/2006 |
| WO | WO 2006/034341 A2 | 3/2006 |
| WO | WO 2006/040568 A1 | 4/2006 |
| WO | WO 2007/002325 A1 | 1/2007 |
| WO | WO 2007/002433 A1 | 1/2007 |
| WO | WO 2007/024680 A1 | 3/2007 |
| WO | WO 2007/035428 A1 | 3/2007 |
| WO | WO 2007/042786 A2 | 4/2007 |
| WO | WO 2007/044420 A1 | 4/2007 |
| WO | WO 2007/048070 A2 | 4/2007 |
| WO | WO 2007/075869 A2 | 7/2007 |
| WO | WO 2007/129195 A2 | 11/2007 |
| WO | WO 2007/138277 A1 | 12/2007 |
| WO | WO 2008/049856 A1 | 5/2008 |
| WO | WO 2008/063888 A2 | 5/2008 |
| WO | WO 2008/068171 A1 | 6/2008 |
| WO | WO 2008/074749 A1 | 6/2008 |
| WO | WO 2008/080015 A2 | 7/2008 |
| WO | WO 2008/112913 A1 | 9/2008 |
| WO | WO 2008/124393 A1 | 10/2008 |
| WO | WO 2008/144253 A1 | 11/2008 |
| WO | WO 2008/151183 A1 | 12/2008 |
| WO | WO 2008/151304 A1 | 12/2008 |
| WO | WO 2009/017822 A2 | 2/2009 |
| WO | WO 2009/028655 A1 | 3/2009 |
| WO | WO 2009/032694 A1 | 3/2009 |
| WO | WO 2009/145360 A1 | 12/2009 |
| WO | WO 2009/152027 A1 | 12/2009 |
| WO | WO 2009/155017 A2 | 12/2009 |
| WO | WO 2010/008847 A2 | 1/2010 |
| WO | WO 2010/051781 A1 | 5/2010 |
| WO | WO 2010/125799 A1 | 11/2010 |
| WO | WO 2010/144909 A1 | 12/2010 |
| WO | WO 2011/115725 A2 | 9/2011 |
| WO | WO 2013/014162 A1 | 1/2013 |
| WO | WO 2013/040436 A2 | 3/2013 |
| WO | WO 2013/074986 A1 | 5/2013 |
| WO | WO 2013/136070 A1 | 9/2013 |
| WO | WO 2013/154778 A1 | 10/2013 |
| WO | WO 2014/063061 A1 | 4/2014 |
| WO | WO 2014/063068 A1 | 4/2014 |
| WO | WO 2015/013635 A1 | 1/2015 |
| WO | WO 2015/058126 A1 | 4/2015 |
| WO | WO 2015/058140 A1 | 4/2015 |
| WO | WO 2015/117087 A1 | 8/2015 |
| WO | WO 2015/154022 A1 | 10/2015 |
| WO | WO 2015/164604 A1 | 10/2015 |
| WO | WO 2015/164614 A1 | 10/2015 |
| WO | WO 2016/014542 A1 | 1/2016 |
| WO | WO 2016/014551 A1 | 1/2016 |
| WO | WO 2016/023014 A2 | 2/2016 |
| WO | WO 2016/105528 A2 | 6/2016 |
| WO | WO 2017/037576 A1 | 3/2017 |

OTHER PUBLICATIONS

U.S. Appl. No. 14/921,894, filed Oct. 23, 2015, Gray et al.
U.S. Appl. No. 15/538,763, filed Jun. 22, 2017, Gray et al.
PCT/US2012/065618, Mar. 19, 2013, International Search Report and Written Opinion.
PCT/US2012/065618, May 30, 2014, International Preliminary Report on Patentability.
PCT/US2013/065708, Feb. 4, 2014, International Search Report and Written Opinion.
PCT/US2013/065708, Apr. 30, 2015, International Preliminary Report on Patentability.
PCT/US2013/065689, Mar. 4, 2014, International Search Report and Written Opinion.

(56) References Cited

OTHER PUBLICATIONS

PCT/US2013/065689, Apr. 30, 2015, International Preliminary Report on Patentability.
PCT/US2013/065698, Feb. 20, 2014, International Search Report and Written Opinion.
PCT/US2013/065698, Apr. 30, 2015, International Preliminary Report on Patentability.
PCT/US2014/061232, Dec. 23, 2014, International Search Report and Written Opinion.
PCT/US2015/027312, Jul. 10, 2015, International Search Report and Written Opinion.
PCT/US2015/027312, Nov. 3, 2016, International Preliminary Report on Patentability.
PCT/US2015/027294, Jul. 10, 2015, International Search Report and Written Opinion.
PCT/US2015/027294, Nov. 3, 2016, International Preliminary Report on Patentability.
PCT/US2010/038518, Dec. 22, 2011, International Preliminary Report on Patentability.
PCT/US2010/038518, Aug. 6, 2010, International Search Report and Written Opinion.
EP 10786967.9, Oct. 23, 2012, Extended European Search Report.
EP 10844280.7, Apr. 17, 2013, Extended European Search Report.
EP 15160591.2, Jul. 14, 2015, Partial European Search Report.
EP 15160591.2, Nov. 2, 2015, Partial European Search Report.
PCT/US2010/062310, Oct. 4, 2011, International Search Report and Written Opinion.
PCT/US2010/062310, Jul. 12, 2012, International Preliminary Report on Patentability.
PCT/US2015/000297, Mar. 4, 2016, International Search Report and Written Opinion.
PCT/US2015/000297, Jul. 6, 2017, International Preliminary Report on Patentability.
PCT/US2016/037086, Sep. 2, 2016, International Search Report and Written Opinion.
PCT/US2016/037086, Dec. 21, 2017, International Preliminary Report on Patentability.
PCT/US2016/024345, Aug. 9, 2016, Invitation to Pay Additional Fees.
PCT/US2016/024345, Oct. 6, 2016, International Search Report and Written Opinion.
PCT/US2016/024345, Oct. 12, 2017, International Preliminary Report on Patentability.
PCT/US2016/051118, Dec. 1, 2016, Invitation to Pay Additional Fees.
PCT/US2016/051118, Mar. 13, 2017, International Search Report and Written Opinion.
PCT/US2011/025423, May 31, 2011, Invitation to Pay Additional Fees.
PCT/US2011/025423, Nov. 5, 2012, International Search Report and Written Opinion.
PCT/US2011/025423, Nov. 29, 2012, International Preliminary Report on Patentability.
Partial Supplementary European Search Report for EP 16773870.7, dated Jul. 12, 2018.
International Preliminary Report on Patentability for PCT/US2016/051118, dated Mar. 22, 2018.
Peifer et al., Small-molecule inhibitors of PDK1. ChemMedChem. Dec. 2008;3(12):1810-38. doi: 10.1002/cmdc.200800195.
Williamson et al., Structure-guided design of pyrazolo[1,5-a]pyrimidines as inhibitors of human cyclin-dependent kinase 2. Bioorg Med Chem Lett. Feb. 15, 2005;15(4):863-7.
Akira et al., Toll-like receptor signalling. Nat Rev Immunol. Jul. 2004;4(7):499-511.
Attoub et al., The c-kit tyrosine kinase inhibitor STI571 for colorectal cancer therapy. Cancer Res. Sep. 1, 2002;62(17):4879-83.
Beeler et al., Role of the JNK-interacting protein 1/islet brain 1 in cell degeneration in Alzheimer disease and diabetes. Brain Res Bull. Oct. 28, 2009;80(4-5):274-81. doi: 10.1016/j.brainresbull.2009.07.006. Epub Jul. 16, 2009

Bloom et al., The requirement for Phr1 in CNS axon tract formation reveals the corticostriatal boundary as a choice point for cortical axons. Genes Dev. Oct. 15, 2007;21(20):2593-606. Epub Sep. 27, 2007.
Carvajal et al., KIT as a therapeutic target in metastatic melanoma. JAMA. Jun. 8, 2011;305(22):2327-34. doi: 10.1001/jama.2011.746.
Chen et al., Antiapoptotic and trophic effects of dominant-negative forms of dual leucine zipper kinase in dopamine neurons of the substantia nigra in vivo. J Neurosci. Jan. 16, 2008;28(3):672-80. doi: 10.1523/JNEUROSCI.2132-07.2008.
Fan et al., Dual leucine zipper-bearing kinase (DLK) activates p46SAPK and p38mapk but not ERK2. J Biol Chem. Oct. 4, 1996;271(40):24788-93.
Fernandes et al., JNK2 and JNK3 are major regulators of axonal injury-induced retinal ganglion cell death. Neurobiol Dis. May 2012;46(2):393-401. doi: 10.1016/j.nbd.2012.02.003. Epub Feb. 14, 2012.
Hirai et al., The c-Jun N-terminal kinase activator dual leucine zipper kinase regulates axon growth and neuronal migration in the developing cerebral cortex. J Neurosci. Nov. 15, 2006;26(46):11992-2002.
Itoh et al., Impaired regenerative response of primary sensory neurons in ZPK/DLK gene-trap mice. Biochem Biophys Res Commun. May 29, 2009;383(2):258-62. doi: 10.1016/j.bbrc.2009.04.009. Epub Apr. 7, 2009.
Joh et al., Ginsenoside Rb1 and its metabolite compound K inhibit IRAK-1 activation—the key step of inflammation. Biochem Pharmacol. Aug. 1, 2011;82(3):278-86. doi: 10.1016/j.bcp.2011.05.003. Epub May 12, 2011.
Kanakaraj et al., Interleukin (IL)-1 receptor-associated kinase (IRAK) requirement for optimal induction of multiple IL-1 signaling pathways and IL-6 production. J Exp Med. Jun. 15, 1998;187(12):2073-9.
Lorenzo et al., Expression of proto-oncogene c-kit in high risk prostate cancer. Eur J Surg Oncol. Nov. 2004;30(9):987-92.
Marelli et al., Tumor targeting via integrin ligands. Front. Oncol., Aug. 30, 2013. https://doi.org/10.3389/fonc.2013.00222.
Matsuyama et al., Activation of Discoidin Domain Receptor 1 Isoform b with Collagen Up-Regulates Chemokine Production in Human Macrophages: Role of p38 Mitogen-Activated Protein Kinase and NF-κB. J Immunol Feb. 15, 2004, 172 (4) 2332-2340; DOI: https://doi.org/10.4049/jimmunol.172.4.2332.
Powers et al., Discovery and initial SAR of inhibitors of interleukin-1 receptor-associated kinase-4. Bioorg Med Chem Lett. Jun. 1, 2006;16(11):2842-5. Epub Mar. 24, 2006.
Roberts et al., Antiangiogenic and antitumor activity of a selective PDGFR tyrosine kinase inhibitor, CP-673,451. Cancer Res. Feb. 1, 2005;65(3):957-66.
Rubin et al., KIT activation is a ubiquitous feature of gastrointestinal stromal tumors. Cancer Res. Nov. 15, 2001;61(22):8118-21.
Sengupta et al., DLK induces developmental neuronal degeneration via selective regulation of proapoptotic JNK activity. Journal of Cell Biology 2011;194(5):751-764. DOI https://doi.org/10.1083/jcb.201103153.
Shin et al., Dual leucine zipper kinase is required for retrograde injury signaling and axonal regeneration. Neuron. Jun. 21, 2012;74(6):1015-22. doi: 10.1016/j.neuron.2012.04.028.
Srivastava et al., Augmentation of therapeutic responses in melanoma by inhibition of IRAK-1,-4. Cancer Res. Dec. 1, 2012;72(23):6209-16. doi: 10.1158/0008-5472.CAN-12-0337. Epub Oct. 4, 2012.
Wang et al., IRAK-4 inhibitors for inflammation. Curr Top Med Chem. 2009;9(8):724-37.
Wietek et al., IRAK-4: a new drug target in inflammation, sepsis, and autoimmunity. Mol Interv. Jul. 2002;2(4):212-5.
Yasuda et al., The stem cell factor/c-kit receptor pathway enhances proliferation and invasion of pancreatic cancer cells. Mol Cancer. Oct. 18, 2006;5:46.
International Search Report and Written Opinion for PCT/US2012/065618, dated Mar. 19, 2013.
International Preliminary Report on Patentability for PCT/US2012/065618, dated May 30, 2014.

(56) References Cited

OTHER PUBLICATIONS

International Search Report and Written Opinion for PCT/US2013/065708, dated Feb. 4, 2014.
International Preliminary Report on Patentability for PCT/US2013/065708, dated Apr. 30, 2015.
International Search Report and Written Opinion for PCT/US2013/065689, dated Mar. 4, 2014.
International Preliminary Report on Patentability for PCT/US2013/065689, dated Apr. 30, 2015.
International Search Report and Written Opinion for PCT/US2013/065698, dated Feb. 20, 2014.
International Preliminary Report on Patentability for PCT/US2013/065698, dated Apr. 30, 2015.
International Search Report and Written Opinion for PCT/US2014/061232, dated Dec. 23, 2014.
International Search Report and Written Opinion for PCT/US2015/027312, dated Jul. 10, 2015.
International Preliminary Report on Patentability for PCT/US2015/027312, dated Nov. 3, 2016.
International Search Report and Written Opinion for PCT/US2015/027294, dated Jul. 10, 2015.
Extended European Search Report for EP 10786967.9, dated Oct. 23, 2012.
International Search Report and Written Opinion for PCT/US2010/038518, dated Aug. 6, 2010.
International Preliminary Report on Patentability for PCT/US2010/038518, dated Dec. 22, 2011.
Extended European Search Report for EP 10844280.7, dated Apr. 17, 2013.
Partial European Search Report for EP 15160591.2, dated Jul. 14, 2015.
Extended European Search Report for EP 15160591.2, dated Nov. 2, 2015.
International Search Report and Written Opinion for PCT/US2010/062310, dated Oct. 4, 2011.
International Preliminary Report on Patentability for PCT/US2010/062310, dated Jul. 12, 2012.
International Search Report and Written Opinion for PCT/US2015/000297, dated Mar. 4, 2016.
International Preliminary Report on Patentability PCT/US2015/000297, dated Jul. 6, 2017.
International Search Report and Written Opinion for PCT/US2016/037086, dated Sep. 2, 2016.
International Preliminary Report on Patentability for PCT/US/2016/037086, dated Dec. 21, 2017.
Invitation to Pay Additional Fees for PCT/US2016/024345, mailed Aug. 9, 2016.
International Search Report and Written Opinion for PCT/US2016/024345, dated Oct. 6, 2016.
International Preliminary Report on Patentability for PCT/US2016/024345, dated Oct. 12, 2017.
Invitation to Pay Additional Fees for PCT/US2016/051118, mailed Dec. 1, 2016.
International Search Report and Written Opinion for PCT/US2016/051118, dated Mar. 13, 2017.
Invitation to Pay Additional Fees for PCT/US2011/025423, mailed May 31, 2011.
International Search Report and Written Opinion from PCT/US2011/025423, dated Nov. 5, 2012.
International Preliminary Report on Patentability for PCT/US2011/025423, dated Nov. 29, 2012.
CAS Registry No. 916173-61-0, STN Entry Date Dec. 21, 2006.
CAS Registry No. 769961-42-4, STN Entry Date Oct. 27, 2004.
CAS Registry No. 769961-59-3, STN Entry Date Oct. 27, 2004.
CAS Registry No. 1334419-59-8, STN Entry Date Dec. 30, 2013.
GenBank Accession No. M80629. Lapidot-Lifson et al., Dec. 31, 1994. 2 pages.
GenBank Accession No. NP_001790. Yang et al., Oct. 6, 2016. 4 pages.
PubChem-CID-68365059. Available at https://pubchem.ncbi.nlm.nih.gov/compound/68365059. Accessed Jun. 17, 2016.
Uniprot No. Q9NYV4. Last modified Mar. 15, 2017. 14 pages.
Akhtar et al., TFIIH kinase places bivalent marks on the carboxy-terminal domain of RNA polymerase II. Mol Cell. May 15, 2009;34(3):387-93. doi: 10.1016/j.molcel.2009.04.016.
Bajrami et al., Genome-wide profiling of genetic synthetic lethality identifies CDK12 as a novel determinant of PARP1/2 inhibitor sensitivity. Cancer Res. Jan. 1, 2014;74(1):287-97. doi: 10.1158/0008-5472.CAN-13/2541. Epub Nov. 15, 2013.
Bartkowiak et al., CDK12 is a transcription elongation-associated CTD kinase, the metazoan ortholog of yeast Ctk1. Genes Dev. Oct. 15, 2010;24(20):2303-16. doi: 10.1101/gad.1968210.
Bell et al., Integrated genomic analyses of ovarian carcinoma. Nature. Jun. 29, 2011;474(7353):609-15. doi: 10.1038/nature10166.
Ben-Av et al., Induction of vascular endothelial growth factor expression in synovial fibroblasts by prostaglandin E and interleukin-1: a potential mechanism for inflammatory angiogenesis. FEBS Letters 1995;372:83-7.
Benezra et al., In vivo angiogenic activity of interleukins. Archives of Opthamology 1990;108:573.
Berge et al., Pharmaceutical salts. J. Pharmaceutical Sciences 1977 66:1-19.
Blazek et al., The Cyclin K/Cdk12 complex maintains genomic stability via regulation of expression of DNA damage response genes. Genes Dev. Oct. 15, 2011;25(20):2158-72. doi: 10.1101/gad.16962311.
Blazek et al., the cyclin K/Cdk12 complex: an emerging new player in the maintenance of genome stability. Cell Cycle. Mar. 15, 2012;11(6):1049-50. doi: 10.4161/cc.11.6.19678. Epub Mar. 15, 2012.
Bosken et al., The structure and substrate specificity of human Cdk12/Cyclin K. Nat Commun. Mar. 24, 2014;5:3505. doi: 10.1038/ncomms4505.
Brower et al., Tumor Angiogenesis: New drugs on the block. Nature Biotechnology 1999;17:963-8.
Brunton et al., eds., Chemotherapy of Neoplastic Diseases. In Goodman & Gilman's the Pharmacological Basis of Therapeutics. 2008; 11th edition:853-908.
Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.
Cappuzzo et al., Increased MET gene copy number negatively affects survival of surgically resected non-small-cell lung cancer patients. J Clin Oncol. Apr. 1, 2009;27(10):1667-74. doi: 10.1200/JCO.2008.19.1635. Epub Mar. 2, 2009.
Castillo et al., suzuki reaction on pyridinium N-haloheteroarylaminides: regioselective synthesis of 3,5-disubstituted 2-aminopyrazines. Available Online Nov. 22, 2007; 2008; 64(7);1351-1370.
Chakraborty et al., Developmental expression of the cyclo-oxygenase-1 and cyclo-oxygenase-2 genes in the peri-implantation mouse uterus and their differential regulation by the blastocyst and ovarian steroids. Journal of Molecular Endocrinology 1996;16:107-122.
Chen et al., Cdk12 and Cdk13 regulate axonal elongation through a common signaling pathway that modulates Cdk5 expression. Exp Neurol. Nov. 2014;261:10-21. doi: 10.1016/j.expneurol.2014.06.024. Epub Jul. 3, 2014.
Chiarugi et al., Cox-2, iNOS and p53 as play-makers of tumor angiogenesis. International Journal of Molecular Medicine 1998;2:715-9.
Choi et al., Development of 'DFG-out' inhibitors of gatekeeper mutant kinases. Bioorg Med Chem Lett. Aug. 15, 2012;22(16):5297-302. doi: 10.1016/j.bmcl.2012.06.036. Epub Jun. 23, 2012.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009. Supplementary Materials.
Chong et al., Positive and negative regulation of Raf kinase activity and function by phosphorylation EMBO J. Jul. 16, 2001;20(14):3716-27.

(56) References Cited

OTHER PUBLICATIONS

Christensen et al., Cytoreductive antitumor activity of PF-2341066, a novel inhibitor of anaplastic lymphoma kinase and c-Met, in experimental models of anaplastic large-cell lymphoma. Mol Cancer Ther. Dec. 2007;6(12 Pt 1):3314-22.
Christensen et al., Targeting transcriptional addictions in small cell lung cancer with a covalent CDK7 inhibitor. Cancer Cell. Dec. 8, 2014;26(6):909-22.
Christian et al., Flavopiridol in chronic lymphocytic leukemia: a concise review. Clin Lymphoma Myeloma. 2009;9 Suppl 3:S179-85. doi: 10.3816/CLM.2009.s.009.
Davies et al., Mutations of the BRAF gene in human cancer Nature. Jun. 27, 2002;417(6892):949-54. Epub Jun. 9, 2002.
Davis et al., Comprehensive analysis of kinase inhibitor selectivity. Nat Biotechnol. Oct. 30, 2011;29(11):1046-51. doi: 10.1038/nbt.1990.
Desai et al., Effects of phosphorylation by CAK on cyclin binding by CDC2 and CDK2. Mol Cell Biol. Jan. 1995;15(1):345-50.
Diaz-Flores et al., Intense vascular sprouting from rat femoral vein induced by prostaglandins E1 and E2. Anatomical Record 1994;238:68-76.
Downward, Targeting RAS signalling pathways in cancer therapy Nat Rev Cancer. Jan. 2003;3(1):11-22.
Drapkin et al., Human cyclin-dependent kinase-activating kinase exists in three distinct complexes. Proc Natl Acad Sci U S A. Jun. 25, 1996;93(13):6488-93.
Ercan et al., Reactivation of ERK signaling causes resistance to EGFR kinase inhibitors. Cancer Discov. Oct. 2012;2(10):934-47.
Even et al., CDC2L5, a Cdk-like kinase with RS domain, interacts with the ASF/SF2-associated protein p32 and affects splicing in vivo. J Cell Biochem. Oct. 15, 2006;99(3):890-904.
Fernandez et al., Neovascularization produced by angiotensin I.Journal of Laboratory and Clinical Medicine 1985;105(2):141-5.
Filippakopoulos et al., Selective inhibition of BET bromodomains. Nature. Dec. 23, 2010;468(7327):1067-73.
Finn et al., Dasatinib, an orally active small molecule inhibitor of both the src and abl kinases, selectively inhibits growth of basal-type/"triple-negative" breast cancer cell lines growing in vitro. Breast Cancer Res Treat. Nov. 2007;105(3):319-26. Epub Feb. 1, 2007.
Fizazi, The role of Src in prostate cancer. Ann Oncol. Nov. 2007;18(11):1765-73. Epub Apr. 10, 2007.
Fleisher et al., Improved oral drug delivery: solubility limitations overcome by the use of prodrugs. Advanced Drug Delivery Reviews 1996;19:115-30.
Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.
Fry et al., Specific inhibition of cyclin-dependent kinase 4/6 by PD 0332991 and associated antitumor activity in human tumor xenografts. Mol Cancer Ther. Nov. 2004;3(11):1427-38.
Garnett et al., Guilty as charged: B-RAF is a human oncogene Cancer Cell. Oct. 2004;6(4):313-9.
Glover-Cutter et al., TFIIH-associated Cdk7 kinase functions in phosphorylation of C-terminal domain Ser7 residues, promoter-proximal pausing, and termination by RNA polymerase II. Mol Cell Biol. Oct. 2009;29(20):5455-64. doi: 10.1128/MCB.00637-09. Epub Aug. 10, 2009.
Gojo et al., The cyclin-dependent kinase inhibitor flavopiridol induces apoptosis in multiple myeloma cells through transcriptional repression and down-regulation of Mcl-1. Clin Cancer Res. Nov. 2002;8(11):3527-38.
Gu et al., Effect of novel CAAX peptidomimetic farnesyltransferase inhibitor on angiogenesis in vitro and in vivo. European Journal of Cancer 1999;35(9):1394-1401.
Harada et al., Expression and regulation of vascular endothelial growth factor in osteoblasts. Clinical Orthopedics 1995;313:76-80.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Hla et al., Human cyclooxygenase-2 cDNA. Proceedings of the National Academy of Sciences 1992;89(16):7384-8.
Hur et al., Clinical stage EGFR inhibitors irreversibly alkylate Bmx kinase. Bioorg Med Chem Lett. Nov. 15. 2008;18(22):5916-9. doi: 10.1016/j.bmcl.2008.07.062. Epub Jul. 18, 2008.
Iorns et al., CRK7 modifies the MAPK pathway and influences the response to endocrine therapy. Carcinogenesis. Oct. 2009;30(10):1696-701. doi: 10.1093/carcin/bgp187. Epub Aug. 3, 2009.
Janne et al., Factors underlying sensitivity of cancers to small-molecule kinase inhibitors. Nat Rev Drug Discov. Sep. 2009;8(9):709-23. doi: 10.1038/nrd2871. Epub Jul. 24, 2009.
Joshi et al., Ovarian cancer-associated mutations disable catalytic activity of CDK12, a kinase that promotes homologous recombination repair and resistance to cisplatin and poly(ADP-ribose) polymerase inhibitors. J Biol Chem. Mar. 28, 2014;289(13):9247-53. doi: 10.1074/jbc.M114.551143. Epub Feb. 19, 2014.
Jouve et al., Oxidative cyclization of n-methyl- and n-benzoylpyridylthioureas. Preparation of new thiazolo[4,5-b] and [5,4-b] pyridine derivatives. J Heterocyclic Chemistry. 2003;40(2):261-68.
Kaldis et al., Analysis of CAK activities from human cells. Eur J Biochem. Jul. 2000;267(13):4213-21.
Kantarjian et al., Dasatinib versus imatinib in newly diagnosed chronic-phase chronic myeloid leukemia. N Engl J Med. Jun. 17, 2010;362(24):2260-70.
Kauraniemi et al., New amplified and highly expressed genes discovered in the ERBB2 amplicon in breast cancer by cDNA microarrays. Cancer Res. Nov. 15, 2001;61(22):8235-40.
Kim et al., Discovery of pyrrolopyridine-pyridone based inhibitors of Met kinase: synthesis, X-ray crystallographic analysis, and biological activities. J Med Chem. Sep. 11, 2008;51(17):5330-41. doi: 10.1021/jm800476q. Epub Aug. 9, 2008.
Kim et al., Inhibition of vascular endothelial growth factor-induced angiogenesis suppresses tumour growth in vivo. Nature 1993;362:841.
King et al., Demonstration of a genetic therapeutic index for tumors expressing oncogenic BRAF by the kinase inhibitor SB-590885. Cancer Res. Dec. 1, 2006;66(23):11100-5.
Ko et al., CrkRS: a novel conserved Cdc2-related protein kinase that colocalises with SC35 speckles. J Cell Sci. Jul. 2001;114(Pt 14):2591-603.
Koivunen et al., EML4-ALK fusion gene and efficacy of an ALK kinase inhibitor in lung cancer. Clin Cancer Res. Jul. 1, 2008;14(13):4275-83. doi: 10.1158/1078-0432.CCR-08-0168.
Konig et al., The novel cyclin-dependent kinase inhibitor flavopiridol downregulates Bcl-2 and induces growth arrest and apoptosis in chronic B-cell leukemia lines. Blood. Dec. 1, 1997;90(11):4307-12.
Kwiatkowski et al., Targeting transcription regulation in cancer with a covalent CDK7 inhibitor. Nature. Jul. 31, 2014;511(7511):616-20.
Kwong et al., Targeted therapy for melanoma: rational combinatorial approaches. Oncogene. Jan. 2, 2014;33(1):1-9. doi: 10.1038/onc.2013.34. Epub Feb. 18, 2013.
Larochelle et al., Requirements for Cdk7 in the assembly of Cdk1/cyclin B and activation of Cdk2 revealed by chemical genetics in human cells. Mol Cell. Mar. 23, 2007;25(6):839-50.
Lavis et al., Bright ideas for chemical biology. ACS Chem Biol. Mar. 20, 2008;3(3):142-55. doi: 10.1021/cb700248m.
Lee et al., BRAF mutations in non-Hodgkin's lymphoma. Br J Cancer. Nov. 17, 2003;89(10):1958-60.
Lin et al., Phase II study of flavopiridol in relapsed chronic lymphocytic leukemia demonstrating high response rates in genetically high-risk disease. J Clin Oncol. Dec. 10, 2009;27(35):6012-8.
Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.
Liu et al., Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin

(56) References Cited

OTHER PUBLICATIONS (mTOR) inhibitor for the treatment of cancer. J Med Chem. Oct. 14, 2010;53(19):7146-55. doi: 10.1021/jm101144f.
Liu et al., Salt-inducible kinase is involved in the regulation of corticotropin-releasing hormone transcription in hypothalamic neurons in rats. Endocrinology. Jan. 2012;153(1):223-33. doi: 10.1210/en.2011-1404. Epub Nov. 22, 2011.
Liu et al., Two cyclin-dependent kinases promote RNA polymerase II transcription and formation of the scaffold complex. Mol Cell Biol. Feb. 2004;24(4):1721-35.
Llambi et al., Apoptosis and oncogenesis: give and take in the BCL-2 family. Curr Opin Genet Dev. Feb. 2011;21(1):12-20. doi: 10.1016/j.gde.2010.12.001. Epub Jan. 13, 2011.
Lyne et al., Identification of amidoheteroaryls as potent inhibitors of mutant (V600E) B-Raf kinase with in vivo activity. Bioorg Med Chem Lett. Feb. 1, 2009;19(3):1026-9. doi: 10.1016/j.bmcl.2008.10.053. Epub Oct. 15, 2008.
Majima et al., Significant Roles of Inducible Cyclooxygenase (COX)-2 in Angiogenesis in Rat Sponge Implants. Japanese Journal of Pharmacology 1997;75;105-14.
Mallinson et al., Macrocycles in new drug discovery. Future Med Chem. Jul. 2012;4(11):1409-38. doi: 10.4155/fmc.12.93.
March, Advanced Organic Chemistry Reactions, Mechanisms and Structure. 4th ed. 1992:383-386.
Marques et al., A new subfamily of high molecular mass CDC2-related kinases with PITAI/VRE motifs. Biochem Biophys Res Commun. Dec. 29, 2000;279(3):832-7.
Mukaiyama et al., The unexpected and the unpredictable in organic synthesis. Tetrahedron Jul. 1999;55(29):8609-70.
Neklesa et al., Small-molecule hydrophobic tagging-induced degradation of HaloTag fusion proteins. Nat Chem Biol. Jul. 3, 2011;7(8):538-43. doi: 10.1038/nchembio.597.
Obenauf et al., Therapy-induced tumour secretomes promote resistance and tumour progression. Nature. Apr. 16, 2015;520(7547):368-72. doi: 10.1038/nature14336. Epub Mar. 25, 2015.
Odingo et al., Synthesis and evaluation of the 2,4-diaminoquinazoline series as anti-tubercular agents. Bioorg Med Chem. Dec. 15, 2014;22(24):6965-79. doi: 10.1016/j.bmc.2014.10.007. Epub Oct. 22, 2014.
Ou et al., Activity of crizotinib (PF02341066), a dual mesenchymal-epithelial transition (MET) and anaplastic lymphoma kinase (ALK) inhibitor, in a non-small cell lung cancer patient with de novo MET amplification. J Thorac Oncol. May 2011;6(5):942-6. doi: 10.1097/JTO.0b013e31821528d3.
Robinson et al., Discovery of the hemifumarate and (alpha-L-alanyloxy)methyl ether as prod rugs of an anti rheumatic oxindole: prod rugs for the enolic OH group. J. Med. Chem. 1996;39:108.
Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.
Seed et al., The Inhibition of colon-26 Adenocarcinoma Development and Angiogenesis by Topical Diclofenac in 2.5% Hyaluronan. Cancer Research 1997;57:1625-9.
Serizawa et al., Association of Cdk-activating kinase subunits with transcription factor TFIIH. Nature. Mar. 16, 1995;374(6519):280-2.
Sharma et al., A chromatin-mediated reversible drug-tolerant state in cancer cell subpopulations. Cell. Apr. 2, 2010;141(1):69-80.
Shiekhattar et al., Cdk-activating kinase complex is a component of human transcription factor TFIIH. Nature. Mar. 16, 1995;374(6519):283-7.
Smith et al., Recent advances in the research and development of RAF kinase inhibitors. Curr. Top Med. Chem. 2006; 6(11):1071-89.
Smith et al., The effect of the nature of the amine leaving group on the nature of the E2 transition state for the reaction of 1-phenylethylammonium ions sodium ethoxide in ethanol. Can J Chem. Mar. 28, 1989;67:1457-67.

Stanovnik et al., The Tautomerism of Heterocycles: Substituent Tautomerism of Six-Membered Ring Heterocycles. Advances in Heterocyclic Chemistry. 2006;91:1-134.
Stuhlmiller et al., Inhibition of Lapatinib-Induced Kinome Reprogramming in ERBB2-Positive Breast Cancer by Targeting Bet Family Bromodomains. Cell Rep. Apr. 21, 2015;11(3):390-404.
Takemori et al., Inactivation of HDACS by SIK1 in AICAR-treated C2C12 myoblasts. Endocr J. 2009;56(1):121-30. Epub Oct. 22, 2008.
Terai et al., Activation of the FGF2-FGFR1 autocrine pathway: a novel mechanism of acquired resistance to gefitinib in NSCLC. Mol Cancer Res. Jul. 2013;11(7):759-67.
Tsai et al., Discovery of a selective inhibitor of oncogenic B-Raf kinase with potent antimelanoma activity. Proc Natl Acad Sci U S A. Feb. 26, 2008;105(8):3041-6. doi: 10.1073/pnas.0711741105. Epub Feb. 19, 2008.
Tsujii et al., Cyclooxygenase regulates angiogenesis induced by colon cancer cells. Cell. May 29, 1998;93(5):705-16.
Wang et al., Ligand-associated ERBB2/3 activation confers acquired resistance to FGFR inhibition in FGFR3-dependent cancer cells. Oncogene. Apr. 23, 2015;34(17):2167-77. doi: 10.1038/onc.2014.161. Epub Jun. 9, 2014.
Wang et al., Pharmacophore and structure-activity relationships of integrase inhibition within a dual inhibitor scaffold of HIV reverse transcriptase and integrase. Bioorg Med Chem. Jun. 15, 2010;18(12):4202-11. doi: 10.1016/j.bmc.2010.05.004. Epub May 7, 2010.
Wellbrock et al., The RAF proteins take centre stage Nat Rev Mol Cell Biol. Nov. 2004;5(11):875-85.
Wilen et al., Strategies in optical resolutions. Tetrahedron 33:2725 (1977).
Yalpani, Cholesterol Lowering Drugs. Chemistry and Industry Feb. 1996;3:85-89.
Zambon et al., Small molecule inhibitors of BRAF in clinical trials. Bioorg Med Chem Lett. Jan. 15, 2012;22(2):789-92. doi: 10.1016/j.bmcl.2011.11.060. Epub Dec. 3, 2011.
Zang et al., Genetic and structural variation in the gastric cancer kinome revealed through targeted deep sequencing. Cancer Res. Jan. 1, 2011;71(1):29-39. doi: 10.1158/0008-5472.CAN-10-1749. Epub Nov. 19, 2010.
Zebisch et al., Back to the roots: the remarkable RAF oncogene story Cell Mol Life Sci. Jun. 2006;63(11):1314-30.
Zhang et al., Discovery of potent and selective covalent inhibitors of JNK. Chem Biol. Jan. 27, 2012;19(1):140-54. doi: 10.1016/j.chembiol.2011.11.010.
Zhou et al., Novel mutant-selective EGFR kinase inhibitors against EGFR T790M. Nature. Dec. 24, 2009;462(7276):1070-4.
Ziche et al., Role of prostaglandin E1 and copper in angiogenesis. Journal of the National Cancer Institute 1982;69(2):475.
U.S. Appl. No. 16/202,961, filed Nov. 28, 2018, Gray et al.
U.S. Appl. No. 16/130,975, filed Sep. 13, 2018, Gray et al.
U.S. Appl. No. 16/009,715, filed Jun. 15, 2018, Gray et al.
U.S. Appl. No. 16/179,833, filed Nov. 2, 2018, Gray et al.
U.S. Appl. No. 16/735,532, filed Dec. 11, 2017, Hammerman et al.
U.S. Appl. No. 16/758,982, filed Mar. 9, 2018, Gray et al.
U.S. Appl. No. 16/583,974, filed Dec. 5, 2012, Gray et al.
EP 16773870.7, Oct. 17, 2018, Extended European Search Report.
Extended European Search Report for EP 15773870.7, dated Oct. 17, 2018.
EP 16773870.7, Jul. 12, 2018, Partial Supplementary European Search Report.
PCT/US2016/051118, Mar. 22, 2018, International Preliminary Report on Patentability.
Partial Supplementary Search Report for EP 16808476.2, dated Mar. 7, 2019.
Extended European Search Report for EP 16845194.6, dated Mar. 1, 2019.
Blachly et al., Emerging drug profile: cyclin-dependent kinase inhibitors. Leuk Lymphoma. Oct. 2013;54(10):2133-43. doi: 10.3109/10428194.2013.783911. Epub Jul. 29, 2013.
Dent et al. Synergistic combinations of signaling pathway inhibitors: mechanisms for improved cancer therapy. Drug Resist Updat. Jun. 2009;12(3):65-73. doi: 10.1016/j.drup.2009.03.001.

(56) References Cited

OTHER PUBLICATIONS

Fiskus et al., BET protein antagonist JQ1 is synergistically lethal with FLT3 tyrosine kinase inhibitor (TKI) and overcomes resistance to FLT3-TKI in AML cells expressing FLT-ITD. Mol Cancer Ther. Oct. 2014; 13(10): 2315-2327. Published online Jul. 22, 2014. doi: 10.1158/1535-7163.MCT-14-0258.

Fleming et al., Synergistic inhibition of ErbB signaling by combined treatment with seliciclib and ErbB-targeting agents. Clin Cancer Res. Jul. 1, 2008;14(13):4326-35. doi: 10.1158/1078-0432.CCR-07-4633.

Girotti et al., No longer an untreatable disease: How targeted and immunotherapies have changed the management of melanoma patients. Mol Oncol. Sep. 2014; 8(6): 1140-1158. Published online Aug. 15, 2014. doi: 10.1016/j.molonc.2014.07.027.

Katt et al., Dissemination from a Solid Tumor: Examining the Multiple Parallel Pathways. Trends Cancer. Jan. 2018;4(1):20-37. doi: 10.1016/j.trecan.2017.12.002. Epub Jan. 10, 2018.

McAuley et al., CARMA3 Is a Critical Mediator of G Protein-Coupled Receptor and Receptor Tyrosine Kinase-Driven Solid Tumor Pathogenesis. Front Immunol. Aug. 15, 2018;9:1887. doi: 10.3389/fimmu.2018.01887. eCollection 2018.

Orzaez et al., Intrinsic caspase-8 activation mediates sensitization of erlotinib-resistant tumor cells to erlotinib/cell-cycle inhibitors combination treatment. Cell Death Dis. Oct. 25, 2012;3:e415. doi: 10.1038/cddis.2012.155.

Sidow et al., Concepts in solid tumor evolution. Trends Genet. Apr. 2015;31(4):208-14. doi: 10.1016/j.tig.2015.02.001. Epub Feb. 27, 2015.

Tian et al., mTOR Signaling in Cancer and mTOR Inhibitors in Solid Tumor Targeting Therapy. Int J Mol Sci. Feb. 11, 2019;20(3). pii: E755. doi: 10.3390/ijms20030755.

Vora et al., CDK 4/6 inhibitors sensitize PIK3CA Mutant Breast Cancer to PI3K inhibitors. Cancer Cell. Jul. 14, 2014;26(1):136-149. Published online Jul. 4, 2014. doi: 10.1016/j.ccr.2014.05.020.

EP 16808476.2, Mar. 7, 2019, Partial Supplementary European Search Report.

EP 16845194.6, Mar. 1, 2019, Extended European Search Report.

\* cited by examiner

Table 1. Evaluation of Exemplified Compounds in NB cells (IC50 nM)

| | MYCN-amplified KELLY | MYCN-nonamplified SH-SY5Y |
|---|---|---|
| SB1-E-23 (1-3) | 17.29 | 42.70 |
| SB1-E-17 | 24.90 | 320.11 |
| SB1-E-21 | 76.31 | 662.16 |
| SB1-E-16 | 154.77 | 525.87 |
| Dinaciclib | 3.85 | 13.28 |

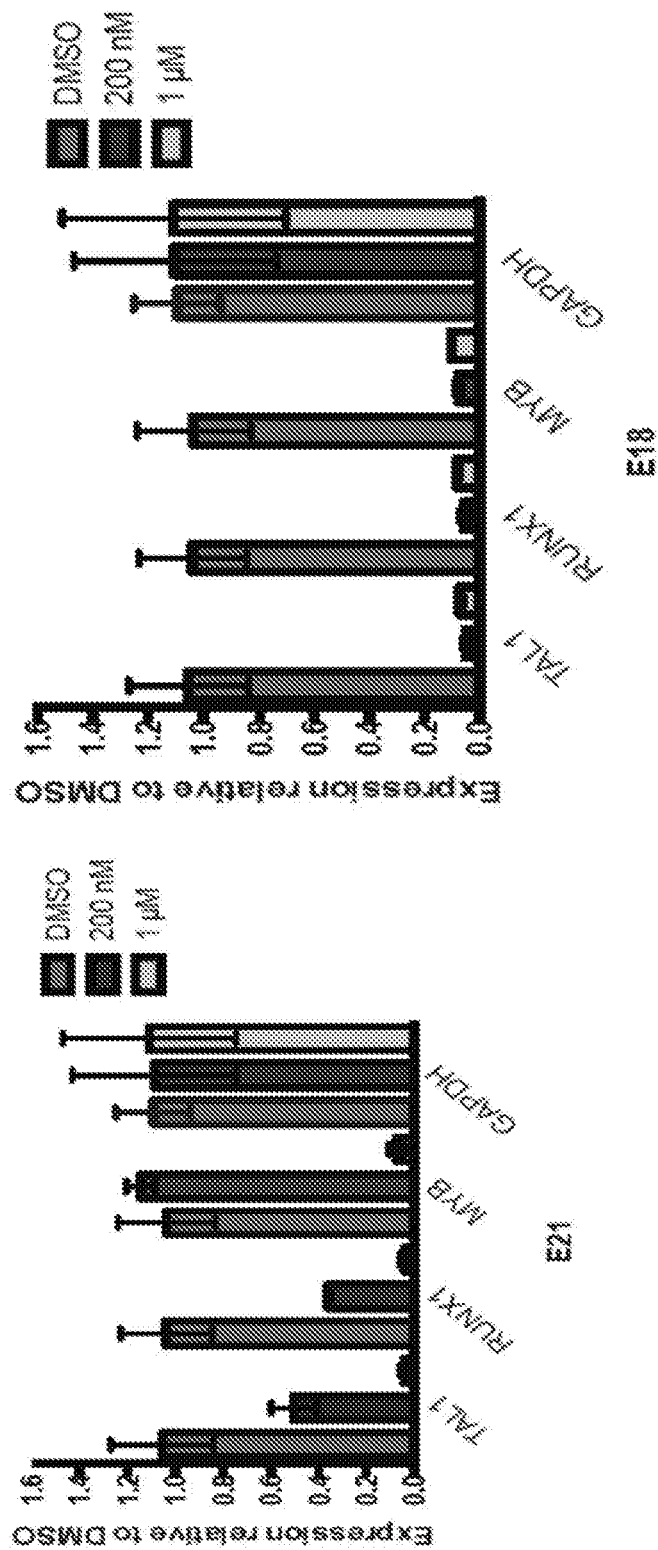
Figure 6 - continued

Table A4. Jurkat cells treated with indicated compounds at 1μM.*

| Kinase | Reference | Sequence | SEQ ID NO: | Labeling Site | E9 1μM |
|---|---|---|---|---|---|
| ABL, ARG | UniRef100_P00519, UniRef100_P42684 | LMTGDTYTAHAGAKFPIK | 1 | Activation Loop | 10.4 |
| ABL, ARG | UniRef100_P00519, UniRef100_P42684 | YSLTVAVKTLKEDTMEVEEFLK | 2 | Lys1 | 15.1 |
| ACK | UniRef100_Q07912 | TVSVAVKCLKPDVLSQPEAMDDFIR | 3 | Lys1 | 12 |
| AKT1 | UniRef100_P31749 | GTFGKVILVK | 4 | ATP Loop | 14.8 |
| AKT2, AKT3 | UniRef100_Q9Y243, UniRef100_P31751 | GTFGKVILVR | 5 | ATP Loop | 20.3 |
| AMPKa1 | UniRef100_Q96E92 | IGHYILGDTLGVGTFGKVK | 6 | ATP Loop | 15.2 |
| AMPKa1 | UniRef100_Q96E92 | VGKHELTGHKVAVKILNR | 7 | Lys1 | 0.9 |
| AMPKa1, AMPKa2 | UniRef100_P54646, UniRef100_Q96E92 | VAVKILNR | 8 | Lys1 | 12.6 |
| AMPKa1, AMPKa2 | UniRef100_P54646, UniRef100_Q96E92 | DLKPENVLLDAHMNAK | 9 | Lys2 | 4.5 |
| ARAF | UniRef100_P10398 | DLKSNNIFLHEGLTVK | 10 | Lys2 | 11.7 |
| ATR | UniRef100_Q13535 | FYIMMCKPK | 11 | ATP | 17.4 |
| AurA | UniRef100_O14965 | FILALKVLFK | 12 | Lys1 | 51.7 |
| AurA | UniRef100_O14965 | DIKPENLLLGSAGELK | 13 | Lys2 | 55.7 |
| AurA, AurB, AurC | UniRef100_O14965, UniRef100_Q9UQB9, UniRef100_Q96GD4 | GKFGNVYLAR | 14 | ATP Loop | 11.7 |
| AurB | UniRef100_Q96GD4 | SHFIVALKVLFK | 15 | Lys1 | 34.4 |
| BARK1 | UniRef100_P25098 | DLKPANILLDEHGHVR | 16 | Lys2 | -5.8 |
| BRAF | UniRef100_P15056 | DLKSNNIFLHEDLTVK | 17 | Lys2 | 7.4 |
| CaMK1d | UniRef100_Q8IU85 | LFAVKCIPK | 18 | Lys1 | 8.1 |
| CaMK1d | UniRef100_Q8IU85 | DLKPENLLYYSQDEESK | 19 | Lys2 | 13.4 |
| CaMK2a, CaMK2b, CaMK2d, CaMK2g | UniRef100_Q53H78, UniRef100_Q13557, UniRef100_Q13555, UniRef100_Q9UQM7 | DLKPENLLLASK | 20 | Lys2 | 0 |
| CaMK2d | UniRef100_Q13557 | IPTGQEYAAKIINTKK | 21 | Lys1 | 6 |
| CaMK2g | UniRef100_Q13555 | TSTQEYAAKIINTK | 22 | Lys1 | 0.3 |
| CaMK4 | UniRef100_Q16566 | IVEHQVLMKTVCGTPGYCAPEILR | 23 | Activation Loop | 29.9 |
| CaMK4 | UniRef100_Q16566 | GTQKPYALKVLK | 24 | Lys1 | 6.7 |
| CaMK4 | UniRef100_Q16566 | DLKPENLLYATPAPDAPLK | 25 | Lys2 | 43.6 |

Figure 10

| Kinase | UniRef ID | Peptide | # | Site | Value |
|---|---|---|---|---|---|
| CaMKK2 | UniRef100_Q96RR4 | LAYNENDNTYYAMKVLSK | 26 | Lys1 | 10.3 |
| CaMKK2 | UniRef100_Q96RR4 | DIKPSNLLVGEDGHIK | 27 | Lys2 | -9.6 |
| CCRK | UniRef100_Q8IZL9 | DLKPANLLISASGQLK | 28 | Lys2 | -6.5 |
| CDC2 | UniRef100_Q5H9N4 | DLKPQNLLIDDKGTIK | 29 | Lys2 | -12.9 |
| CDC2 | UniRef100_Q5H9N4 | DLKPQNLLIDDK | 30 | Lys2 | -32.6 |
| CDK10 | UniRef100_Q15131 | DLKVSNLLMTDK | 31 | Lys2 | 18.2 |
| CDK11, CDK8 | UniRef100_P49336, UniRef100_Q9BWU1 | DLKPANILVMGEGPER | 32 | Lys2 | -5.7 |
| CDK2 | UniRef100_P24941 | LTGEVVALKK | 33 | Lys1 | -48.7 |
| CDK2 | UniRef100_P24941 | DLKPQNLLINTEGAIK | 34 | Lys2 | -29.1 |
| CDK5 | UniRef100_Q00535 | NRETHEIVALKR | 35 | Lys1 | 4.5 |
| CDK5 | UniRef100_Q00535 | DLKPQNLLINR | 36 | Lys2 | -10.6 |
| CDK6 | UniRef100_Q00534 | DLKPQNILVTSSGQIK | 37 | Lys2 | -9.4 |
| CDK7 | UniRef100_P50613 | DKNTNQIVAIKK | 38 | Lys1 | 17.5 |
| CDK7 | UniRef100_P50613 | DLKPNNLLLDENGVLK | 39 | Lys2 | 5.8 |
| CDK9 | UniRef100_P50750 | DMKAANVLITR | 40 | Lys2 | 27.7 |
| CDK13 | UniRef100_Q14004 | DIKCSNILLNNR | 41 | Lys2 | 77.6 |
| CHK1 | UniRef100_B4DT73 | DIKPENLLLDER | 42 | Lys2 | -7.7 |
| CHK1 | UniRef100_B4DT73 | LSKGDGLEFK | 43 | Protein Kinase Domain | 7.9 |
| CHK2 | UniRef100_O96017 | VAIKIISK | 44 | Lys1 | 18.2 |
| CHK2 | UniRef100_O96017 | DLKPENVLLSSQEEDCLIK | 45 | Lys2 | -6 |
| CK1a | UniRef100_P48729 | DIKPDNFLMGIGR | 46 | Lys2 | 10.8 |
| CK1d, CK1e | UniRef100_P49674, UniRef100_P48730 | DVKPDNFLMGLGKK | 47 | Lys2 | 27.3 |
| CK1g2 | UniRef100_P78368 | DVKPENFLVGRPGTK | 48 | Lys2 | 13.6 |
| CK2a1 | UniRef100_P68400 | GGPNIITLADIVKDPVSR | 49 | Protein Kinase Domain | -31.5 |
| CK2a2 | UniRef100_P19784 | DVKPHNVMIDHQQK | 50 | Lys2 | -3 |
| CLK1 | UniRef100_P49759 | LTHTDLKPENILFVQSDYTEAYNPK | 51 | Lys2 | 54.2 |
| CLK3 | UniRef100_P49761 | YEIVGNLGEGTFGKVVECLDHAR | 52 | ATP Loop | 16.1 |
| CDK12 | UniRef100_Q9NYV4 | DIKCSNILLNNSGQIK | 53 | Lys2 | 81.7 |
| CSK | UniRef100_P41240 | VSDFGLTKEASSTQDTGKLPVK | 54 | Activation Loop | -0.9 |
| CSK | UniRef100_P41240 | VAVKCIK | 55 | Lys1 | -7.6 |
| DGKA | UniRef100_P23743 | IDPVPNTHPLLVFVNPKSGGK | 56 | ATP | -37.4 |
| DGKH | UniRef100_Q86XP1 | ATFSFCVSPLLVFVNSKSGDNQGVK | 57 | ATP | -18 |
| DNAPK | UniRef100_P78527 | KGGSWIQEINVAEK | 58 | ATP | -1.9 |
| DNAPK | UniRef100_P78527 | EHPFLVKGGEDLR | 59 | ATP | 21.7 |

Figure 10 (continued)

| | | | | | |
|---|---|---|---|---|---|
| DRAK1 | UniRef100_Q9UEE5 | DVVHLDLKPQNILLTSESPLGDIK | 60 | Lys2 | 17.9 |
| eEF2K | UniRef100_O00418 | YIKYNSNSGFVR | 61 | ATP | 8.8 |
| EphB2 | UniRef100_P29323 | FLEDDTSDPTYTSALGGKIPIR | 62 | Activation Loop | -23.4 |
| Erk1 | UniRef100_P27361 | DLKPSNLLINTTCDLK | 63 | Lys2 | -1.7 |
| Erk2 | UniRef100_P28482 | DLKPSNLLLNTTCDLK | 64 | Lys2 | -2.3 |
| Erk5 | UniRef100_Q13164 | DLKPSNLLVNENCELK | 65 | Lys2 | 0.2 |
| FAK | UniRef100_Q05397 | CIGEGQFGDVHQGIYMSPENPALAVAIKTCK | 66 | Lys1 | -13.5 |
| FER | UniRef100_P16591 | QEDGGVYSSSGLKQIPIK | 67 | Activation Loop | -2.2 |
| FER | UniRef100_P16591 | TSVAVKTCKEDLPQELK | 68 | Lys1 | 0.2 |
| FGR | UniRef100_P09769 | LIKDDEYNPCQGSKFPIK | 69 | Activation Loop | -6.6 |
| FRAP | UniRef100_P42345 | IQSIAPSLQVITSKQRPR | 70 | ATP | -15.5 |
| FYN | UniRef100_P06241 | VAIKTLKPGTMSPESFLEEAQIMK | 71 | Lys1 | -21.6 |
| FYN, SRC, YES | UniRef100_P12931, UniRef100_P07947, UniRef100_P06241 | QGAKFPIKWTAPEAALYGR | 72 | Activation Loop | 5.8 |
| GCK | UniRef100_Q12851 | DTVTSELAAVKIVK | 73 | Lys1 | -6 |
| GCK | UniRef100_Q12851 | DIKGANLLLTLQGDVK | 74 | Lys2 | -1.4 |
| GCN2 | UniRef100_Q9P2K8 | LDGCCYAVKR | 75 | Lys1 | -1.8 |
| GCN2 | UniRef100_Q9P2K8 | DLKPVNIFLDSDDHVK | 76 | Lys2 | 6.4 |
| GPRK5 | UniRef100_P34947 | DLKPENILLDDYGHIR | 77 | Lys2 | 17.9 |
| GPRK6 | UniRef100_P43250 | DLKPENILLDDHGHIR | 78 | Lys2 | 16.3 |
| GSK3A | UniRef100_P49840 | DIKPQNLLVDPDTAVLK | 79 | Lys2 | 6.6 |
| GSK3B | UniRef100_P49841 | DIKPQNLLLDPDTAVLK | 80 | Lys2 | 8 |
| HPK1 | UniRef100_Q92918 | DKVSGDLVALKMVK | 81 | Lys1 | 21.3 |
| HPK1 | UniRef100_Q92918 | DIKGANILINDAGEVR | 82 | Lys1 | 10.7 |
| IKKa | UniRef100_O15111 | DLKPENIVLQDVGGK | 83 | Lys2 | 18.7 |
| IKKb | UniRef100_O14920 | WHNQETGEQIAIKQCR | 84 | Lys1 | 14.3 |
| IKKb | UniRef100_O14920 | DLKPENIVLQQGEQR | 85 | Lys2 | 16.9 |
| IKKe | UniRef100_Q14164 | SGELVAVKVFNTTSYLRPR | 86 | Lys1 | 22.4 |
| IKKe, TBK1 | UniRef100_Q14164, UniRef100_Q9UHD2 | DIKPGNIMR | 87 | Lys2 | 26.9 |
| ILK | UniRef100_Q13418 | WQGNDIVVKVLK | 88 | Lys1 | 22.3 |
| ILK | UniRef100_Q13418 | ISMADVKFSFQCPGR | 89 | Protein Kinase Domain | -16.4 |
| IRAK1 | UniRef100_P51617 | AIQFLHQDSPSLIHGDIKSSNVLLDEF | 90 | Lys2 | -1.3 |

Figure 10 (continued)

| | | | | | |
|---|---|---|---|---|---|
| IRAK4 | UniRef100_Q9NWZ3 | GYVNNTTVAVKK | 91 | Lys1 | 30.1 |
| IRAK4 | UniRef100_Q9NWZ3 | DIKSANILLDEAFTAK | 92 | Lys2 | 10.8 |
| IRE1 | UniRef100_O75460 | DLKPHNILISMPNAHGK | 93 | Lys2 | 2.4 |
| ITK | UniRef100_Q08881 | FVLDDQYTSSTGTKFPVK | 94 | Activation Loop | 18.9 |
| ITK | UniRef100_Q08881 | VAIKTIR | 95 | Lys1 | 16.8 |
| ITPK1 | UniRef100_Q13572 | ESIFFNSHNVSKPESSSVLTELDKIEGVFERPSDEVIR | 96 | ATP | 5.5 |
| JAK1 domain1 | UniRef100_P23458 | QLASALSYLEDKDLVHGNVCTKNLLLAR | 97 | Protein Kinase Domain | 26.5 |
| JAK1 domain2 | UniRef100_P23458 | IGDFGLTKAIETDKEYYTVK | 98 | Activation Loop | 35.2 |
| JAK1 domain2 | UniRef100_P23458 | YDPEGDNTGEQVAVKSLKPESGGNHIADLKK | 99 | Lys1 | 38.3 |
| JNK1, JNK2, JNK3 | UniRef100_P45983, UniRef100_P53779, UniRef100_P45984 | DLKPSNIVVK | 100 | Lys2 | -3.6 |
| JNK2 | UniRef100_P45984 | YQQLKPIGSGAQGIVCAAFDTVLGINVAVKK | 101 | Lys1 | -15.3 |
| KHS1 | UniRef100_Q9Y4K4 | NVHTGELAAVKIIK | 102 | Lys1 | -2 |
| KHS1 | UniRef100_Q9Y4K4 | DIKGANILLTDHGDVK | 103 | Lys2 | 4.8 |
| KHS2 | UniRef100_Q8IVH8 | NVNTGELAAIKVIK | 104 | Lys1 | 8.9 |
| LATS1 | UniRef100_O95835 | ALYATKTLR | 105 | Lys1 | 7.2 |
| LATS1 | UniRef100_O95835 | DIKPDNILIDR | 106 | Lys2 | 3.5 |
| LATS2 | UniRef100_Q9NRM7 | DIKPDNILIDLDGHIK | 107 | Lys2 | 11.7 |
| LCK | UniRef100_P06239 | EGAKFPIKWTAPEAINYGTFTIK | 108 | Activation Loop | 5.6 |
| LKB1 | UniRef100_Q15831 | DIKPGNLLLTTGGTLK | 109 | Lys2 | 2.6 |
| LOK | UniRef100_O94804 | NKETGALAAAKVIETK | 110 | Lys1 | 11.4 |
| LOK | UniRef100_O94804 | DLKAGNVLMTLEGDIR | 111 | Lys2 | 4.3 |
| MAP2K1 | UniRef100_Q02750 | IMHRDVKPSNILVNSR | 112 | Lys2 | 17.5 |
| MAP2K1, MAP2K2 | UniRef100_P36507, UniRef100_Q02750 | DVKPSNILVNSR | 113 | Lys2 | -2.4 |
| MAP2K2 | UniRef100_P36507 | HQIMHRDVKPSNILVNSR | 114 | Lys2 | 2.7 |
| MAP2K3 | UniRef100_P46734 | HAQSGTIMAVKR | 115 | Lys1 | 9.6 |
| MAP2K3 | UniRef100_P46734 | DVKPSNVLINK | 116 | Lys2 | 26.7 |
| MAP2K4 | UniRef100_P45985 | MVHKPSGQIMAVKR | 117 | Lys1 | 17.9 |
| MAP2K4 | UniRef100_P45985 | DIKPSNILLDR | 118 | Lys2 | 10.2 |
| MAP2K5 | UniRef100_Q13163 | DVKPSNMLVNTR | 119 | Lys2 | 8 |
| MAP2K6 | UniRef100_P52564 | HVPSGQIMAVKR | 120 | Lys1 | 9.4 |
| MAP2K6 | UniRef100_P52564 | DVKPSNVLINALGQVK | 121 | Lys2 | -7.8 |
| MAP2K7 | UniRef100_O14733 | DVKPSNILLDER | 122 | Lys2 | -0.4 |

Figure 10 (continued)

| Gene | UniRef | Peptide | # | Site | Value |
|---|---|---|---|---|---|
| MAP3K1 | UniRef100_Q13233 | DVKGANLLIDSTGQR | 123 | Lys2 | -6.9 |
| MAP3K15, MAP3K5, MAP3K6 | UniRef100_Q99683, UniRef100_O95382, UniRef100_Q6ZN16 | IAIKEIPER | 124 | Lys1 | 12.5 |
| MAP3K2 | UniRef100_Q9Y2U5 | ELAVKQVQFDPDSPETSKEVNALECEIQLLK | 125 | Lys1 | 8.8 |
| MAP3K2, MAP3K3 | UniRef100_Q9Y2U5, UniRef100_Q99759 | DIKGANILR | 126 | Lys2 | 11.7 |
| MAP3K3 | UniRef100_Q99759 | ELASKQVQFDPDSPETSKEVSALECEIQLLK | 127 | Lys1 | 5.6 |
| MAP3K4 | UniRef100_Q9Y6R4 | DIKGANIFLTSSGLIK | 128 | Lys2 | -3.9 |
| MAP3K5 | UniRef100_Q99683 | DIKGDNVLINTYSGVLK | 129 | Lys2 | 13.5 |
| MAPKAPK3 | UniRef100_Q16644 | QVLGLGVNGKVLECFHR | 130 | ATP Loop | -9.5 |
| MAPKAPK3 | UniRef100_Q16644 | CALKLLYDSPK | 131 | Lys1 | 0.4 |
| MARK1, MARK2 | UniRef100_Q7KZI7, UniRef100_Q9P0L2 | EVAVKIIDK | 132 | Lys1 | 11.7 |
| MARK2 | UniRef100_Q7KZI7 | EVAVKIIDKTQLNSSSLQK | 133 | Lys1 | 16.4 |
| MARK2 | UniRef100_Q7KZI7 | FIVHRDLKAENLLLDADMNIK | 134 | Lys2 | 17.4 |
| MARK2, MARK3 | UniRef100_P27448, UniRef100_Q7KZI7 | DLKAENLLLDADMNIK | 135 | Lys2 | 14.4 |
| MARK3 | UniRef100_P27448 | EVAIKIIDKTQLNPTSLQK | 136 | Lys1 | 15 |
| MARK3, MARK4 | UniRef100_Q96L34, UniRef100_P27448 | EVAIKIIDK | 137 | Lys1 | 12.6 |
| MARK4 | UniRef100_Q96L34 | EVAIKIIDKTQLNPSSLQK | 138 | Lys1 | -6 |
| MARK4 | UniRef100_Q96L34 | DLKAENLLLDAEANIK | 139 | Lys2 | 3.5 |
| MAST3 | UniRef100_O60307 | DLKPDNLLITSLGHIK | 140 | Lys2 | 0.7 |
| MASTL | UniRef100_Q96GX5 | GAFGKVYLGQK | 141 | ATP Loop | -7 |
| MASTL | UniRef100_Q96GX5 | LYAVKVVK | 142 | Lys1 | 6.2 |
| MLK1 | UniRef100_P80192 | DLKSSNILILQK | 143 | Lys2 | -4.6 |
| MLK2 | UniRef100_Q02779 | DLKSINILILEAIENHNLADTVLK | 144 | Lys2 | 0.5 |
| MLK3 | UniRef100_Q16584 | GELVAVKAAR | 145 | Lys1 | 20.3 |
| MLK3 | UniRef100_Q16584 | DLKSNNILLLQPIESDDMEHK | 146 | Lys2 | 7.4 |
| MLKL | UniRef100_Q8NB16 | APVAIKVFK | 147 | Lys1 | -25.9 |
| MPSK1 | UniRef100_O75716 | LGEGGFSYVDLVEGLHDGHFYALKR | 148 | Lys1 | 5.8 |
| MPSK1 | UniRef100_O75716 | DLKPTNILLGDEGQPVLMDLGSMNQACIHVEGSR | 149 | Lys2 | 6.8 |
| MSK1 | UniRef100_O75582 | DIKLENILLDSNGHVVL | 150 | Lys2 | 27.4 |

Figure 10 (continued)

| | | | | | |
|---|---|---|---|---|---|
| domain1 | | TDFGLSK | | | |
| MSK2 domain1 | UniRef100_O75676 | DLKLENVLLDSEGHIVL TDFGLSK | 151 | Lys2 | -21.6 |
| MST1 | UniRef100_Q13043 | ETGQIVAIKQVPVESDL QEIIK | 152 | Lys1 | -1.6 |
| MST1, MST2 | UniRef100_Q13188, UniRef100_Q13043 | DIKAGNILLNTEGHAK | 153 | Lys2 | -0.4 |
| MST2 | UniRef100_Q13188 | ESGQVVAIKQVPVESD LQEIIK | 154 | Lys1 | -7.1 |
| MST3 | UniRef100_Q9Y6E0 | VVAIKIIDLEEAEDEIEDI QQEITVLSQCDSPYVT K | 155 | Lys1 | 0.1 |
| MST3 | UniRef100_Q9Y6E0 | DIKAANVLLSEHGEVK | 156 | Lys2 | 12.3 |
| MST4 | UniRef100_Q9P289 | TQQVVAIKIIDLEEAED EIEDIQQEITVLSQCDS SYVTK | 157 | Lys1 | -21.2 |
| MST4, YSK1 | UniRef100_O00506, UniRef100_Q9P289 | DIKAANVLLSEQGDVK | 158 | Lys2 | 5.9 |
| NDR1 | UniRef100_Q15208 | DTGHVYAMKILR | 159 | Lys1 | 4.4 |
| NDR1 | UniRef100_Q15208 | DIKPDNLLLDSK | 160 | Lys2 | 2.8 |
| NDR2 | UniRef100_Q9Y2H1 | DTGHIYAMKILR | 161 | Lys1 | 7.2 |
| NDR2 | UniRef100_Q9Y2H1 | DIKPDNLLLDAK | 162 | Lys2 | 9.4 |
| NEK1 | UniRef100_Q96PY6 | DIKSQNIFLTK | 163 | Lys2 | 11.6 |
| NEK3 | UniRef100_P51956 | SKNIFLTQNGK | 164 | Activation Loop | 7.7 |
| NEK4 | UniRef100_P51957 | DLKTQNVFLTR | 165 | Lys2 | 36.8 |
| NEK6, NEK7 | UniRef100_Q8TDX7, UniRef100_Q9HC98 | DIKPANVFITATGVVK | 166 | Lys2 | -9.9 |
| NEK7 | UniRef100_Q8TDX7 | AACLLDGVPVALKK | 167 | Lys1 | -0.5 |
| NEK8 | UniRef100_Q86SG6 | DLKTQNILLDK | 168 | Lys2 | -1.9 |
| NEK9 | UniRef100_Q8TD19 | RTEDDSLVVWKEVDLT R | 169 | Lys1 | -23.6 |
| NEK9 | UniRef100_Q8TD19 | DIKTLNIFLTK | 170 | Lys2 | 33.2 |
| NLK | UniRef100_Q9UBE8 | DIKPGNLLVNSNCVLK | 171 | Lys2 | 14.3 |
| OSR1 | UniRef100_C9JIG9, UniRef100_O95747 | DVKAGNILLGEDGSVQ IADFGVSAFLATGGDIT R | 172 | Lys2 | 4.6 |
| p38a | UniRef100_Q16539 | DLKPSNLAVNEDCELK | 173 | Lys2 | 15.9 |
| p38a | UniRef100_Q16539 | QELNKTIWEVPER | 174 | Protein Kinase Domain | 6.5 |
| p38b | UniRef100_Q15759 | QELNKTVWEVPQR | 175 | Protein Kinase Domain | 1.4 |
| p38d, p38g | UniRef100_O15264, UniRef100_P53778 | DLKPGNLAVNEDCELK | 176 | Lys2 | 32.6 |
| p70S6K | UniRef100_P23443 | DLKPENIMLNHQGHVK | 177 | Lys2 | 6.5 |
| p70S6K, p70S6Kb | UniRef100_Q9UBS0, UniRef100_P23443 | GGYGKVFQVR | 178 | ATP Loop | -9.6 |

Figure 10 (continued)

| | | | | | |
|---|---|---|---|---|---|
| p70S6Kb | UniRef100_Q9UBS0 | DLKPENIMLSSQGHIK | 179 | Lys2 | 15.2 |
| PAK2 | UniRef100_Q13177 | IGQGASGTVFTATDVALGQEVAIKQINLQK | 180 | Lys1 | 12.5 |
| PAN3 | UniRef100_Q58A45 | VMDPTKILITGK | 181 | ATP | 8.1 |
| PCTAIRE1 | UniRef100_Q00536 | SKLTDNLVALKEIR | 182 | Lys1 | 11.9 |
| PCTAIRE 1, PCTAIRE 3 | UniRef100_Q00536, UniRef100_Q07002 | DLKPQNLLINER | 183 | Lys2 | 8.6 |
| PCTAIRE 2 | UniRef100_Q00537 | DLKPQNLLINEK | 184 | Lys2 | 10.4 |
| PCTAIRE 2, PCTAIRE 3 | UniRef100_Q00537, UniRef100_Q07002 | SKLTENLVALKEIR | 185 | Lys1 | 14 |
| PDK1 | UniRef100_O15530 | EYAIKILEK | 186 | Lys1 | 6.8 |
| PEK | UniRef100_Q9NZJ5 | DLKPSNIFFTMDDVVK | 187 | Lys2 | 4.8 |
| PHKg2 | UniRef100_P15735 | ATGHEFAVKIMEVTAER | 188 | Lys1 | 15.8 |
| PI4KA, PI4KAP2 | UniRef100_A4QPH2, UniRef100_P42356 | SGTPMQSAAKAPYLAK | 189 | ATP | 23 |
| PI4KB | UniRef100_Q9UBF8 | VPHTQAVVLNSKDK | 190 | ATP | 6.6 |
| PI4KB | UniRef100_Q9UBF8 | LLSVIVKCGDDLRQELLAFQVLK | 191 | ATP | 2.8 |
| PIK3C2B | UniRef100_O00750 | VIFKCGDDLRQDMLTLQMIR | 192 | ATP | 18 |
| PIK3C3 | UniRef100_Q8NEB9 | TEDGGKYPVIFKHGDDLRQDQLILQIISLMDK | 193 | ATP | 27.6 |
| PIK3C3 | UniRef100_Q8NEB9 | TEDGGKYPVIFKHGDDLR | 194 | ATP | 29.8 |
| PIK3CA | UniRef100_P42336 | RPLWLNWENPDIMSELLFQNNEIIFKNGDDLRQDMLTLQIIR | 195 | ATP | 89.1 |
| PIK3CB | UniRef100_P42338 | VFGEDSVGVIFKNGDDLRQDMLTLQMLR | 196 | ATP | 25 |
| PIK3CD | UniRef100_O00329 | TKVNWLAHNVSKDNRQ | 197 | ATP | 0.2 |
| PIK3CD | UniRef100_O00329 | VNWLAHNVSKDNRQ | 198 | ATP | 9.6 |
| PIK3CG | UniRef100_P48736 | KKPLWLEFK | 199 | ATP | 0.9 |
| PIP4K2A | UniRef100_P48426 | AKELPTLKDNDFINEGQK | 200 | ATP | 20.4 |
| PIP4K2B | UniRef100_P78356 | AKDLPTFKDNDFLNEGQK | 201 | ATP | 1.5 |
| PIP4K2C | UniRef100_Q8TBX8 | VKELPTLKDMDFLNK | 202 | ATP | 9.1 |
| PIP4K2C | UniRef100_Q8TBX8 | TLVIKEVSSEDIADMHSNLSNYHQYIVK | 203 | ATP | 4.7 |
| PIP5K3 | UniRef100_Q9Y2I7 | GGKSGAAFYATEDDRFILK | 204 | ATP | 21.8 |

Figure 10 (continued)

| | | | | | |
|---|---|---|---|---|---|
| PITSLRE | UniRef100_P21127 | DLKTSNLLLSHAGILK | 205 | Lys2 | 11.4 |
| PKCa | UniRef100_P17252 | KGTEELYAIKILK | 206 | Lys1 | 8.2 |
| PKCa, PKCb | UniRef100_P05771, UniRef100_P17252 | DLKLDNVMLDSEGHIK | 207 | Lys2 | 42.8 |
| PKCh | UniRef100_P24723 | VKETGDLYAVKVLK | 208 | Lys1 | 35.5 |
| PKCi | UniRef100_P41743 | IYAMKVVK | 209 | Lys1 | 29.6 |
| PKCi | UniRef100_P41743 | DLKLDNVLLDSEGHIK | 210 | Lys2 | 2.6 |
| PKD1, PKD2 | UniRef100_Q9BZL6, UniRef100_Q15139 | NIVHCDLKPENVLLAS ADPFPQVK | 211 | Lys2 | -1.8 |
| PKD2 | UniRef100_Q9BZL6 | DVAVKVIDK | 212 | Lys1 | -7.6 |
| PKD3 | UniRef100_O94806 | DVAIKVIDK | 213 | Lys1 | 13.9 |
| PKD3 | UniRef100_O94806 | NIVHCDLKPENVLLAS AEPFPQVK | 214 | Lys2 | -5.8 |
| PKN1 | UniRef100_Q16512 | VLLSEFRPSGELFAIKA LK | 215 | Lys1 | 33.7 |
| PKN1 | UniRef100_Q16512 | DLKLDNLLLDTEGYVK | 216 | Lys2 | 2.1 |
| PKN2 | UniRef100_Q16513 | DLKLDNLLLDTEGFVK | 217 | Lys2 | -3.9 |
| PKR | UniRef100_P19525 | IGDFGLVTSLKNDGKR | 218 | Activation Loop | -2.2 |
| PKR | UniRef100_P19525 | DLKPSNIFLVDTK | 219 | Lys2 | -9.4 |
| PLK1 | UniRef100_P53350 | CFEISDADTKEVFAGKI VPK | 220 | Lys1 | 60.4 |
| PLK1 | UniRef100_P53350 | DLKLGNLFLNEDLEVK | 221 | Lys2 | 58.8 |
| PRP4 | UniRef100_Q13523 | CNILHADIKPDNILVNE SK | 222 | Lys2 | 14.5 |
| PRP4 | UniRef100_Q13523 | AAGIGKDFKENPNLR | 223 | Protein Kinase Domain | 16.9 |
| PRPK | UniRef100_Q96S44 | FLSGLELVKQGAEAR | 224 | ATP Loop | 33.3 |
| PYK2 | UniRef100_Q14289 | YIEDEDYYKASVTR | 225 | Activation Loop | 33.3 |
| QSK | UniRef100_Q9Y2K2 | VAIKIIDKTQLDEENLKK | 226 | Lys1 | 8.6 |
| RAF1 | UniRef100_P04049 | DMKSNNIFLHEGLTVK | 227 | Lys2 | -4.7 |
| ROCK1, ROCK2 | UniRef100_O75116, UniRef100_Q13464 | DVKPDNMLLDK | 228 | Lys2 | -3.9 |
| RSK1 domain1 | UniRef100_Q15418 | LTDFGLSKEAIDHEKK | 229 | Activation Loop | 0 |
| RSK1 domain1 | UniRef100_Q15418 | KVTRPDSGHLYAMKVL K | 230 | Lys1 | -3 |
| RSK1 domain1, RSK2 domain1, RSK3 domain1 | UniRef100_P51812, UniRef100_Q15418, UniRef100_Q15349 | DLKPENILLDEEGHIK | 231 | Lys2 | 5.2 |
| RSK1 domain2 | UniRef100_Q15418 | DLKPSNILYVDESGNP ECLR | 232 | Lys2 | -10.4 |
| RSK2 domain1 | UniRef100_P51812 | VLGQGSFGKVFLVK | 233 | ATP Loop | -18.6 |
| RSK2 | UniRef100_P51812 | LTDFGLSKESIDHEKK | 234 | Activation Loop | 5.8 |

Figure 10 (continued)

| | | domain1 | | | |
|---|---|---|---|---|---|
| RSK2 domain2 | UniRef100_P51812 | DLKPSNILYVDESGNPESIR | 235 | Lys2 | -13.8 |
| RSKL1 | UniRef100_Q96S38 | VLGVIDKVLLVMDTR | 236 | ATP | 0.8 |
| SGK3 | UniRef100_Q96BR1 | FYAVKVLQK | 237 | Lys1 | 5.5 |
| SGK3 | UniRef100_Q96BR1 | IVYRDLKPENILLDSVGHVVLTDFGLCK | 238 | Lys2 | 33.7 |
| SLK | UniRef100_Q9H2G2 | AQNKETSVLAAAKVIDTK | 239 | Lys1 | 1.1 |
| SLK | UniRef100_Q9H2G2 | DLKAGNILFTLDGDIK | 240 | Lys2 | 11.3 |
| SMG1 | UniRef100_Q96Q15 | DTVTIHSVGGTITILPTKTKPK | 241 | ATP | -1.5 |
| SMG1 | UniRef100_Q96Q15 | SYPYLFKGLEDLHLDER | 242 | ATP | 46.5 |
| SNRK | UniRef100_Q9NRH2 | VAVKVIDK | 243 | Lys1 | 3.6 |
| SNRK | UniRef100_Q9NRH2 | DLKPENVVFFEK | 244 | Lys2 | 1 |
| SRPK1 | UniRef100_Q96SB4 | IIHTDIKPENILLSVNEQYIR | 245 | Lys2 | -5.8 |
| SRPK1, SRPK2 | UniRef100_P78362, UniRef100_Q96SB4 | FVAMKVVK | 246 | Lys1 | -18.5 |
| STLK3 | UniRef100_Q9UEW8 | DLKAGNILLGEDGSVQIADFGVSAFLATGGDVTR | 247 | Lys2 | 15.8 |
| STLK5 | UniRef100_Q7RTN6 | YSVKVLPWLSPEVLQQNLQGYDAK | 248 | Activation Loop | -18.6 |
| STLK5 | UniRef100_Q7RTN6 | SVKASHILISVDGK | 249 | Lys2 | -6.5 |
| STLK6 | UniRef100_Q9C0K7 | HTPTGTLVTIKITNLENCNEER | 250 | Lys1 | -7.3 |
| STLK6 | UniRef100_Q9C0K7 | SIKASHILISGDGLVTLSGLSHLHSLVK | 251 | Lys2 | 5.9 |
| TAK1 | UniRef100_O43318 | DLKPPNLLLVAGGTVLK | 252 | Lys2 | 21.5 |
| TAO1, TAO3 | UniRef100_Q7L7X3, UniRef100_Q9H2K8 | DIKAGNILLTEPGQVK | 253 | Lys2 | 11.1 |
| TAO2 | UniRef100_Q9UL54 | DVKAGNILLSEPGLVK | 254 | Lys2 | 1.6 |
| TBK1 | UniRef100_Q9UHD2 | TGDLFAIKVFNNISFLRPVDVQMR | 255 | Lys1 | 20.3 |
| TLK1 | UniRef100_Q9UKI8 | YAAVKIHQLNK | 256 | Lys1 | 4.8 |
| TLK1 | UniRef100_Q9UKI8 | YLNEIKPPIIHYDLKPGNILLVDGTACGEIK | 257 | Lys2 | 10.9 |
| TLK2 | UniRef100_Q86UE8 | YVAVKIHQLNK | 258 | Lys1 | 2.4 |
| TLK2 | UniRef100_Q86UE8 | YLNEIKPPIIHYDLKPGNILLVNGTACGEIK | 259 | Lys2 | -1.7 |
| TYK2 domain2 | UniRef100_P29597 | IGDFGLAKAVPEGHEYYR | 260 | Activation Loop | 4.6 |
| ULK1 | UniRef100_O75385 | DLKPQNILLSNPAGR | 261 | Lys2 | 4.6 |
| ULK3 | UniRef100_D3DW67 | EVVAIKCVAK | 262 | Lys1 | -15.8 |
| ULK3 | UniRef100_D3DW67 | NISHLDLKPQNILLSSL | 263 | Lys2 | -7.2 |

Figure 10 (continued)

| | | EKPHLK | | | |
|---|---|---|---|---|---|
| Wnk1, Wnk2 | UniRef100_Q9Y3S1, UniRef100_D3DUP1 | GSFKTVYK | 264 | ATP Loop | -62.6 |
| Wnk1, Wnk2, Wnk3 | UniRef100_Q9Y3S1, UniRef100_D3DUP1, UniRef100_Q9BYP7 | DLKCDNIFITGPTGSVK | 265 | Lys2 | -77.2 |
| Wnk1, Wnk2, Wnk4 | UniRef100_Q96J92, UniRef100_Q9Y3S1, UniRef100_D3DUP1 | IGDLGLATLKR | 266 | Activation Loop | 4.1 |
| YSK1 | UniRef100_O00506 | EVVAIKIIDLEEAEDEIEDIQQEITVLSQCDSPYITR | 267 | Lys1 | -13 |
| ZAK | UniRef100_Q9NYL2 | WISQDKEVAVKK | 268 | Lys1 | -6.9 |
| ZAP70 | UniRef100_P43403 | ISDFGLSKALGADDSYYTAR | 269 | Activation Loop | 7.6 |
| ZAP70 | UniRef100_P43403 | QIDVAIKVLK | 270 | Lys1 | -9.2 |
| ZC1/HGK | UniRef100_O95819 | TGQLAAIKVMDVTEDEEEEIKLEINMLKK | 271 | Lys1 | 14.6 |
| ZC1/HGK, ZC2/TNIK, ZC3/MINK | UniRef100_O95819, UniRef100_Q9UKE5, UniRef100_Q8N4C8 | DIKGQNVLLTENAEVK | 272 | Lys2 | 1.4 |
| ZC2/TNIK | UniRef100_Q9UKE5 | TGQLAAIKVMDVTGDEEEEIKQEINMLKK | 273 | Lys1 | -2.1 |

Figure 10 (continued)

*Table A1. Labeling Site Key Information.*

| Lys1 | Conserved Lysine 1 |
|---|---|
| Lys2 | Conserved Lysine 2 |
| ATP Loop | ATP binding loop. |
| Activation Loop | Activation loop |
| ATP | ATP site in non-canonical kinase (e.g. lipid kinase) |
| Protein Kinase Domain | Other lysine within kinase domain, possibly not in ATP binding site |
| Other | Labeling of residue outside of the protein kinase domain, possibly not in ATP binding site |
|  | >90% Inhibition |
|  | 75 - 90% Inhibition |
|  | 50 - 75% Inhibition |
|  | 35 - 50% Inhibition |
|  | No change |
|  | > 100% increase in MS signal |
| Not colored | Variable or weak data not reaching significance despite >35% inhibition |

Figure 10 (continued)

| CDK7 | CDK12 | CDK13 | CDK7 | CDK12 | CDK13 |
|---|---|---|---|---|---|
| CDKN1A | UBASH3A | RPL35A | TRAF5 | HNRNPA1 | HNRNPC |
| MYC | TRAF6 | RPL31 | TET1 | FLI1 | RPS11 |
| RUNX1 | TERF2 | RPS14 | ADAMTS1 | FANCI | EEF1A1 |
| MYB | TAL1 | RPL37A | RBM39 | FANCF | EIF4B |
| TAL1 | SRSF1 | RPL41 | DDX17 | FANCD2 | |
| GATA3 | SRPK1 | RPL4 | UBXN8 | ETS1 | |
| KLF2 | SNRPE | RPL26 | N4BP2L2 | ERG | |
| HNRPDL | SNRPD2 | RPS3 | TEX19 | ERCC4 | |
| ASCL1 | SNRPD1 | RPL12 | CDCA7 | E2F8 | |
| MYCN | SMC3 | SNRPD2 | ING5 | E2F7 | |
| INSM1 | SMC1B | EIF4E | GNL3 | E2F6 | |
| NEUROD1 | SMC1 | INTS8 | PRPF4B | E2F5 | |
| NEUROG1 | SMAD6 | RPL39 | OTUD6B | E2F3 | |
| FOXG1 | SMAD4 | RPS7 | ZNF586 | CSTF3 | |
| FOXA1 | SMAD1 | RPS5 | ZCCHC8 | CHEK2 | |
| SOX2 | SET | EEF2 | PAPOLA | CHEK1 | |
| SOX4 | RUNX1 | EIF3H | MAP2K7 | CHD1 | |
| BCL11A | RFC5 | EIF3E | MGA | CENPA | |
| OTX2 | RFC4 | NPM3 | GIMAP4 | CDC6 | |
| PHOX2B | RAD51D | SNRNP40 | KIF1B | CCDC138 | |
| PLK2 | RAD51C | SNRPG | KAT5 | BUB1B | |
| TAF1 | POLA1 | POLR2L | CCNL1 | BRCA1 | |
| CTGF | PIK3R3 | RPL38 | NUP98 | BCL2 | |
| WEE1 | PARP9 | RPL11 | ZNF295 | BCL11B | |
| SDIM | PARP1 | RPL17 | RBM23 | ATR | |
| JUN | ORC3L | RPL7 | RFC3 | ATM | |
| PIM1 | OBFC2A | EIF3K | S1PR1 | APEX1 | |
| IL8 | NEK9 | RPL14 | FDXACB1 | | |
| FOS1 | NDC80 | POLR2H | CCDC94 | | |
| MCPH1 | MYC | SNRPB | SRSF6 | | |
| PRPF38B | MYB | EEF1D | RAD50 | | |
| C9orf41 | MED13 | EIF3G | GIMAP6 | | |
| ZNF248 | MDC1 | RPS12 | MSI2 | | |
| JMJD6 | MCL1 | RPS23 | xiap | | |
| CHORDC1 | JMJD1C | SNORA38 | mcl1 | | |
| ZNF37A | HNRPDL | EMG1 | | | |
| RABGGTB | HNRNPH1 | RPL37 | | | |
| IL7R | HNRNPC | RPL13 | | | |

Figure 11

- WT CDK12/13 WT HAP1 cells
  (IC50 = 90 nM)
- CDK12 C1039S/ CDK13 C1017S
  HAP1 cells
  (IC50 = 350 nM)

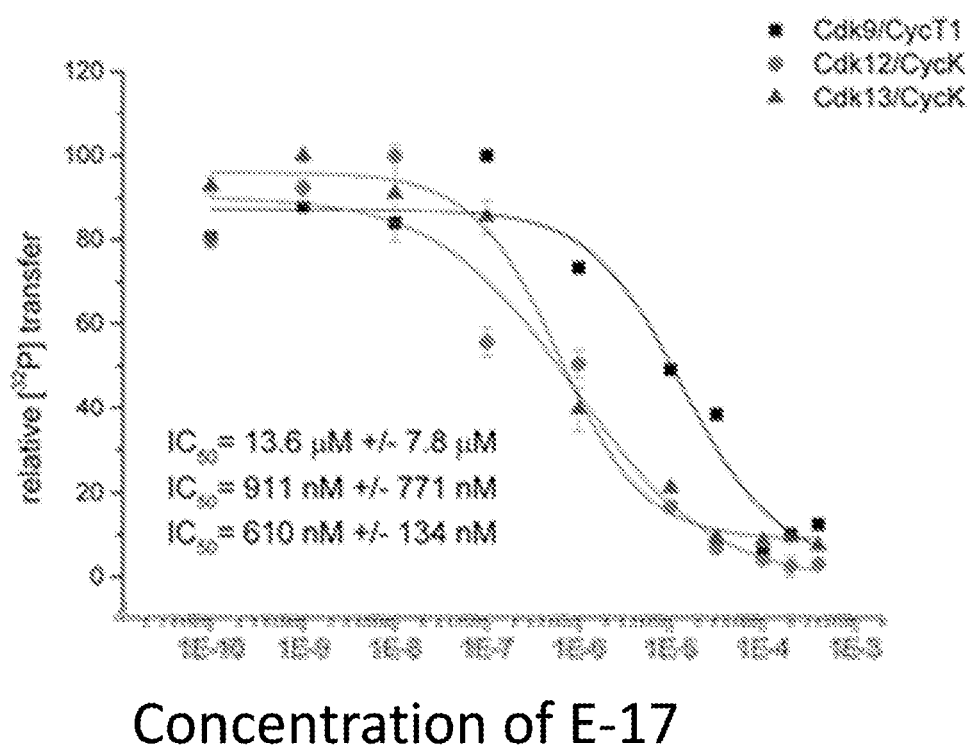
Concentration of E-17
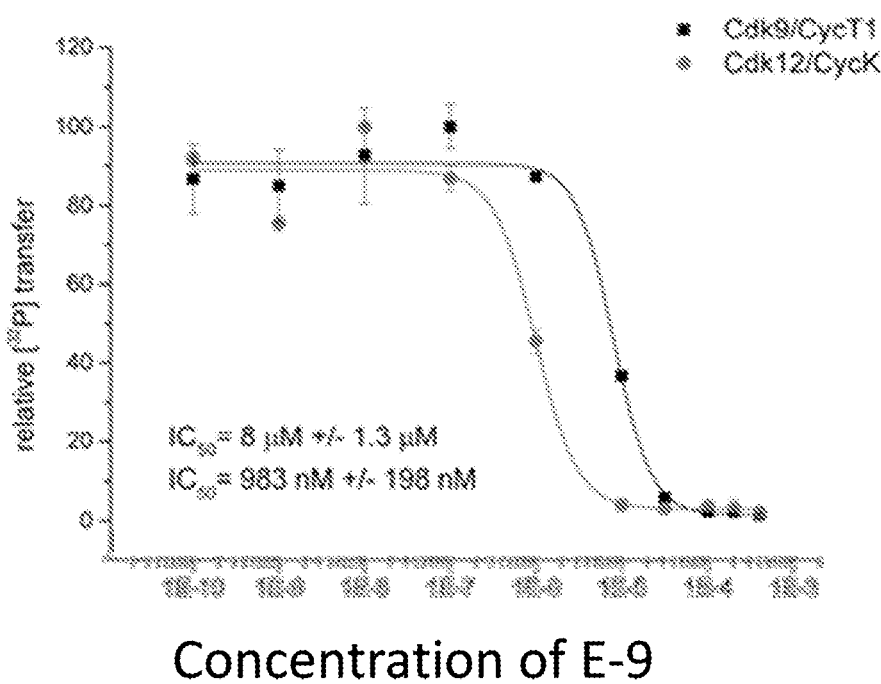
Concentration of E-9
Figure 15

INHIBITORS OF CYCLIN-DEPENDENT KINASES

RELATED APPLICATIONS

This application is a national stage filing under 35 U.S.C. § 371 of international PCT application, PCT/US2016/024345, filed Mar. 25, 2016, which claims priority under 35 U.S.C. § 119(e) to U.S. provisional application, U.S. Ser. No. 62/139,352, filed Mar. 27, 2015, each of which is incorporated herein by reference.

GOVERNMENT SUPPORT

This invention was made with government support under grant number 1 R01 CA179483-01A1 awarded by the National Institutes of Health. The government has certain rights in the invention.

BACKGROUND OF THE INVENTION

The members of the cyclin-dependent kinase (CDK) family play critical regulatory roles in cell proliferation. There are currently twenty known mammalian CDKs. While CDK7-CDK13 have been linked to transcription, only CDK1, 2, 4, and 6 show demonstrable association with the cell cycle.

Unique among the mammalian CDKs, CDK7 has consolidated kinase activities, regulating both the cell cycle and transcription. In the cytosol, CDK7 exists as a heterotrimeric complex and is believed to function as a CDK1/2-activating kinase (CAK), whereby phosphorylation of conserved residues in CDK1/2 by CDK7 is required for full catalytic CDK activity and cell cycle progression (Desai et al., "Effects of phosphorylation by CAK on cyclin binding by CDC2 and CDK2." Mol. Cell Biol. 15, 345-350 (1995); Kaldis et al., "Analysis of CAK activities from human cells." Eur. J. Biochem. 267, 4213-4221 (2000); Larochelle et al., "Requirements for CDK7 in the assembly of CDK1/cyclin B and activation of CDK2 revealed by chemical genetics in human cells." Mol. Cell 25, 839-850 (2007)). In the nucleus, CDK7 forms the kinase core of the RNA polymerase (RNAP) II general transcription factor complex and is charged with phosphorylating the C-terminal domain (CTD) of RNAP II, a requisite step in gene transcriptional initiation (Serizawa. et al., "Association of CDK-activating kinase subunits with transcription factor TFIIH." Nature 374, 280-282 (1995); Shiekhattar et al., "CDK-activating kinase complex is a component of human transcription factor TFIIH." Nature 374, 283-287 (1995); Drapkin et al., "Human cyclin-dependent kinase-activating kinase exists in three distinct complexes." Proc. Natl. Acad. Sci. U.S.A. 93, 6488-6493 (1996); Liu. et al., "Two cyclin-dependent kinases promote RNA polymerase II transcription and formation of the scaffold complex." Mol. Cell Biol. 24, 1721-1735 (2004); Akhtar et al., "TFIIH kinase places bivalent marks on the carboxy-terminal domain of RNA polymerase II." Mol. Cell 34, 387-393 (2009); Glover-Cutter et al., "TFIIH-associated CDK7 kinase functions in phosphorylation of C-terminal domain Ser7 residues, promoter-proximal pausing, and termination by RNA polymerase II." Mol. Cell Biol. 29, 5455-5464 (2009)). Together, the two functions of CDK7, i.e., CAK and CTD phosphorylation, support critical facets of cellular proliferation, cell cycling, and transcription.

CDK12 and CDK13 were identified in cDNA screens for cell cycle regulators. Because their cyclin partners were not yet known, they were initially named CRKRS and CDC2L5 (Ko et al., J. Cell Sci., 2001, 114, 2591-2603; Marques et al., Biochem Biophys Res Commun., 2000, 279(3):832-837), respectively. They were found to be 1490- and 1512-amino acid proteins, respectively, with a conserved central CTD kinase domain and degenerate RS domains identified in their N- and C-terminal regions (Even et al., J Cell Biochem., 2006, 99(3), 890-904).

Evidence has shown CDK12 and CDK13 play an important role in cancer development. A comprehensive genomic approach identified CDK12 to be one of the most frequently somatically mutated genes in high-grade serous ovarian cancer, the most fatal form of the disease (Erratum, Nature, 2011, 474(7353), 609-615). Several identified point mutations in the kinase domain point to the critical importance of the kinase activity of CDK12 for the development/progression of this disease. CDK12 has also been found to contribute to the development of breast cancer. Notably, CDK12 is located on chromosome 17, within the 17q21 locus that contains several candidate genes for breast cancer susceptibility (Kauraniemi et al., Cancer Res., 2001, 61(22), 8235-8240), and it is co-amplified with the tyrosine kinase receptor ERBB2, a protein amplified and overexpressed in about 20% of breast tumors. Gene fusion between CDK12 and ERBB2 was also detected in gastric cancer (Zang et al., Cancer Res., 2011, 71(1), 29-39). CDK12 is also implicated in the modification of tamoxifen sensitivity in estrogen-positive breast cancer via the modulation of the mitogen-activated protein kinase pathway (Iorns et al., Carcinogenesis, 2009, 30(10):1696-1701).

Due to the important regulatory functions of kinases, such as CDK7, CDK12, and CDK13, in cell cycle control, cell proliferation, differentiation, and apoptosis, it is important to develop modulators of the activities of these kinases, including selective modulators, for use as research tools as well as therapeutic agents in the treatment of diseases.

SUMMARY OF THE INVENTION

Cyclin dependent kinases (CDKs), e.g., CDK7, CDK12, and CDK13 are key regulators of the cell cycle. Their successive activation and inactivation drives the cycle forward. The activity of CDKs is regulated by multiple mechanisms such as positive and negative phosphorylation, binding of regulatory proteins like cyclins, and CDK inhibitors. Most CDKs require the phosphorylation of a threonine residue located in the T-loop to achieve full kinase activity. This threonine residue is conserved in all CDKs that function in cell cycle regulation. The enzyme responsible for this phosphorylation is therefore termed CDK-activating-kinase or CAK. CAK complexes have been found to be composed of CDK7, CDK12, CDK13, cyclin H, and MAT1. Besides its CAK function, CDK7, CDK12, and CDK13 also play a role in transcription and possibly in DNA repair. This suggests that the CDK7, CDK12, and CDK13 enzyme complexes are involved in multiple functions in the cell, e.g., cell cycle control, apoptosis, transcription regulation, and DNA repair.

The present invention provides compounds of Formulae (I)-(III), and pharmaceutically acceptable salts, solvates, hydrates, polymorphs, co-crystals, tautomers, stereoisomers, isotopically labeled derivatives, prodrugs, and compositions thereof. The compounds of Formulae (I)-(III), and pharmaceutically acceptable salts, solvates, hydrates, polymorphs, co-crystals, tautomers, stereoisomers, isotopically labeled derivatives, prodrugs, and compositions thereof, may inhibit the activity of a kinase. The compounds described herein can selectively inhibit specific CDK subtypes, for example, CDK7, CDK12, or CDK13. In certain embodiments, the compounds of Formulae (I)-(III) are selective for CDK7 compared to other kinases. In certain embodiments, the compounds of Formulae (I)-(III) are selective for CDK12 and/or CDK13 compared to other kinases. The present invention also provides methods of using the inventive compounds, and pharmaceutically acceptable salts, solvates, hydrates, polymorphs, co-crystals, tautomers, stereoisomers, isotopically labeled derivatives, prodrugs, and compositions thereof, to study the inhibition of a kinase (e.g., CDK7, CDK12, and/or CDK13) and as therapeutics for the prevention and/or treatment of diseases associated with the overexpression and/or aberrant activity of a kinase (e.g., CDK7, CDK12, and/or CDK13). In certain embodiments, the inventive compounds are used for the prevention and/or treatment of proliferative diseases (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases) in a subject.

Since the discovery of selective inhibitors of CDK7, CDK12, and CDK13 has been hampered by the high sequence and structural similarities of the kinase domain of CDK family members, the development of selective inhibitors of the transcriptional cyclin-dependent kinases (tCDKs) will allow dissection of their individual contributions to the regulation of transcription and evaluation of their therapeutic potential. Without wishing to be bound by any particular theory, the inventive compounds' selectivity for CDK7, CDK12, and/or CDK13 may be due to the compounds' ability to covalently modify a specific cysteine residue of these kinases (e.g., Cys312 of CDK7, Cys1039 of CDK12, Cys1017 of CDK13).

In one aspect, the present invention provides compounds of Formula (I):

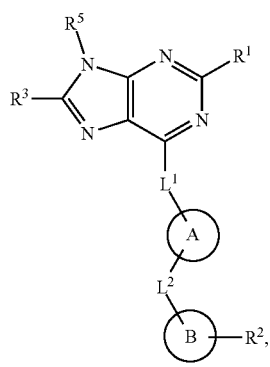
(I)

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^5$, Ring A, Ring B, $L^1$, and $L^2$ are as defined herein.

In one aspect, the present invention provides compounds of Formula (II):

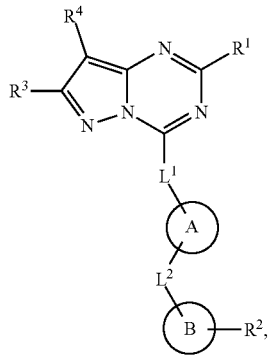
(II)

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^4$, Ring A, Ring B, $L^1$, and $L^2$ are as defined herein.

In one aspect, the present invention provides compounds of Formula (III):

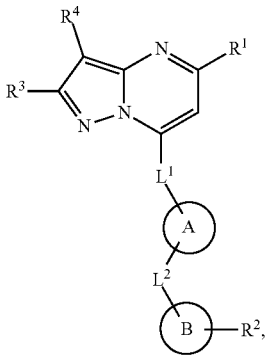
(III)

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^4$, Ring A, Ring B, $L^1$, and $L^2$ are as defined herein.

In another aspect, the present disclosure provides pharmaceutical compositions including a compound described herein, and optionally a pharmaceutically acceptable excipient. In certain embodiments, the pharmaceutical compositions described herein include a therapeutically or prophylactically effective amount of a compound described herein. The pharmaceutical composition may be useful for treating a proliferative disease in a subject in need thereof, preventing a proliferative disease in a subject in need thereof, inhibiting the activity of a protein kinase in a subject, biological sample, tissue, or cell, and/or inducing apoptosis in a cell. In certain embodiments, the proliferative disease is an acute inflammatory disease. In certain embodiments, the acute inflammatory disease is rheumatoid arthritis, Crohn's disease, or fibrosis.

In another aspect, the present invention provides methods for treating and/or preventing a proliferative disease. Exemplary proliferative diseases which may be treated include cancer, benign neoplasm, diseases associated with angiogenesis, inflammatory diseases, autoinflammatory diseases, and autoimmune diseases. In certain embodiments, the cancer is one or more selected from the group consisting of pancreatic cancer, lung cancer (e.g. small cell lung cancer (SCLC), and non-small cell lung cancer), prostate cancer, breast cancer, ovarian cancer, kidney cancer, liver cancer, Ewing's sarcoma, osteosarcoma, brain cancer, neuroblastoma, and colorectal cancer.

Another aspect of the invention relates to methods of inhibiting the activity of a kinase (e.g., CDK (e.g., CDK7, CDK12, CDK13)) in a biological sample or subject. In certain embodiments, the method involves the selective inhibition of CDK7. In certain embodiments, the method involves the selective inhibition of CDK12. In certain embodiments, the method involves the selective inhibition of CDK13.

Also provided by the present invention are methods of inhibiting transcription of one or more genes in the cell of a biological sample or subject. The transcription of genes affected by the activity of CDK7 may be inhibited by a compound of the invention. In certain embodiments, these genes are one or more selected from the group consisting of MYC, RUNX1, MYB, TAL1, GATA3, KLF2, HNRPDL, p21, ASCL1, MYCN, INSM1, NEUROD1, NEUROG1, FOXG1, FOXA1, SOX2, SOX4, BCL11A, OTX2, GAT2, PHOX2B, PLK2, TAF1, CTGF, WEE1, SDIM, JUN, PIM1, IL8, FOS1. The transcription of genes affected by the activity of CDK12 may be inhibited by a compound of the invention. In certain embodiments, these genes are one or more selected from the group consisting of BRCA1, FANCI, ATR, FANCD2, APEX1, NEK9, CHEK1, CHEK2, ATM, RAD51C, RAD51D, ORC3L, MDC1, TERF2, ERCC4, FANCF, PARP9, RUNX1, MYB, TAL1, MCL1, MYC, BCL2, ETS1, EWS-FLI. The transcription of genes affected by the activity of CDK13 may be inhibited by a compound of the invention. In certain embodiments, the gene is SNORA38.

The present invention also provides methods of inhibiting cell growth in a biological sample or subject. In still another aspect, the present invention provides methods of inducing apoptosis of a cell in a biological sample or subject.

In yet another aspect, the present invention provides compounds of Formulae (I)-(III), and pharmaceutically acceptable salts, solvates, hydrates, polymorphs, co-crystals, tautomers, stereoisomers, isotopically labeled derivatives, prodrugs, and compositions thereof, for use in the treatment of a disease (e.g., a proliferative disease such as cancer) in a subject.

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. A kit described herein may also include information (e.g. prescribing information) as required by a regulatory agency such as the U.S. Food and Drug Administration (FDA).

The present invention provides methods for administering to a subject in need thereof an effective amount of a compound, or pharmaceutical composition thereof, as described herein. Also described are methods for contacting a cell with an effective amount of a compound, or pharmaceutical composition thereof, as described herein. In certain embodiments, a method described herein further includes administering to the subject an additional pharmaceutical agent. In certain embodiments, a method described herein further includes contacting the cell with an additional pharmaceutical agent. The methods described herein may further include performing radiotherapy, immunotherapy, and/or transplantation on the subject.

The details of one or more embodiments of the invention are set forth herein. Other features, objects, and advantages of the invention will be apparent from the Detailed Description, the Examples, and the Claims.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 10 shows KiNativ™ kinome profiling of compound E9.

FIG. 11 shows exemplified downstream genes. Transcription of these downstream genes are affected by the activities of CDK7, CDK12, and CDK13.

Figure 1:
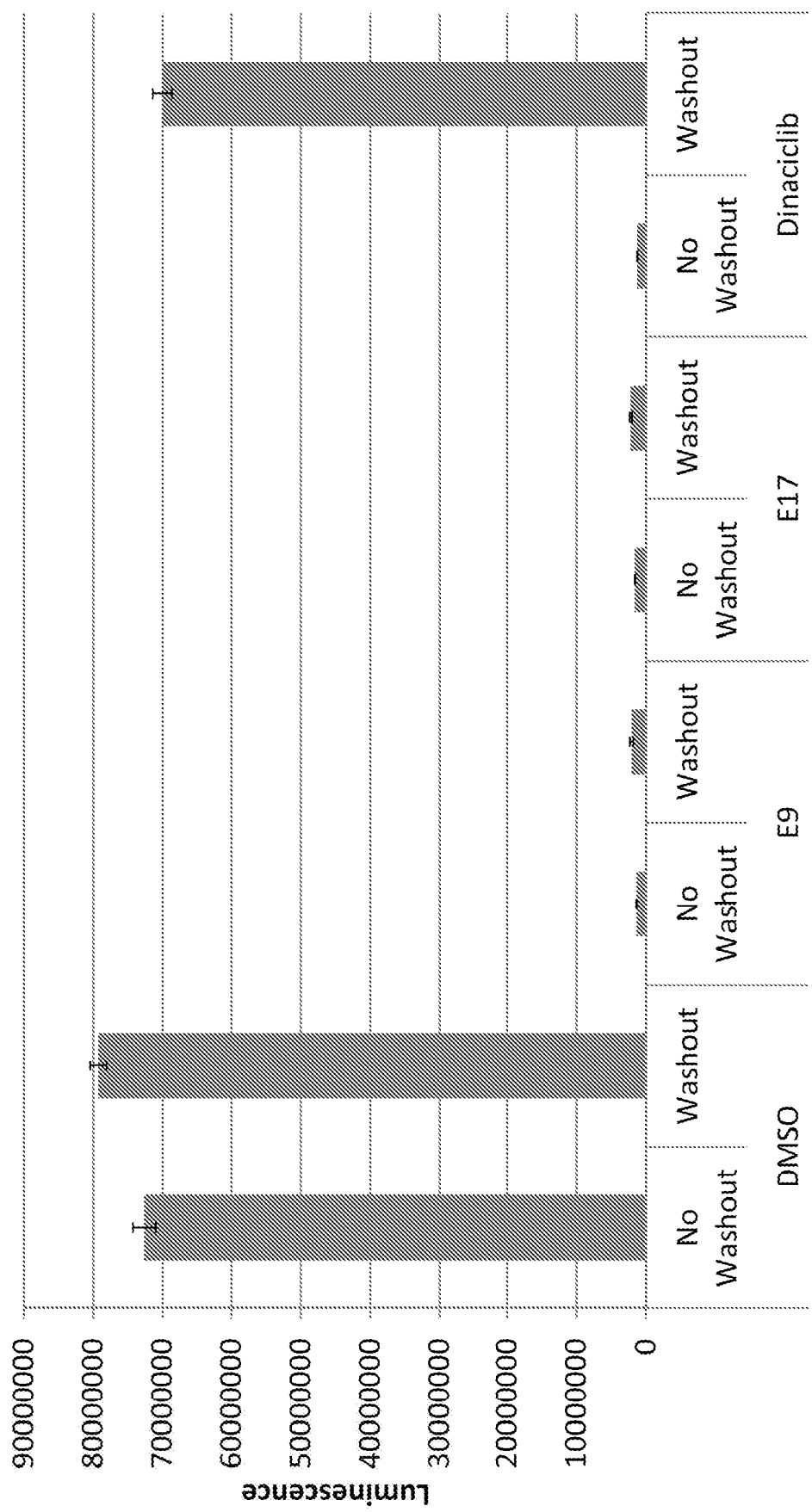
FIG. 1 shows inhibition of Jurkat cell viability by compounds E9, E17, and dinaciclib. Specifically, compounds E9 and E11 irreversibly inhibit Jurkat cell viability. The antiproliferative effects of compounds E9 and E17 are present with and without washout, while dinaciclib's effects are abolished with washout. Cells were treated with each compound for 4 hours and either no washout (no washout) or had compound removed by washing cells with media (washout). Sixty-eight (68) hours after washout, the cells were assayed for antiproliferative effects. Error bars indicate +/−SD.

Results were graphed as fraction of the DMSO control at 72 hours. All data points were performed in biological triplicate. Error bars are +/−SD.

FIG. 15 shows the profiling of E-9 and E11 in the HAP1 cell proliferation assay. HAP1 cells expressing inhibitor-refractory mutations in CDK12 (C1039S) and CDK13 (C1017S) were 4-fold less sensitive to E17 compared to control wild type HAP1 cells. This result indicates that a significant portion of intracellular E17 activity comes from covalent inhibition of CDK12 and/or CDK13. Mutation of these targeted cysteines to a less nucleophilic serine is sufficient to rescue a significant portion of anti-proliferative activity at concentrations less than 350 nM.

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions*, p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

In a formula, ⌇ is a single bond where the stereochemistry of the moieties immediately attached thereto is not specified, - - - is absent or a single bond, and ═ or ═ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$). In certain embodiments, the alkyl group is a substituted $C_{1-10}$ alkyl (such as substituted $C_{1-6}$ alkyl, e.g., —CF$_3$). In certain embodiments, the alkyl group is unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is substituted $C_{1-10}$ alkyl (such as substituted $C_{1-6}$ alkyl, e.g., —CF$_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —CHF$_2$, —CH$_2$F, —CF$_3$, —CH$_2$CF$_3$, —CF$_2$CF$_3$, —CF$_2$CF$_2$CF$_3$, —CCl$_3$, —CFCl$_2$, —CF$_2$Cl, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and for 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is unsubstituted heteroC$_{1-10}$ alkyl. In certain embodiments, the heteroalkyl group is substituted heteroC$_{1-10}$ alkyl.

"Alkenyl" refers to a radical of a straight-chain or branched hydrocarbon group having from 2 to 20 carbon atoms, one or more carbon-carbon double bonds, and no triple bonds ("C$_{2-20}$ alkenyl"). In some embodiments, an alkenyl group has 2 to 10 carbon atoms ("C$_{2-10}$ alkenyl"). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted C$_{2-10}$ alkenyl. In certain embodiments, the alkenyl group is substituted C$_{2-10}$ alkenyl. In an alkenyl group, a C=C double bond for which the stereochemistry is not specified (e.g., —CH=CHCH$_3$ or

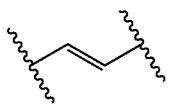 [SMILES: */C=C/*]

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, and sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and for 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted ("unsubstituted heteroalkenyl") or substituted ("substituted heteroalkenyl") with one or more substituents. In certain embodiments, the heteroalkenyl group is unsubstituted heteroC$_{2-10}$ alkenyl. In certain embodiments, the heteroalkenyl group is substituted heteroC$_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("C$_{2-20}$ alkynyl"). In some embodiments, an alkynyl group has 2 to 10 carbon atoms ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted C$_{2-10}$ alkynyl. In certain embodiments, the alkynyl group is substituted C$_{2-10}$ alkynyl.

The term "heteroalkynyl" refers to an alkynyl group that includes at least one heteroatom (e.g., 1, 2, 3, or 4 heteroatoms) selected from oxygen, nitrogen, and sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted ("unsubstituted heteroalkynyl") or substituted ("substituted heteroalkynyl") with one or more substituents. In certain embodiments, the heteroalkynyl group is unsubstituted heteroC$_{2-10}$ alkynyl. In certain embodiments, the heteroalkynyl group is substituted heteroC$_{2-10}$ alkynyl.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or Spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered, non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups, wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" refers to an optionally substituted alkyl group substituted by an optionally substituted aryl group. "Aralkyl" is a subset of "alkyl" and refers to an alkyl group substituted with an aryl group, wherein the point of attachment is on the alkyl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered, monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Alkyl, alkenyl, alkynyl, carbocyclyl, heterocyclyl, aryl, and heteroaryl groups, which are divalent linking groups, are further referred to using the suffix -ene, e.g., alkylene, alkenylene, alkynylene, carbocyclylene, heterocyclylene, arylene, and heteroarylene. Thus, alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, NR$^{bb}$P(=O)(R$^{aa}$)$_2$, —NR$^{bb}$P(O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups; or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2$$R^{aa}$, =N$R^{bb}$, or =NO$R^{cc}$; wherein $X^-$ is a counterion;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)($R^{aa}$)$_2$, —P(=O)(O$R^{cc}$)$_2$, —P(=O)N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; wherein X is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3^+$$X^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)(O$R^{ee}$)$_2$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of 0 is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two 0 groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$$X^-$, —NH(C$_{1-6}$ alkyl)$_2^+$$X^-$, —NH$_2$(C$_{1-6}$ alkyl)$^+$$X^-$, —NH$_3^+$$X^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH(C$_{1-6}$ alkyl))$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, ethanoate, propanoate, benzoate, glycerate, lactate, tartrate, glycolate, and the like). Exemplary counterions further include BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —O$R^{aa}$, —ON($R^{bb}$)$_2$, —OC(=O)S$R^{aa}$, —OC(=O)$R^{aa}$, —OCO$_2$$R^{aa}$, —OC(=O)N($R^{bb}$)$_2$, —OC(=N$R^{bb}$)$R^{aa}$, —OC(=N$R^{bb}$)O$R^{aa}$, —OC(=N$R^{bb}$)N $(R^{bb})_2$, —OS(=O)$R^{aa}$, —OSO$_2R^{aa}$, —OSi($R^{aa}$)$_3$, —OP($R^{cc}$)$_2$, —OP($R^{cc}$)$_3^+$X$^-$, —OP(O$R^{cc}$)$_2$, —OP(O$R^{cc}$)$_3^+$X$^-$, —OP(=O)($R^{aa}$)$_2$, —OP(=O)(O$R^{cc}$)$_2$, and —OP(=O)(N($R^{bb}$))$_2$, wherein X$^-$, $R^{aa}$, $R^{bb}$, and $R^{cc}$ are as defined herein.

The term "amino" refers to the group —NH$_2$. The term "substituted amino," by extension, refers to a monosubstituted amino, disubstituted amino, or trisubstituted amino. In certain embodiments, the "substituted amino" is a monosubstituted amino or disubstituted amino group.

The term "sulfonyl" refers to a group selected from —SO$_2$N($R^{bb}$)$_2$, —SO$_2R^{aa}$, and —SO$_2$O$R^{aa}$, wherein $R^{aa}$ and $R^{bb}$ are as defined herein.

The term "sulfinyl" refers to the group —S(=O)$R^{aa}$, wherein $R^{aa}$ is as defined herein.

"Acyl" refers to a moiety selected from the group consisting of —C(=O)$R^{aa}$, —CHO, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein. In other instances, "acyl" refers to a group having the general formula: —C(=O)$R^{X1}$, C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, —C(=S)S($R^{X1}$), —C(=N$R^{X1}$)$R^{X1}$, C(=N$R^{X1}$)O$R^{X1}$, —C(=N$R^{X1}$)S$R^{X1}$, or —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen, or sulfur atom, e.g., a group selected from ketones (—C(=O)$R^{aa}$), carboxylic acids (—CO$_2$H), aldehydes (—CHO), esters (—CO$_2R^{aa}$, —C(=O)S$R^{aa}$, —C(=S)S$R^{aa}$), amides (—C(=O)N($R^{bb}$)$_2$, —C(=O)N$R^{bb}$SO$_2R^{aa}$, —C(=S)N($R^{bb}$)$_2$), and imines (—C(=N$R^{bb}$)$R^{aa}$, —C(=N$R^{bb}$)O$R^{aa}$), —C(=N$R^{bb}$)N($R^{bb}$)$_2$), wherein $R^{aa}$ and $R^{bb}$ are as defined herein.

The term "silyl" refers to the group —Si($R^{aa}$)$_3$, wherein $R^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O) (O$R^{cc}$)$_2$, —P(=O)($R^{aa}$)$_2$, —P(=O)(N($R^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)SR", —C(=S)S$R^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and are as defined herein. Nitrogen protecting groups are well $R^{dd}$ known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl) methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $—S(=O)_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N-dimethylaminomethylene) amine, N,N-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, $—R^{aa}$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3{}^+X^-$, $—P(OR^{cc})_2$, $—P(OR^{cc})_3{}^+X^-$, $—P(=O)(R^{aa})_2$, $—P(=O)(OR^{cc})_2$, and $—P(=O)(N(R^{bb})_2)_2$, wherein $X^-$, $R^{aa}$, $R^{bb}$, and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-tfichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, $-R^{aa}$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(R^{cc})_3^+X^-$, $-P(OR^{cc})_2$, $-(OR^{cc})_3^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms" or "carbon units") and does not include hydrogen atoms or heteroatoms. However, a non-chain substituent of a hydrocarbon chain may include any atoms, including hydrogen atoms, carbon atoms, and heteroatoms. For example, hydrocarbon chain $-C^AH(C^BH_2C^CH_3)-$ includes one chain atom $C^A$, one hydrogen atom on $C^A$, and non-chain substituent $-(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, $-CH(C_2H_5)-$ is a $C_1$ hydrocarbon chain, and

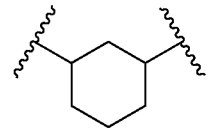 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., $-(CH_2)_4-$). A hydrocarbon chain may also be unsaturated and include one or more C=C and/or C≡C bonds anywhere in the hydrocarbon chain. For instance, $-CH=CH-(CH_2)_2-$, $-CH_2-C\equiv C-CH_2-$, and $-C\equiv C-CH=CH-$ are all examples of a unsubstituted and unsaturated hydrocarbon chain. In certain embodiments, the hydrocarbon chain is unsubstituted (e.g., $-C\equiv C-$ or $-(CH_2)_4-$). In certain embodiments, the hydrocarbon chain is substituted (e.g., $-CH(C_2H_5)-$ and $-CF_2-$). Any two substituents on the hydrocarbon chain may be joined to form an optionally substituted carbocyclyl, optionally substituted heterocyclyl, optionally substituted aryl, or optionally substituted heteroaryl ring. For instance,

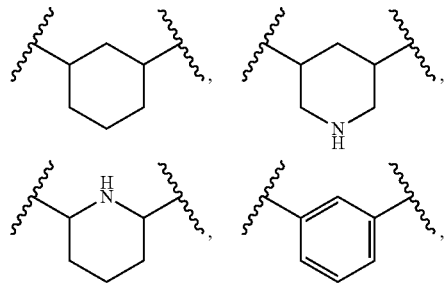

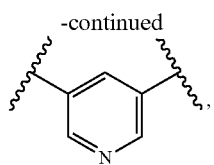

and

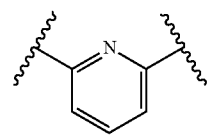 [SMILES: *c1cccc(*)n1]

are all examples of a hydrocarbon chain. In contrast, in certain embodiments,

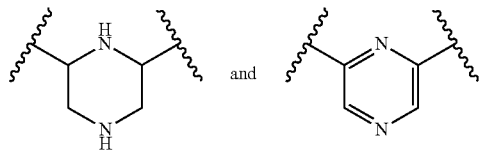 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

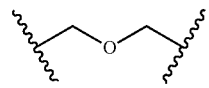

is a $C_3$ hydrocarbon chain wherein one chain atom is replaced with an oxygen atom.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Other exemplary leaving groups include, but are not limited to, activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

As used herein, the term "salt" refers to any and all salts, and encompasses pharmaceutically acceptable salts. The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, hippurate, and the like. Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5H$_2$O)), and polyhydrates (x is a number greater than 1, e.g., dihydrates (R·2H$_2$O) and hexahydrates (R·6H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Calm and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "co-crystal" refers to a crystalline structure composed of at least two components. In certain embodiments, a co-crystal may contain a compound of the present invention and one or more other component, including but not limited to, atoms, ions, molecules, or solvent molecules. In certain embodiments, a co-crystal may contain a compound of the present invention and one or more components related to said compound, including not limited to, an isomer, tautomer, salt, solvate, hydrate, synthetic precursor, synthetic derivative, fragment or impurity of said compound. Co-crystals may be useful to improve the properties (e.g., solubility, stability, and ease of formulation) of a compound of the present invention.

The term "isotopes" refers to variants of a particular chemical element such that, while all isotopes of a given element share the same number of protons in each atom of the element, those isotopes differ in the number of neutrons. The term "radioactivity" or "radioactive decay" refers to the process by which a nucleus of an unstable isotope (e.g., $^{18}$F) loses energy by emitting particles or rays (e.g., alpha particles, beta particles, and gamma rays) of electromagnetic radiation. Such an unstable isotope or a material including the unstable isotope is referred to as "radioactive." The Curie (Ci) is a non-SI (non-International System of Units) unit of radioactivity and is defined as 1 Ci=3.7×10$^{10}$ decays per second. The term "specific activity" refers to the unit radioactivity of a material (e.g., any compound disclosed herein, or a salt, tautomer, stereoisomer, or isotopically labeled derivative (e.g., $^{18}$F-labeled derivative) thereof). In certain embodiments, the term "specific activity" refers to the radioactivity of a material per micromole (μmol) of the material.

The term "isotopically labeled derivative" or "isotopically labeled" refers to a compound wherein one or more atoms in the compound (or in an associated ion or molecule of a salt, hydrate, or solvate) has been replaced with an isotope of the same element. For the given element or position in the molecule the isotope will be enriched, or present in a higher percentage of all atoms of the element or of all atoms at the position in the molecule in a sample, relative to an unlabeled variant. In certain embodiments, the enriched isotope will be a stable isotope. In certain embodiments, the enriched isotope will be an unstable or radioactive isotope (e.g., a radionuclide). In certain embodiments, the enriched isotope may be detected by a measurement technique, including but not limited to nuclear magnetic resonance, mass spectrometry, infrared spectroscopy, or a technique that measures radioactive decay.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "inhibition", "inhibiting", "inhibit," or "inhibitor" refer to the ability of a compound to reduce, slow, halt or prevent activity of a particular biological process (e.g., activity of a bromodomain and/or a bromodomain-containing protein) in a cell relative to vehicle.

As used herein the term "inhibit" or "inhibition" in the context of enzymes, for example, in the context of CDK (e.g., CDK7, CDK12, CDK13), refers to a reduction in the activity of the enzyme. In some embodiments, the term refers to a reduction in the level of enzyme activity, e.g., CDK (e.g., CDK7, CDK12, CDK13) activity, to a level that is statistically significantly lower than an initial level, which may, for example, be a baseline level of enzyme activity. In some embodiments, the term refers to a reduction in the level of enzyme activity, e.g., CDK (e.g., CDK7, CDK12, CDK13) activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

When a compound, pharmaceutical composition, method, use, or kit is referred to as "selectively," "specifically," or "competitively" binding a first protein or a first chromatin, the compound, pharmaceutical composition, method, use, or kit binds the first protein or the first chromatin with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein or second chromatin that is different from the first protein and the first chromatin. When a compound, pharmaceutical composition, method, use, or kit is referred to as "selectively," "specifically," or "competitively" modulating (e.g., increasing or inhibiting) the activity of a bromodomain-containing protein, the compound, pharmaceutical composition, method, use, or kit modulates the activity of the bromodomain-containing protein to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the bromodomain-containing protein.

The term "aberrant activity" refers to activity deviating from normal activity, that is, abnormal activity. The term "increased activity" refers to activity higher than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from another biological sample.

The terms "administer," "administering," or "administration" refers to implanting, absorbing, ingesting, injecting, inhaling, or otherwise introducing a compound described herein, or a composition thereof, into, in, or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "prevent," "preventing," or "prevention" refers to a prophylactic treatment of a subject who has not and had not been diagnosed with a disease but is at risk of developing the disease. The term "prevent," "preventing," or "prevention" also refers to a prophylactic treatment of a subject who was suffering from a disease or has not been diagnosed with the disease, but is at risk of regression or recurrence of the disease. In certain embodiments, the subject is at a higher risk of developing the disease or at a higher risk of regression of the disease than an average healthy member of a population.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for inhibiting CDK (e.g., CDK7, CDK12, CDK13). In certain embodiments, a therapeutically effective amount is an amount sufficient for treating an acute inflammatory disease (e.g., rheumatoid arthritis, Crohn's disease, or fibrosis) and/or a proliferative disease (e.g., cancer, benign neoplasm, diseases associated with angiogenesis, inflammatory diseases, autoimmune diseases, pancreatic cancer, lung cancer (e.g. small cell lung cancer (SCLC), non-small cell lung cancer), prostate cancer, breast cancer, ovarian cancer, kidney cancer, liver cancer, Ewing's sarcoma, osteosarcoma, brain cancer, neuroblastoma, and colorectal cancer). In certain embodiments, a therapeutically effective amount is an amount sufficient for inhibiting CDK (e.g., CDK7, CDK12, CDK13) and for treating an acute inflammatory disease (e.g., rheumatoid arthritis, Crohn's disease, or fibrosis) and/or a proliferative disease (e.g., cancer, benign neoplasm, diseases associated with angiogenesis, inflammatory diseases, autoinflammatory diseases, autoimmune diseases, pancreatic cancer, lung cancer (e.g. small cell lung cancer (SCLC), and non-small cell lung cancer), prostate cancer, breast cancer, ovarian cancer, kidney cancer, liver cancer, Ewing's sarcoma, osteosarcoma, brain cancer, neuroblastoma, and colorectal cancer).

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for inhibiting CDK (e.g., CDK7, CDK12, CDK13). In certain embodiments, a prophylactically effective amount is an amount sufficient for treating an acute inflammatory disease (e.g., rheumatoid arthritis, Crohn's disease, or fibrosis) and/or a proliferative disease (e.g., cancer, benign neoplasm, diseases associated with angiogenesis, inflammatory diseases, autoinflammatory diseases, autoimmune diseases, pancreatic cancer, lung cancer (e.g. small cell lung cancer (SCLC), and non-small cell lung cancer), prostate cancer, breast cancer, ovarian cancer, kidney cancer, liver cancer, Ewing's sarcoma, osteosarcoma, brain cancer, neuroblastoma, and colorectal cancer). In certain embodiments, a prophylactically effective amount is an amount sufficient for inhibiting CDK (e.g., CDK7, CDK12, CDK13) and for treating acute inflammatory disease (e.g., rheumatoid arthritis, Crohn's disease, or fibrosis) and/or a proliferative disease (e.g., cancer, benign neoplasm, diseases associated with angiogenesis, inflammatory diseases, autoinflammatory diseases, autoimmune diseases, pancreatic cancer, lung cancer (e.g. small cell lung cancer (SCLC), and non-small cell lung cancer), prostate cancer, breast cancer, ovarian cancer, kidney cancer, liver cancer, Ewing's sarcoma, osteosarcoma, brain cancer, neuroblastoma, and colorectal cancer).

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, diseases associated with angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated as in the growth of normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast, triple negative breast cancer (TNBC)); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "hematological malignancy" refers to tumors that affect blood, bone marrow, and/or lymph nodes. Exemplary hematological malignancies include, but are not limited to, leukemia, such as acute lymphoblastic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt's lymphoma, Waldenstrom's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hay fever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosus, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. Exemplary human protein kinases include, but are not limited to, AAK1, ABL, ACK, ACTR2, ACTR2B, AKT1, AKT2, AKT3, ALK, ALK1, ALK2, ALK4, ALK7, AMPKa1, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLIK1, CLIK1L, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRK1A, DYRK1B, DYRK2, DYRK3, DYRK4, EGFR, EphA1, EphA10, EphA2, EphA3, EphA4, EphA5, EphA6, EphA7, EphA8, EphB1, EphB2, EphB3, EphB4, EphB6, Erk1, Erk2, Erk3, Erk3ps1, Erk3ps2, Erk3ps3, Erk3ps4, Erk4, Erk5, Erk7, FAK, FER, FERps, FES, FGFR1, FGFR2, FGFR3, FGFR4, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obscn, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgK050ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK (e.g., SIK1, SIK2), skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, and ZC4/NRK.

The term "SRC family kinase" refers to a family of non-receptor tyrosine protein kinases that includes nine members: SRCA subfamily that includes c-SRC (proto-oncogene tyrosine-protein kinase SRC), YES (proto-oncogene tyrosine-protein kinase Yes), FYN (proto-oncogene tyrosine-protein kinase FYN), and FGR (Gardner-Rasheed feline sarcoma viral (v-FGR) oncogene homolog); SRCB subfamily that includes LCK (lymphocyte-specific protein tyrosine kinase), HCK (tyrosine-protein kinase HCK, hemopoietic cell kinase), BLK (tyrosine-protein kinase BLK), and LYN (tyrosine-protein kinase LYN); and FRK (Fyn-related kinase).

The term "CDK" refers to a cyclin-dependent kinase. A CDK binds a cyclin (e.g., Cyclin H), which is a regulatory protein. CDKs phosphorylate their substrates at serines and threonines. The consensus sequence for the phosphorylation site in the amino acid sequence of a CDK substrate is [S/T*]PX[K/R], where S/T* is the phosphorylated serine or threonine, P is proline, X is any amino acid, K is lysine, and R is arginine CDKs include CDK1, CDK2, CDK3, CDK4, CDK5, CDK6, CDK7, CDK8, CDK9, CDK10, CDK11, CDK12, CDK13, CDK14, CDK15, CDK16, CDK17, CDK18, CDK19 and CDK20.

CDK7, cyclin-dependent kinase 7, is a CDK, wherein the substrate is Cyclin H, MAT1 (e.g., MNAT1), or Cyclin H and MAT1. CDK7 is alternatively referred to as CAK1, HCAK, MO15, STK1, CDKN7, and p39MO15. Non-limiting examples of the nucleotide and protein sequences for human CDK7 are described in GenBank Accession Number NP_001790, incorporated herein by reference. The amino acid sequence of this CDK7 is as follows:

```
MALDVKSRAKRYEKLDFLGEGQFATVYKARDKNTNQIVAIKKIKLGHRSEA

KDGINRTALREIKLLQELSHPNIIGLLDAFGHKSNISLVFDFMETDLEVII

KDNSLVLTPSHIKAYMLMTLQGLEYLHQHWILHRDLKPNNLLLDENGVLKL

ADFGLAKSFGSPNRAYTHQVVTRWYRAPELLFGARMYGVGVDMWAVGCILA

ELLLRVPFLPGDSDLDQLTRIFETLGTPTEEQWPDMCSLPDYVTFKSFPGI

PLHHIFSAAGDDLLDLIQGLFLFNPCARITATQALKMKYFSNRPGPTPGCQ

LPRPNCPVETLKEQSNPALAIKRKRTEALEQGGLPKKLIF
```

CDK12, cyclin-dependent kinase 12, is a CDK, wherein the substrate is Cyclin K or Flavopiridol. CDK12 is alternatively referred to as Cdc2-related kinase, CDC2-related protein kinase 7, Cell division cycle 2-related protein kinase 7, Cell division protein kinase 12, CRK7, CRKR, CRKRS, cyclin-dependent kinase 12, or KIAA0904. Non-limiting examples of the nucleotide and protein sequences for human CDK12 are described in Uniprot Number Q9NYV4, which is incorporated herein by reference. The amino acid sequence of this CDK12 is as follows: MPNSERHGGK-KDGSGGASGTLQPSSGGGSSNSRERHRLVSKH-KRHKSKHSKDMGLVTPEA

```
MPNSERHGGKKDGSGGASGTLQPSSGGGSSNSRERHRLVSKHKRHKSKDM

GLVTPEAASLGTVIKPLVEYDDISSDSDTFSDDMAFKLDRRENDERRGSD

RSDRLHKHRHHQHRRSRDLLKAKQTEKEKSQEVSSKSGSMKDRISGSSKR

SNEETDDYGKAQVAKSSSKESRSSKLHKEKTRKERELKSGHKDRSKSHRK

RETPKSYKTVDSPKRRSRSPHRKWSDSSKQDDSPSGASYGQDYDLSPSRS

HTSSNYDSYKKSPGSTSRRQSVSPPYKEPSAYQSSTRSPSPYSRRQRSVS

PYSRRRSSSYERSGSYSGRSPSPYGRRRSSSPFLSKRSLSRSPLPSRKSMK

RSSRSPAYSRHSSSHSKKKRSSSRSRHSSISPVRLPLNSSLGAELSRKKK

ERAAAAAAAKMDGKESKGSPVFLPRKENSSVEAKDSGLESKKLPRSVKLEK

SAPDTELVNVTHLNTEVKNSSDTGKVKLDENSEKHLVKDLKAQGTRDSKP

IALKEEIVTPKETETSEKETPPPLPTIASPPPPLPTTTPPPQTPPLPPLP
```

PIPALPQQPPLPPSQPAFSQVPASSTSTLPPSTHSKTSAVSSQANSQPPV

QVSVKTQVSVTAAIPHLKTSTLPPLPLPPLLPGDDDMDSPKETLPSK-
PVKKE

KEQRTRHLLTDLPLPPELPGGDLSPPDSPEPKAITPPQQPYKKRPKICCPR

YGERRQTESDWGKRCVDKFDIIGIIGEGTYGQVYKAKDKDTGELVALKK-
VRL

DNEKEGFPITAIREIKILRQLIHRSVVNMKEIVTDKQDALDFKKDKGAFYL

VFEYMDHDLMGLLESGLVHFSEDHIKSFMKQLMEGLEYCHKKNELHRDIKC

SNILLNNSGQIKLADEGLARLYNSEESRPYTNKVITLWYRPPELLLGEERY

TPAIDVWSCGCILGELFTKKPIFQANLELAQLELISRLCGSPCPAVWPDVI

KLPYENTMKPKKQYRRRLREEFSFIPSAALDLLDHMLTLDPSKRCTAEQTL

QSDFLKDVELSKMAPPDLPHWQDCHELWSKKRRRQRQSGVVVEEPPPSKT

SRKETTSGTSTEPVKNSSPAPPQPAPGKVESGAGDAIGLADITQQLNQSE

LAVLLNLLQSQTDLSIPQMAQLLNIHSNPEMQQQLEALNQSISALTEATSQ

QQDSETMAPEESLKEAPSAPVILPSAEQTTLEASSTPADMQNILAVLLSQL

MKTQEPAGSLEENNSDKNSGPQGPRRTPTMPQEEAAACPPHILPPEKRPP

EPPGPPPPPPPPLVEGDLSSAPQELNPAVTAALLQLLSQPEAEPPGHLPH

EHQALRPMEYSTRPRPNRTYGNTDGPETGFSAIDTDERNSGPALTESLVQ

TLVKNRTFSGSLSHLGESSSYQGTGSVQFPGDQDLRFARVPLALHPVVGQ

PFLKAEGSSNSVVHAETKLQNYGELGPGTTGASSSGAGLHWGGPTQSSA

YGKLYRGPTRVPPRGGRGRGVPY

CDK13, cyclin-dependent kinase 13, is a CDK, wherein the relevant cyclin is cyclin K and a reference inhibitor is the pan-CDK inhibitor Flavopiridol and the c-terminal domain (CTD) of RNA-polymerase II is a physiological substrate. CDK13 is alternatively referred to as CHED; CDC2L; CDC2L5; or hCDK13. Non-limiting examples of the nucleotide and protein sequences for human CDK12 are described in GenBank Accession Number M80629, which is incorporated herein by reference. The amino acid sequence of this CDK13 is as follows:

MPSSSDTALGGGGGLSWAEKKLEERRKRRRFLSPQQPPLLLPLLQPQLLQP

PPPPPPLLFLAAPGTAAAAAAAAASSSCFSPGPPLEVKRLARGKRRAGGR

QKRRRGPRAGQEAEKRRVFSLPQPQQDGGGGASSGGGVTPLVEYEDVSSQS

EQGLLLGGASAATAATAAGGTGGSGGSPASSSGTQRRGEGSERRPRRDRRS

SSGRSKERHREHRRRDGQRGGSEASKSRSRHSHSGEERAEVAKSGSSSSSG

GRRKSASATSSSSSSRKDRDSKAHRSRTKSSKEPPSAYKEPPKAYREDKTE

PKAYRRRRSLSPLGGRDDSPVSHRASQSLRSRKSPSPAGGGSSPYSRRLPR

SPSPYSRRRSPSYSRHSSYERGGDVSPSPYSSSSWRRSRSPYSPVLRRSGK

SRSRSPYSSRHSRSRSRHRLSRSRSRHSSISPSTLTLKSSLAAELNKNKKA

RAAEAARAAEAAKAAEATKAAEAAAKAAKASNTSTPTKGNTETSASASQTN

HVKDVKKIKIEHAPSPSSGGTLKNDKAKTKPPLQVTKVENNLIVDKATKKA

VIVGKESKSAATKEESVSLKEKTKPLTPSIGAKEKEQHVALVTSTLPPLPL

PPMLPEDKEADSLRGNISVKAVKKEVEKKLRCLLADLPLPPELPGGDDLSK

SPEEKKTATQLHSKRRPKICGPRYGETKEKDIDWGKRCVDKFDIIGIIGEG

TYGQVYKARDKDTGEMVALKKVRLDNEKEGFPITAIREIKILRQLTHQSII

NMKEIVTDKEDALDFKKDKGAFYLVFEYMDHDLMGLLESGLVHFNENHIKS

FMRQLMEGLDYCHKKNFLHRDIKCSNILLNNRGQIKLADFGLARLYSSEES

RPYTNKVITLWYRPPELLLGEERYTPAIDVWSCGCILGELFTKKPIFQANQ

ELAQLELISRICGSPCPAVWPDVIKLPYENTMKPKKQYRRKLREEFVFIPA

AALDLFDYMLALDPSKRCTAEQALQCEFLRDVEPSKMPPPDLPLWQDCHEL

WSKKRRRQKQMGMTDDVSTIKAPRKDLSLGLDDSRTNTPQGVLPSSQLKSQ

GSSNVAPVKTGPGQHLNHSELAILLNLLQSKTSVNMADFVQVLNIKVNSET

QQQLNKINLPAGILATGEKQTDPSTPQQESSKPLGGIQPSSQTIQPKVETD

AAQAAVQSAFAVLLTQLIKAQQSKQKDVLLEERENGSGHEASLQLRPPPEP

STPVSGQDDLIQHQDMRILELTPEPDRPRILPPDQRPPEPPEPPPVTEEDL

DYRTENQHVPTTSSSLTDPHAGVKAALLQLLAQHQPQDDPKREGGIDYQAG

DTYVSTSDYKDNFGSSSFSSAPYVSNDGLGSSSAPPLERRSFIGNSDIQSL

DNYSTASSHSGGPPQPSAFSESFPSSVAGYGDIYLNAGPMLFSGDKDHRFE

YSHGPIAVLANSSDPSTGPESTHPLPAKMHNYNYGGNLQENPSGPSLMHGQ

TWTSPAQGPGYSQGYRGHISTSTGRGRGRGLPY

DETAILED DESCRIPTION OF CERTAIN EMBODIMENTS OF THE INVENTION

Cyclin dependent kinases (CDKs) are key regulators of the cell cycle. Their successive activation and inactivation drives the cycle forward. The activity of CDKs is regulated by multiple mechanisms such as positive and negative phosphorylation, binding of regulatory proteins like cyclins, and CDK inhibitors. CDK7 plays a critical role in the regulation of RNA polymerase II-mediated transcription of protein-encoding genes. Disruption of CDK7, CDK12, and/or CDK13 signaling cause defects in transcription. However, a complete understanding of how these disruptions affect global transcription is lacking. Furthermore, the absence of selective inhibitors of CDK7, CDK12, and CDK13 has hindered investigation of the transcriptional and functional consequences of acute and long-term inhibition of these kinases under normal and pathological conditions. The present invention provides selective CDK7, CDK12, and/or CDK13 inhibitors and analogs, which have the ability to covalently modify a cysteine residue located outside of the canonical kinase domain (i.e., Cys312 of CDK7, Cys1039 of CDK12, and Cys1017 of CDK13). Selective covalent inhibitors of these kinases may be useful in the treatment of various proliferative diseases including cancer.

The present invention provides compounds, which inhibit the activity of a kinase, for the prevention and/or treatment of a subject with a proliferative disease. In certain embodiments, the inventive compounds inhibit the activity of cyclin-dependent kinase (CDK). In certain embodiments, the inventive compounds inhibit the activity of a cyclin-dependent kinase 7 (CDK7). In certain embodiments, the inventive compounds inhibit the activity of a cyclin-dependent kinase 12 (CDK12). In certain embodiments, the inventive compounds inhibit the activity of a cyclin-dependent kinase 13 (CDK13). The present invention also provides methods of using the compounds described herein, e.g., as biological probes to study the inhibition of the activity of a kinase (e.g., CDK (e.g. CDK7, CDK12, and/or CDK13)), and as therapeutics, e.g., in the prevention and/or treatment of diseases associated with the overexpression and/or aberrant activity of a kinase (e.g., CDK (e.g. CDK7, CDK12, and/or CDK13)). In certain embodiments, the diseases are proliferative diseases. The proliferative diseases that may be treated and/or prevented include, but are not limited to, cancers (e.g., breast cancer, leukemia, melanoma, multiple myeloma), benign neoplasms, diseases associated with angiogenesis, inflammatory diseases, autoinflammatory diseases, and autoimmune diseases. Also provided by the present disclosure are pharmaceutical compositions, kits, methods, and uses including a compound of Formula (I) as described herein.

Compounds

Aspects of the present disclosure relate to the compounds described herein. The compounds described herein are purine, pyrazolo-triazine, and pyrazolo-pyrimidine containing compounds that are useful in treating and/or preventing proliferative diseases in a subject, inhibiting the activity of a protein kinase (e.g., CDK) in a subject or biological sample, and inducing apoptosis of a cell. In certain embodiments, a compound described herein is a compound of any one of Formulae (I)-(III), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I), or a pharmaceutically acceptable salt thereof. In certain embodiments, a compound described herein is a compound of Formula (II), or a pharmaceutically acceptable salt thereof. In certain embodiments, a compound described herein is a compound of Formula (III), or a pharmaceutically acceptable salt thereof.

In certain embodiments, a compound described herein is of Formula (I):

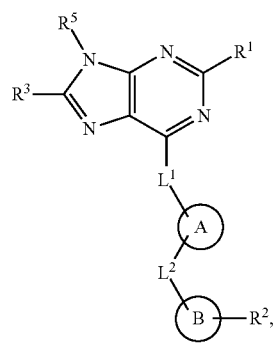

(I)

or a pharmaceutically acceptable salt thereof, wherein:

$R^1$ is optionally substituted alkyl, optionally substituted alkenyl, optionally substituted alkynyl, optionally substituted carbocyclyl, optionally substituted aryl, optionally substituted heterocyclyl, optionally substituted heteroaryl, $-NR^aR^b$, $-OR^b$, $-SR^b$, $-C(=O)R^b$, $-C(=O)OR^b$, or $-C(=O)NR^aR^b$, wherein each instance of $R^a$ and $R^b$ is independently hydrogen, optionally substituted alkyl, optionally substituted alkenyl, optionally substituted alkynyl, optionally substituted carbocyclyl, optionally substituted aryl, optionally substituted heterocyclyl, optionally substituted aryl, optionally substituted heteroaryl, or a nitrogen protecting group when attached to nitrogen, or an oxygen protecting group when attached to oxygen, or a sulfur protecting group when attached to sulfur; or $R^a$ and $R^b$ are joined to form an optionally substituted heterocyclic or optionally substituted heteroaryl ring;

$R^3$ is hydrogen, halogen, or optionally substituted $C_1$-$C_6$ alkyl;

$R^5$ is hydrogen, optionally substituted $C_1$-$C_6$ alkyl, or a nitrogen protecting group;

$L^1$ is a bond, $-NR^{L1}-(CH_2)_t-$, $-O-$, or $-S-$;

$R^{L1}$ is hydrogen, optionally substituted $C_1$-$C_6$ alkyl, or a nitrogen protecting group;

t is 0 or an integer between 1 and 5, inclusive;

Ring A is optionally substituted carbocyclyl, optionally substituted heterocyclyl, optionally substituted aryl, or optionally substituted heteroaryl;

$L^2$ is a bond, optionally substituted $C_{1-4}$ alkylene, $-C(=O)-$, $-NR^{L2}-$, $-C(=O)NR^{L2}-$, $-NR^{L2}C(=O)-$, $-O-$, or $-S-$, wherein $R^{L2}$ is hydrogen, optionally substituted $C_1$-$C_6$ alkyl, or a nitrogen protection group;

Ring B is absent, optionally substituted carbocyclyl, optionally substituted heterocyclyl, optionally substituted aryl, or optionally substituted heteroaryl; and $R^2$ is any of Formulae (i-1)-(i-41):

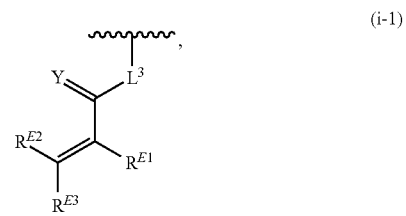

(i-1)

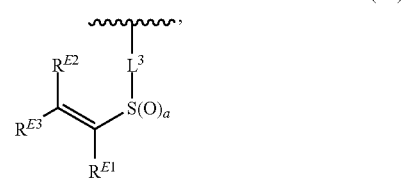

(i-2)

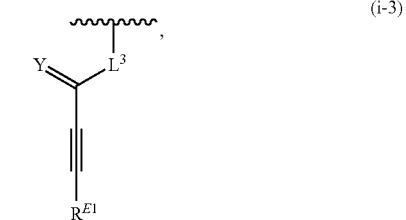

(i-3)

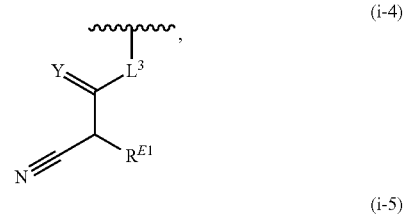

(i-4)

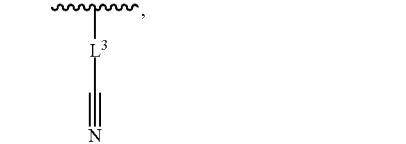

(i-5)

-continued
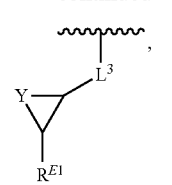 (i-6)
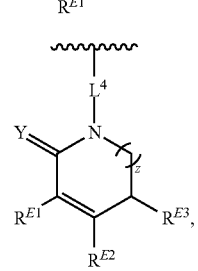 (i-7)
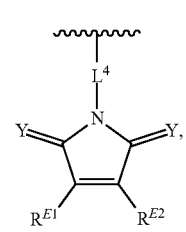 (i-8)
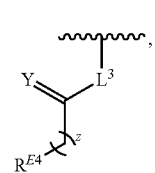 (i-9)
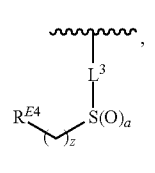 (i-10)
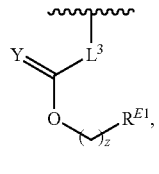 (i-11)
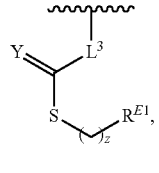 (i-12)
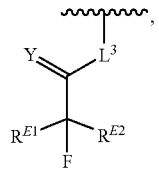 (i-13)
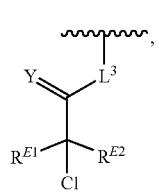 (i-14)
-continued
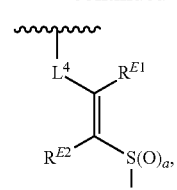 (i-15)
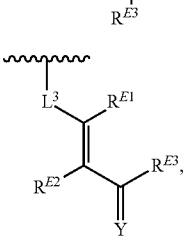 (i-16)
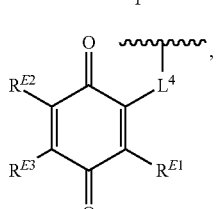 (i-17)
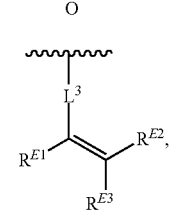 (i-18)
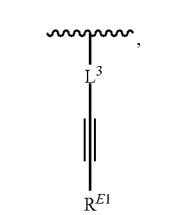 (i-19)
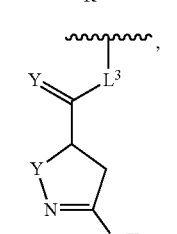 (i-20)
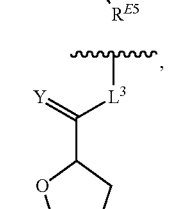 (i-21)
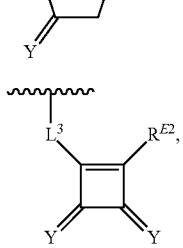 (i-22)

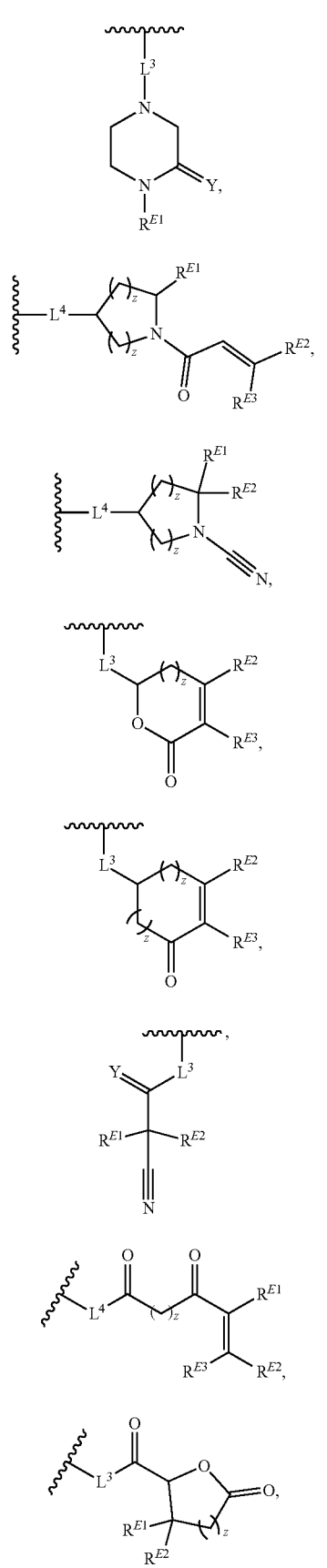
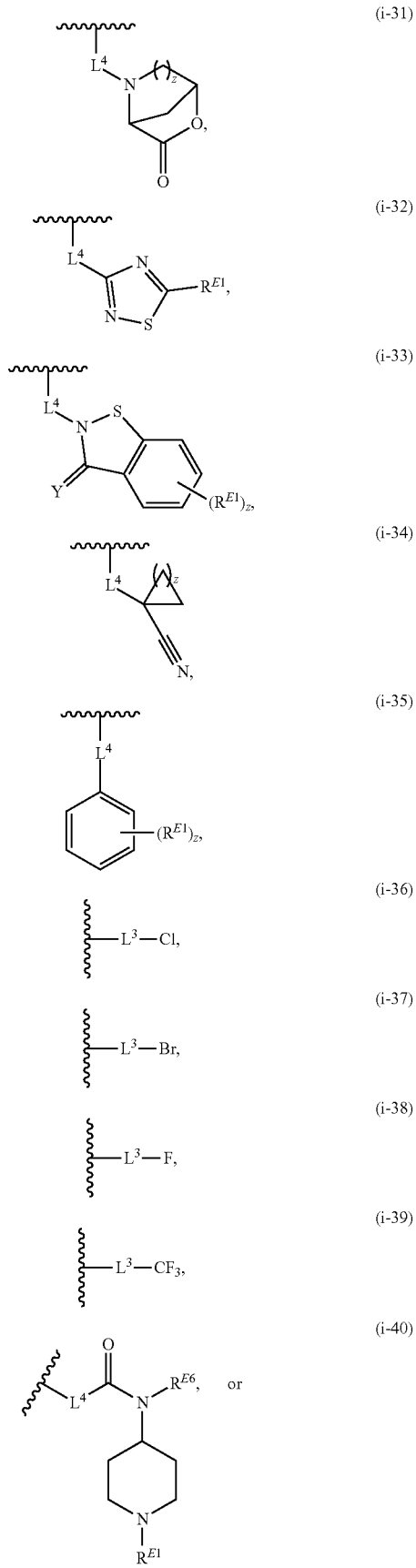

-continued (i-41)

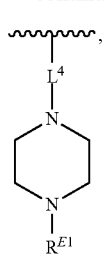

wherein:

$L^3$ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

$L^4$ is a bond or an optionally substituted, branched or unbranched $C_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, and —SR$^{EE}$, wherein each occurrence of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted $C_{1-6}$ alkyl, or a nitrogen protecting group;

each instance of Y is independently O, S, or NR$^{E7}$, wherein R$^{E7}$ is hydrogen, substituted or unsubstituted $C_{1-6}$ alkyl, or a nitrogen protecting group;

a is 1 or 2; and each instance of z is independently 0, 1, 2, 3, 4, 5, or 6, as valency permits; and provided that the compound is not

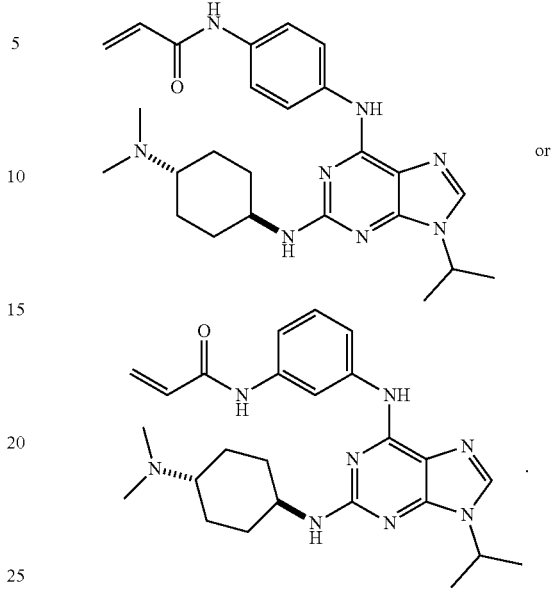

In certain embodiments, a compound described herein is of Formula (II):

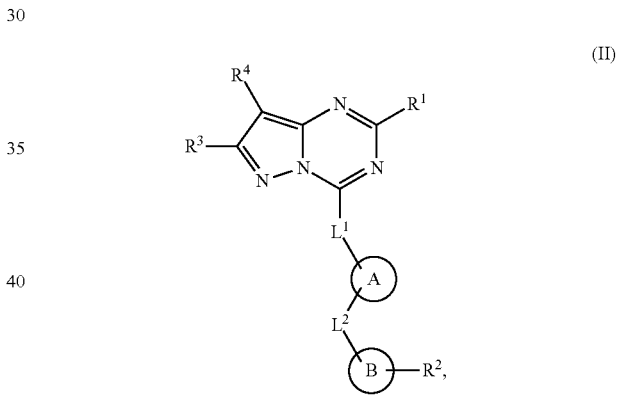

(II)

or a pharmaceutically acceptable salt thereof, wherein:

R$^1$ is optionally substituted alkyl, optionally substituted alkenyl, optionally substituted alkynyl, optionally substituted carbocyclyl, optionally substituted aryl, optionally substituted heterocyclyl, optionally substituted heteroaryl, —NR$^a$R$^b$, —OR$^b$, —SR$^b$, —C(=O)R$^b$, —C(=O)OR$^b$, or —C(=O)NR$^a$R$^b$, wherein each instance of R$^a$ and R$^b$ is independently hydrogen, optionally substituted alkyl, optionally substituted alkenyl, optionally substituted alkynyl, optionally substituted carbocyclyl, optionally substituted aryl, optionally substituted heterocyclyl, optionally substituted aryl, optionally substituted heteroaryl, or a nitrogen protecting group when attached to nitrogen, or an oxygen protecting group when attached to oxygen, or a sulfur protecting group when attached to sulfur; or R$^a$ and R$^b$ are joined to form an optionally substituted heterocyclic or optionally substituted heteroaryl ring;

each of R$^3$ and R$^4$ is independently hydrogen, halogen, or optionally substituted $C_1$-$C_6$ alkyl;

$L^1$ is a bond, —NR$^{L1}$—(CH$_2$)$_t$—, —O—, or —S—;

R$^{L1}$ is hydrogen, optionally substituted $C_1$-$C_6$ alkyl, or a nitrogen protecting group;

t is 0 or an integer between 1 and 5, inclusive;

Ring A is optionally substituted carbocyclyl, optionally substituted heterocyclyl, optionally substituted aryl, or optionally substituted heteroaryl;

$L^2$ is a bond, optionally substituted $C_{1-4}$ alkylene, —C(=O)—, —NR$^{L2}$—, —C(=O)NR$^{L2}$—, —NR$^{L2}$C(=O)—, —O—, or —S—, wherein $R^{L2}$ is hydrogen, optionally substituted $C_1$-$C_6$ alkyl, or a nitrogen protection group;

Ring B is absent, optionally substituted carbocyclyl, optionally substituted heterocyclyl, optionally substituted aryl, or optionally substituted heteroaryl; and $R^2$ is any of Formulae (i-1)-(i-41):

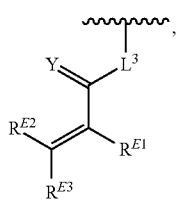 (i-1)

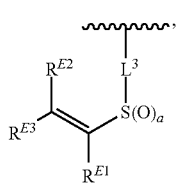 (i-2)

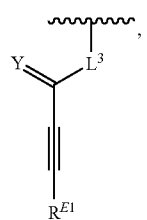 (i-3)

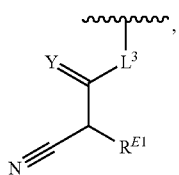 (i-4)

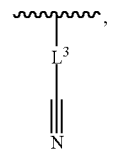 (i-5)

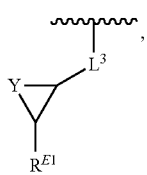 (i-6)

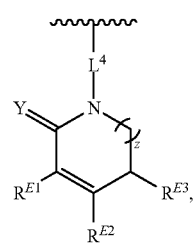 (i-7)

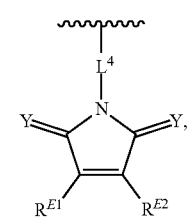 (i-8)

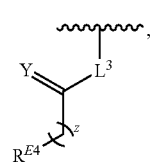 (i-9)

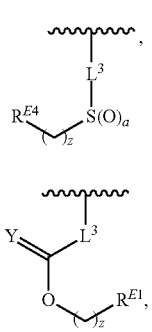 (i-10)

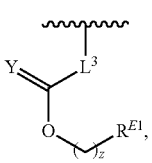 (i-11)

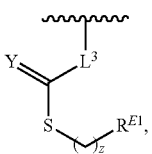 (i-12)

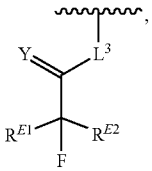 (i-13)

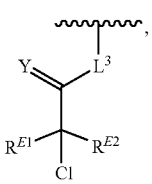 (i-14)

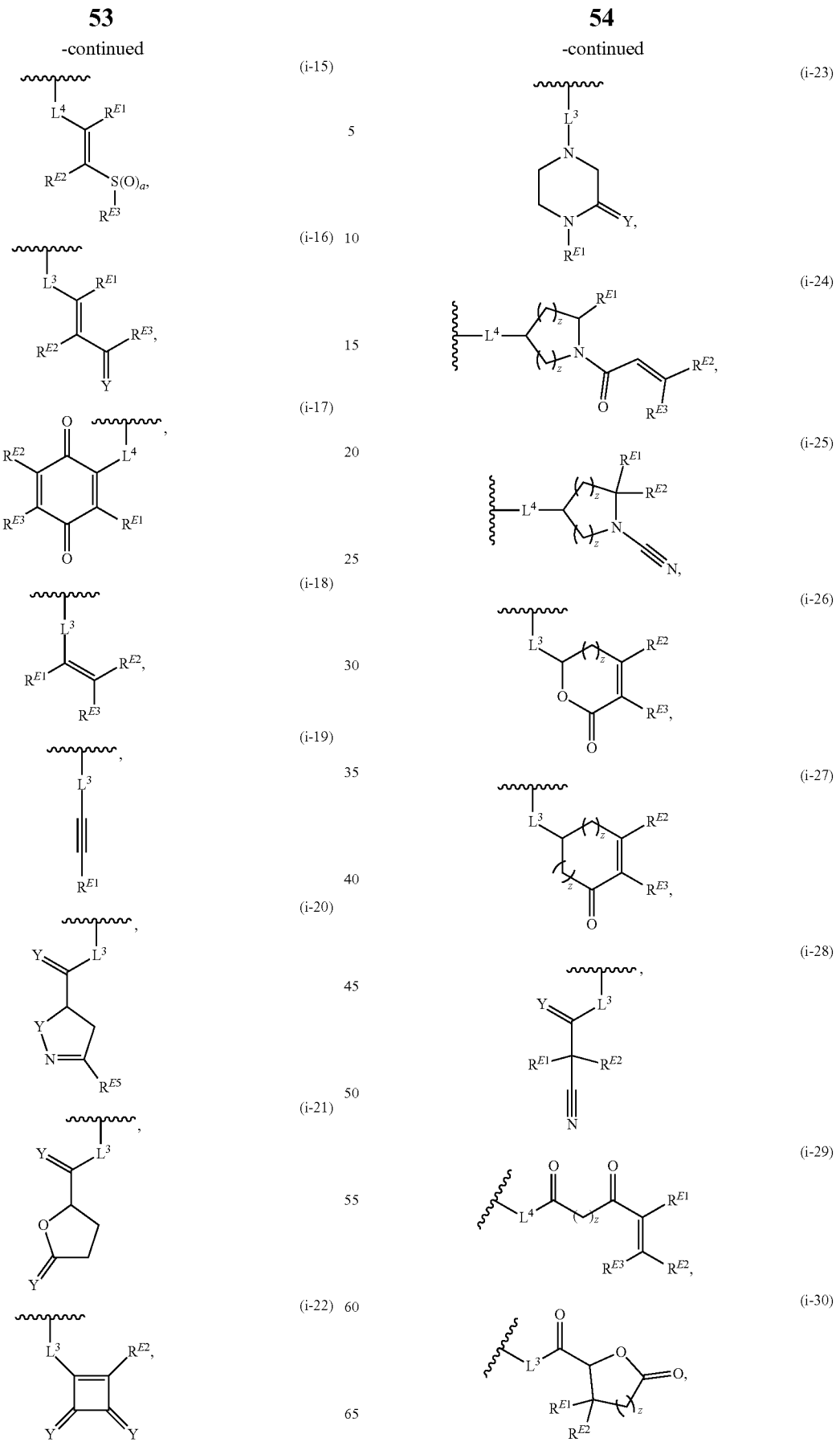

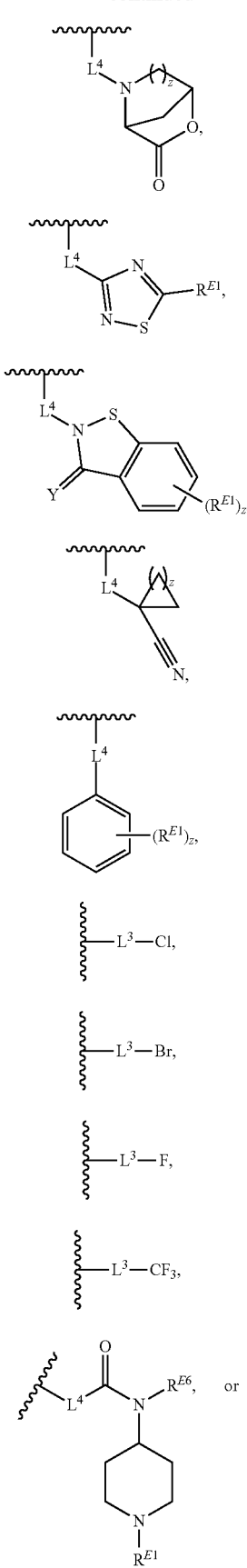

wherein:

$L^3$ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3}$a is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

$L^4$ is a bond or an optionally substituted, branched or unbranched $C_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, and —SR$^{EE}$, wherein each occurrence of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring;

or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted $C_{1-6}$ alkyl, or a nitrogen protecting group;

each instance of Y is independently O, S, or NR$^{E7}$, wherein R$^{E7}$ is hydrogen, substituted or unsubstituted $C_{1-6}$ alkyl, or a nitrogen protecting group;

a is 1 or 2; and each instance of z is independently 0, 1, 2, 3, 4, 5, or 6, as valency permits.

In certain embodiments, a compound described herein is of Formula (III):

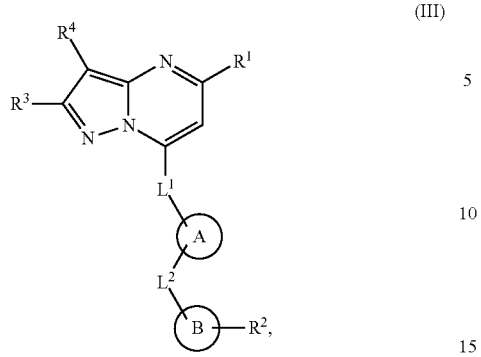 (III)

or a pharmaceutically acceptable salt thereof, wherein:

$R^1$ is optionally substituted alkyl, optionally substituted alkenyl, optionally substituted alkynyl, optionally substituted carbocyclyl, optionally substituted aryl, optionally substituted heterocyclyl, optionally substituted heteroaryl, $-NR^aR^b$, $-OR^b$, $-SR^b$, $-C(=O)R^b$, $-C(=O)OR^b$, or $-C(=O)NR^aR^b$, wherein each instance of $R^a$ and $R^b$ is independently hydrogen, optionally substituted alkyl, optionally substituted alkenyl, optionally substituted alkynyl, optionally substituted carbocyclyl, optionally substituted aryl, optionally substituted heterocyclyl, optionally substituted aryl, optionally substituted heteroaryl, or a nitrogen protecting group when attached to nitrogen, or an oxygen protecting group when attached to oxygen, or a sulfur protecting group when attached to sulfur; or $R^a$ and $R^b$ are joined to form an optionally substituted heterocyclic or optionally substituted heteroaryl ring;

each of $R^3$ and $R^4$ is independently hydrogen, halogen, or optionally substituted $C_1$-$C_6$ alkyl;

$L^1$ is a bond, $-NR^{L1}-(CH_2)_t-$, $-O-$, or $-S-$;

$R^{L1}$ is hydrogen, optionally substituted $C_1$-$C_6$ alkyl, or a nitrogen protecting group;

t is 0 or an integer between 1 and 5, inclusive;

Ring A is optionally substituted carbocyclyl, optionally substituted heterocyclyl, optionally substituted aryl, or optionally substituted heteroaryl;

$L^2$ is a bond, optionally substituted $C_{1-4}$ alkylene, $-C(=O)-$, $-NR^{L2}-$, $-C(=O)NR^{L2}-$, $-NR^{L2}C(=O)-$, $-O-$, or $-S-$, wherein $R^{L2}$ is hydrogen, optionally substituted $C_1$-$C_6$ alkyl, or a nitrogen protection group;

Ring B is absent, optionally substituted carbocyclyl, optionally substituted heterocyclyl, optionally substituted aryl, or optionally substituted heteroaryl; and $R^2$ is any of Formulae (i-1)-(i-41):

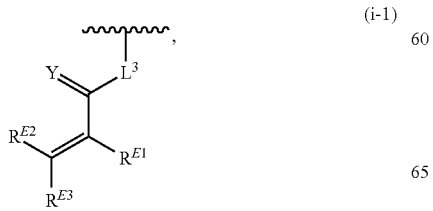 (i-1)

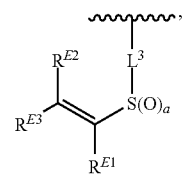 (i-2)

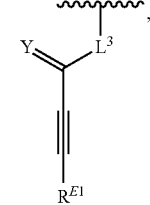 (i-3)

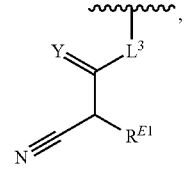 (i-4)

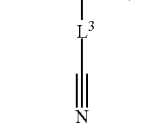 (i-5)

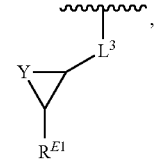 (i-6)

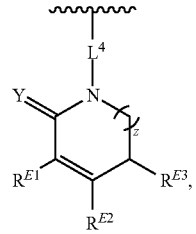 (i-7)

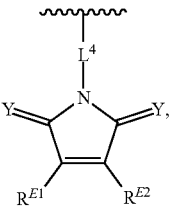 (i-8)

(i-9)

-continued
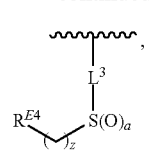 (i-10)
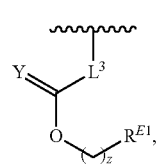 (i-11)
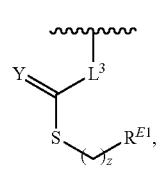 (i-12)
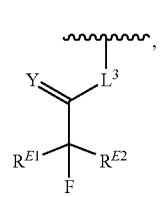 (i-13)
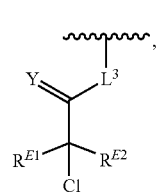 (i-14)
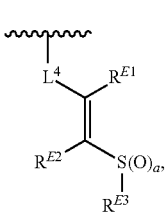 (i-15)
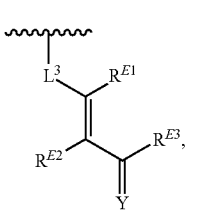 (i-16)
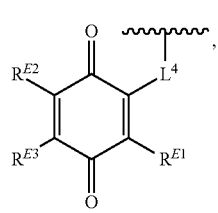 (i-17)
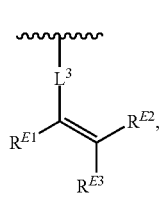 (i-18)
-continued
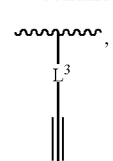 (i-19)
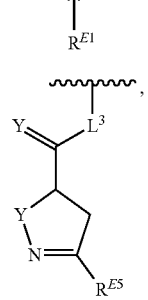 (i-20)
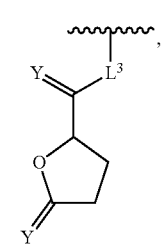 (i-21)
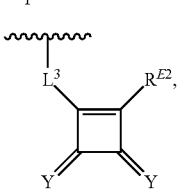 (i-22)
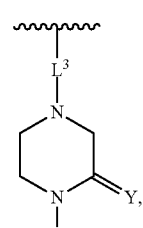 (i-23)
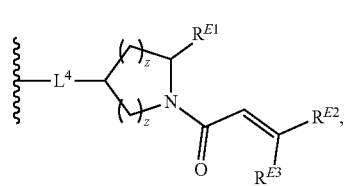 (i-24)
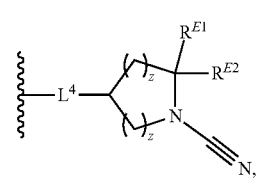 (i-25)
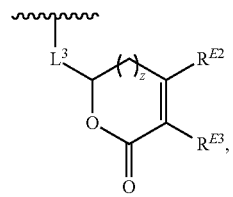 (i-26)

(i-27) 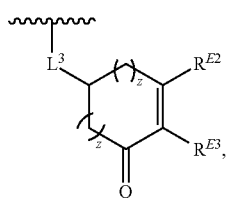

(i-28) 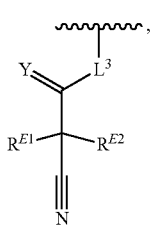

(i-29) 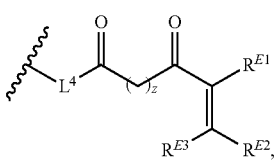

(i-30) 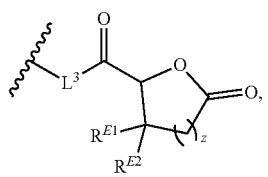

(i-31) 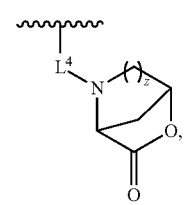

(i-32) 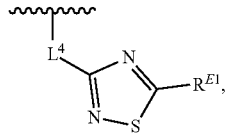

(i-33) 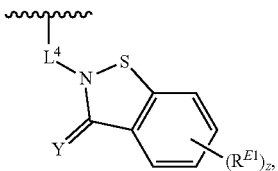

(i-34) 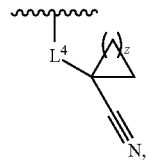

(i-35) 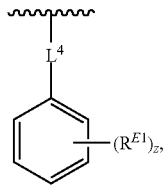

(i-36) 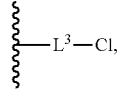

(i-37) 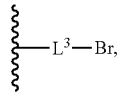

(i-38) 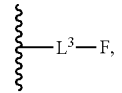

(i-39) 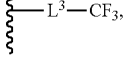

(i-40) 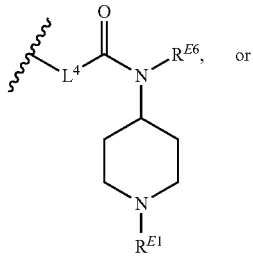 or (i-41) 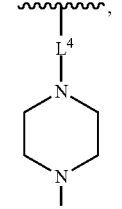, wherein:

$L^3$ is a bond or an optionally substituted $C_{1-4}$ hydrocarbon chain, optionally wherein one or more carbon units of the hydrocarbon chain are independently replaced with —C=O—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{L3b}$ groups are joined to form an optionally substituted carbocyclic or optionally substituted heterocyclic ring;

$L^4$ is a bond or an optionally substituted, branched or unbranched $C_{1-6}$ hydrocarbon chain;

each of $R^{E1}$, $R^{E2}$, and $R^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, and —SR$^{EE}$, wherein each occurrence of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two $R^{EE}$ groups are joined to form an optionally substituted heterocyclic ring;

or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

$R^{E6}$ is hydrogen, substituted or unsubstituted $C_{1-6}$ alkyl, or a nitrogen protecting group;

each instance of Y is independently O, S, or NR$^{E7}$, wherein $R^{E7}$ is hydrogen, substituted or unsubstituted $C_{1-6}$ alkyl, or a nitrogen protecting group;

a is 1 or 2; and each instance of z is independently 0, 1, 2, 3, 4, 5, or 6, as valency permits.

As generally defined herein in Formulae (I)-(III), $R^1$ is optionally substituted alkyl, optionally substituted alkenyl, optionally substituted alkynyl, optionally substituted carbocyclyl, optionally substituted aryl, optionally substituted heterocyclyl, optionally substituted heteroaryl, —NR$^a$R$^b$, —OR$^b$, —SR$^b$, —C(=O)R$^b$, —C(=O)OR$^b$, or —C(=O)NR$^a$R$^b$, wherein each instance of R$^a$ and R$^b$ is independently hydrogen, optionally substituted alkyl, optionally substituted alkenyl, optionally substituted alkynyl, optionally substituted carbocyclyl, optionally substituted aryl, optionally substituted heterocyclyl, optionally substituted aryl, optionally substituted heteroaryl, or a nitrogen protecting group when attached to nitrogen, or an oxygen protecting group when attached to oxygen, or a sulfur protecting group when attached to sulfur; or R$^a$ and R$^b$ are joined to form an optionally substituted heterocyclic or optionally substituted heteroaryl ring.

In certain embodiments, $R^1$ is optionally substituted alkyl. In certain embodiments, $R^1$ is unsubstituted alkyl. In certain embodiments, $R^1$ is substituted alkyl. In certain embodiments, $R^1$ is substituted alkyl. In certain embodiments, $R^1$ is optionally substituted carbocyclylalkyl, optionally substituted arylalkyl, optionally substituted heterocyclylalkyl, or optionally substituted heteroarylalkyl. In certain embodiments, $R^1$ is optionally substituted heteroaryl. In certain embodiments, $R^1$ is optionally substituted monocyclic heteroaryl. In certain embodiments, $R^1$ is optionally substituted 5-membered heteroaryl. In certain embodiments, $R^1$ is optionally substituted 6-membered heteroaryl. In certain embodiments, $R^1$ is optionally substituted heterocyclyl. In certain embodiments, $R^1$ is optionally substituted monocyclic heterocyclyl. In certain embodiments, $R^1$ is optionally substituted 5-membered heterocyclyl. In certain embodiments, $R^1$ is optionally substituted 6-membered heterocyclyl. In certain embodiments, $R^1$ is —OR$^b$, wherein R$^b$ is as defined herein. In certain embodiments, $R^1$ is —OR$^b$, wherein R$^b$ is optionally substituted alkyl, optionally substituted carbocyclyl, optionally substituted aryl, optionally substituted heterocyclyl, optionally substituted aryl, optionally substituted heteroaryl, or an oxygen protecting group. In certain embodiments, $R^1$ is —SR$^b$, wherein R$^b$ is as defined herein. In certain embodiments, $R^1$ is —SR$^b$, wherein R$^b$ is optionally substituted alkyl, optionally substituted carbocyclyl, optionally substituted aryl, optionally substituted heterocyclyl, optionally substituted aryl, optionally substituted heteroaryl, or a sulfur protecting group. In certain embodiments, $R^1$ is —C(=O)R$^b$, wherein R$^b$ is as defined herein. In certain embodiments, $R^1$ is —C(=O)R$^b$, wherein R$^b$ is optionally substituted alkyl, optionally substituted carbocyclyl, optionally substituted aryl, optionally substituted heterocyclyl, optionally substituted aryl, optionally substituted heteroaryl. In certain embodiments, $R^1$ is —C(=O)OR$^b$, wherein R$^b$ is as defined herein. In certain embodiments, $R^1$ is —C(=O)OR$^b$, wherein R$^b$ is optionally substituted alkyl, optionally substituted carbocyclyl, optionally substituted aryl, optionally substituted heterocyclyl, optionally substituted aryl, optionally substituted heteroaryl, or an oxygen protecting group. In certain embodiments, $R^1$ is C(=O)NR$^a$R$^b$, wherein R$^a$ and R$^b$ are as defined herein. In certain embodiments, $R^1$ is C(=O)NR$^a$R$^b$, wherein each instance of R$^a$ and R$^b$ is independently optionally substituted alkyl, optionally substituted carbocyclyl, optionally substituted aryl, optionally substituted heterocyclyl, optionally substituted aryl, optionally substituted heteroaryl, or a nitrogen protecting group, or R$^a$ and R$^b$ are taken together with the nitrogen to form an optionally substituted heterocyclyl ring. In certain embodiments, $R^1$ is C(=O)NR$^a$R$^b$, wherein R$^a$ is hydrogen or optionally substituted alkyl, and R$^b$ is independently optionally substituted alkyl, optionally substituted carbocyclyl, optionally substituted aryl, optionally substituted heterocyclyl, optionally substituted aryl, optionally substituted heteroaryl, or a nitrogen protecting group, or R$^a$ and R$^b$ are taken together with the nitrogen to form an optionally substituted heterocyclyl ring.

In certain embodiments, $R^1$ is —NR$^a$R$^b$, wherein R$^a$ and R$^b$ are as defined herein. In certain embodiments, $R^1$ is —NR$^a$R$^b$, wherein each of R$^a$ and R$^b$ is independently hydrogen, optionally substituted alkyl, optionally substituted carbocyclyl, or a nitrogen protecting group. In certain embodiments, $R^1$ is —NR$^a$R$^b$, wherein R$^a$ is hydrogen, optionally substituted alkyl, or optionally substituted carbocyclyl; and R$^b$ is independently hydrogen, optionally substituted alkyl, or a nitrogen protecting group.

In certain embodiments of Formulae (I)-(III), $R^1$ is of Formula (n-1):

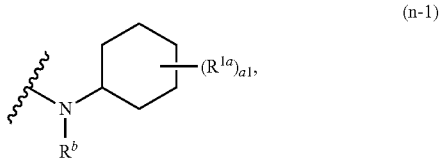

(n-1)

wherein:

each instance of $R^{1a}$ is independently hydrogen, halogen, optionally substituted $C_1$-$C_6$ alkyl, —N(R$^{N1}$)$_2$, or —OR$^{O1}$;

each instance of $R^{N1}$ is independently hydrogen, optionally substituted $C_1$-$C_6$ alkyl, or a nitrogen protecting group;

$R^{O1}$ is independently hydrogen, optionally substituted $C_1$-$C_6$ alkyl, or an oxygen protecting group; and a1 is 0 or an integer between 1 and 6, inclusive.

In certain embodiments, a1 is 1. In certain embodiments, a1 is 2. In certain embodiments, a1 is 3.

In certain embodiments, $R^{1a}$ is optionally substituted $C_1$-$C_6$ alkyl. In certain embodiments, $R^{1a}$ is unsubstituted $C_1$-$C_6$ alkyl. In certain embodiments, $R^{1a}$ is methyl or ethyl. In certain embodiments, $R^{1a}$ is substituted $C_1$-$C_6$ alkyl. In certain embodiments, $R^{1a}$ is hydroxy $C_1$-$C_6$ alkyl. In certain embodiments, $R^{1a}$ is —$CH_2OH$. In certain embodiments, $R^{1a}$ is —$CH_2CH_2OH$. In certain embodiments, $R^{1a}$ is —$N(R^{N1})_2$, wherein $R^{N1}$ is as defined herein. In certain embodiments, $R^{1a}$ is —$NHR^{N1}$, wherein $R^{N1}$ is as defined herein. In certain embodiments, $R^{1a}$ is —$NHR^{N1}$, wherein $R^{N1}$ is hydrogen or optionally substituted $C_1$-$C_6$ alkyl. In certain embodiments, $R^{1a}$ is —$NH_2$. In certain embodiments, $R^{1a}$ is —$NHR^{N1}$, wherein $R^{N1}$ is optionally substituted $C_1$-$C_6$ alkyl. In certain embodiments, $R^{1a}$ is —$NHR^{N1}$, wherein $R^{N1}$ is unsubstituted $C_1$-$C_6$ alkyl. In certain embodiments, $R^{1a}$ is —$NHR^{N1}$, wherein $R^{N1}$ is methyl or ethyl. In certain embodiments, $R^{1a}$ is —$NHCH_3$. In certain embodiments, $R^{1a}$ is —$NHR^{N1}$, wherein $R^{N1}$ is a nitrogen protecting group. In certain embodiments, $R^{1a}$ is —$N(CH_3)R^{N1}$, wherein $R^{N1}$ is optionally substituted $C_1$-$C_6$ alkyl. In certain embodiments, $R^{1a}$ is —$N(CH_3)R^{N1}$, wherein $R^{N1}$ is unsubstituted $C_1$-$C_6$ alkyl. In certain embodiments, $R^{1a}$ is —$N(CH_3)R^{N1}$, wherein $R^{N1}$ is methyl or ethyl. In certain embodiments, $R^{1a}$ is —$N(CH_3)_2$. In certain embodiments, $R^{1a}$ is —$N(CH_3)R^{N1}$, wherein $R^{N1}$ is a nitrogen protecting group.

In certain embodiments of Formulae (I)-(III), $R^1$ is —$NR^aR^b$, wherein $R^a$ and $R^b$ are joined to form an optionally substituted heterocyclic or optionally substituted heteroaryl ring. In certain embodiments, $R^1$ is of one of the following formulae:

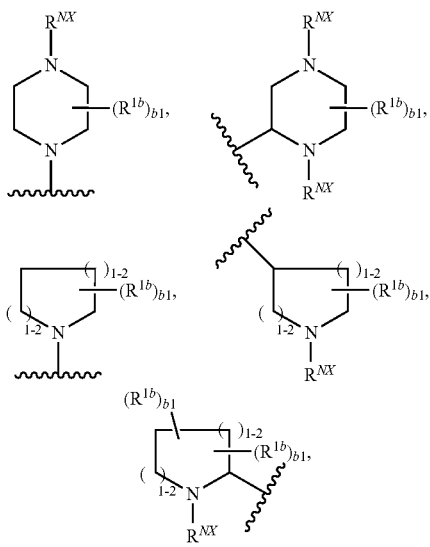

wherein:

each instance of $R^{NX}$ is independently hydrogen, optionally substituted alkyl, optionally substituted alkenyl, optionally substituted alkynyl, optionally substituted carbocyclyl, optionally substituted aryl, optionally substituted heterocyclyl, optionally substituted heteroaryl, or a nitrogen protecting group;

each instance of $R^{1b}$ is independently hydrogen, halogen, optionally substituted $C_1$-$C_6$ alkyl, —$N(R^{N1})_2$, or —$OR^{O1}$;

each instance of $R^{N1}$ is independently hydrogen, optionally substituted $C_1$-$C_6$ alkyl, or a nitrogen protecting group;

$R^{O1}$ is independently hydrogen, optionally substituted $C_1$-$C_6$ alkyl, or an oxygen protecting group; and b1 is 0 or an integer between 1 and 6, inclusive, as valency permits.

In certain embodiments, $R^1$ is of Formula (n-2):

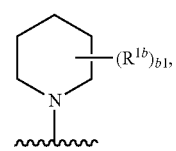

wherein:

each instance of $R^{1b}$ is independently hydrogen, halogen, optionally substituted $C_1$-$C_6$ alkyl, —$N(R^{N1})_2$, or —$OR^{O1}$;

each instance of $R^{N1}$ is independently hydrogen, optionally substituted $C_1$-$C_6$ alkyl, or a nitrogen protecting group;

$R^{O1}$ is independently hydrogen, optionally substituted $C_1$-$C_6$ alkyl, or an oxygen protecting group; and b1 is 0 or an integer between 1 and 6, inclusive.

In certain embodiments, b1 is 1. In certain embodiments, b1 is 2. In certain embodiments, b1 is 3.

In certain embodiments, $R^{1b}$ is optionally substituted $C_1$-$C_6$ alkyl. In certain embodiments, $R^{1b}$ is unsubstituted $C_1$-$C_6$ alkyl. In certain embodiments, $R^{1b}$ is methyl or ethyl. In certain embodiments, $R^{1b}$ is substituted $C_1$-$C_6$ alkyl. In certain embodiments, $R^{1b}$ is hydroxy $C_1$-$C_6$ alkyl. In certain embodiments, $R^{1b}$ is —$CH_2OH$. In certain embodiments, $R^{1b}$ is —$CH_2CH_2OH$. In certain embodiments, $R^{1b}$ is —$N(R^{N1})_2$, wherein $R^{N1}$ is as defined herein. In certain embodiments, $R^{1b}$ is —$NHR^{N1}$, wherein $R^{N1}$ is as defined herein. In certain embodiments, $R^{1b}$ is —$NHR^{N1}$, wherein $R^{N1}$ is hydrogen or optionally substituted $C_1$-$C_6$ alkyl. In certain embodiments, $R^{1b}$ is —$NH_2$. In certain embodiments, $R^{1b}$ is —$NHR^{N1}$, wherein $R^{N1}$ is optionally substituted $C_1$-$C_6$ alkyl. In certain embodiments, $R^{1b}$ is —$NHR^{N1}$, wherein $R^{N1}$ is unsubstituted $C_1$-$C_6$ alkyl. In certain embodiments, $R^{1b}$ is —$NHR^{N1}$, wherein $R^{N1}$ is methyl or ethyl. In certain embodiments, $R^{1b}$ is —$NHCH_3$. In certain embodiments, $R^{1b}$ is —$NHR^{N1}$, wherein $R^{N1}$ is a nitrogen protecting group. In certain embodiments, $R^{1b}$ is —$N(CH_3)R^{N1}$, wherein $R^{N1}$ is optionally substituted $C_1$-$C_6$ alkyl. In certain embodiments, $R^{1b}$ is —$N(CH_3)R^{N1}$, wherein $R^{N1}$ is unsubstituted $C_1$-$C_6$ alkyl. In certain embodiments, $R^{1b}$ is —$N(CH_3)R^{N1}$, wherein $R^{N1}$ is methyl or ethyl. In certain embodiments, $R^{1b}$ is —$N(CH_3)_2$. In certain embodiments, $R^{1b}$ is —$N(CH_3)R^{N1}$, wherein $R^{N1}$ is a nitrogen protecting group.

In certain embodiments, $R^{NX}$ is hydrogen. In certain embodiments, $R^{NX}$ is optionally substituted alkyl. In certain embodiments, $R^{NX}$ is unsubstituted $C_1$-$C_6$ alkyl (e.g. methyl or ethyl). In certain embodiments, $R^{NX}$ is substituted $C_1$-$C_6$ alkyl. In certain embodiments, $R^{NX}$ is a nitrogen protecting group.

In certain embodiments of Formulae (I)-(III), $R^1$ is optionally substituted carbocyclyl. In certain embodiments, $R^1$ is optionally substituted monocyclic carbocyclyl. In certain embodiments, $R^1$ is optionally substituted cyclopentyl. In certain embodiments, $R^1$ is optionally substituted cyclohexyl of Formula (n-3)

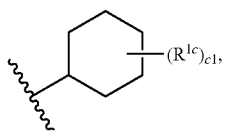

(n-3)

wherein:

each instance of $R^{1c}$ is independently hydrogen, halogen, optionally substituted $C_1$-$C_6$ alkyl, —$N(R^{N1})_2$, or —$OR^{O1}$;

each instance of $R^{N1}$ is independently hydrogen, optionally substituted $C_1$-$C_6$ alkyl, or a nitrogen protecting group;

$R^{O1}$ is independently hydrogen, optionally substituted $C_1$-$C_6$ alkyl, or an oxygen protecting group; and c1 is 0 or an integer between 1 and 6, inclusive.

In certain embodiments, c1 is 1. In certain embodiments, c1 is 2. In certain embodiments, c1 is 3.

In certain embodiments, $R^{1c}$ is optionally substituted $C_1$-$C_6$ alkyl. In certain embodiments, $R^{1c}$ is unsubstituted $C_1$-$C_6$ alkyl. In certain embodiments, $R^{1c}$ is methyl or ethyl. In certain embodiments, $R^{1c}$ is substituted $C_1$-$C_6$ alkyl. In certain embodiments, $R^{1c}$ is hydroxy $C_1$-$C_6$ alkyl. In certain embodiments, $R^{1c}$ is —$CH_2OH$. In certain embodiments, $R^{1c}$ is —$CH_2CH_2OH$. In certain embodiments, $R^{1c}$ is —$N(R^{N1})_2$, wherein $R^{N1}$ is as defined herein. In certain embodiments, $R^{1c}$ is —$NHR^{N1}$, wherein $R^{N1}$ is as defined herein. In certain embodiments, $R^{1c}$ is —$NHR^{N1}$, wherein $R^{N1}$ is hydrogen or optionally substituted $C_1$-$C_6$ alkyl. In certain embodiments, $R^{1c}$ is —$NH_2$. In certain embodiments, $R^{1c}$ is —$NHR^{N1}$, wherein $R^{N1}$ is optionally substituted $C_1$-$C_6$ alkyl. In certain embodiments, $R^{1c}$ is —$NHR^{N1}$, wherein $R^{N1}$ is unsubstituted $C_1$-$C_6$ alkyl. In certain embodiments, $R^{1c}$ is —$NHR^{N1}$, wherein $R^{N1}$ is methyl or ethyl. In certain embodiments, $R^{1c}$ is —$NHCH_3$. In certain embodiments, $R^{1c}$ is —$NHR^{N1}$, wherein $R^{N1}$ is a nitrogen protecting group. In certain embodiments, $R^{1c}$ is —$N(CH_3)R^{N1}$, wherein $R^{N1}$ is optionally substituted $C_1$-$C_6$ alkyl. In certain embodiments, $R^{1c}$ is —$N(CH_3)R^{N1}$, wherein $R^{N1}$ is unsubstituted $C_1$-$C_6$ alkyl. In certain embodiments, $R^{1c}$ is —$N(CH_3)R^{N1}$, wherein $R^{N1}$ is methyl or ethyl. In certain embodiments, $R^{1c}$ is —$N(CH_3)_2$. In certain embodiments, $R^{1c}$ is —$N(CH_3)R^{N1}$, wherein $R^{N1}$ is a nitrogen protecting group.

In certain embodiments of Formulae (I)-(III), $R^1$ is optionally substituted aryl. In certain embodiments, $R^1$ is optionally substituted monocyclic aryl. In certain embodiments, $R^1$ is optionally substituted phenyl of Formula (n-4)

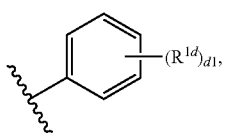

(n-4)

wherein:

each instance of $R^{1d}$ is independently hydrogen, halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —C(=O)$R^C$, —C(=O)$OR^A$, —OC(=O)$R^C$, —C(=O)N($R^B$)$_2$, —$NR^B$C(=O)$R^C$, —OC(=O)N($R^B$)$_2$, —$NR^B$C(=O)$OR^A$, —$NR^B$C(=O)N($R^B$)$_2$, S(=O)$R^C$, —$SO_2R^C$, —$NR^B SO_2 R^C$, or —$SO_2$N($R^B$)$_2$;

each instance of $R^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to oxygen, or a sulfur protecting group when attached to sulfur;

each instance of $R^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group, or two $R^B$ groups are taken together with their intervening atoms to form an optionally substituted heterocyclic ring; and d1 is 0 or an integer between 1 and 5, inclusive.

In certain embodiments, d1 is 0. In certain embodiments, d1 is 1. In certain embodiments, d1 is 2. In certain embodiments, d1 is 3.

In certain embodiments, $R^{1d}$ is hydrogen. In certain embodiments, $R^{1d}$ is halogen (e.g. F, Cl, Br, or I). In certain embodiments, $R^{1d}$ is optionally substituted alkyl. In certain embodiments, $R^{1d}$ is unsubstituted alkyl. In certain embodiments, $R^{1d}$ is methyl or ethyl.

As generally defined herein in Formulae (I)-(III), $R^3$ is hydrogen, halogen, or optionally substituted $C_1$-$C_6$ alkyl. In certain embodiments, $R^3$ is hydrogen. In certain embodiments, $R^3$ is halogen (e.g. F, Cl, Br, or I). In certain embodiments, $R^3$ is optionally substituted $C_1$-$C_6$ alkyl. In certain embodiments, $R^3$ is unsubstituted $C_1$-$C_6$ alkyl. In certain embodiments, $R^3$ is methyl, ethyl, n-propyl, or isopropyl. In certain embodiments, $R^3$ is substituted $C_1$-$C_6$ alkyl.

As generally defined herein in Formulae (II)-(III), $R^4$ is hydrogen, halogen, or optionally substituted $C_1$-$C_6$ alkyl. In certain embodiments, $R^4$ is hydrogen. In certain embodiments, $R^4$ is halogen (e.g. F, Cl, Br, or I). In certain embodiments, $R^4$ is optionally substituted $C_1$-$C_6$ alkyl. In certain embodiments, $R^4$ is unsubstituted $C_1$-$C_6$ alkyl. In certain embodiments, $R^4$ is methyl, ethyl, n-propyl, or isopropyl. In certain embodiments, $R^4$ is substituted $C_1$-$C_6$ alkyl.

As generally defined herein in Formula (I), $R^5$ is hydrogen, optionally substituted $C_1$-$C_6$ alkyl, or a nitrogen protecting group. In certain embodiments, $R^5$ is hydrogen. In certain embodiments, $R^5$ is optionally substituted $C_1$-$C_6$ alkyl. In certain embodiments, $R^5$ is unsubstituted $C_1$-$C_6$ alkyl. In certain embodiments, $R^5$ is methyl, ethyl, n-propyl, or isopropyl. In certain embodiments, $R^5$ is substituted $C_1$-$C_6$ alkyl. In certain embodiments, $R^5$ is nitrogen protecting group. In certain embodiments, $R^5$ is nitrogen protecting group.

As generally defined herein in Formulae (I)-(III), $L^1$ is a bond, —$NR^{L1}$—($CH_2$)$_t$—, —O—, or —S—, wherein $R^{L1}$ is hydrogen, optionally substituted $C_1$-$C_6$ alkyl, or a nitrogen protecting group, wherein t is 0 or an integer between 1 and 5, inclusive. In certain embodiments, $L^1$ is a bond. In certain embodiments, $L^1$ is —O—. In certain embodiments, $L^1$ is —S—. In certain embodiments, $L^1$ is —$NR^{L1}$—($CH_2$)$_t$—, wherein $R^{L1}$ is hydrogen, optionally substituted $C_1$-$C_6$ alkyl, or a nitrogen protecting group. In certain embodiments, t is 0. In certain embodiments, t is 1. In certain embodiments, t is 2. In certain embodiments, t is 3. In certain embodiments, t is 4. In certain embodiments, t is 5. In certain embodiments, $L^1$ is —NR$^{L1}$—, wherein R$^{L1}$ is hydrogen, optionally substituted C$_1$-C$_6$ alkyl, or a nitrogen protecting group. In certain embodiments, L$^1$ is —NH—. In certain embodiments, L$^1$ is —NH—. In certain embodiments, L$^1$ is —NR$^{L1}$—, wherein R$^{L1}$ is optionally substituted C$_1$-C$_6$ alkyl. In certain embodiments, L$^1$ is —NR$^{L1}$—, wherein R$^{L1}$ is unsubstituted C$_1$-C$_6$ alkyl. In certain embodiments, L$^1$ is —NR$^{L1}$—, wherein R$^{L1}$ is methyl or ethyl. In certain embodiments, L$^1$ is —NR$^{L1}$—, wherein R$^{L1}$ is substituted C$_1$-C$_6$ alkyl. In certain embodiments, L$^1$ is —NR$^{L1}$—, wherein R$^{L1}$ is a nitrogen protecting group (e.g. Boc). In certain embodiments, L$^1$ is —NR$^{L1}$—CH$_2$—, wherein R$^{L1}$ is hydrogen, optionally substituted C$_1$-C$_6$ alkyl, or a nitrogen protecting group. In certain embodiments, L$^1$ is —NHCH$_2$—. In certain embodiments, L$^1$ is —NR$^{L1}$—CH$_2$—, wherein R$^{L1}$ is optionally substituted C$_1$-C$_6$ alkyl. In certain embodiments, L$^1$ is —NR$^{L1}$—CH$_2$—, wherein R$^{L1}$ is unsubstituted C$_1$-C$_6$ alkyl. In certain embodiments, L$^1$ is —NR$^{L1}$—CH$_2$—, wherein R$^{L1}$ is methyl or ethyl. In certain embodiments, L$^1$ is —NR$^{L1}$—CH$_2$—, wherein R$^{L1}$ is substituted C$_1$-C$_6$ alkyl. In certain embodiments, L$^1$ is —NR$^{L1}$—CH$_2$—, wherein R$^{L1}$ is a nitrogen protecting group (e.g. Boc).

As generally defined herein in Formulae (I)-(III), L$^2$ is a bond, optionally substituted C$_{1-4}$ alkylene, —C(=O)—, —NR$^{L2}$—, —C(=O)NR$^{L2}$—, —NR$^{L2}$C(=O)—, —O—, or —S—, wherein R$^{L2}$ is hydrogen, optionally substituted C$_1$-C$_6$ alkyl, or a nitrogen protection group. In certain embodiments, L$^2$ is a bond. In certain embodiments, L$^2$ is —O—. In certain embodiments, L$^2$ is —S—. In certain embodiments, L$^2$ is optionally substituted C$_{1-4}$ alkylene. In certain embodiments, L$^2$ is unsubstituted C$_{1-4}$ alkylene. In certain embodiments, L$^2$ is —CH$_2$—. In certain embodiments, L$^2$ is —(CH$_2$)$_2$—. In certain embodiments, L$^2$ is —(CH$_2$)$_3$—. In certain embodiments, L$^2$ is —(CH$_2$)$_4$—. In certain embodiments, L$^2$ is —C(=O)—. In certain embodiments, L$^2$ is —NR$^{L2}$—, wherein R$^{L2}$ is hydrogen, optionally substituted C$_1$-C$_6$ alkyl, or a nitrogen protecting group. In certain embodiments, L$^2$ is —NH—. In certain embodiments, L$^2$ is —NH—. In certain embodiments, L$^2$ is —NR$^{L2}$—, wherein R$^{L2}$ is optionally substituted C$_1$-C$_6$ alkyl. In certain embodiments, L$^2$ is —NR$^{L2}$—, wherein R$^{L2}$ is unsubstituted C$_1$-C$_6$ alkyl. In certain embodiments, L$^2$ is —NR$^{L2}$—, wherein R$^{L2}$ is methyl or ethyl. In certain embodiments, L$^2$ is —NR$^{L2}$—, wherein R$^{L2}$ is substituted C$_1$-C$_6$ alkyl. In certain embodiments, L$^2$ is —NR$^{L2}$—, wherein R$^{L2}$ is a nitrogen protecting group (e.g. Boc). In certain embodiments, L$^2$ is —C(=O)NR$^{L2}$—, wherein R$^{L2}$ is hydrogen, optionally substituted C$_1$-C$_6$ alkyl, or a nitrogen protecting group. In certain embodiments, L$^2$ is —C(=O)NH—. In certain embodiments, L$^2$ is —C(=O) wherein R$^{L2}$ is optionally substituted C$_1$-C$_6$ alkyl. In certain embodiments, L$^2$ is —C(=O)NR$^{L2}$—, wherein R$^{L2}$ is unsubstituted C$_1$-C$_6$ alkyl. In certain embodiments, L$^2$ is —C(=O)NR$^{L2}$—, wherein R$^{L2}$ is methyl or ethyl. In certain embodiments, L$^2$ is —C(=O)NR$^{L2}$—, wherein R$^{L2}$ is substituted C$_1$-C$_6$ alkyl. In certain embodiments, L$^2$ is —C(=O)NR$^{L2}$—, wherein R$^{L2}$ is a nitrogen protecting group (e.g. Boc). In certain embodiments, L$^2$ is —NR$^{L2}$C(=O)—, wherein R$^{L2}$ is hydrogen, optionally substituted C$_1$-C$_6$ alkyl, or a nitrogen protecting group. In certain embodiments, L$^2$ is —NHC(=O)—. In certain embodiments, L$^2$ is —NR$^{L2}$C(=O)—, wherein R$^{L2}$ is optionally substituted C$_1$-C$_6$ alkyl. In certain embodiments, L$^2$ is —NR$^{L2}$C(O)—, wherein R$^{L2}$ is unsubstituted C$_1$-C$_6$ alkyl. In certain embodiments, L$^2$ is —NR$^{L2}$C(=O)—, wherein R$^{L2}$ is methyl or ethyl. In certain embodiments, L$^2$ is —NR$^{L2}$C(=O)—, wherein R$^{L2}$ is substituted C$_1$-C$_6$ alkyl. In certain embodiments, L$^2$ is —NR$^{L2}$C(=O)—, wherein R$^{L2}$ is a nitrogen protecting group (e.g. Boc).

In certain embodiments of Formula (I), R$^3$ is hydrogen and R$^5$ is optionally substituted C$_1$-C$_6$ alkyl or a nitrogen protecting group. In certain embodiments of Formula (I), R$^3$ is hydrogen and R$^5$ is optionally substituted C$_1$-C$_6$ alkyl. In certain embodiments of Formula (I), R$^3$ is hydrogen and R$^5$ is unsubstituted C$_1$-C$_6$ alkyl. In certain embodiments of Formula (I), R$^3$ is hydrogen and R$^5$ is methyl, ethyl, n-propyl, or isopropyl.

In certain embodiments of Formula (II) or (III), R$^3$ is hydrogen and R$^4$ is optionally substituted C$_1$-C$_6$ alkyl or a nitrogen protecting group. In certain embodiments of Formula (II) or (III), R$^3$ is hydrogen and R$^4$ is optionally substituted C$_1$-C$_6$ alkyl. In certain embodiments of Formula (II) or (III), R$^3$ is hydrogen and R$^4$ is unsubstituted C$_1$-C$_6$ alkyl. In certain embodiments of Formula (II) or (III), R$^3$ is hydrogen and R$^4$ is methyl, ethyl, n-propyl, or isopropyl.

In certain embodiments of Formula (I), R$^1$ is optionally substituted carbocyclyl; R$^3$ is hydrogen; and R$^5$ is optionally substituted C$_1$-C$_6$ alkyl or a nitrogen protecting group. In certain embodiments of Formula (I), R$^1$ is optionally substituted cyclohexyl; R$^3$ is hydrogen; and R$^5$ is optionally substituted C$_1$-C$_6$ alkyl. In certain embodiments of Formula (I), R$^1$ is mono-substituted cyclohexyl; R$^3$ is hydrogen; and R$^5$ is unsubstituted C$_1$-C$_6$ alkyl. In certain embodiments of Formula (I), R$^1$ is optionally substituted aryl; R$^3$ is hydrogen; and R$^5$ is optionally substituted C$_1$-C$_6$ alkyl or a nitrogen protecting group. In certain embodiments of Formula (I), R$^1$ is optionally substituted phenyl; R$^3$ is hydrogen; and R$^5$ is optionally substituted C$_1$-C$_6$ alkyl. In certain embodiments of Formula (I), R$^1$ is mono-substituted phenyl; R$^3$ is hydrogen; and R$^5$ is unsubstituted C$_1$-C$_6$ alkyl. In certain embodiments of Formula (I), R$^1$ is —NR$^a$R$^b$, wherein R$^a$ and R$^b$ are as defined herein; R$^3$ is hydrogen; and R$^5$ is optionally substituted C$_1$-C$_6$ alkyl or a nitrogen protecting group. In certain embodiments of Formula (I), R$^1$ is —NR$^a$R$^b$, wherein R$^a$ is optionally substituted carbocyclyl and R$^b$ is hydrogen or optionally substituted alkyl; R$^3$ is hydrogen; and R$^5$ is optionally substituted C$_1$-C$_6$ alkyl. In certain embodiments of Formula (I), R$^1$ is —NR$^a$R$^b$, wherein R$^a$ is optionally substituted cyclohexyl and R$^b$ is hydrogen; R$^3$ is hydrogen; and R$^5$ is unsubstituted C$_1$-C$_6$ alkyl. In certain embodiments of Formula (I), R$^1$ is —NR$^a$R$^b$, wherein R$^a$ and R$^b$ are joined to form an optionally substituted heterocylic ring; R$^3$ is hydrogen; and R$^5$ is optionally substituted C$_1$-C$_6$ alkyl. In certain embodiments of Formula (I), R$^1$ is —NR$^a$R$^b$, wherein R$^a$ and R$^b$ are joined to form an optionally substituted piperidine ring; R$^3$ is hydrogen; and R$^5$ is unsubstituted C$_1$-C$_6$ alkyl. In certain embodiments of Formula (I), R$^1$ is —NR$^a$R$^b$, wherein R$^a$ and R$^b$ are joined to form a mono-substituted piperidine ring; R$^3$ is hydrogen; and R$^5$ is unsubstituted C$_1$-C$_6$ alkyl.

In certain embodiments of Formula (II) or (III), R$^3$ is hydrogen and R$^4$ is optionally substituted C$_1$-C$_6$ alkyl or a nitrogen protecting group. In certain embodiments of Formula (II) or (III), R$^3$ is hydrogen and R$^4$ is optionally substituted C$_1$-C$_6$ alkyl. In certain embodiments of Formula (II) or (III), R$^3$ is hydrogen and R$^4$ is unsubstituted C$_1$-C$_6$ alkyl. In certain embodiments of Formula (II) or (III), R$^3$ is hydrogen and R$^4$ is methyl, ethyl, n-propyl, or isopropyl.

In certain embodiments of Formula (II) or (III), R$^1$ is optionally substituted carbocyclyl; R$^3$ is hydrogen; and R$^4$ is optionally substituted C$_1$-C$_6$ alkyl or a nitrogen protecting group. In certain embodiments of Formula (II) or (III), R$^1$ is optionally substituted cyclohexyl; R$^3$ is hydrogen; and R$^4$ is optionally substituted $C_1$-$C_6$ alkyl. In certain embodiments of Formula (II) or (III), $R^1$ is mono-substituted cyclohexyl; $R^3$ is hydrogen and $R^4$ is unsubstituted $C_1$-$C_6$ alkyl. In certain embodiments of Formula (II) or (III), $R^1$ is optionally substituted aryl; $R^3$ is hydrogen and $R^4$ is optionally substituted $C_1$-$C_6$ alkyl or a nitrogen protecting group. In certain embodiments of Formula (II) or (III), $R^1$ is optionally substituted phenyl; $R^3$ is hydrogen; and $R^4$ is optionally substituted $C_1$-$C_6$ alkyl. In certain embodiments of Formula (II) or (III), $R^1$ is mono-substituted phenyl; $R^3$ is hydrogen; and $R^4$ is unsubstituted $C_1$-$C_6$ alkyl. In certain embodiments of Formula (II) or (III), $R^1$ is —$NR^aR^b$, wherein $R^a$ and $R^b$ are as defined herein; $R^3$ is hydrogen; and $R^4$ is optionally substituted $C_1$-$C_6$ alkyl or a nitrogen protecting group. In certain embodiments of Formula (II) or (III), $R^1$ is —$NR^aR^b$, wherein $R^a$ is optionally substituted carbocyclyl and $R^b$ is hydrogen or optionally substituted alkyl; $R^3$ is hydrogen and $R^4$ is optionally substituted $C_1$-$C_6$ alkyl. In certain embodiments of Formula (II) or (III), $R^1$ is —$NR^aR^b$, wherein $R^a$ is optionally substituted cyclohexyl and $R^b$ is hydrogen; $R^3$ is hydrogen; and $R^4$ is unsubstituted $C_1$-$C_6$ alkyl. In certain embodiments of Formula (II) or (III), $R^1$ is —$NR^aR^b$, wherein $R^a$ and $R^b$ are joined to form an optionally substituted heterocylic ring; $R^3$ is hydrogen; and $R^4$ is optionally substituted $C_1$-$C_6$ alkyl. In certain embodiments of Formula (II) or (III), $R^1$ is —$NR^aR^b$, wherein $R^a$ and $R^b$ are joined to form an optionally substituted piperidine ring; $R^3$ is hydrogen; and $R^4$ is unsubstituted $C_1$-$C_6$ alkyl. In certain embodiments of Formula (II) or (III), $R^1$ is —$NR^aR^b$, wherein $R^a$ and $R^b$ are joined to form a mono-substituted piperidine ring; $R^3$ is hydrogen; and $R^4$ is methyl, ethyl, n-propyl, or isopropyl.

Compounds of any one of Formulae (I)-(III) include Ring A between linker $L^1$ and linker $L^2$. Ring A may be optionally substituted carbocyclyl, optionally substituted heterocyclyl, optionally substituted aryl, or optionally substituted heteroaryl. In certain embodiments, Ring A is optionally substituted carbocyclyl. In certain embodiments, Ring A is optionally substituted heterocyclyl. In certain embodiments, Ring A is optionally substituted aryl. In certain embodiments, Ring A is optionally substituted heteroaryl. In certain embodiments, Ring A is optionally substituted phenyl. In certain embodiments, Ring A is phenyl substituted with only $L^1$ and $L^2$. In certain embodiments, Ring A is optionally substituted cyclohexyl. In certain embodiments, Ring A is optionally substituted piperidinyl. In certain embodiments, Ring A is optionally substituted piperizinyl. In certain embodiments, Ring A is optionally substituted pyridinyl. In certain embodiments, Ring A is optionally substituted pyrimidinyl.

In certain embodiments of Formulae (I)-(III), linkers $L^1$ and $L^2$ are attached "ortho" or 1.2 to Ring A. In certain embodiments, linkers $L^1$ and $L^2$ are attached "meta" or 1.3 to Ring A. In certain embodiments, linkers $L^1$ and $L^2$ are attached "para" or 1.4 to ring A.

In certain embodiments of Formulae (I)-(III), Ring A is

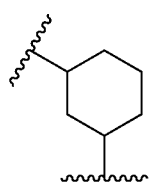 [SMILES: *C1CCCC(*)C1]

or

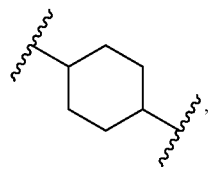 [SMILES: *C1CCC(*)CC1]

wherein each ring atom is optionally substituted. In certain embodiments, Ring A is

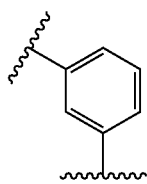 or 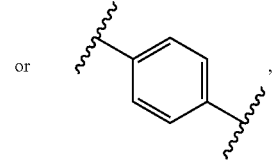

wherein each ring atom is optionally substituted. In certain embodiments, Ring A is

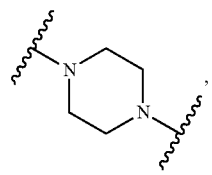 [SMILES: *N1CCN(*)CC1]

wherein each ring atom is optionally substituted. In certain embodiments, Ring A is

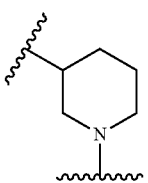 or 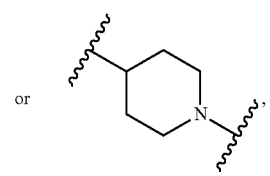

wherein each ring atom is optionally substituted, and $L^1$ and $L^2$ may attach to ring A at either indicated position. In certain embodiments, Ring A is

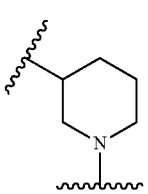 or 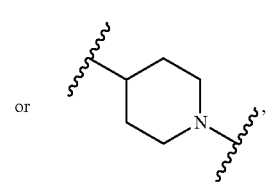

wherein each ring atom is optionally substituted, and $L^1$ and $L^2$ may attach to ring A at either indicated position. In certain embodiments, Ring A is

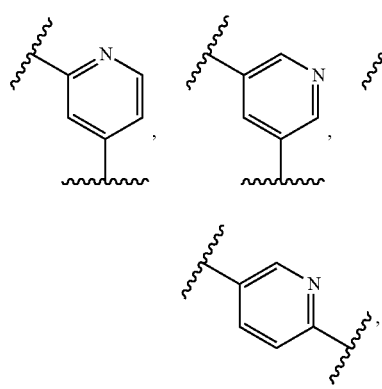

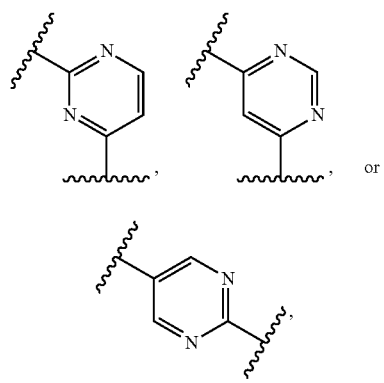

wherein each ring atom is optionally substituted, and $L^1$ and $L^2$ may attach to ring A at either indicated position. In certain embodiments, Ring A is

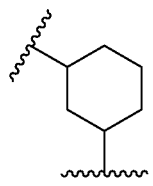 [SMILES: *C1CCCC(*)C1]

or

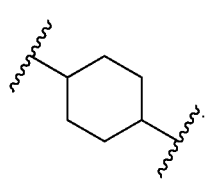 [SMILES: *C1CCC(*)CC1]

wherein each ring atom is optionally substituted, and $L^1$ and $L^2$ may attach to ring A at either indicated position.

In certain embodiments of Formulae (I)-(III), Ring A is

In certain embodiments, Ring A is

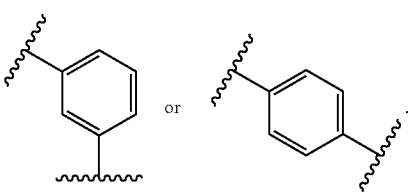 [SMILES: *c1cccc(*)c1 ; *c1ccc(*)cc1]

In certain embodiments, Ring A is

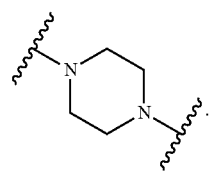

In certain embodiments, Ring A is

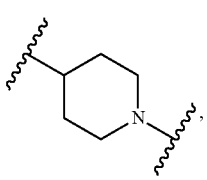 [SMILES: *C1CCN(*)CC1]

or

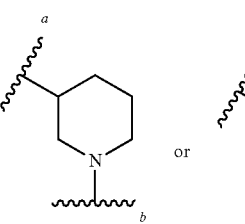

$L^1$ and $L^2$ may attach to ring A at either indicated position. In certain embodiments, Ring A is wherein $L^1$ is attached to position a and $L^2$ is attached to position b. In certain embodiments, Ring A is

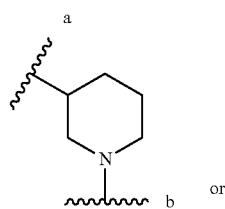 [SMILES: *C1CCCN(*)C1]

or

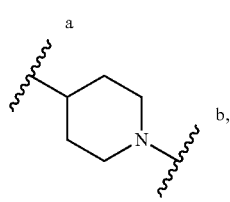

wherein L² is attached to position a and L¹ is attached to position b. In certain embodiments, Ring A is

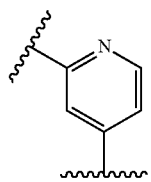, 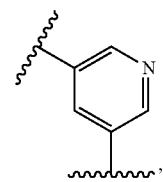, 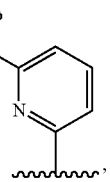, or

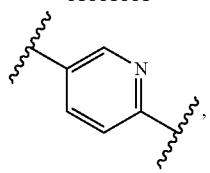, wherein L¹ and L² may attach to ring A at either indicated position. In certain embodiments, Ring A is

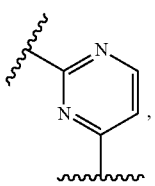, 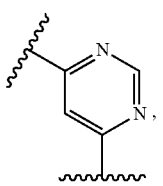, 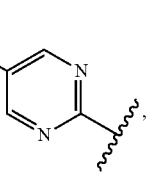, wherein L¹ and L² may attach to ring A at either indicated position.

Compounds of Formulae (I)-(III) include Ring B between linker L² and group R². In certain embodiments, linker L² is a bond, such that Ring B is directly attached to Ring A. Ring B may absent, optionally substituted carbocyclyl, optionally substituted heterocyclyl, optionally substituted aryl, or optionally substituted heteroaryl. In certain embodiments, Ring B is absent, such that L² is directly attached to R². In certain embodiments, Ring B is absent and linker L² is a bond, such that Ring A is directly attached to R². In certain embodiments, Ring B is optionally substituted carbocyclyl. In certain embodiments, Ring B is optionally substituted heterocyclyl. In certain embodiments, Ring B is optionally substituted aryl. In certain embodiments, Ring B is option- ally substituted heteroaryl. In certain embodiments, Ring B is optionally substituted phenyl. In certain embodiments, Ring B is optionally substituted cyclohexyl. In certain embodiments, Ring B is optionally substituted piperidinyl. In certain embodiments, Ring B is optionally substituted piperizinyl. In certain embodiments, Ring B is optionally substituted pyridinyl. In certain embodiments, Ring B is optionally substituted pyrimidinyl.

In certain embodiments of Formulae (I)-(III), linker L² and group R² are attached "ortho" or 1.2 to each other on Ring B. In certain embodiments, linkers L² and group R² are attached "meta" or 1.2 to each other on Ring B. In certain embodiments, linkers L² and R² are attached "para" or 1.4 to each other on Ring B.

In certain embodiments of Formulae (I)-(III), Ring B is

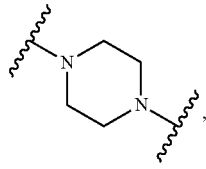 [SMILES: *N1CCN(*)CC1]

wherein each ring atom is optionally substituted. In certain embodiments, Ring B is

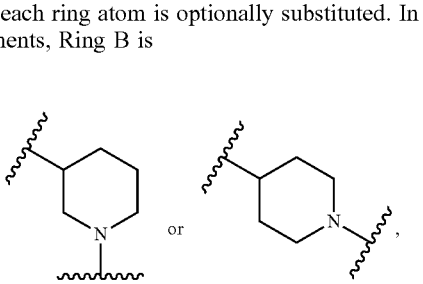

wherein each ring atom is optionally substituted. In certain embodiments, Ring B is wherein each ring atom is optionally substituted. In certain embodiments, Ring B is wherein each ring atom is optionally substituted, and L² and R² may attach to Ring B at either indicated position. In certain embodiments, Ring B is

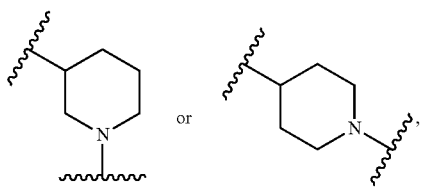 [SMILES: *C1CCCN(*)C1 ; *C1CCN(*)CC1] or , wherein each ring atom is optionally substituted, and L² and R² may attach to Ring B at either indicated position. In certain embodiments, Ring B is

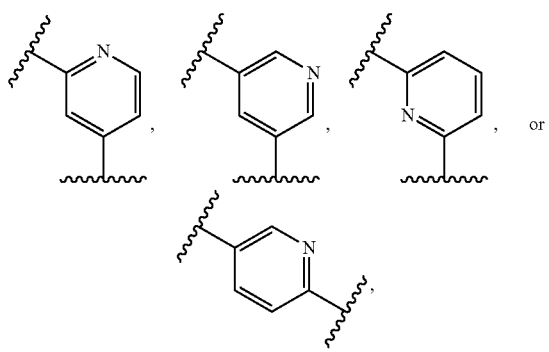

wherein each ring atom is optionally substituted, and L² and R² may attach to Ring B at either indicated position. In certain embodiments, Ring B is

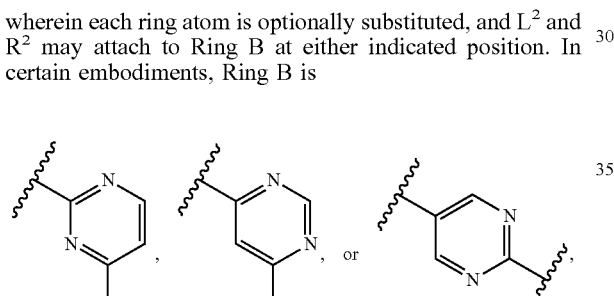

wherein each ring atom is optionally substituted, and L² and R² may attach to Ring B at either indicated position.

In certain embodiments of Formulae (I)-(III), Ring B is

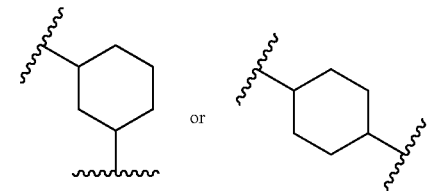 [SMILES: *C1CCCC(*)C1 ; *C1CCC(*)CC1] or ,

In certain embodiments, Ring B is

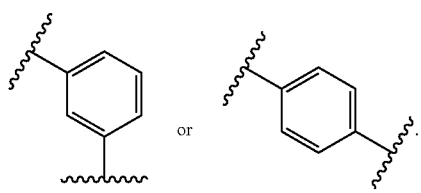 [SMILES: *c1cccc(*)c1 ; *c1ccc(*)cc1] or .

In certain embodiments, Ring B is

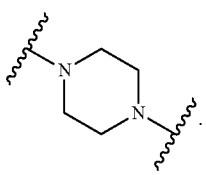 [SMILES: *N1CCN(*)CC1]

In certain embodiments, Ring B is

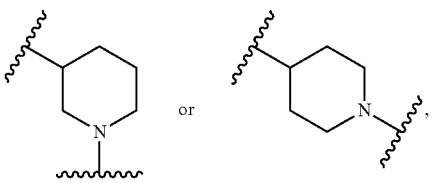 [SMILES: *C1CCCN(*)C1 ; *C1CCN(*)CC1] or ,

L² and R² may attach to Ring B at either indicated position. In certain embodiments, Ring B is

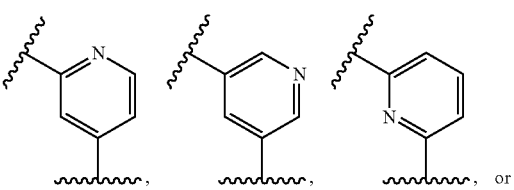

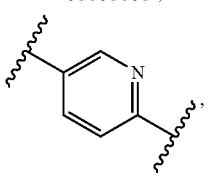 , wherein L² and R² may attach to Ring B at either indicated position. In certain embodiments, Ring B is

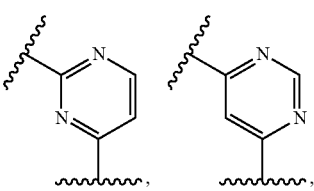 ,

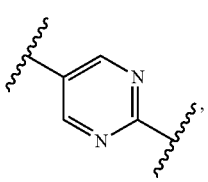 , wherein L² and R² may attach to Ring B at either indicated position.

Compounds of Formulae (I)-(III) include R² attached to Ring B. In certain embodiments, Ring B is absent, such that R² is directly attached to linker L². In certain embodiments, Ring B is absent and $L^2$ is a bond, such that $R^2$ is directly attached to Ring A. In certain embodiments, $R^2$ comprises an electrophilic moiety. In certain embodiments, $R^2$ comprises a Michael acceptor moiety. The electrophilic moiety (e.g., Michael acceptor moiety) may react with a cysteine residue of a kinase (e.g., CDK (e.g., CDK7)) to allow for covalent attachment of the compound to the kinase. In certain embodiments, the electrophilic moiety (e.g., Michael acceptor moiety) may react with a cysteine residue of a kinase (e.g., CDK (e.g., CDK7)). In certain embodiments, the electrophilic moiety (e.g., Michael acceptor moiety) may react with the Cys312 residue of CDK7. In certain embodiments, the covalent attachment is irreversible. In certain embodiments, the covalent attachment is reversible.

As generally defined herein in Formulae (I)-(III), $R^2$ may be any one of Formulae (i-1)-(i-41). In certain embodiments, $R^2$ is of Formula (i-1):

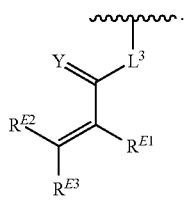

(i-1)

In certain embodiments, $R^2$ is of Formula (i-2):

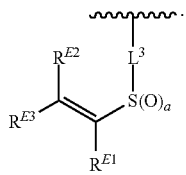

(i-2)

In certain embodiments, $R^2$ is of Formula (i-3):

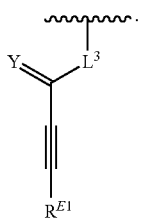

(i-3)

In certain embodiments, $R^2$ is of Formula (i-4):

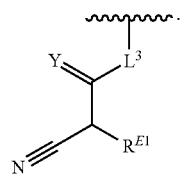

(i-4)

In certain embodiments, $R^2$ is of Formula (i-5):

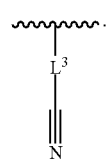

(i-5)

In certain embodiments, $R^2$ is of Formula (i-6):

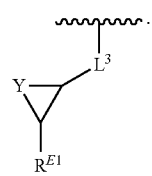

(i-6)

In certain embodiments, $R^2$ is of Formula (i-7):

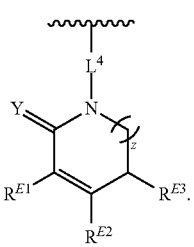

(i-7)

In certain embodiments, $R^2$ is of Formula (i-8):

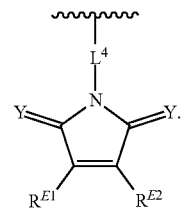

(i-8)

In certain embodiments, $R^2$ is of Formula (i-9):

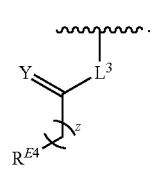

(i-9)

In certain embodiments, $R^2$ is of Formula (i-10):

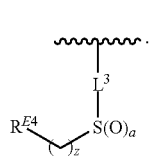
(i-10)

In certain embodiments, $R^2$ is of Formula (i-11):

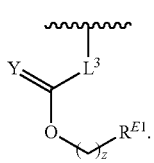
(i-11)

In certain embodiments, $R^2$ is of Formula (i-12):

(i-12)

In certain embodiments, $R^2$ is of Formula (i-13):

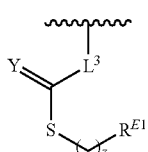
(i-13)

In certain embodiments, $R^2$ is of Formula (i-14):

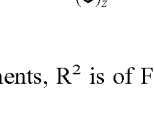
(i-14)

In certain embodiments, $R^2$ is of Formula (i-15):

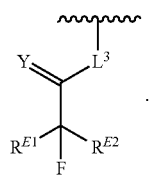
(i-15)

In certain embodiments, $R^2$ is of Formula (i-16):

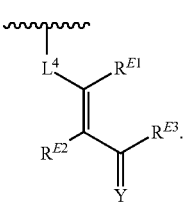
(i-16)

In certain embodiments, $R^2$ is of Formula (i-17):

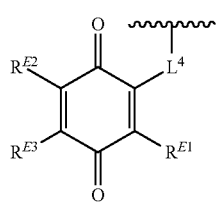
(i-17)

In certain embodiments, $R^2$ is of Formula (i-18):

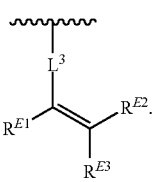
(i-18)

In certain embodiments, $R^2$ is of Formula (i-19):

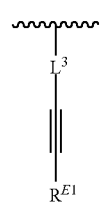
(i-19)

In certain embodiments, $R^2$ is of Formula (i-20):

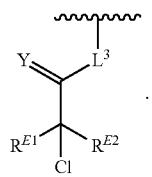
(i-20)

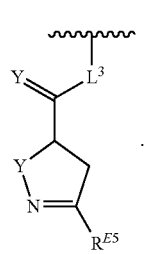

In certain embodiments, $R^2$ is of Formula (i-21):

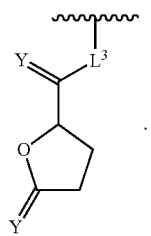
(i-21)

In certain embodiments, $R^2$ is of Formula (i-22):

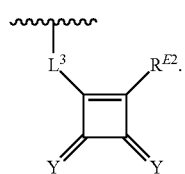
(i-22)

In certain embodiments, $R^2$ is of Formula (i-23):

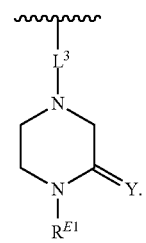
(i-23)

In certain embodiments, $R^2$ is of Formula (i-24):

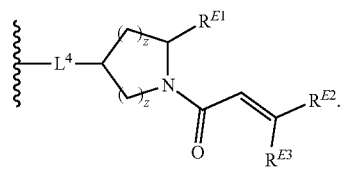
(i-24)

In certain embodiments, $R^2$ is of Formula (i-25):

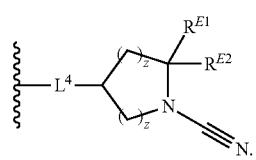
(i-25)

In certain embodiments, $R^2$ is of Formula (i-26):

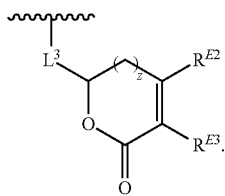
(i-26)

In certain embodiments, $R^2$ is of Formula (i-27):

(i-27)

In certain embodiments, $R^2$ is of Formula (i-28):

(i-28)

In certain embodiments, $R^2$ is of Formula (i-29):

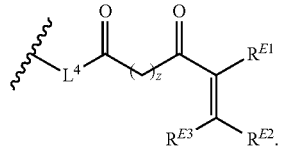
(i-29)

In certain embodiments, $R^2$ is of Formula (i-30):

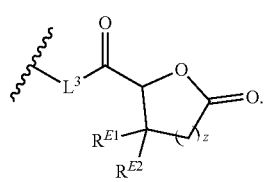
(i-30)

In certain embodiments, $R^2$ is of Formula (i-31):

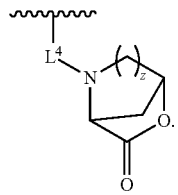

(i-31)

In certain embodiments, $R^2$ is of Formula (i-32):

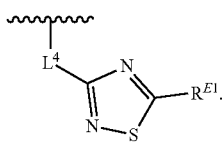

(i-32)

In certain embodiments, $R^2$ is of Formula (i-33):

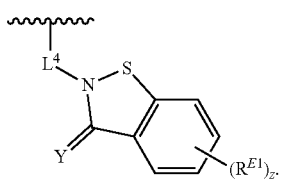

(i-33)

In certain embodiments, $R^2$ is of Formula (i-34):

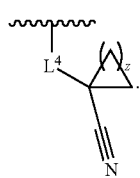

(i-34)

In certain embodiments, $R^2$ is of Formula (i-35):

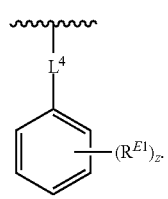

(i-35)

In certain embodiments, $R^2$ is of Formula (i-36):

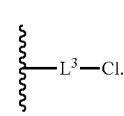

(i-36)

In certain embodiments, $R^2$ is of Formula (i-37):

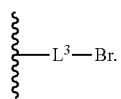

(i-37)

In certain embodiments, $R^2$ is of Formula (i-38):

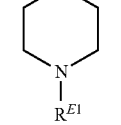

(i-38)

In certain embodiments, $R^2$ is of Formula (i-39):

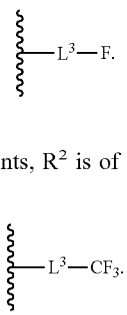

(i-39)

In certain embodiments, $R^2$ is of Formula (i-40):

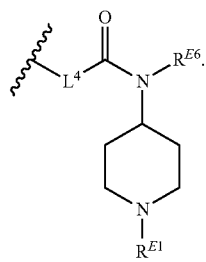

(i-40)

In certain embodiments, $R^2$ is of Formula (i-41):

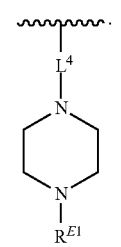

(i-41)

In certain embodiments, $R^2$ is of Formula (i-1a):

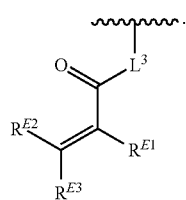

(i-1a)

In certain embodiments, $R^2$ is of Formula (i-1b):

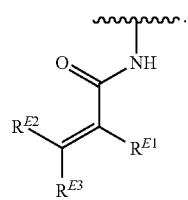
(i-1b)

In certain embodiments, $R^2$ is of Formula (i-1c):

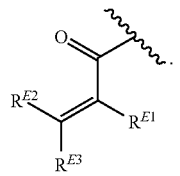
(i-1c)

In certain embodiments, $R^2$ is of Formula (i-1d):

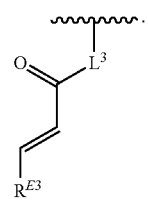
(i-1d)

In certain embodiments, $R^2$ is of Formula (i-1e):

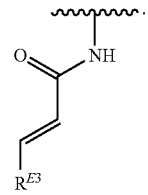
(i-1e)

In certain embodiments, $R^2$ is of Formula (i-1f):

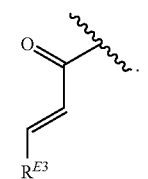
(i-1f)

In certain embodiments, $R^2$ is of Formula (i-1g):

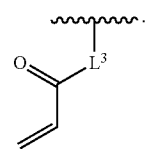
(i-1g)

In certain embodiments, $R^2$ is

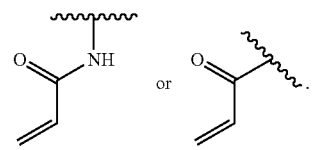

In certain embodiments, $R^2$ is of Formula (i-1h):

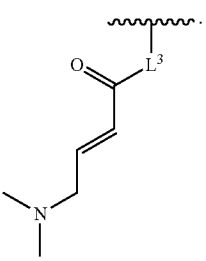
(i-1h)

In certain embodiments, $R^2$ is

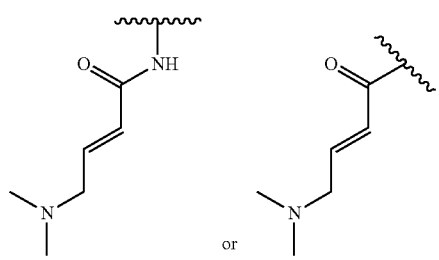

In certain embodiments, $R^2$ is of Formula (i-1a):

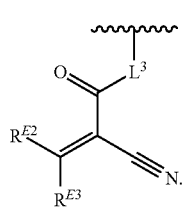
(i-1a)

In certain embodiments, R² is of Formula (i-1b):

(i-1b)

In certain embodiments, R² is of Formula (i-1c):

(i-1c)

In certain embodiments, R² is of Formula (i-18a):

(i-18a)

In certain embodiments, R² is of Formula (i-18b):

(i-18b)

In certain embodiments, R² is of Formula (i-18c):

(i-18c)

In certain embodiments, R² is of Formula (i-15a):

(i-15a)

In certain embodiments, R² is of Formula (i-15b):

(i-15b)

In certain embodiments, R² is of Formula (i-15c):

(i-15c)

R² may contain linker L³ or L⁴. In certain embodiments, L³ is a bond. L³ is an optionally substituted $C_{1-4}$ hydrocarbon chain. In certain embodiments, L³ is an optionally substituted $C_{1-4}$ hydrocarbon chain, wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—. In certain embodiments, L³ is an optionally substituted $C_{1-4}$ hydrocarbon chain, wherein one carbon unit of the hydrocarbon chain is replaced with —NR$^{L3a}$— (e.g., —NH—). In certain embodiments, L³ is of the formula: —(CH$_2$)$_{1-4}$—NR$^{L3a}$— (e.g., —(CH$_2$)$_{1-4}$—NH—) or —NR$^{L3a}$—CH$_2$)$_{1-4}$— (e.g., —NH—CH$_2$)$_{1-4}$—). In certain embodiments, L³ is —NR$^{L3a}$—. In certain embodiments, L³ is —NR$^{L3a}$(C=O)—. In certain embodiments, L³ is —(C=O)NR$^{L3a}$—. In certain embodiments, L³ is —NH—. In certain embodiments, L³ is —(C=O)—. In certain embodiments, L³ is —NH(C=O)—. In certain embodiments, L³ is —(C=O)NH—. In certain embodiments, L³ is —O—. In certain embodiments, L³ is —S—. In certain embodiments, L⁴ is a bond. In certain embodiments, L⁴ is an optionally substituted $C_{1-4}$ hydrocarbon chain.

Linker L³ may contain groups R$^{L3a}$ or R$^{L3b}$. In certain embodiments, R$^{L3a}$ is hydrogen. In certain embodiments, at least one instance of $R^{L3b}$ is hydrogen. In certain embodiments, each instance of $R^{L3b}$ is hydrogen. In certain embodiments, at least one instance of $R^{L3b}$ is —Cl, —Br, or —I. In certain embodiments, each instance of $R^{L3b}$ is —Cl, —Br, or —I. In certain embodiments, at least one instance of $R^{L3b}$ is —F. In certain embodiments, each instance of $R^{L3b}$ is —F. In certain embodiments, at least one instance of $R^{L3b}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, two $R^{EM}$ groups are joined to form an optionally substituted carbocyclic or optionally substituted heterocyclic ring.

$R^2$ may contain groups $R^{E1}$, $R^{E2}$, and/or $R^{E3}$. In certain embodiments, $R^{E1}$ is hydrogen. In certain embodiments, $R^{E2}$ is hydrogen. In certain embodiments, $R^{E3}$ is hydrogen. In certain embodiments, $R^{E1}$ is —Cl, —Br, or —I. In certain embodiments, $R^{E2}$ is —Cl, —Br, or —I. In certain embodiments, $R^{E3}$ is —Cl, —Br, or —I. In certain embodiments, $R^{E1}$ is —F. In certain embodiments, $R^{E2}$ is —F. In certain embodiments, $R^{E3}$ is —F. In certain embodiments, $R^{E1}$ is optionally substituted alkyl (e.g., substituted or unsubstituted $C_{1-6}$ alkyl). In certain embodiments, $R^{E2}$ is optionally substituted alkyl (e.g., substituted or unsubstituted $C_{1-6}$ alkyl). In certain embodiments, $R^{E3}$ is optionally substituted alkyl (e.g., substituted or unsubstituted $C_{1-6}$ alkyl). In certain embodiments, $R^{E1}$ is optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$. In certain embodiments, $R^{E2}$ is optionally substituted alkenyl, optionally substituted alkynyl, optionally substituted carbocyclyl, optionally substituted heterocyclyl, optionally substituted aryl, optionally substituted (heteroaryl, —CN, —CH$_2$OR$^{EE}$, —CH$_2$N(R$^{EE}$)$_2$—, —CH$_2$SR$^{EE}$, —OR$^{EE}$, —N(R$^{EE}$)$_2$, —Si(R$^{EE}$)$_3$, or —SR$^{EE}$. In certain embodiments, $R^{E3}$ is optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$. In certain embodiments, $R^{E1}$ is —N(R$^{EE}$)$_2$. In certain embodiments, $R^{E2}$ is —N(R$^{EE}$)$_2$. In certain embodiments, $R^{E3}$ is —N(R$^{EE}$)$_2$. In certain embodiments, $R^{E1}$ is —N(CH$_3$)$_2$. In certain embodiments, $R^{E2}$ is —N(CH$_3$)$_2$. In certain embodiments, $R^{E3}$ is —N(CH$_3$)$_2$. In certain embodiments, $R^{E1}$ is —CH$_2$N(R$^{EE}$)$_2$. In certain embodiments, $R^{E2}$ is —CH$_2$N(R$^{EE}$) In certain embodiments, $R^{E3}$ is —CH$_2$N(R$^{EE}$)$_2$. In certain embodiments, $R^{E1}$ is —CH$_2$N(CH$_3$)$_2$. In certain embodiments, $R^{E2}$ is —CH$_2$N(CH$_3$)$_2$. In certain embodiments, $R^{E3}$ is —CH$_2$N(CH$_3$)$_2$. In certain embodiments, $R^{E1}$ is —CN. In certain embodiments, $R^{E2}$ is —CN. In certain embodiments, $R^{E3}$ is —CN.

In certain embodiments, $R^{E1}$ and $R^{E3}$ are joined to form an optionally substituted carbocyclic ring. In certain embodiments, $R^{E1}$ and $R^{E3}$ are joined to form an optionally substituted heterocyclic ring. In certain embodiments, $R^{E2}$ and $R^{E3}$ are joined to form an optionally substituted carbocyclic ring. In certain embodiments, $R^{E2}$ and $R^{E3}$ are joined to form an optionally substituted heterocyclic ring. In certain embodiments, $R^{E1}$ and $R^{E2}$ are joined to form an optionally substituted carbocyclic ring. In certain embodiments, $R^{E1}$ and $R^{E2}$ are joined to form an optionally substituted heterocyclic ring.

$R^2$ may contain group $R^{E4}$, where $R^{E4}$ is a leaving group. In certain embodiments, $R^{E4}$ is —Cl, —Br, or —I. In certain embodiments, $R^{E4}$ is —F. In certain embodiments, $R^{E4}$ is —OS(=O)R$^{E4a}$ or —OS(=O)$_2$R$^{E4a}$, wherein $R^{E4a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, $R^{E4}$ is —OR$^{E4a}$. In certain embodiments, $R^{E4}$ is —OMs, —OTf, —OTs, —OBs, or 2-nitrobenzenesulfonyloxy. In certain embodiments, $R^{E4}$ is —OR$^{E4a}$. In certain embodiments, $R^{E4}$ is —OMe, —OCF$_3$, or —OPh. In certain embodiments, $R^{E4}$ is —OC(=O)R$^{E4a}$. In certain embodiments, $R^{E4}$ is —OC(=O)Me, —OC(=O)CF$_3$, —OC(=O)Ph, or —OC(=O)Cl. In certain embodiments, $R^{E4}$ is —OC(=O)OR$^{E4a}$. In certain embodiments, $R^{E4}$ is —OC(=O)OMe or —OC(=O)O(t-Bu).

$R^2$ may contain group $R^{E5}$, where $R^{E5}$ is a halogen. In certain embodiments, $R^{E5}$ is —Cl, —Br, or —I. In certain embodiments, $R^{E5}$ is —F.

$R^2$ may contain group $R^{E6}$. In certain embodiments, $R^{E6}$ is hydrogen. In certain embodiments, $R^{E6}$ is substituted or unsubstituted $C_1$-$C_6$ alkyl. In certain embodiments, $R^{E6}$ is a nitrogen protecting group.

In certain embodiments, a is 1. In certain embodiments, a is 2.

In certain embodiments, z is 0. In certain embodiments, z is 1. In certain embodiments, z is 2. In certain embodiments, z is 3, 4, 5, or 6.

$R^2$ may contain group Y. In certain embodiments, Y is O. In certain embodiments, Y is S. In certain embodiments, Y is NR$^{E7}$. In certain embodiments, Y is NH.

Compounds of Formula (I) may exist as tautomers or mixtures thereof of Formulae (I-a) and (I-b):

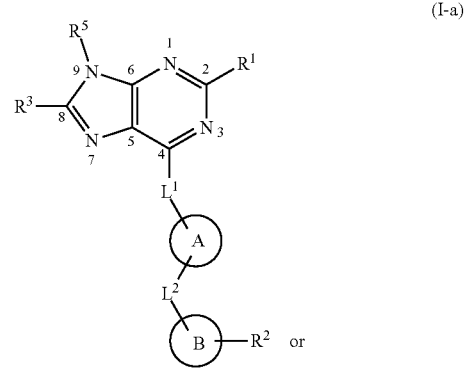

(I-a)

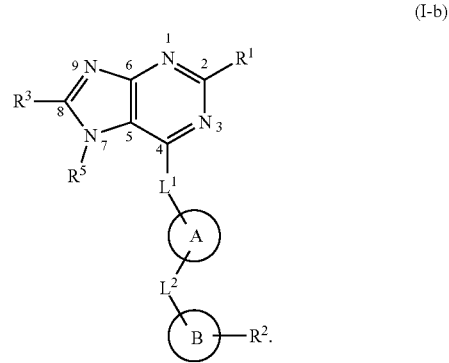

(I-b)

In each tautomer, $R^5$ is attached to different imidazole nitrogens in compounds of each formula. In certain embodiments, $R^5$ is attached to the nitrogen at the position labeled 9, as in Formula (I-a). In certain embodiments, $R^5$ is attached to the nitrogen at the position labeled 7, as in Formula (I-b). In certain embodiments, compounds of Formula (I) may exist as a mixture of compounds of Formulae (I-a) and (I-b), in which case $R^5$ is attached to the nitrogen at the position labeled 9 for components of the mixture corresponding to Formula (I-a), and $R^5$ is attached to the nitrogen at the position labeled 7 for components of the mixture corresponding to Formula (I-b).

In certain embodiments, a compound of Formula (I) is of Formula (I-1):

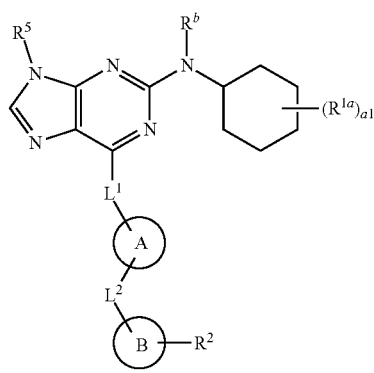

(I-1)

or a pharmaceutically acceptable salt, solvate, hydrate, polymorph, co-crystal, tautomer, stereoisomer, isotopically labeled derivative, or prodrug thereof, wherein $L^1$, $L^2$, Ring A, Ring B, $R^2$, $R^5$, $R^b$, $R^{1a}$, and a1 are as defined herein.

In certain embodiments, a compound of Formula (I) is of Formula (I-1-a):

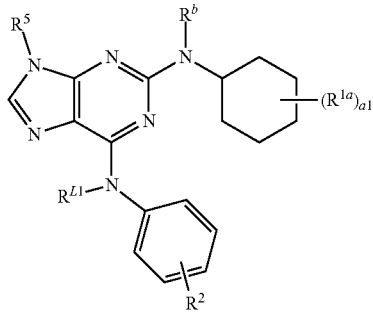

(I-1-a)

or a pharmaceutically acceptable salt, solvate, hydrate, polymorph, co-crystal, tautomer, stereoisomer, isotopically labeled derivative, or prodrug thereof, wherein $R^2$, $R^5$, $R^{L1}$, $R^b$, $R^{1a}$, and a1 are as defined herein.

In certain embodiments, a compound of Formula (I) is of Formula (I-1-a-i):

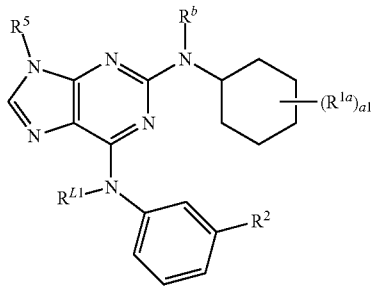

(I-1-a-i)

or a pharmaceutically acceptable salt, solvate, hydrate, polymorph, co-crystal, tautomer, stereoisomer, isotopically labeled derivative, or prodrug thereof, wherein $R^2$, $R^5$, $R^{L1}$, $R^b$, $R^{1a}$, and a1 are as defined herein.

In certain embodiments, a compound of Formula (I) is of Formula (I-1-b):

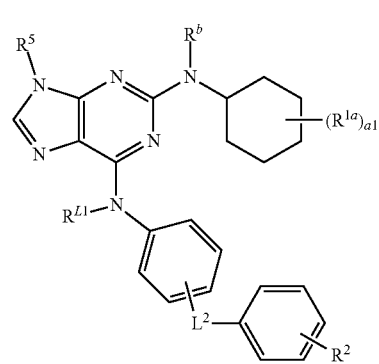

(I-1-b)

or a pharmaceutically acceptable salt, solvate, hydrate, polymorph, co-crystal, tautomer, stereoisomer, isotopically labeled derivative, or prodrug thereof, wherein $R^2$, $L^2$, $R^5$, $R^{L1}$, $R^b$, $R^{1a}$, and a1 are as defined herein.

In certain embodiments, a compound of Formula (I) is of Formula (I-1-b-i):

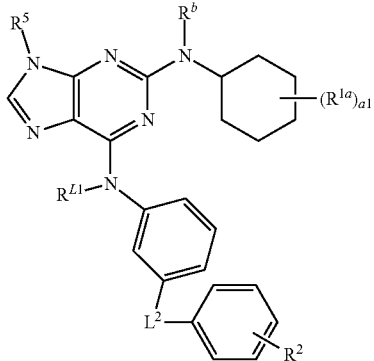

(I-1-b-i)

or a pharmaceutically acceptable salt, solvate, hydrate, polymorph, co-crystal, tautomer, stereoisomer, isotopically labeled derivative, or prodrug thereof, wherein $R^2$, $L^2$, $R^5$, $R^{L1}$, $R^b$, $R^{1a}$, and a1 are as defined herein.

In certain embodiments, a compound of Formula (I) is of Formula (I-1-b-ii):

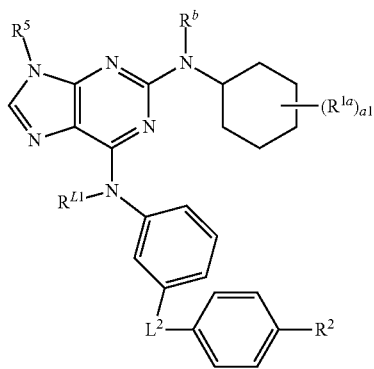

(I-1-b-ii)

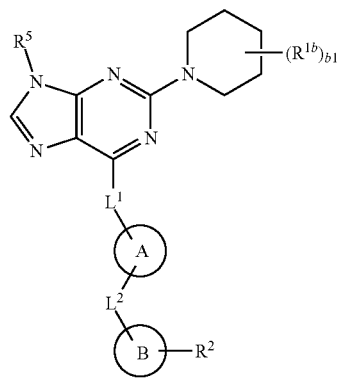
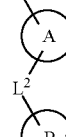

(I-2)

or a pharmaceutically acceptable salt, solvate, hydrate, polymorph, co-crystal, tautomer, stereoisomer, isotopically labeled derivative, or prodrug thereof, wherein $R^2$, $L^2$, $R^5$, $R^{L1}$, $R^b$, $R^{1a}$, and a1 are as defined herein.

In certain embodiments, a compound of Formula (I) is of Formula (I-1-c):

or a pharmaceutically acceptable salt, solvate, hydrate, polymorph, co-crystal, tautomer, stereoisomer, isotopically labeled derivative, or prodrug thereof, wherein $R^2$, $L^2$, $L^1$, Ring A, Ring B, $R^5$, $R^{1b}$, and b1 are as defined herein In certain embodiments, a compound of Formula (I) is of Formula (I-2-a):

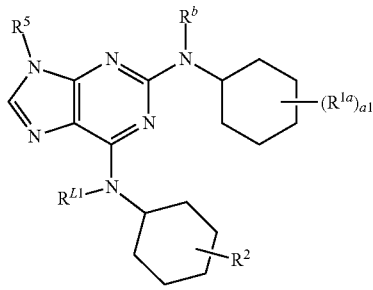

(I-1-c)

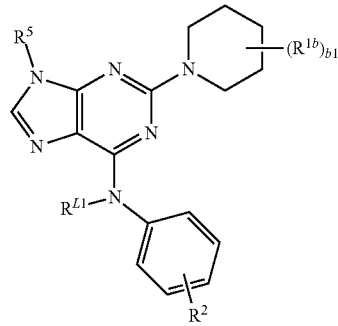

(I-2-a)

or a pharmaceutically acceptable salt, solvate, hydrate, polymorph, co-crystal, tautomer, stereoisomer, isotopically labeled derivative, or prodrug thereof, wherein $R^2$, $R^5$, $R^{L1}$, $R^b$, $R^{1a}$, and a1 are as defined herein.

In certain embodiments, a compound of Formula (I) is of Formula (I-1-c-i):

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^5$, $R^{1b}$, and b1 are as defined herein.

In certain embodiments, a compound of Formula (I) is of Formula (I-2-a-i):

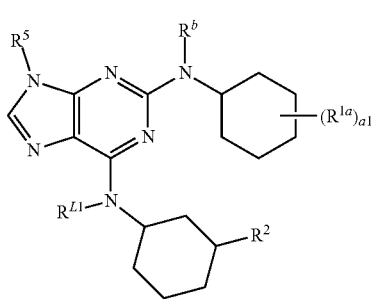

(I-1-c-i)

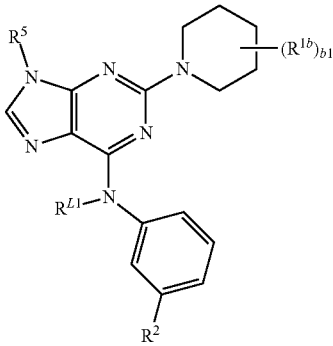

(I-2-a-i)

or a pharmaceutically acceptable salt, solvate, hydrate, polymorph, co-crystal, tautomer, stereoisomer, isotopically labeled derivative, or prodrug thereof, wherein $R^2$, $R^5$, $R^{L1}$, $R^b$, $R^{1a}$, and a1 are as defined herein.

In certain embodiments, a compound of Formula (I) is of Formula (I-2):

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^5$, $R^{1b}$, and b1 are as defined herein.

In certain embodiments, a compound of Formula (I) is of Formula (I-2-b):

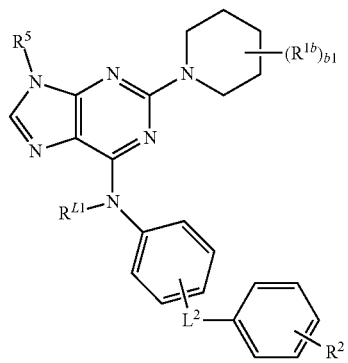

(I-2-b)

or a pharmaceutically acceptable salt, solvate, hydrate, polymorph, co-crystal, tautomer, stereoisomer, isotopically labeled derivative, or prodrug thereof, wherein $R^2$, $L^2$, $R^{L1}$, $R^5$, $R^{1b}$, and b1 are as defined herein.

In certain embodiments, a compound of Formula (I) is of Formula (I-2-b-i):

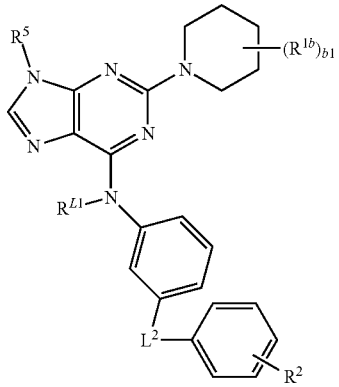

(I-2-b-i)

or a pharmaceutically acceptable salt, solvate, hydrate, polymorph, co-crystal, tautomer, stereoisomer, isotopically labeled derivative, or prodrug thereof, wherein $R^2$, $L^2$, $R^{L1}$, $R^5$, $R^{1b}$, and b1 are as defined herein.

In certain embodiments, a compound of Formula (I) is of Formula (I-2-b-ii):

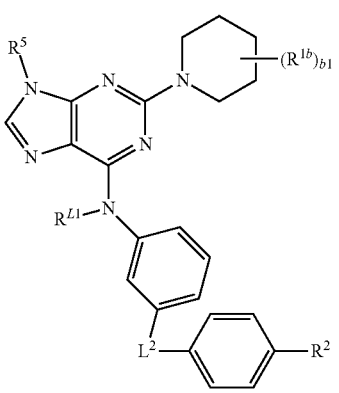

(I-2-b-ii)

or a pharmaceutically acceptable salt, solvate, hydrate, polymorph, co-crystal, tautomer, stereoisomer, isotopically labeled derivative, or prodrug thereof, wherein $R^2$, $L^2$, $R^{L1}$, $R^5$, $R^{1b}$, and b1 are as defined herein.

In certain embodiments, a compound of Formula (I) is of Formula (I-3):

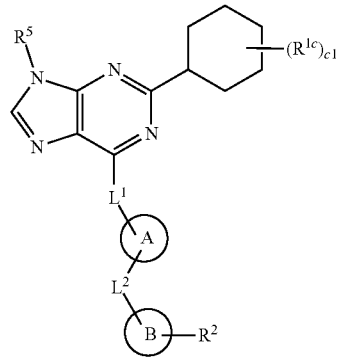

(I-3)

or a pharmaceutically acceptable salt, solvate, hydrate, polymorph, co-crystal, tautomer, stereoisomer, isotopically labeled derivative, or prodrug thereof, wherein $R^2$, $L^2$, $L^1$, Ring A, Ring B, $R^5$, $R^{1c}$, and c1 are as defined herein.

In certain embodiments, a compound of Formula (I) is of Formula (I-3-a):

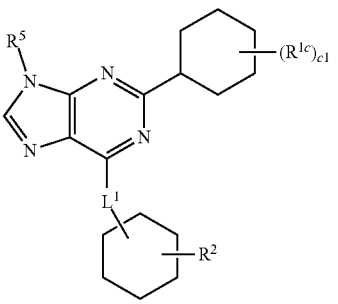

(I-3-a)

or a pharmaceutically acceptable salt, solvate, hydrate, polymorph, co-crystal, tautomer, stereoisomer, isotopically labeled derivative, or prodrug thereof, wherein $R^2$, $L^1$, $R^5$, $R^{1c}$, and c1 are as defined herein.

In certain embodiments, a compound of Formula (I) is of Formula (I-3-a-1):

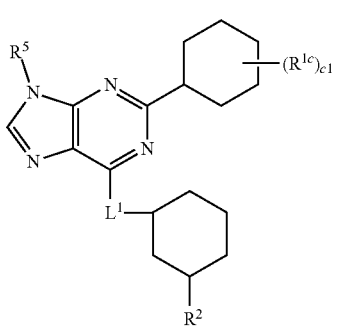

(I-3-a-1)

or a pharmaceutically acceptable salt, solvate, hydrate, polymorph, co-crystal, tautomer, stereoisomer, isotopically labeled derivative, or prodrug thereof, wherein $R^2$, $L^1$, $R^5$, $R^{1c}$, and c1 are as defined herein.

In certain embodiments, a compound of Formula (I) is of Formula (I-3-b):

(I-3-b)

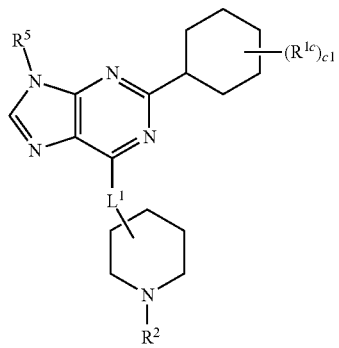

or a pharmaceutically acceptable salt, solvate, hydrate, polymorph, co-crystal, tautomer, stereoisomer, isotopically labeled derivative, or prodrug thereof, wherein $R^2$, $L^1$, $R^5$, $R^{1c}$, and c1 are as defined herein.

In certain embodiments, a compound of Formula (II) is of Formula (I-3-b-i):

(I-3-b-i)

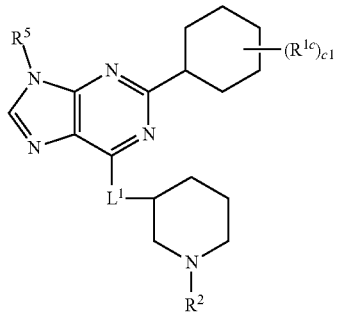

or a pharmaceutically acceptable salt, solvate, hydrate, polymorph, co-crystal, tautomer, stereoisomer, isotopically labeled derivative, or prodrug thereof, wherein $R^2$, $L^1$, $R^5$, $R^{1c}$, and c1 are as defined herein.

In certain embodiments, a compound of Formula (I) is one of the following formulae:

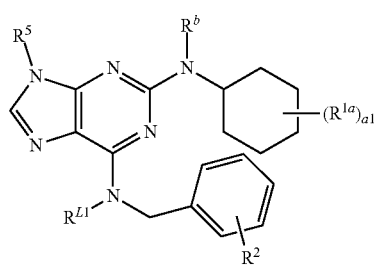

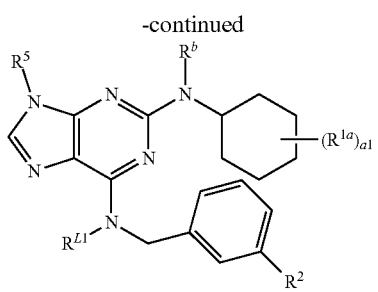

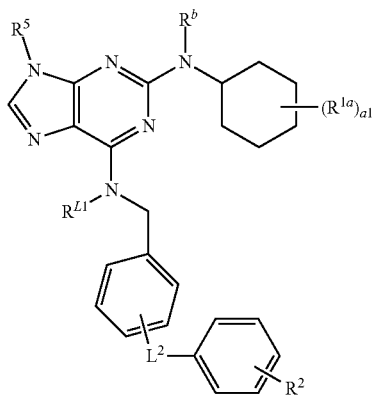

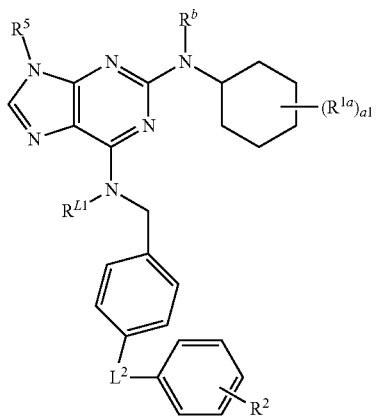

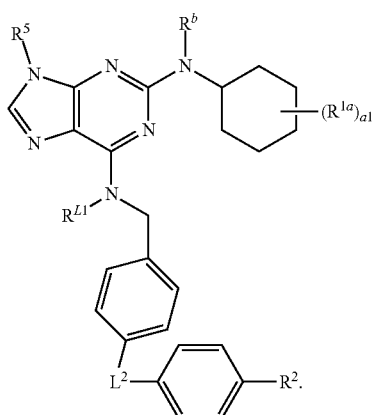

In certain embodiments, a compound of Formula (II) is of Formula (II-1):

(II-1)

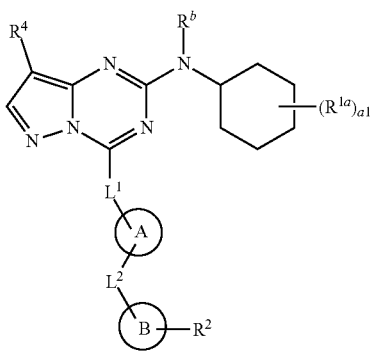

or a pharmaceutically acceptable salt, solvate, hydrate, polymorph, co-crystal, tautomer, stereoisomer, isotopically labeled derivative, or prodrug thereof, wherein $R^2$, $L^1$, $L^2$, Ring A, Ring B, $R^4$, $R^b$, $R^{1a}$, and a1 are as defined herein.

In certain embodiments, a compound of Formula (II) is of Formula (II-1-a):

(II-1-a)

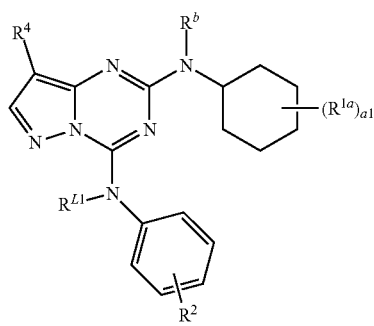

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^b$, $R^{1a}$, and a1 are as defined herein.

In certain embodiments, a compound of Formula (II) is of Formula (II-1-a-i):

(II-1-a-i)

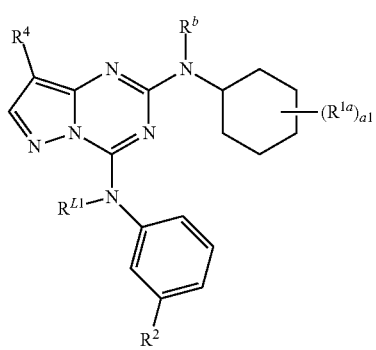

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^b$, $R^{1a}$, and a1 are as defined herein.

In certain embodiments, a compound of Formula (II) is of Formula (II-1-b):

(II-1-b)

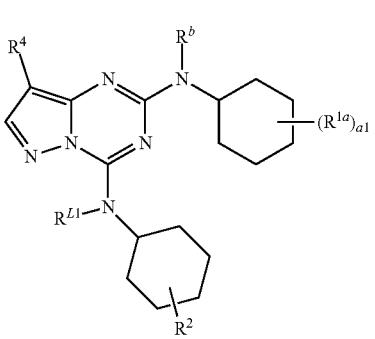

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^b$, $R^{1a}$, and a1 are as defined herein.

In certain embodiments, a compound of Formula (II) is of Formula (II-1-b-i):

(II-1-b-i)

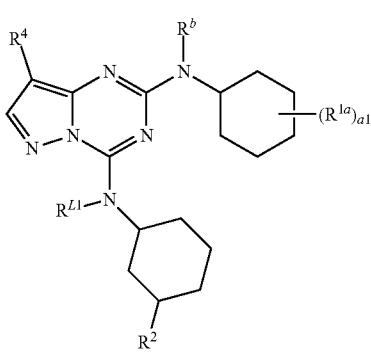

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^b$, $R^{1a}$, and a1 are as defined herein.

In certain embodiments, a compound of Formula (II) is of Formula (II-1-c):

(II-1-c)

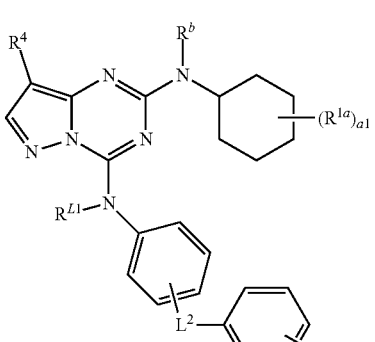

or a pharmaceutically acceptable salt, solvate, hydrate, polymorph, co-crystal, tautomer, stereoisomer, isotopically labeled derivative, or prodrug thereof, wherein $R^2$, $L^2$, $R^{L1}$, $R^4$, $R^b$, $R^{1a}$, and a1 are as defined herein.

In certain embodiments, a compound of Formula (II) is of Formula (II-2):

(II-2)

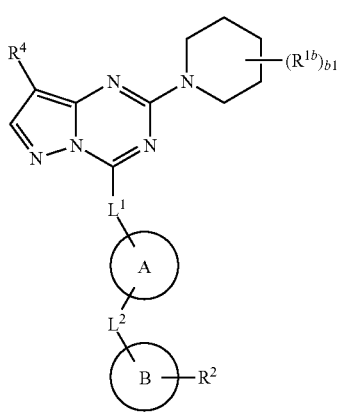

or a pharmaceutically acceptable salt, solvate, hydrate, polymorph, co-crystal, tautomer, stereoisomer, isotopically labeled derivative, or prodrug thereof, wherein $R^2$, $L^1$, $L^2$, Ring A, Ring B, $R^4$, $R^{1b}$, and b1 are as defined herein.

In certain embodiments, a compound of Formula (II) is of Formula (II-2-a):

(II-2-a)

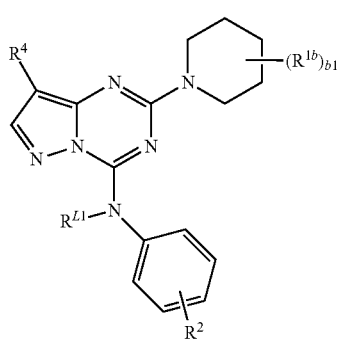

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^{1b}$, and b1 are as defined herein.

In certain embodiments, a compound of Formula (II) is of Formula (II-2-b):

(II-2-b)

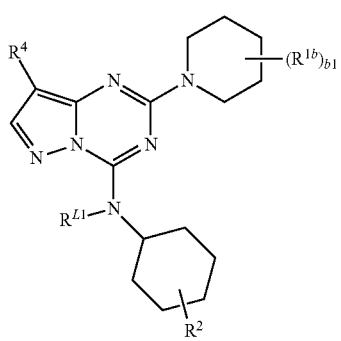

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^{1b}$, and b1 are as defined herein.

In certain embodiments, a compound of Formula (II) is of Formula (II-2-c):

(II-2-c)

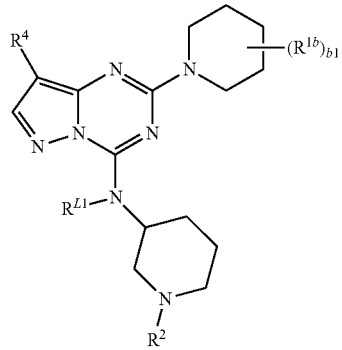

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^{1b}$, and b1 are as defined herein.

In certain embodiments, a compound of Formula (II) is of Formula (II-2-d):

(II-2-d)

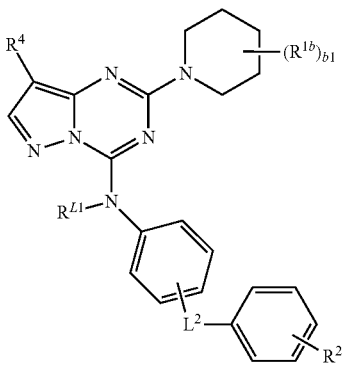

or a pharmaceutically acceptable salt, solvate, hydrate, polymorph, co-crystal, tautomer, stereoisomer, isotopically labeled derivative, or prodrug thereof, wherein $R^2$, $L^2$, $R^{L1}$, $R^4$, $R^{1b}$, and b1 are as defined herein.

In certain embodiments, a compound of Formula (II) is of Formula (II-2-d-i):

(II-2-d-i)

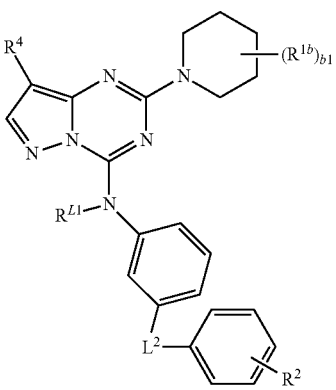

or a pharmaceutically acceptable salt, solvate, hydrate, polymorph, co-crystal, tautomer, stereoisomer, isotopically labeled derivative, or prodrug thereof, wherein $R^2$, $L^2$, $R^{L1}$, $R^4$, $R^{1b}$, and b1 are as defined herein.

In certain embodiments, a compound of Formula (II) is of Formula (II-2-d-ii):

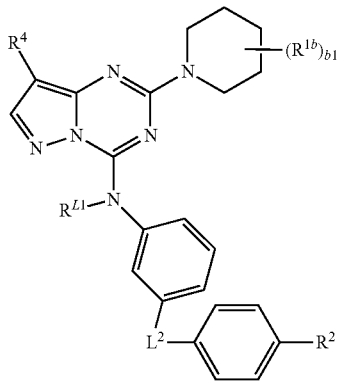

(II-2-d-ii)

or a pharmaceutically acceptable salt, solvate, hydrate, polymorph, co-crystal, tautomer, stereoisomer, isotopically labeled derivative, or prodrug thereof, wherein $R^2$, $L^2$, $R^{L1}$, $R^4$, $R^{1b}$, and b1 are as defined herein.

In certain embodiments, a compound of Formula (II) is of one of the following formulae:

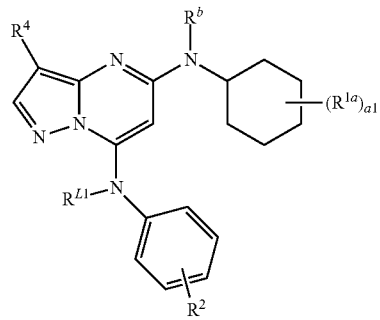

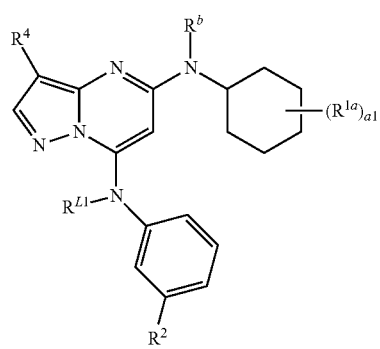

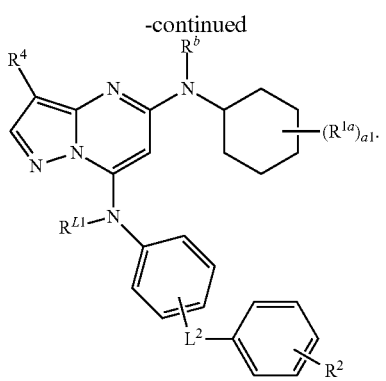

In certain embodiments, a compound of Formula (II) is of one of the following formulae:

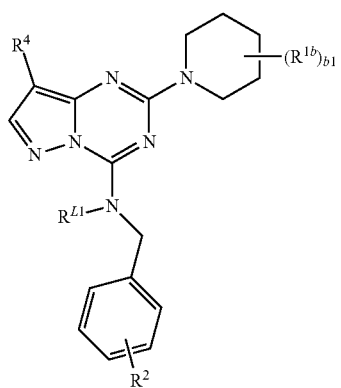

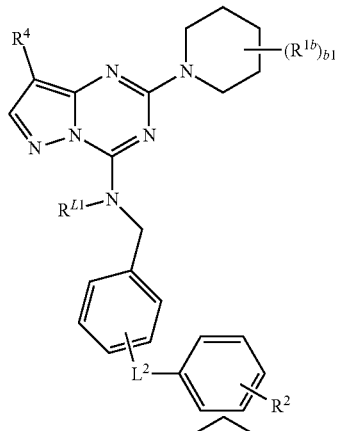

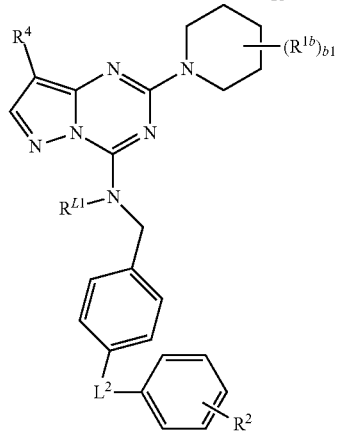

-continued
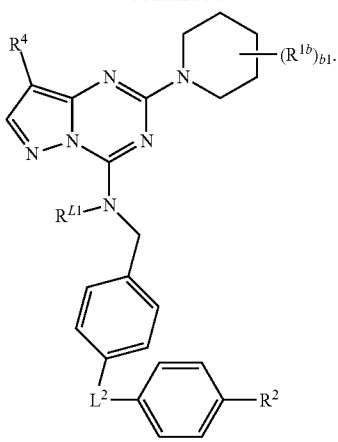
In certain embodiments, a compound of Formula (II) is of the formula:
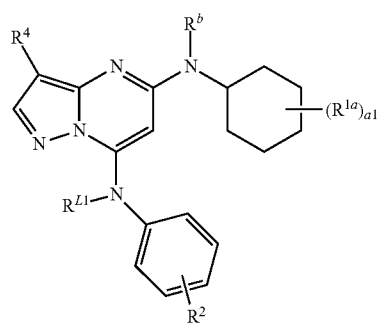
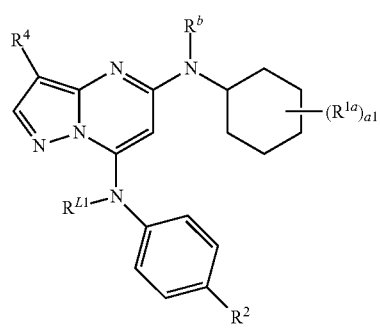
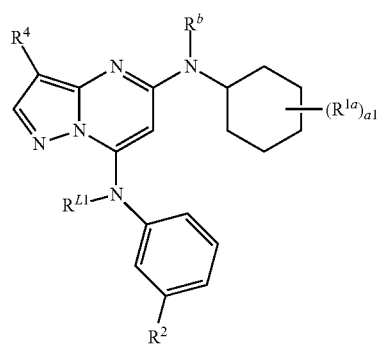
-continued
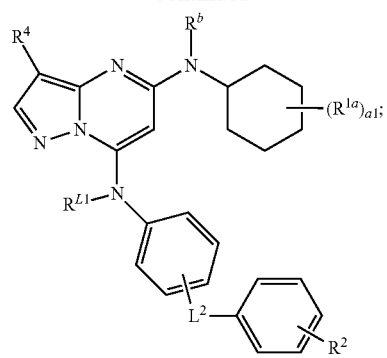
or a pharmaceutically acceptable salt, solvate, hydrate, polymorph, co-crystal, tautomer, stereoisomer, isotopically labeled derivative, or prodrug thereof.
In certain embodiments, a compound of Formula (II) is of the formula:
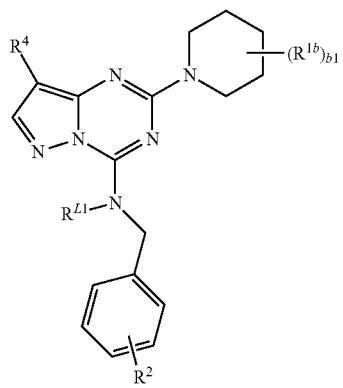
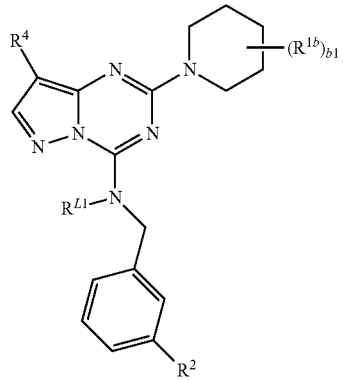
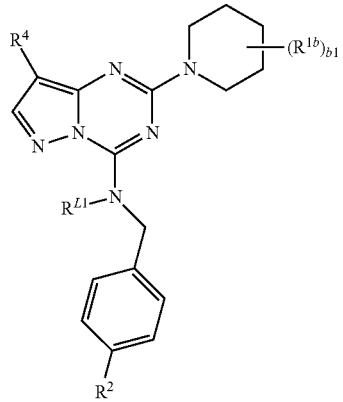

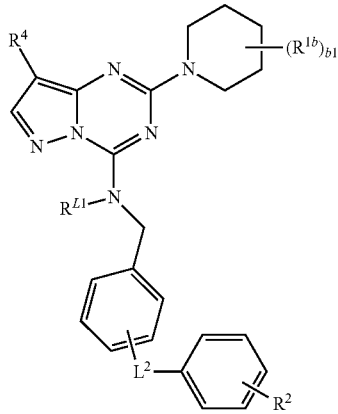

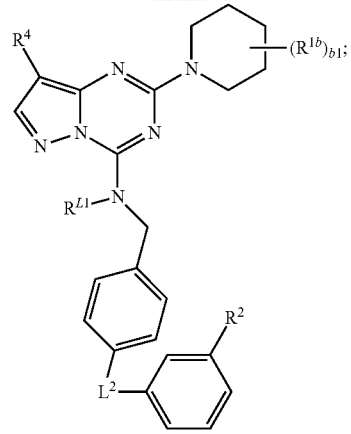

or a pharmaceutically acceptable salt, solvate, hydrate, polymorph, co-crystal, tautomer, stereoisomer, isotopically labeled derivative, or prodrug thereof.

In certain embodiments, a compound of Formula (III) is of Formula (III-1):

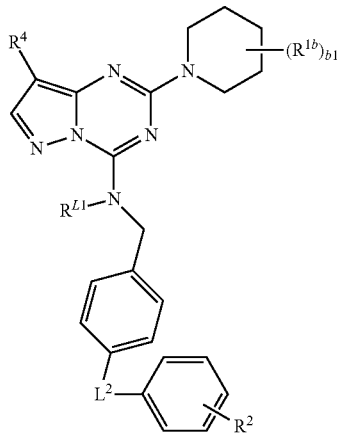

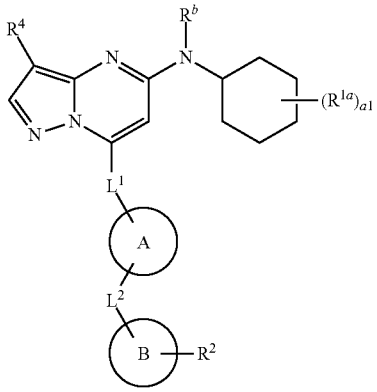

(III-1)

or a pharmaceutically acceptable salt, solvate, hydrate, polymorph, co-crystal, tautomer, stereoisomer, isotopically labeled derivative, or prodrug thereof, wherein $R^2$, $L^2$, $L^1$, Ring A, Ring B, $R^4$, $R^b$, $R^{1a}$, and a1 are as defined herein.

In certain embodiments, a compound of Formula (III) is of Formula (III-1-a):

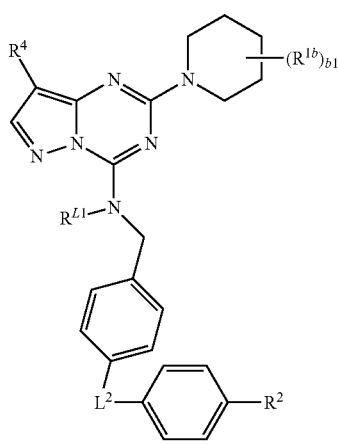

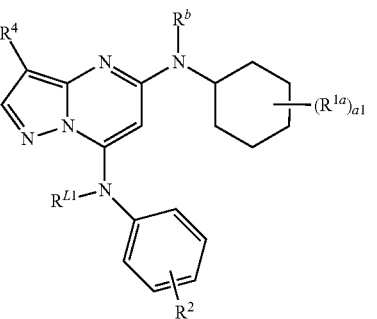

(III-1-a)

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^b$, $R^{1a}$, and a1 are as defined herein.

In certain embodiments, a compound of Formula (III) is of Formula (III-1-a-ii):

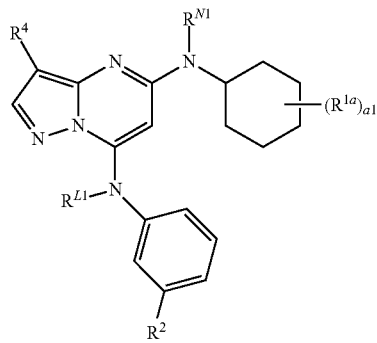

(III-1-a-ii)

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^b$, $R^{1a}$, and a1 are as defined herein.

In certain embodiments, a compound of Formula (III) is of Formula (III-1-b):

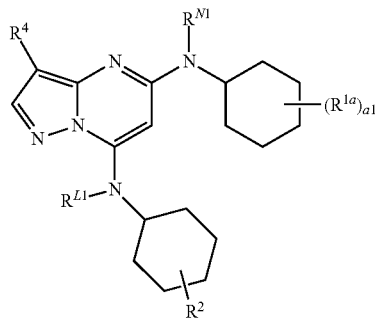

(III-1-b)

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^b$, $R^{1a}$, and a1 are as defined herein.

In certain embodiments, a compound of Formula (III) is of Formula (III-1-b-i):

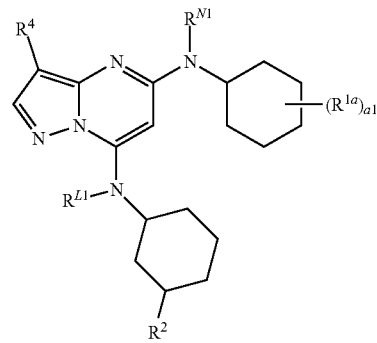

(III-1-b-i)

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^b$, $R^{1a}$, and a1 are as defined herein.

In certain embodiments, a compound of Formula (III) is of Formula (III-1-c):

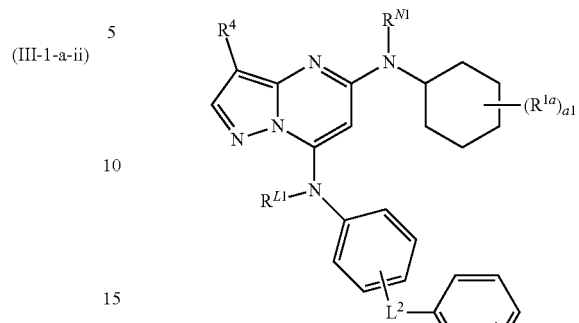

(III-1-c)

or a pharmaceutically acceptable salt, solvate, hydrate, polymorph, co-crystal, tautomer, stereoisomer, isotopically labeled derivative, or prodrug thereof, wherein $R^2$, $L^2$, $R^{L1}$, $R^4$, $R^b$, $R^{1a}$, and a1 are as defined herein.

In certain embodiments, a compound of Formula (III) is of Formula (III-1-c-i):

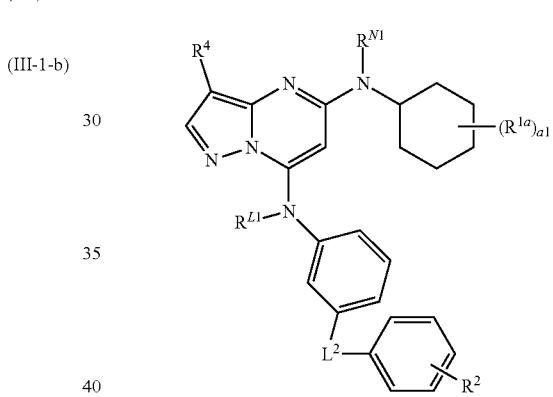

(III-1-c-i)

or a pharmaceutically acceptable salt, solvate, hydrate, polymorph, co-crystal, tautomer, stereoisomer, isotopically labeled derivative, or prodrug thereof, wherein $R^2$, $L^2$, $R^{L1}$, $R^4$, $R^b$, $R^{1a}$, and a1 are as defined herein.

In certain embodiments, a compound of Formula (III) is of Formula (III-1-c-ii):

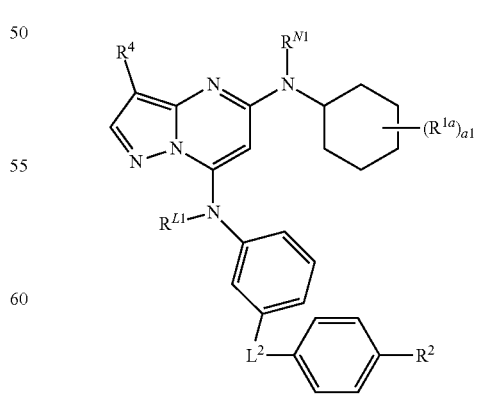

(III-1-c-ii)

or a pharmaceutically acceptable salt, solvate, hydrate, polymorph, co-crystal, tautomer, stereoisomer, isotopically labeled derivative, or prodrug thereof, wherein $R^2$, $L^2$, $R^{L1}$, $R^4$, $R^b$, $R^{1a}$, and a1 are as defined herein.

In certain embodiments, a compound of Formula (III) is of Formula (III-2):

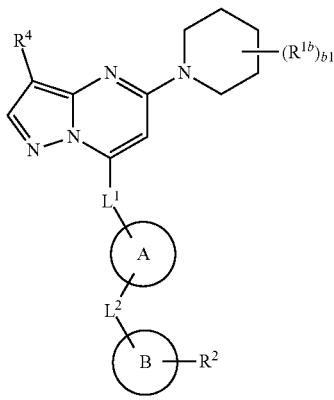

(III-2)

or a pharmaceutically acceptable salt, solvate, hydrate, polymorph, co-crystal, tautomer, stereoisomer, isotopically labeled derivative, or prodrug thereof, wherein $R^2$, $L^1$, $L^2$, Ring A, Ring B, $R^4$, $R^{1b}$, and b1 are as defined herein.

In certain embodiments, a compound of Formula (III) is of Formula (III-2-a):

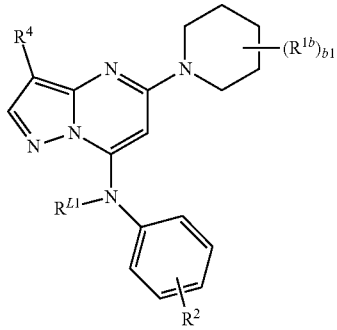

(III-2-a)

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^{1b}$, and b1 are as defined herein.

In certain embodiments, a compound of Formula (III) is of Formula (III-2-a-i):

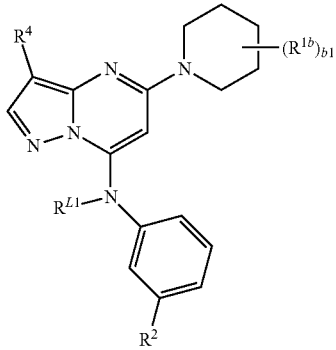

(III-2-a-i)

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^{1b}$, and b1 are as defined herein.

In certain embodiments, a compound of Formula (III) is of Formula (III-2-a-ii):

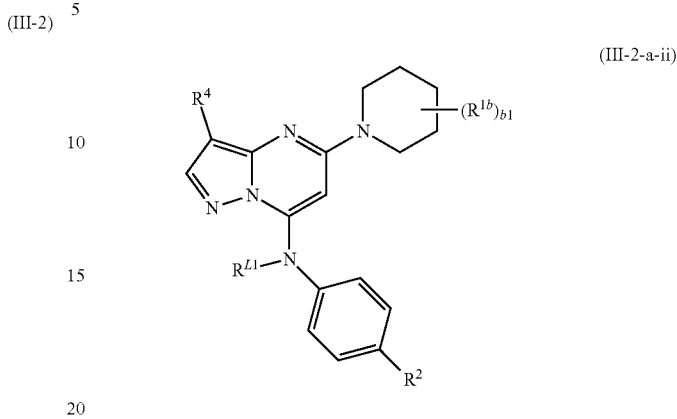

(III-2-a-ii)

or a pharmaceutically acceptable salt, solvate, hydrate, polymorph, co-crystal, tautomer, stereoisomer, isotopically labeled derivative, or prodrug thereof.

In certain embodiments, a compound of Formula (III) is of Formula (III-2-b):

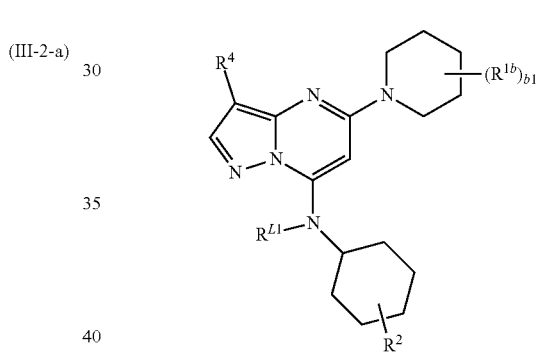

(III-2-b)

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^{1b}$, and b1 are as defined herein.

In certain embodiments, a compound of Formula (III) is of Formula (III-2-b-i):

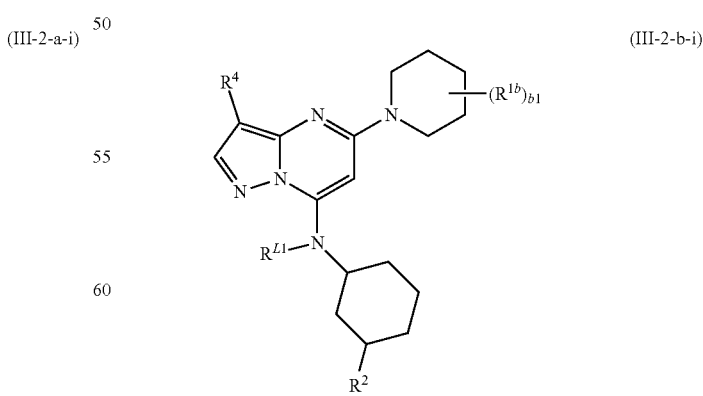

(III-2-b-i)

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^{1b}$, and b1 are as defined herein.

In certain embodiments, a compound of Formula (III) is of Formula (III-2-c):

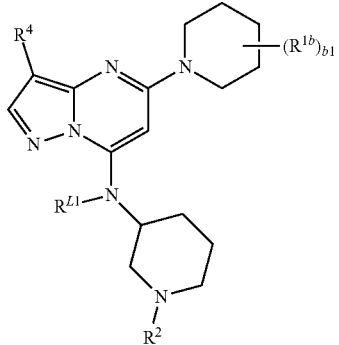

(III-2-c)

or a pharmaceutically acceptable salt, solvate, hydrate, polymorph, co-crystal, tautomer, stereoisomer, isotopically labeled derivative, or prodrug thereof, wherein $R^2$, $R^{L1}$, $R^4$, $R^{1b}$, and b1 are as defined herein.

In certain embodiments, a compound of Formula (III) is of Formula (III-2-d):

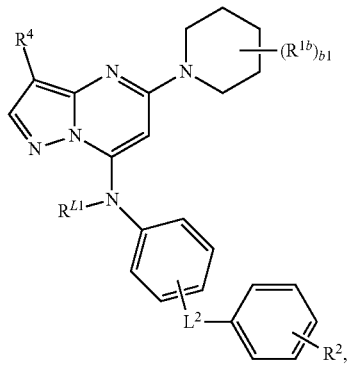

(III-2-d)

or a pharmaceutically acceptable salt, solvate, hydrate, polymorph, co-crystal, tautomer, stereoisomer, isotopically labeled derivative, or prodrug thereof, wherein $R^2$, $L^2$, $R^{L1}$, $R^4$, $R^{1b}$, and b1 are as defined herein.

In certain embodiments, a compound of Formula (III) is of Formula (III-2-d-i):

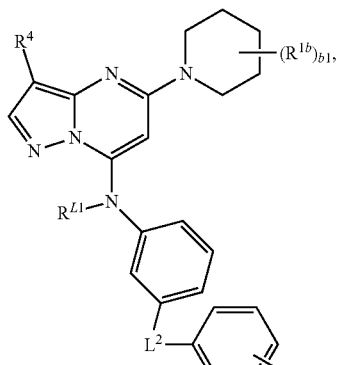

(III-2-d-i)

or a pharmaceutically acceptable salt, solvate, hydrate, polymorph, co-crystal, tautomer, stereoisomer, isotopically labeled derivative, or prodrug thereof, wherein $R^2$, $L^2$, $R^{L1}$, $R^4$, $R^{1b}$, and b1 are as defined herein.

In certain embodiments, a compound of Formula (III) is of Formula (III-2-d-ii):

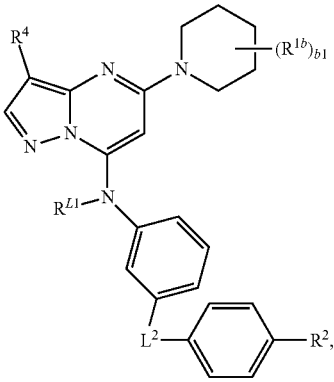

(III-2-d-ii)

or a pharmaceutically acceptable salt, solvate, hydrate, polymorph, co-crystal, tautomer, stereoisomer, isotopically labeled derivative, or prodrug thereof, wherein $R^2$, $L^2$, $R^{L1}$, $R^4$, $R^{1b}$, and b1 are as defined herein.

In certain embodiments, a compound of Formula (III) is of one of the following formulae:

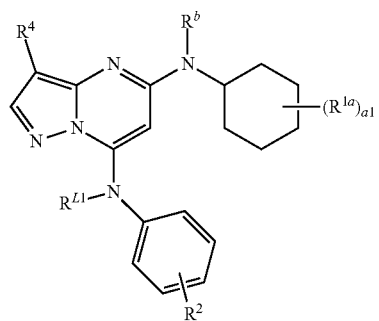

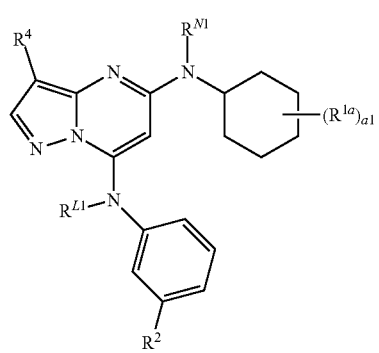

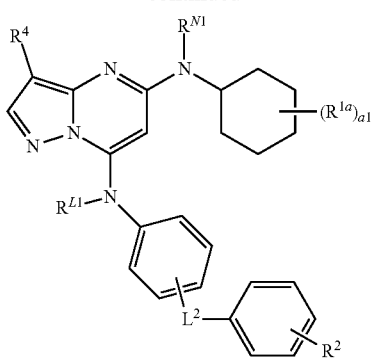
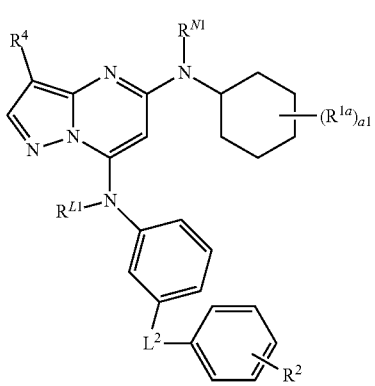
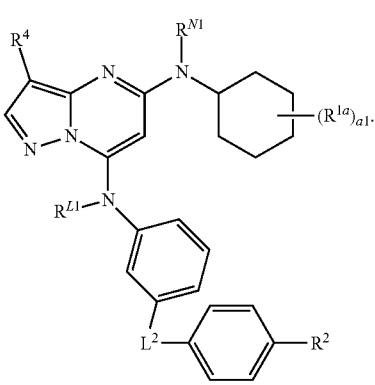
In certain embodiments, a compound of Formula (III) is of one of the following formulae:
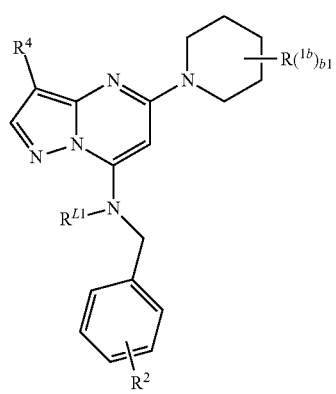
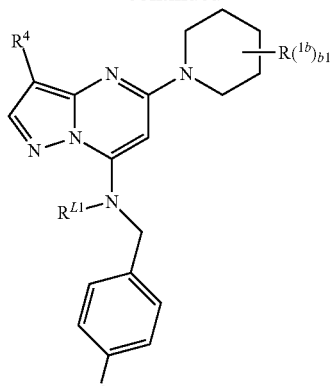
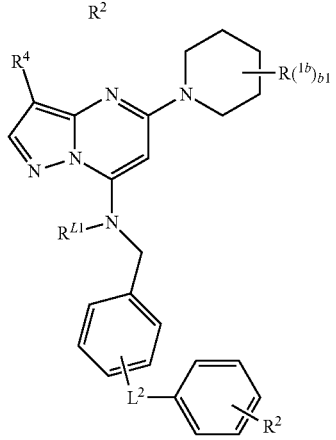
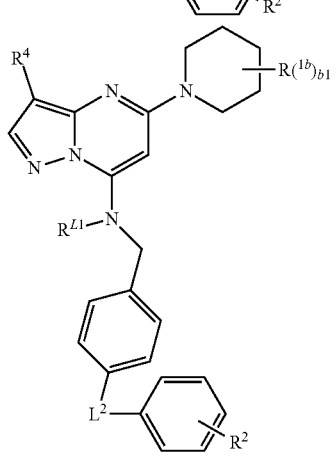
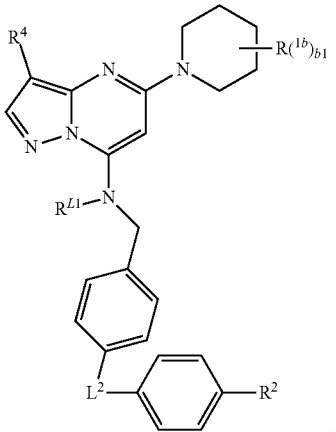

In certain embodiments, a compound of Formula (III) is of the formula:
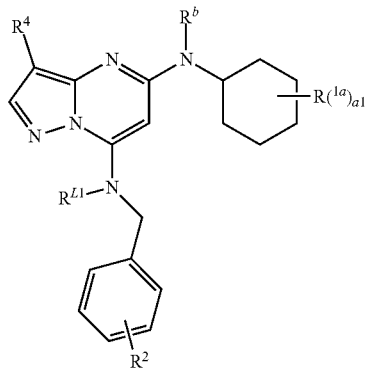
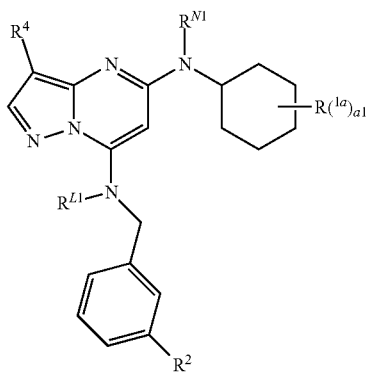
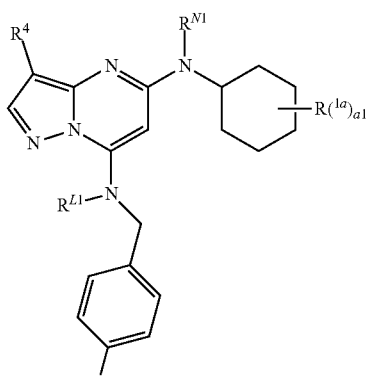
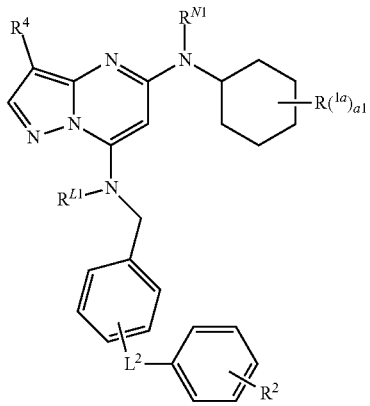
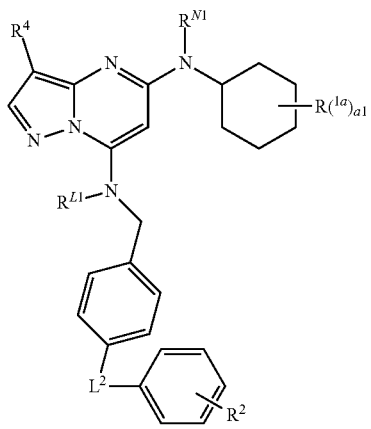
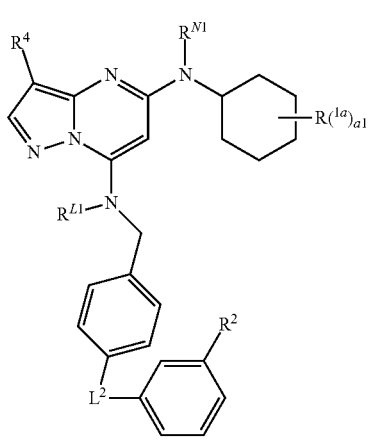
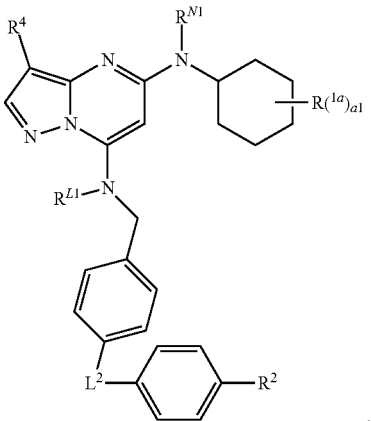
In certain embodiments, a compound of Formula (III) is of the formula:

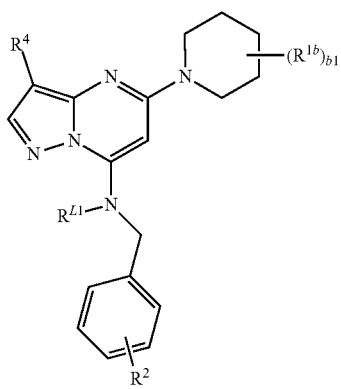
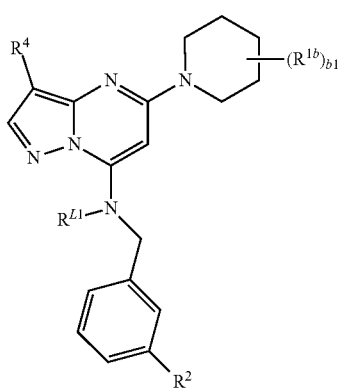
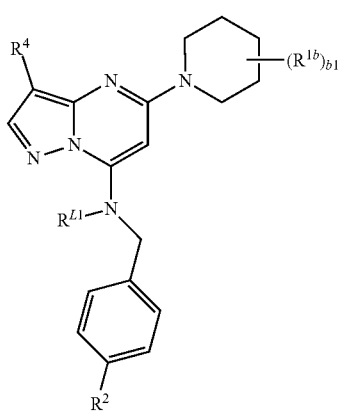
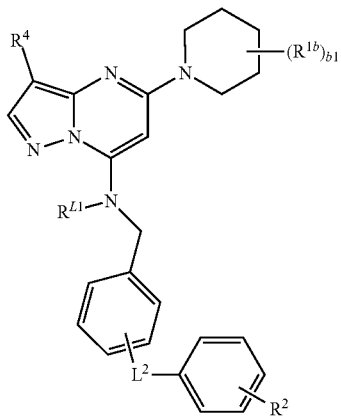
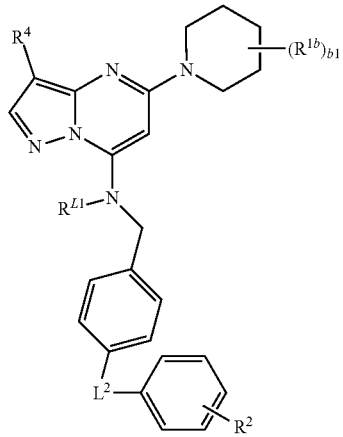
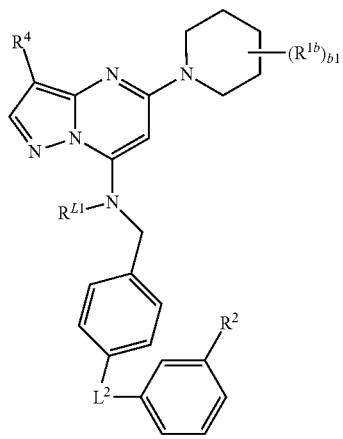
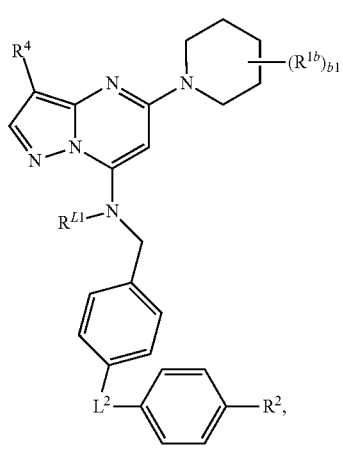
or a pharmaceutically acceptable salt, solvate, hydrate, polymorph, co-crystal, tautomer, stereoisomer, isotopically labeled derivative, or prodrug thereof.
In some embodiments, a compound of Formula (I) is of the formula:

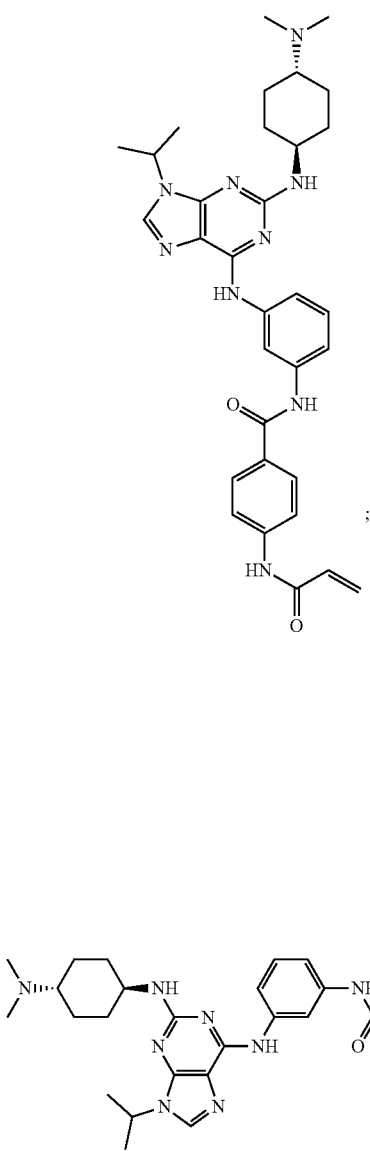
or a pharmaceutically acceptable salt, solvate, hydrate, polymorph, co-crystal, tautomer, stereoisomer, isotopically labeled derivative, or prodrug thereof.
In some embodiments, a compound of Formula (I) is of the formula:

125
-continued
THZ-4-119-1
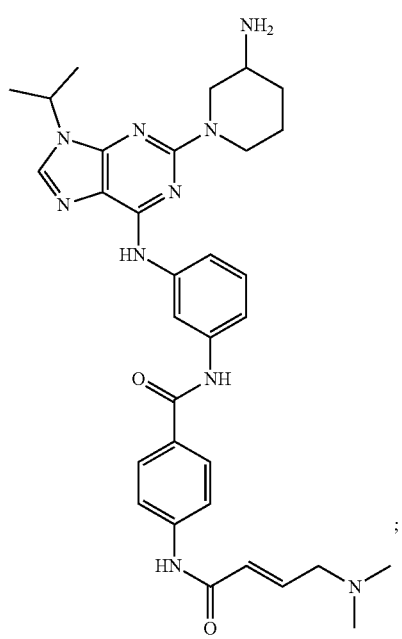
THZ-4-134-1
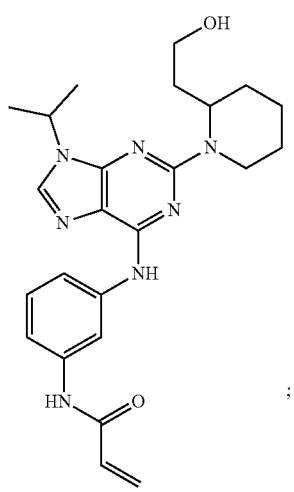
126
MFH-2-67-1
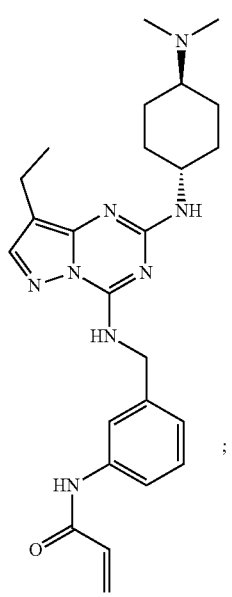
SB1-E-17
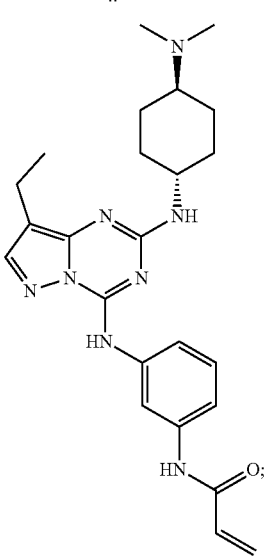
MFH-2-78-1
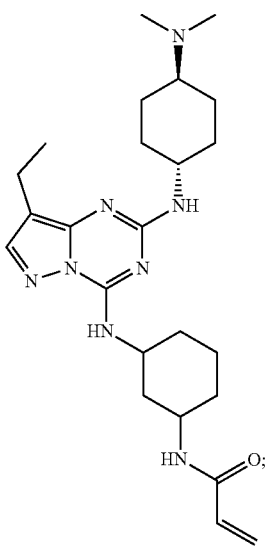
or a pharmaceutically acceptable salt, solvate, hydrate, polymorph, co-crystal, tautomer, stereoisomer, isotopically labeled derivative, or prodrug thereof.
In some embodiments, a compound of Formula (II) is of the formula:

or a pharmaceutically acceptable salt, solvate, hydrate, polymorph, co-crystal, tautomer, stereoisomer, isotopically labeled derivative, or prodrug thereof.

In some embodiments, a compound of Formula (II) is of the formula:

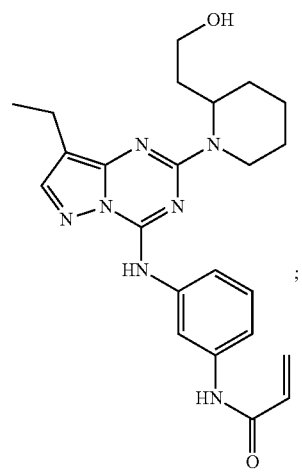

SB1-E-18

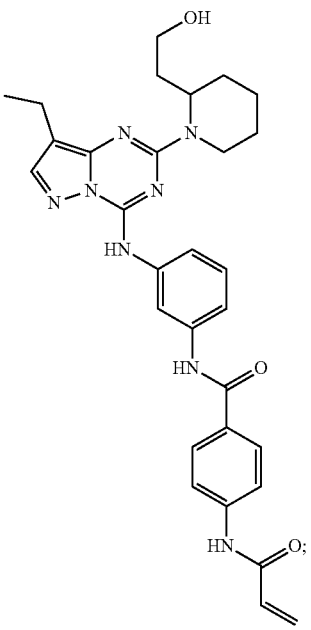

SB1-E-19 or a pharmaceutically acceptable salt, solvate, hydrate, polymorph, co-crystal, tautomer, stereoisomer, isotopically labeled derivative, or prodrug thereof.

In some embodiments, a compound of Formula (III) is of the formula:

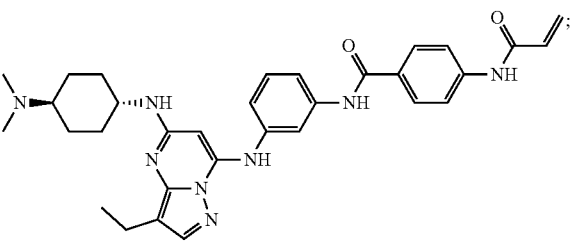

SB1-E-22

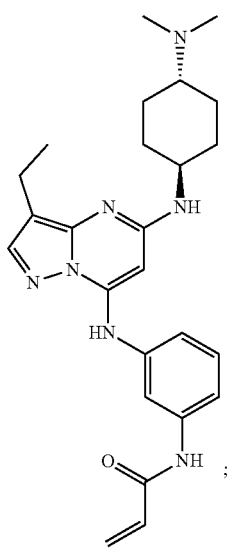

SB1-E-21

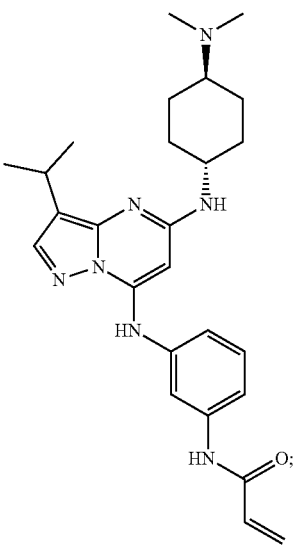

SB1-E-26

SB1-E-25
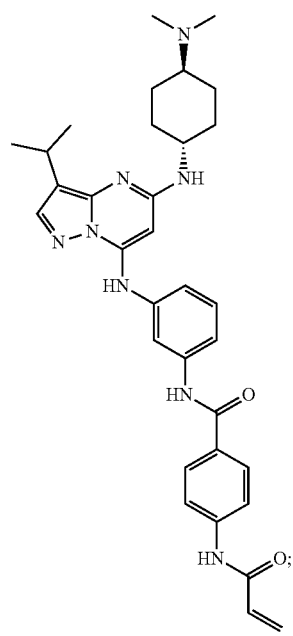
or a pharmaceutically acceptable salt, solvate, hydrate, polymorph, co-crystal, tautomer, stereoisomer, isotopically labeled derivative, or prodrug thereof.
In some embodiments, a compound of Formula (III) is of the formula:
SB1-E-23
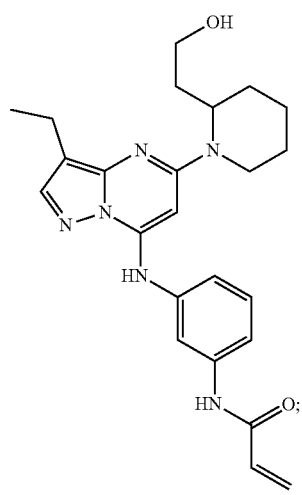
THZ-4-128-1
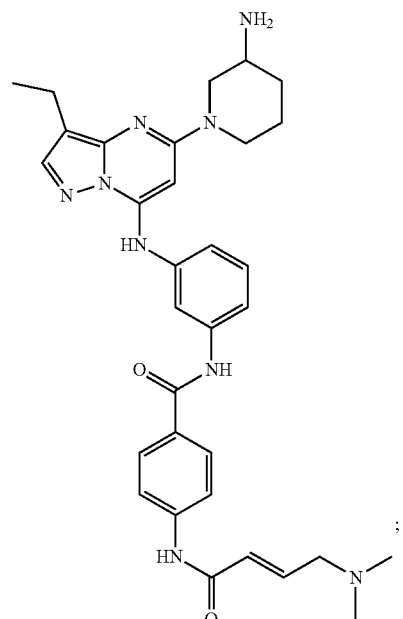
SB1-E-24
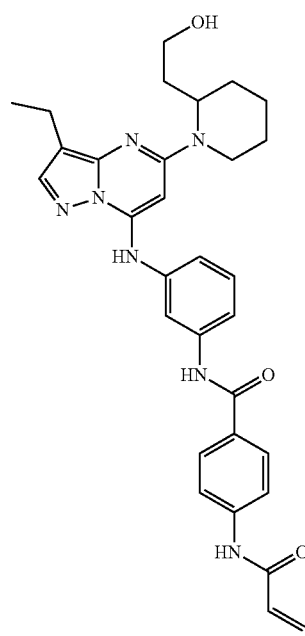
MFH-1-169-1
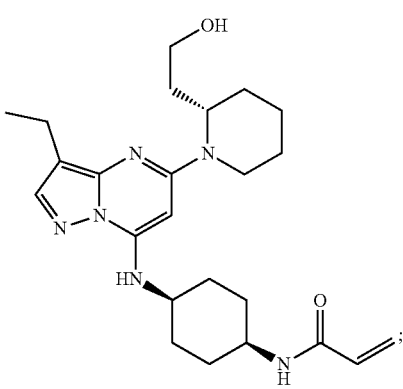

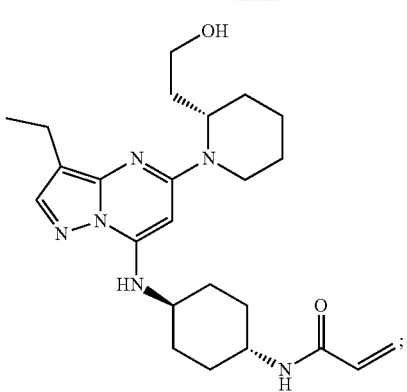

MFH-1-175-1

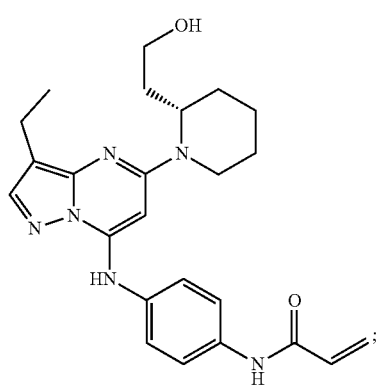

MFH-1-187-1

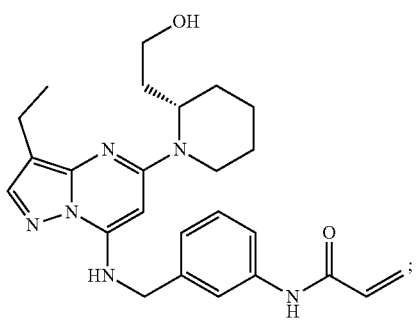

MFH-1-49-1 or a pharmaceutically acceptable salt, solvate, hydrate, polymorph, co-crystal, tautomer, stereoisomer, isotopically labeled derivative, or prodrug thereof.

Pharmaceutical Compositions, Kits, and Administration

The pharmaceutical compositions described herein are useful in treating and/or preventing proliferative diseases (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases) in a subject. The compositions described herein are also useful for inhibiting the activity of a protein kinase (e.g., CDK (e.g., CDK7, CDK12, and/or CDK13)) in a subject, biological sample, tissue, or cell. The compositions described herein are also useful for inducing apoptosis in a cell.

The present disclosure provides pharmaceutical compositions comprising a compound described herein (e.g., a compound of any one of Formulae (I)-(III)), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical composition of the invention comprises a compound described herein, or a pharmaceutically acceptable salt thereof, and optionally a pharmaceutically acceptable excipient. In certain embodiments, a pharmaceutical composition described herein comprises a compound described herein, or a pharmaceutically acceptable salt thereof, and a pharmaceutically acceptable excipient. In certain embodiments, the compound described herein, or a pharmaceutically acceptable salt, solvate, hydrate, polymorph, co-crystal, tautomer, stereoisomer, isotopically labeled derivative, or prodrug thereof, is provided in an effective amount in the pharmaceutical composition.

In certain embodiments, the effective amount is a therapeutically effective amount (e.g., amount effective for treating a proliferative disease in a subject in need thereof). In certain embodiments, the effective amount is an amount effective for inhibiting the activity of a protein kinase (e.g., CDK (e.g., CDK7, CDK12, and/or CDK13)) in a subject in need thereof. In certain embodiments, the effective amount is an amount effective for inhibiting the activity of a protein kinase (e.g., CDK (e.g., CDK7, CDK12, and/or CDK13)) in a cell. In certain embodiments, the effective amount is an amount effective for inducing apoptosis in a cell. In certain embodiments, the effective amount is a prophylactically effective amount (e.g., amount effective for preventing a proliferative disease in a subject in need thereof and/or for keeping a subject in need thereof in remission of a proliferative disease).

In certain embodiments, a protein kinase described herein is a CDK. In certain embodiments, a protein kinase described herein is CDK1, CDK2, CDK3, CDK4, CDK5, CDK6, CDK7, CDK8, CDK9, CDK10, CDK11, CDK12, CDK13, CDK14, CDK15, CDK16, CDK17, CDK18, CDK19, or CDK20. In certain embodiments, a protein kinase described herein is CDK7. In certain embodiments, a protein kinase described herein is CDK12. In certain embodiments, a protein kinase described herein is CDK13. In certain embodiments, a protein kinase described herein is a Src family kinase. In certain embodiments, a protein kinase described herein is SRC. In certain embodiments, a protein kinase described herein is FGR. In certain embodiments, a protein kinase described herein is BUB1B. In certain embodiments, a protein kinase described herein is CHEK2. In certain embodiments, a protein kinase described herein is HIPK4. In certain embodiments, a protein kinase described herein is PRKCQ. In certain embodiments, a protein kinase described herein is RET. In certain embodiments, a protein kinase described herein is MELK. In certain embodiments, a protein kinase described herein is IRAK1, IRAK4, BMX, or PI3K. In certain embodiments, a protein kinase described herein is ABL, ARG, BLK, CSK, EphB1, EphB2, FGR, FRK, FYN, SRC, YES, LCK, LYN, MAP2K5, NLK, p38a, SNRK, or TEC. In certain embodiments, a protein kinase described herein is ABL1(H396P)-phosphorylated, ABL1-phosphorylated, BLK, EPHA4, EPHB2, EPHB3, EPHB4, FGR, JAK3(JH1domain-catalytic), KIT, KIT(L576P), KIT(V559D), PDGFRB, SRC, YES, ABL1(H396P)-nonphosphorylated, ABL1(Y253F)-phosphorylated, ABL1-nonphosphorylated, FRK, LYN, ABL1(Q252H)-nonphosphorylated, DDR1, EPHB1, ERBB4, p38-alpha, ABL2, ABL1(Q252H)-phosphorylated, SIK, EPHA8, MEK5, ABL1(E255K)-phosphorylated, ABL1(F317L)-nonphosphorylated, FYN, LCK, EPHA2, ABL1(M351T)-phosphorylated, TXK, EGFR(L858R), EGFR(L861Q), ERBB2, ERBB3, EPHA5, ABL1(F317I)-nonphosphorylated, EGFR(L747-E749del, A750P), CSK, EPHA1, ABL1(F317L)-phosphorylated, BRAF(V600E), EGFR, KIT-autoinhibited, or EGFR(E746-A750del). In certain embodiments, a protein kinase described herein is ABL1(F317L)-nonphosphorylated, ABL1(H396P)-nonphosphorylated, ABL1(H396P)-phosphorylated, ABL1-phosphorylated, BLK, EPHA4, EPHB2, EPHB3, EPHB4, JAK3(JH1domain-catalytic), KIT, KIT(L576P), KIT(V559D), LYN, PDGFRB, SRC, YES, ABL1-nonphosphorylated, ABL1(Y253F)-phosphorylated, ERBB3, FGR, FRK, p38-alpha, ABL1(F317I)-nonphosphorylated, DDR1, EPHA2, ABL1(Q252H)-phosphorylated, MEK5, ABL1(Q252H)-nonphosphorylated, ABL2, FYN, EPHB1, ABL1(E255K)-phosphorylated, ABL1(F317L)-phosphorylated, EPHA1, ABL1(M351T)-phosphorylated, ERBB4, TXK, LCK, EPHA8, SIK, EPHA5, EGFR(L861Q), CSF1R-autoinhibited, BRAF(V600E), BRK, CSK, KIT(D816V), KIT-autoinhibited, EGFR(L747-T751del,Sins), EGFR(L858R), EGFR(L747-E749del, A750P), or CSF1R.

In certain embodiments, the effective amount is an amount effective for inhibiting the activity of a protein kinase (e.g., CDK (e.g., CDK7, CDK12, and/or CDK13)) by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of a protein kinase (e.g., CDK (e.g., CDK7, CDK12, and/or CDK13)) by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the activity of a protein kinase (e.g., CDK (e.g., CDK7, CDK12, and/or CDK13)) by a range between a percentage described in this paragraph and another percentage described in this paragraph, inclusive.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, German® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

In certain embodiments, an effective amount of a compound for administration one or more times a day to a 70 kg adult human comprises about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compound of the invention is administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents) useful in treating and/or preventing a proliferative disease. The compounds or compositions can be administered in combination with additional pharmaceutical agents that improve their activity (e.g., activity (e.g., potency and/or efficacy) in treating a proliferative disease in a subject in need thereof, in preventing a proliferative disease in a subject in need thereof, and/or in inhibiting the activity of a protein kinase (e.g., CDK (e.g., CDK7, CDK12, and/or CDK13)) in a subject, biological sample, tissue, or cell), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies in treating and/or preventing a proliferative disease. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating a proliferative disease. In certain embodiments, the additional pharmaceutical agent is a pharmaceutical agent useful in preventing a proliferative disease. In certain embodiments, the additional pharmaceutical agent is a pharmaceutical agent useful in inhibiting the activity of a protein kinase (e.g., CDK (e.g., CDK7, CDK12, and/or CDK13)) in a subject, biological sample, tissue, or cell. In certain embodiments, the additional pharmaceutical agent is a pharmaceutical agent useful in inducing apoptosis in a cell. In certain embodiments, the additional pharmaceutical agent is a pharmaceutical agent approved by a regulatory agency (e.g., the US FDA) for treating and/or preventing a proliferative disease. Each additional pharmaceutical agent may be administered at a dose and/or on a time schedule determined for that pharmaceutical agent. The additional pharmaceutical agent(s) may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia Chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is an anti-myelodysplasia agent. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), or a combination thereof.

In certain embodiments, the additional pharmaceutical agent is an anti-macroglobulinemia agent. In certain embodiments, the additional pharmaceutical agent is LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPDX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), or a combination thereof. In certain embodiments, the additional pharmaceutical agent is a protein kinase inhibitor (e.g., tyrosine protein kinase inhibitor). In certain embodiments, the additional pharmaceutical agent is an inhibitor of a Src family kinase. In certain embodiments, the additional pharmaceutical agent is a CDK inhibitor. In certain embodiments, the additional pharmaceutical agent is a CDK7 inhibitor. In certain embodiments, the additional pharmaceutical agent is a CDK12 inhibitor. In certain embodiments, the additional pharmaceutical agent is a CDK13 inhibitor. In certain embodiments, the additional pharmaceutical agent is an inhibitor of one or more protein kinases selected from the group consisting of IRAK1, IRAK4, BMX, and PI3K. In certain embodiments, the additional pharmaceutical agent is an inhibitor of one or more protein kinases selected from the group consisting of BUB1B, CDK2, CDK9, CHEK2, FGR, HIPK4, PRKCQ, RET, SRC, or MELK. In certain embodiments, the additional pharmaceutical agent is an inhibitor of one or more protein kinases selected from the group consisting of ABL, ARG, BLK, CSK, EphB1, EphB2, FGR, FRK, FYN, SRC, YES, LCK, LYN, MAP2K5, NLK, p38a, SNRK, and TEC. In certain embodiments, the additional pharmaceutical agent is an inhibitor of one or more protein kinases selected from the group consisting of ABL1(H396P)-phosphorylated, ABL1-phosphorylated, BLK, EPHA4, EPHB2, EPHB3, EPHB4, FGR, JAK3 (JH1domain-catalytic), KIT, KIT(L576P), KIT(V559D), PDGFRB, SRC, YES, ABL1(H396P)-nonphosphorylated, ABL1(Y253F)-phosphorylated, ABL1-nonphosphorylated, FRK, LYN, ABL1(Q252H)-nonphosphorylated, DDR1, EPHB1, ERBB4, p38-alpha, ABL2, ABL1(Q252H)-phosphorylated, SIK, EPHA8, MEK5, ABL1(E255K)-phosphorylated, ABL1(F317L)-nonphosphorylated, FYN, LCK, EPHA2, ABL1(M351T)-phosphorylated, TXK, EGFR (L858R), EGFR(L861Q), ERBB2, ERBB3, EPHA5, ABL1 (F317I)-nonphosphorylated, EGFR(L747-E749del, A750P), CSK, EPHA1, ABL1(F317L)-phosphorylated, BRAF (V600E), EGFR, KIT-autoinhibited, and EGFR(E746-A750del). In certain embodiments, the additional pharmaceutical agent is an inhibitor of one or more protein kinases selected from the group consisting of ABL1(F317L)-nonphosphorylated, ABL1(H396P)-nonphosphorylated, ABL1 (H396P)-phosphorylated, ABL1-phosphorylated, BLK, EPHA4, EPHB2, EPHB3, EPHB4, JAK3(JH1domain-catalytic), KIT, KIT(L576P), KIT(V559D), LYN, PDGFRB, SRC, YES, ABL1-nonphosphorylated, ABL1(Y253F)-phosphorylated, ERBB3, FGR, FRK, p38-alpha, ABL1(F317I)-nonphosphorylated, DDR1, EPHA2, ABL1(Q252H)-phosphorylated, MEK5, ABL1(Q252H)-nonphosphorylated, ABL2, FYN, EPHB1, ABL1(E255K)-phosphorylated, ABL1(F317L)-phosphorylated, EPHA1, ABL1(M351T)-phosphorylated, ERBB4, TXK, LCK, EPHA8, SIK, EPHA5, EGFR(L861Q), CSF1R-autoinhibited, BRAF (V600E), BRK, CSK, KIT(D816V), KIT-autoinhibited, EGFR(L747-T751del,Sins), EGFR(L858R), EGFR(L747-E749del, A750P), and CSF1R. In certain embodiments, the additional pharmaceutical agent is an anti-angiogenesis agent, anti-inflammatory agent, immunosuppressant, antibacterial agent, anti-viral agent, cardiovascular agent, cholesterol-lowering agent, anti-diabetic agent, anti-allergic agent, pain-relieving agent, or a combination thereof. In certain embodiments, the compounds described herein or pharmaceutical compositions can be administered in combination with an anti-cancer therapy including, but not limited to, transplantation (e.g., bone marrow transplantation, stem cell transplantation), surgery, radiation therapy, immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

In certain embodiments, a kit described herein includes a first container comprising a compound or pharmaceutical composition described herein. In certain embodiments, a kit described herein is useful in treating a proliferative disease (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases) in a subject in need thereof, preventing a proliferative disease in a subject in need thereof, inhibiting the activity of a protein kinase (e.g., CDK (e.g., CDK7, CDK12, or CDK13)) in a subject, biological sample, tissue, or cell, and/or inducing apoptosis in a cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease in a subject in need thereof, preventing a proliferative disease in a subject in need thereof, inhibiting the activity of a protein kinase (e.g., CDK (e.g., CDK7, CDK12, or CDK13)) in a subject, biological sample, tissue, or cell, and/or inducing apoptosis in a cell. A kit described herein may include one or more additional pharmaceutical agents described herein as a separate composition.

Methods of Treatment and Uses

The present invention also provides methods for the treatment or prevention of a proliferative disease (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases).

The compounds described herein may exhibit kinase inhibitory activity; the ability to inhibit cyclin-dependent kinase (CDK); the ability to inhibit cyclin-dependent kinase 7 (CDK7); the ability to inhibit cyclin-dependent kinase 7 (CDK7), without inhibiting another cyclin-dependent kinase (CDK); the ability to inhibit cyclin-dependent kinase 12 (CDK12); the ability to inhibit cyclin-dependent kinase 12 (CDK12), without inhibiting another cyclin-dependent kinase (CDK); the ability to inhibit cyclin-dependent kinase 13 (CDK13); the ability to inhibit cyclin-dependent kinase 13 (CDK13), without inhibiting another cyclin-dependent kinase (CDK); the ability to inhibit cyclin-dependent kinases 12 and 13 (CDK12 and CDK13); the ability to inhibit cyclin-dependent kinases 12 and 13 (CDK12 and CDK13), without inhibiting another cyclin-dependent kinase (CDK); a therapeutic effect and/or preventative effect in the treatment of cancers; a therapeutic effect and/or preventative effect in the treatment of Myc-dependent cancers; and/or a therapeutic profile (e.g., optimum safety and curative effect) that is superior to existing chemotherapeutic agents.

Without wishing to be bound by any particular theory, the compounds described herein are able to bind (e.g., covalently modify) a protein kinase described herein. In certain embodiments, the $R^2$ group of a compound described herein is able to bind (e.g., covalently modify) to the protein kinase. In certain embodiments, the $R^2$ group of a compound described herein is able to covalently bind a cysteine residue of the protein kinase. In certain embodiments, the $R^2$ group of a compound described herein is able to covalently bind Cys312 residue of CDK7. In certain embodiments, the $R^2$ group of a compound described herein is able to covalently bind Cys Cys1039 residue of CDK12. In certain embodiments, the $R^2$ group of a compound described herein is able to covalently bind Cys1017 residue of CDK13.

In another aspect, the present disclosure provides methods of inhibiting the activity of a protein kinase in a subject, the methods comprising administering to the subject an effective amount (e.g., therapeutically effective amount) of a compound, or pharmaceutical composition thereof, as described herein.

In another aspect, the present disclosure provides methods of inhibiting the activity of a protein kinase in a biological sample, the methods comprising contacting the biological sample with an effective amount of a compound, or pharmaceutical composition thereof, as described herein.

In another aspect, the present disclosure provides methods of inhibiting the activity of a protein kinase in a tissue, the methods comprising contacting the tissue with an effective amount of a compound, or pharmaceutical composition thereof, as described herein.

In another aspect, the present disclosure provides methods of inhibiting the activity of a protein kinase in a cell, the methods comprising contacting the cell with an effective amount of a compound, or pharmaceutical composition thereof, as described herein.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

In certain embodiments, a biological sample described herein is a breast tissue, bone marrow, lymph node, spleen, or blood.

In certain embodiments, a cell described herein is in vitro. In certain embodiments, a cell described herein is ex vivo. In certain embodiments, a cell described herein is in vivo. In certain embodiments, a cell described herein is a malignant cell (e.g., malignant blood cell). In certain embodiments, a cell described herein is a malignant hematopoietic stem cell (e.g., malignant myeloid cell or malignant lymphoid cell). In certain embodiments, a cell described herein is a malignant lymphocyte (e.g., malignant T-cell or malignant B-cell). In certain embodiments, a cell described herein is a malignant red blood cell, malignant white blood cell, or malignant platelet. In certain embodiments, a cell described herein is a malignant neutrophil, malignant macrophage, or malignant plasma cell. In certain embodiments, a cell described herein is a carcinoma cell. In certain embodiments, a cell described herein is a carcinoma breast cell. In certain embodiments, a cell described herein is a sarcomas cell. In certain embodiments, a cell described herein is a sarcomas breast cell.

The proliferative disease to be treated or prevented using the compounds described herein may be associated with overexpression of a kinase, such as cyclin-dependent kinase (CDK). The process of eukaryotic cell division may be broadly divided into a series of sequential phases termed G1, S, G2, and M. Correct progression through the various phases of the cell cycle has been shown to be critically dependent upon the spatial and temporal regulation of a family of proteins known as cyclin dependent kinases (CDKs) and a diverse set of their cognate protein partners termed cyclins. CDKs are CDC2 (also known as CDK1) homologous serine-threonine kinase proteins that are able to utilize ATP as a substrate in the phosphorylation of diverse polypeptides in a sequence-dependent context. Cyclins are a family of proteins characterized by a homology region, containing approximately 100 amino acids, termed the "cyclin box" which is used in binding to, and defining selectivity for, specific CDK partner proteins.

Modulation of the expression levels, degradation rates, protein levels, and activity levels of various CDKs and cyclins throughout the cell cycle leads to the cyclical formation of a series of CDK/cyclin complexes, in which the CDKs are enzymatically active. The formation of these complexes controls passage through discrete cell cycle checkpoints and thereby enables the process of cell division to continue. Failure to satisfy the prerequisite biochemical criteria at a given cell cycle checkpoint, i.e., failure to form a required CDK/cyclin complex, can lead to cell cycle arrest and/or cellular apoptosis. Aberrant cellular proliferation can often be attributed to loss of correct cell cycle control. Inhibition of CDK enzymatic activity therefore provides a means by which abnormally dividing cells can have their division arrested and/or be killed. The diversity of CDKs, and CDK complexes, and their critical roles in mediating the cell cycle, provides a broad spectrum of potential therapeutic targets selected on the basis of a defined biochemical rationale.

CDK7, a member of the CDK family, was originally isolated as the catalytic subunit of the trimeric CDK-activating kinase (CAK) complex. This complex, consisting of CDK7, cyclin H, and MAT1, is responsible for activation of the mitotic promoting factor in vitro. The discovery that CDK7 was also a component of the basal transcription repair factor IIH (TFIIH) implicated a dual role for CDK7 in transcription as part of TFIIH and in the control of the cell cycle as the trimeric CAK complex. TFIIH is a multi-subunit protein complex identified as a factor required for RNA polymerase II (RNAP II)-catalyzed transcription, and subsequently this complex was found to play a key role in nucleotide excision repair. CDK7 is a component of at least three complexes, i.e., the trimeric CAK complex, the quaternary complex with the XPD (or ERCC2, a protein involved in transcription-coupled nucleotide excision repair), and the nine-subunit TFIIH complex. The two functions of CDK7 in CAK and CTD phosphorylation support critical facets of cellular proliferation, cell cycling, and transcription. Overexpression of CDK7 may inhibit apoptosis, promote transcription and cell proliferation, and/or disrupt DNA repair, and therefore, cause proliferative diseases. In certain embodiments, the proliferative disease to be treated or prevented using the compounds described herein may be associated with overexpression of a CDK (e.g., CDK7).

Cdk12 and Cdk13 are Cdc2-related proteins that share 92% identity in their kinase domains (Chen et al., *Exp. Neurol.*, 2014, 261, 10-21). CDK12 plays a critical role in cell processes, for example, regulating transcription and splicing machinery by stabilizing the RNAPII and DNA interaction, and regulating DNA damage response (DDR) and maintenance of genomic stability by modulating the expression of DDR genes. Overexpression of CDK12 has been found to correlate, both at the transcriptional and protein level, with pathological parameters of breast cancer disease.

A proliferative disease may be associated with aberrant activity of a CDK (e.g., CDK7, CDK12, and/or CDK13). Aberrant activity of a CDK (e.g., CDK7, CDK12, and/or CDK13) may be an elevated and/or an inappropriate activity of the CDK. Deregulation of cell cycle progression is a characteristic of a proliferative disease, and a majority of proliferative diseases have abnormalities in some component of CDK (e.g., CDK7, CDK12, and/or CDK13) activity, frequently through elevated and/or inappropriate CDK activation. Inhibition of the catalytic activity of CDK7, CDK12, and/or CDK13 would be expected to inhibit cell cycle progression by blocking the phosphorylation of cell cycle CDKs, and would additionally inhibit transcription of effectors of cell division. In certain embodiments, CDK7 is not overexpressed, and the activity of CDK7 is elevated and/or inappropriate. In certain other embodiments, CDK7 is overexpressed, and the activity of CDK7 is elevated and/or inappropriate. In certain embodiments, CDK12 is not overexpressed, and the activity of CDK12 is elevated and/or inappropriate. In certain embodiments, CDK12 is overexpressed, and the activity of CDK12 is elevated and/or inappropriate. In certain other embodiments, CDK13 is not overexpressed, and the activity of CDK13 is elevated and/or inappropriate. In certain other embodiments, CDK13 is overexpressed, and the activity of CDK13 is elevated and/or inappropriate. The compounds described herein, and pharmaceutically acceptable salts, solvates, hydrates, polymorphs, co-crystals, tautomers, stereoisomers, isotopically labeled derivatives, prodrugs, and compositions thereof, may inhibit the activity of CDK7 and be useful in treating and/or preventing proliferative diseases. The compounds described herein, and pharmaceutically acceptable salts, solvates, hydrates, polymorphs, co-crystals, tautomers, stereoisomers, isotopically labeled derivatives, prodrugs, and compositions thereof, may inhibit the activity of CDK12 and/or CDK13 and be useful in treating and/or preventing proliferative diseases.

A proliferative disease may also be associated with inhibition of apoptosis of a cell in a biological sample or subject. All types of biological samples described herein or known in the art are contemplated as being within the scope of the invention. Apoptosis is the process of programmed cell death. Inhibition of apoptosis may result in uncontrolled cell proliferation and, therefore, may cause proliferative diseases. The cell cycle CDKs (CDK1, 2, 4, and 6) are activated by phosphorylation by CDK7/cyclin H (also called CAK). Inhibition of CDK7 would therefore result in cell-cycle arrest at multiple points in the cell cycle due to failure to activate the cell cycle CDKs. CDK 7 activates transcription by phosphorylating the CTD of RNAP II. Inhibition of CTD phosphorylation has been shown to inhibit transcription and reduce expression of short lived proteins, including those involved in apoptosis regulation. It is appreciated in the art that stalling of RNA polymerase may activate p53 (also known as protein 53 or tumor protein 53, a tumor suppressor protein that is encoded in humans by the TP53 gene), leading to apoptosis. Thus, inhibition of the activity of CDK7 are expected to cause cytotoxicity by inducing apoptosis. The compounds described herein, and pharmaceutically acceptable salts, solvates, hydrates, polymorphs, co-crystals, tautomers, stereoisomers, isotopically labeled derivatives, prodrugs, and compositions thereof, may induce apoptosis, and therefore, be useful in treating and/or preventing proliferative diseases.

The CycK/Cdk12 complex regulates phosphorylation of Ser2 in the C-terminal domain of RNA polymerase II and expression of a small subset of human genes, as revealed in expression microarrays. Through regulation of expression of DNA damage response genes (i.e. oncogenes), CycK/Cdk12 protects cells from genomic instability. In certain embodiments, the DNA damage response genes are BRCA1, BRCA2, HER1, HER2, ATR, FANCI, or FANCD2. In certain embodiments, the DNA damage response genes are BRCA1, HER2, ATR, FANCI, and FANCD2. In certain embodiments, the DNA damage response genes are BRCA1. In certain embodiments, the DNA damage response genes are HER2.

In certain embodiments, the proliferative disease to be treated or prevented using the compounds described herein is cancer. All types of cancers disclosed herein or known in the art are contemplated as being within the scope of the invention. In certain embodiments, the proliferative disease is a cancer associated with dependence on BCL-2 anti-apoptotic proteins (e.g., MCL-1 and/or XIAP). In certain embodiments, the proliferative disease is a cancer associated with dependence on BCL-2 anti-apoptotic proteins (e.g., MCL-1 and/or XIAP). In certain embodiments, the proliferative disease is a cancer associated with overexpression of MYC (a gene that codes for a transcription factor). In certain embodiments, the cancer is a MYC-dependent cancer. In certain embodiments, the proliferative disease is a cancer associated with amplification of BRCA1. In certain embodiments, the proliferative disease is a cancer associated with amplification of HER2. In certain embodiments, the proliferative disease is a hematological malignancy. In certain embodiments, the proliferative disease is a blood cancer. In certain embodiments, the proliferative disease is a hematological malignancy. In certain embodiments, the proliferative disease is leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myelogenous leukemia (AML). In certain embodiments, the proliferative disease is acute monocytic leukemia (AMoL). In certain embodiments, the proliferative disease is lymphoma. In some embodiments, the proliferative disease is Burkitt's lymphoma. In certain embodiments, the proliferative disease is a Hodgkin's lymphoma. In certain embodiments, the proliferative disease is a non-Hodgkin's lymphoma. In certain embodiments, the proliferative disease is multiple myeloma. In certain embodiments, the proliferative disease is melanoma. In certain embodiments, the proliferative disease is colorectal cancer. In certain embodiments, the proliferative disease is breast cancer. In certain embodiments, the proliferative disease is recurring breast cancer. In certain embodiments, the proliferative disease is mutant breast cancer. In certain embodiments, the proliferative disease is HER2+ breast cancer. In certain embodiments, the proliferative disease is HER2− breast cancer. In certain embodiments, the proliferative disease is triple-negative breast cancer (TNBC). In certain embodiments, the proliferative disease is a bone cancer. In certain embodiments, the proliferative disease is osteosarcoma. In certain embodiments, the proliferative disease is Ewing's sarcoma. In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is non-small cell lung cancer. In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis.

In certain embodiments, the proliferative disease is an acute inflammatory disease. In certain embodiments, the acute inflammatory disease is rheumatoid arthritis, Crohn's disease, or fibrosis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

Another aspect of the invention relates to methods of inhibiting the activity of a kinase in a biological sample or subject. In certain embodiments, the kinase is CDK. In certain embodiments, the kinase is CDK7. In certain embodiments, the kinase is CDK12. In certain embodiments, the kinase is CDK13. In certain embodiments, the activity of the kinase is aberrant activity of the kinase. In certain embodiments, the inhibition of the activity of the kinase is irreversible. In other embodiments, the inhibition of the activity of the kinase is reversible. In certain embodiments, the methods of inhibiting the activity of the kinase include attaching a compound described herein to the kinase.

Also provided in the present invention are methods of inhibiting transcription of genes in a biological sample or subject. In certain embodiments, the genes which may have their transcription inhibited by the activity of CDK7, CDK12, and/or CDK13 are listed in FIG. 11. In certain embodiments, the transcription of genes affected by the activity of CDK7 may be inhibited by a compound of the invention. In certain embodiments, the genes which may have their transcription inhibited by the activity of CDK7 are one or more selected from the group consisting of MYC, RUNX1, MYB, TAL1, GATA3, KLF2, HNRPDL, p21, ASCL1, MYCN, INSM1, NEUROD1, NEUROG1, FOXG1, FOXA1, SOX2, SOX4, BCL11A, OTX2, GAT2, PHOX2B, PLK2, TAF1, CTGF, WEE1, SDIM, JUN, PIM1, IL8, and FOS1. In certain embodiments, the genes which may have their transcription inhibited by the activity of CDK7 include MYC, KLF2, E2F2, CDK6, CCND3, E2F3, HNRPDL, TET1, IL7R, BRCA1, BRCA2, HER1, and HER2. In certain embodiments, the transcription of genes affected by the activity of CDK12 may be inhibited by a compound of the invention. In certain embodiments, the genes which may have their transcription inhibited by the activity of CDK12 are one or more selected from the group consisting of BRCA1, FANCI, ATR, FANCD2, APEX1, NEK9, CHEK1, CHEK2, ATM, RAD51C, RAD51D, ORC3L, MDC1, TERF2, ERCC4, FANCF, PARP9, RUNX1, MYB, TAL1, MCL1, MYC, BCL2, ETS1, and EWS-FLI. In certain embodiments, the transcription of genes affected by the activity of CDK13 may be inhibited by a compound of the invention. In certain embodiments, the genes which may have their transcription inhibited by the compounds herein are SNORA38.

The present invention also provides methods of inhibiting cell growth in a biological sample or subject.

In still another aspect, the present invention provides methods of inducing apoptosis of a cell in a biological sample or a subject.

In certain embodiments, the methods described herein include administering to a subject or contacting a biological sample with an effective amount of a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include administering to a subject or contacting a biological sample with an effective amount of a compound described herein, or a pharmaceutically acceptable salt thereof, or a pharmaceutical composition thereof. In certain embodiments, the compound is contacted with a biological sample. In certain embodiments, the compound is administered to a subject. In certain embodiments, the compound is administered in combination with one or more additional pharmaceutical agents described herein. The additional pharmaceutical agent may be an anti-proliferative agent. In certain embodiments, the additional pharmaceutical agent is an anti-cancer agent. The additional pharmaceutical agent may also be a kinase inhibitor. In certain embodiments, the additional pharmaceutical agent is an inhibitor of a CDK. In certain embodiments, the additional pharmaceutical agent is an inhibitor of CDK7. In certain embodiments, the additional pharmaceutical agent is a selective inhibitor of CDK7. In certain embodiments, the additional pharmaceutical agent is a nonselective inhibitor of CDK7. In certain embodiments, the additional pharmaceutical agent is an inhibitor of CDK12. In certain embodiments, the additional pharmaceutical agent is a selective inhibitor of CDK12. In certain embodiments, the additional pharmaceutical agent is a nonselective inhibitor of CDK12. In certain embodiments, the additional pharmaceutical agent is an inhibitor of CDK13. In certain embodiments, the additional pharmaceutical agent is a selective inhibitor of CDK13. In certain embodiments, the additional pharmaceutical agent is a nonselective inhibitor of CDK13. In certain embodiments, the additional pharmaceutical agent is an inhibitor of another CDK. In certain embodiments, the additional pharmaceutical agent is a selective inhibitor of another CDK. In certain embodiments, the additional pharmaceutical agent is a nonselective inhibitor of another CDK. In certain embodiments, the additional pharmaceutical agent is flavopiridol, triptolide, SNS-032 (BMS-387032), PHA-767491, PHA-793887, BS-181, (S)—CR8, (R)—CR8, or NU6140. In certain embodiments, the additional pharmaceutical agent is an inhibitor of a mitogen-activated protein kinase (MAPK). In certain embodiments, the additional pharmaceutical agent is an inhibitor of a glycogen synthase kinase 3 (GSK3). In certain embodiments, the additional pharmaceutical agent is an inhibitor of an AGC kinase. In certain embodiments, the additional pharmaceutical agent is an inhibitor of a calmodulin-dependent kinase (CaM Kinase). In certain embodiments, the additional pharmaceutical agent is an inhibitor of a casein kinase 1. In certain embodiments, the additional pharmaceutical agent is an inhibitor of a STE kinase. In certain embodiments, the additional pharmaceutical agent is an inhibitor of a tyrosine kinase.

In some embodiments, the additional pharmaceutical agent is a topoisomerase inhibitor, a MCL1 inhibitor, a BCL-2 inhibitor, a BCL-xL inhibitor, a BRD4 inhibitor, a BRCA1 inhibitor, BRCA2 inhibitor, HER1 inhibitor, HER2 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-(((R)-1-methoxypropan-2-yl)amino)cyclohexyl)amino)-[2,4'-bipyridin]-6-yl)amino)methyl)tetrahydro-2H-pyran-4-carbonitrile, JIB04, or cisplatin. In some embodiments, the additional pharmaceutical agent is etoposide, obatoclax, or navitoclax, and the disease to be treated is breast cancer, e.g., triple-negative breast cancer, HER2 positive breast cancer, HER2 negative breast cancer, ER-positive breast cancer, ER-negative breast cancer, or ER/PR-positive breast cancer. In some embodiments, the additional pharmaceutical agent is etoposide, JIB04, or cisplatin, and the disease to be treated is Ewing's sarcoma. In some embodiments, the additional pharmaceutical agent is JQ1 or NVP2, and the disease to be treated is leukemia, e.g., acute myelogenous leukemia, myeloblastic leukemia, promyelocytic leukemia, myelomonocytic leukemia, monocytic leukemia, monoblastic leukemia, or megakaryoblastic leukemia. In certain embodiments, a pharmaceutical composition described herein further comprises a combination of the additional pharmaceutical agents described herein.

The inventive compounds or compositions may synergistically augment inhibition of CDK7 induced by the additional pharmaceutical agent(s) in the biological sample or subject. The inventive compounds or compositions may synergistically augment inhibition of CDK12 and/or CDK13 induced by the additional pharmaceutical agent(s) in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

In some embodiments, the activity of a protein kinase is non-selectively inhibited by the compounds or pharmaceutical compositions described herein. In some embodiments, the activity of a protein kinase described herein is selectively inhibited by the compounds or pharmaceutical compositions described herein, compared to the activity of a different protein (e.g., a different protein kinase). In certain embodiments, the activity of CDK (e.g., CDK7, CDK12, or CDK13) is selectively inhibited by a compound or pharmaceutical composition described herein, compared to the activity of a different protein. In certain embodiments, the activity of CDK7 is selectively inhibited by a compound or pharmaceutical composition described herein, compared to the activity of a different CDK protein. In certain embodiments, the activity of CDK7 is selectively inhibited by a compound or pharmaceutical composition described herein, compared to the activity of CDK12. In certain embodiments, the activity of CDK7 is selectively inhibited by a compound or pharmaceutical composition described herein, compared to the activity of CDK13. In certain embodiments, the activity of CDK7 is selectively inhibited by a compound or pharmaceutical composition described herein, compared to the activity of CDK12 and the activity of CDK13. In certain embodiments, the activity of CDK12 is selectively inhibited by a compound or pharmaceutical composition described herein, compared to the activity of CDK7. In certain embodiments, the activity of CDK13 is selectively inhibited by a compound or pharmaceutical composition described herein, compared to the activity of CDK7. In certain embodiments, the activity of CDK12 and the activity of CDK13 are selectively inhibited by a compound or pharmaceutical composition described herein, compared to the activity of CDK7.

The selectivity of a compound or pharmaceutical composition described herein in inhibiting the activity of a protein kinase over a different protein (e.g., a different protein kinase) may be measured by the quotient of the $IC_{50}$ value of the compound or pharmaceutical composition in inhibiting the activity of the different protein over the $IC_{50}$ value of the compound or pharmaceutical composition in inhibiting the activity of the protein kinase. The selectivity of a compound or pharmaceutical composition described herein for a protein kinase over a different protein may also be measured by the quotient of the $K_d$ value of an adduct of the compound or pharmaceutical composition and the different protein over the $K_d$ value of an adduct of the compound or pharmaceutical composition and the protein kinase. In certain embodiments, the selectivity is at least 2-fold, at least 3-fold, at least 5-fold, at least 10-fold, at least 30-fold, at least 100-fold, at least 300-fold, at least 1,000-fold, at least 3,000-fold, at least 10,000-fold, at least 30,000-fold, or at least 100,000-fold. In certain embodiments, the selectivity is not more than 100,000-fold, not more than 10,000-fold, not more than 1,000-fold, not more than 100-fold, not more than 10-fold, or not more than 2-fold. Combinations of the above-referenced ranges (e.g., at least 2-fold and not more than 10,000-fold) are also within the scope of the disclosure.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Synthesis of the Compounds

The compounds provided herein can be prepared from readily available starting materials using the following general methods and procedures. Reactions were monitored by thin layer chromatography (TLC) with 0.25 mm E. Merck pre-coated silica gel plates (60 $F_{254}$) and Waters LCMS system (Waters 2489 UV/Visible Detector, Waters 3100 Mass, Waters 515 HPLC pump, Waters 2545 Binary Gradient Module, Waters Reagent Manager, Waters 2767 Sample Manager) using SunFire™ C18 column (4.6×50 mm, 5 μm particle size): solvent gradient=95% A at 0 min, 0% A at 5 min; solvent A=0.5% TFA in Water; solvent B=Methanol; flow rate: 1.5 mL/min Purification of reaction products was carried out by flash chromatography using CombiFlash®Rf with Teledyne Isco RediSep®Rf High Performance Gold or Silicycle SiliaSep™ High Performance columns (4 g, 12 g, 24 g, 40 g, 80 g or 120 g) or by Waters preparative HPLC system with a C18 column: solvent gradient=100% A at 0 min, 0% A at 15 min; solvent A=0.5% TFA in Water; solvent B=Methanol; flow rate: 20 mL/min. The purity of all compounds was over 95% and was analyzed with Waters LCMS system. $^1$H NMR and $^{13}$C NMR spectra were obtained using a Varian Inova-600 or 400 MHz spectrometer. Chemical shifts are reported relative to chloroform (δ=7.24) for $^1$H NMR or dimethyl sulfoxide (δ=2.50) for $^1$H NMR and dimethyl sulfoxide (δ=39.51) for $^{13}$C NMR. Data are reported as (br=broad, s=singlet, d=doublet, t=triplet, q=quartet, m=multiplet).

Example 1. 4-Acrylamido-N-(3-((2-(2-(2-hydroxyethyl)piperidin-1-yl)-9-isopropyl-9H-purin-6-yl)amino)phenyl)benzamide (THZ-4-124-1)

The synthesis of THZ-4-124-1 follows Synthetic Scheme 1. The reagents and conditions used for the synthesis are: (1) NMP, DIPEA, 100° C. (2) pyridine, 80° C. (3) NMP, 135° C. (4) SnCl$_2$, Ethyl acetate and Methanol (5) acryl chloride, acetonitrile, 0° C.

Synthetic Scheme 1.

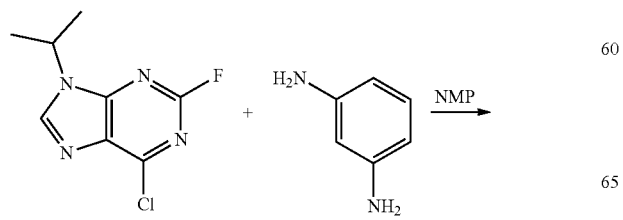

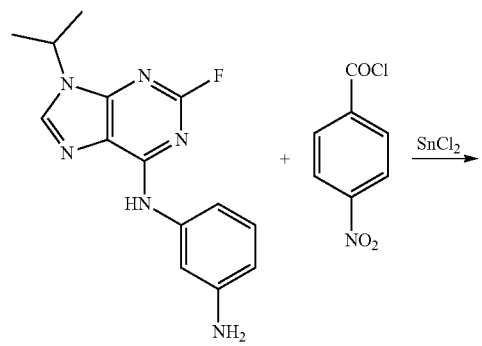

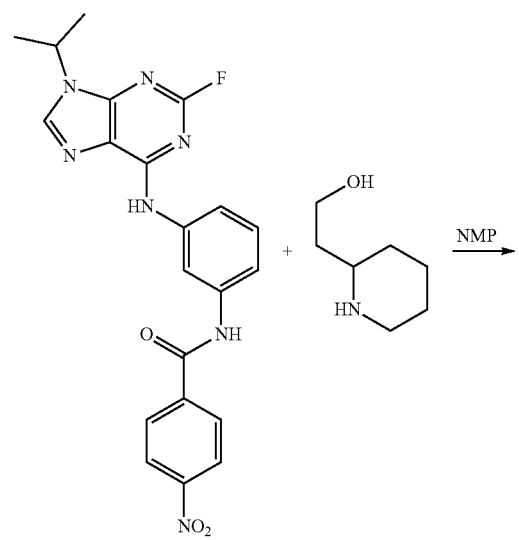

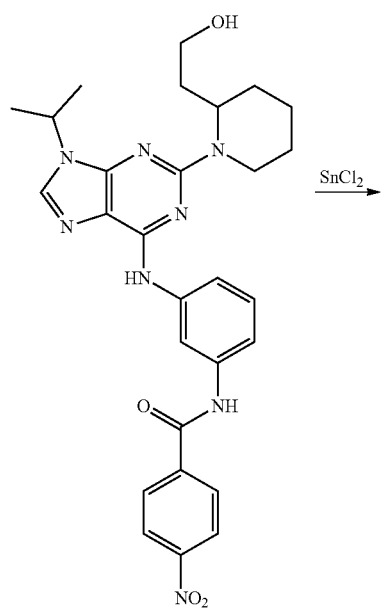

-continued

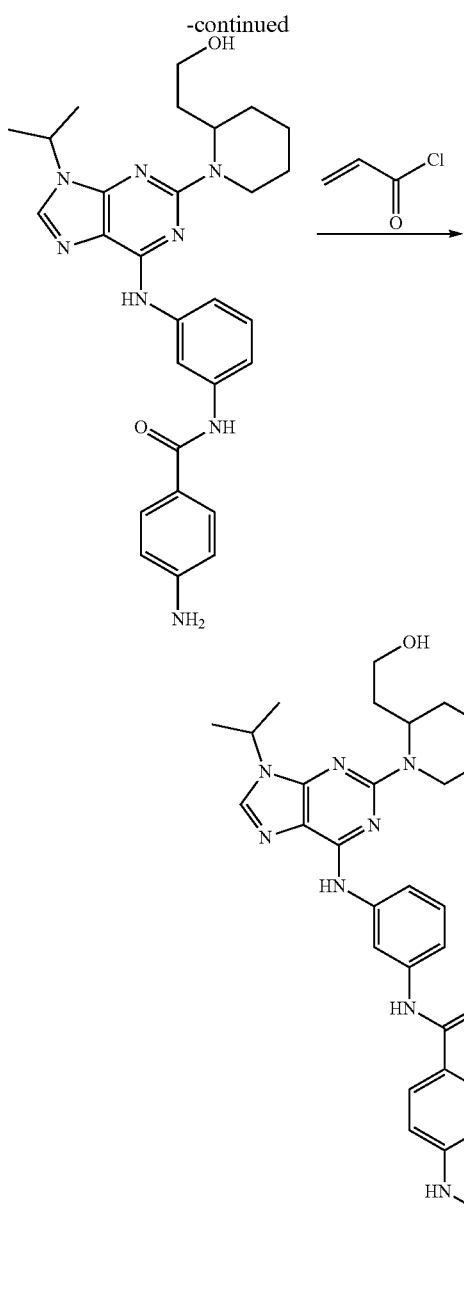

N1-(2-Fluoro-9-isopropyl-9H-purin-6-yl)benzene-1,3-diamine

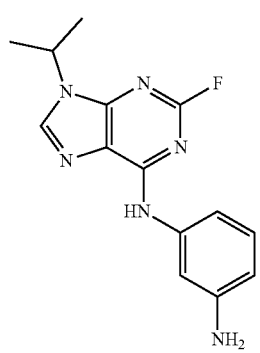 [SMILES: CC(C)n1cnc2c(Nc3cccc(N)c3)nc(F)nc21]

To a solution of 6-chloro-2-fluoro-9-isopropyl-9H-purine (214 mg) in NMP (N-Methyl-2-pyrrolidone) was added benzene-1,3-diamine (130 mg, 1.2 equiv) and diisopropylethylamine (129 mg, 1.0 equiv). The solution was heated for 2 h at 100° C. The cooled solution was diluted with 100 mL of ethyl acetate and then washed with water. The separation by silica gel with $CH_2Cl_2$/methanol (10/1) to give of the product (225 mg, 79%).

N-(3-((2-Fluoro-9-isopropyl-9H-purin-6-yl)amino)phenyl)-4-nitrobenzamide

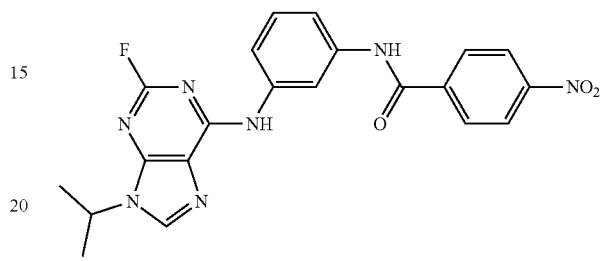

To a stirred solution of the above product (225 mg, 0.80 mmol) in 10 mL of pyridine was added 4-nitrobenzoyl chloride (219 mg, 1.5 equiv) and resulting solution was heated to 80° C. The reaction mixture was stirred for 2 h and concentrated under reduced pressure. The crude was purified by silica gel with $CH_2Cl_2$/methanol (10/1) to give of the product (285 mg, 82%).

N-(3-((2-(2-(2-Hydroxyethyl)piperidin-1-yl)-9-isopropyl-9H-purin-6-yl)amino)phenyl)-4-nitrobenzamide

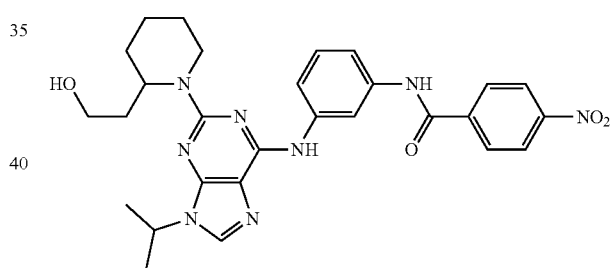

The nitro compound (285 mg, 0.65 mmol) obtained from above reaction was dissolved in 3 mL of NMP and then was added with 2-(piperidin-2-yl)ethanol (170 mg, 2.0 equiv). The solution was heated to 135° C. for 2h and then cooled down to RT. The product was purified by HPLC to give the product (105 mg, 30%).

4-Amino-N-(3-((2-(2-(2-hydroxyethyl)piperidin-1-yl)-9-isopropyl-9H-purin-6-yl)amino)phenyl)benzamide

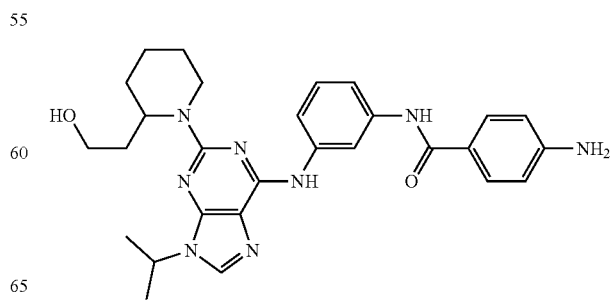

The nitro compound from step 3 (105 mg, 0.19 mmol) was suspended in 5 mL of ethyl acetate/methanol (5:1) and treated with SnCl$_2$ (91 mg, 2.5 equiv). After stirring for 2 h at 80° C., the reaction mixture was cooled to room temperature and poured into saturated aqueous NaHCO$_3$. The mixture was stirred for 10 min and the aqueous phase was then extracted with 30 mL of chloroform and 2-propanol (4:1). The combined organic layer was washed with water and brine, dried over MgSO$_4$, filtered through a pad of celite and concentrated under reduced pressure. The resulting crude product was purified by flash column chromatography with CH$_2$Cl$_2$/methanol (10/1) to provide the title compound (68 mg, 70%).

4-Acrylamido-N-(3-((2-(2-(2-hydroxyethyl)piperidin-1-yl)-9-isopropyl-9H-purin-6-yl)amino)phenyl)benzamide

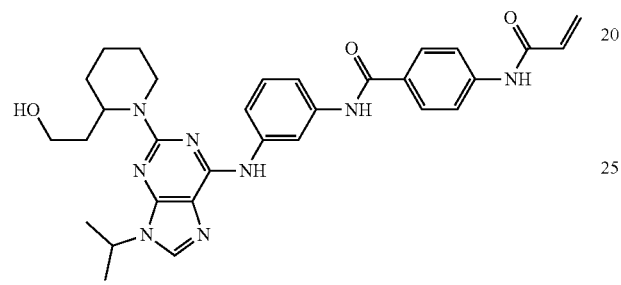

To the solution of the aniline (26 mg, 0.05 mmol)) obtained above in 5 mL of acetonitrile was added diisopropylethylamine (13 mg, 2.0 equiv). The reaction mixture was cooled to 0° C. and then treated with 4-chlorobut-2-enoyl chloride (15 mg, 3.0 equiv) in CH$_2$Cl$_2$. After the stirring for 10 min at 0° C., the reaction was then quenched with Sat. NaHCO$_3$ and extracted with 30 mL of chloroform and 2-propanol (4:1). The solvent was removed at reduce pressure and the crude was purified with HPLC to give the final product THZ-4-124-1 (15 mg, 55%) MS 569 (M+1), $^1$H NMR (DMSO-d6): 10.42 (s, 1H), 10.15 (s, 1H), 9.53 (s, 1H), 8.40 (d, J=12.0 Hz, 2H), 7.93 (d, J=7.2 Hz, 2H), 7.79 (d, J=7.2 Hz, 2H), 7.52 (d, J=7.2 Hz, 1H), 7.27 (m, 2H), 6.43 (m, 1H), 6.28 (d, J=15 Hz, 1H), 5.78 (d, J=9.6 Hz, 1H), 4.99 (s, 1H), 4.65 (m, 2H), 3.45 (m, 2H), 2.88 (t, J=6.8 Hz, 1H), 1.85 (m, 1H), 1.72 (m, 1H), 1.52 (s, 6H), 1.61-1.30 (m, 12H).

Example 2. 4-Acrylamido-N-(3-((2-((trans-4-(dimethylamino)cyclohexyl)amino)-9-isopropyl-9H-purin-6-yl)amino)phenyl)benzamide (THZ-5-38-1)

Synthetic Scheme 2

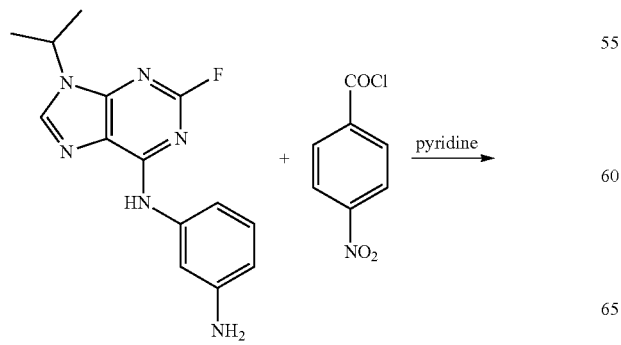

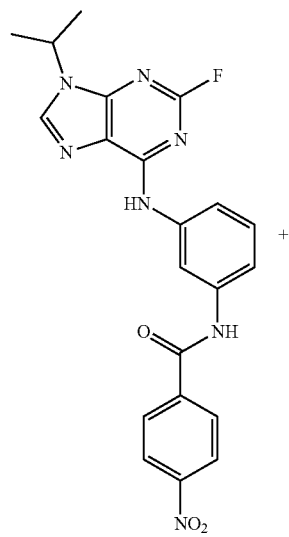

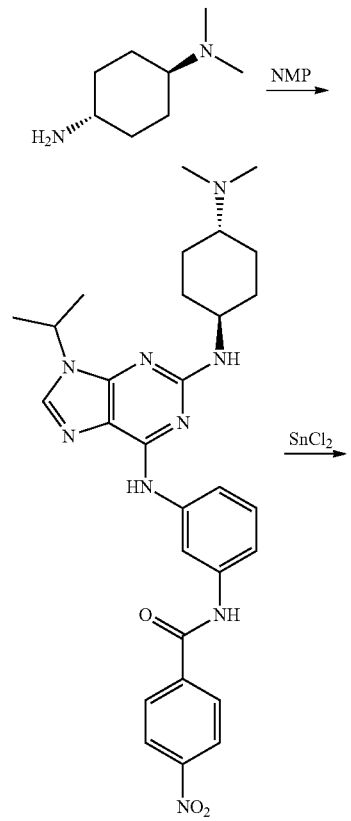

162

N-(3-((2-Fluoro-9-isopropyl-9H-purin-6-yl)amino)phenyl)-4-nitrobenzamide

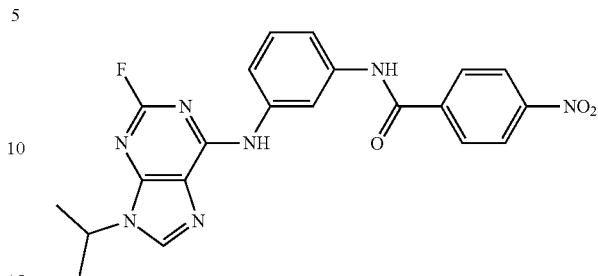

To a stirred solution of N1-(2-fluoro-9-isopropyl-9H-purin-6-yl)benzene-1,3-diamine (286 mg, 1.0 mmol) in 10 mL of pyridine was added 4-nitrobenzoyl chloride (277 mg, 1.5 equiv) and resulting solution was heated to 80° C. The reaction mixture was stirred for 2 h and concentrated under reduced pressure. The crude was purified by silica gel with CH$_2$Cl$_2$/methanol (10/1) to give of the product (326 mg, 75%)

N-(3-((2-(((1r,4r)-4-(dimethylamino)cyclohexyl)amino)-9-isopropyl-9H-purin-6-yl)amino)phenyl)-4-nitrobenzamide

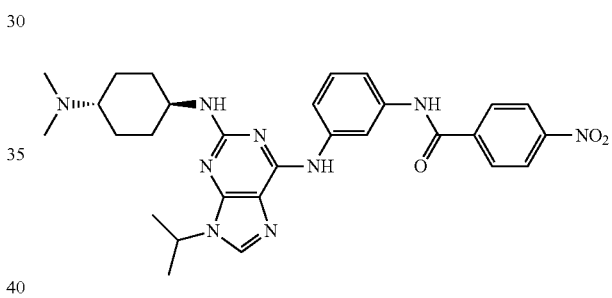

The nitro compound (326 mg, 0.75 mmol) obtained from above reaction was dissolved in 3 mL of NMP and then was added with trans-N1,N1-dimethylcyclohexane-1,4-diamine (213 mg, 2.0 equiv). The solution was heated to 135° C. for 2h and then cooled down to RT. The product was purified by HPLC to give the product (208 mg, 50%).

4-Amino-N-(3-((2-((trans-4-(dimethylamino)cyclohexyl)amino)-9-isopropyl-9H-purin-6-yl)amino)phenyl)benzamide

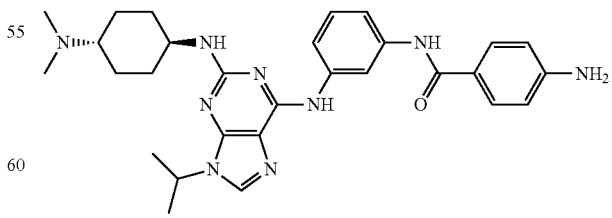

The nitro compound from step 2 (208 mg, 0.37 mmol) was suspended in 5 mL of ethyl acetate/methanol (5:1) and treated with SnCl$_2$ (177 mg, 2.5 equiv). After stirring for 2 h at 80° C., the reaction mixture was cooled to room -continued

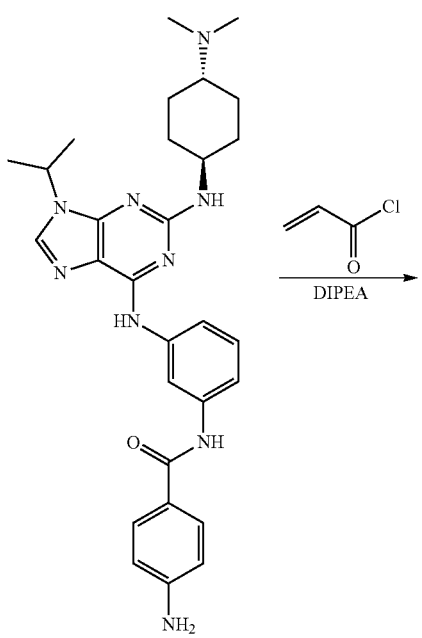

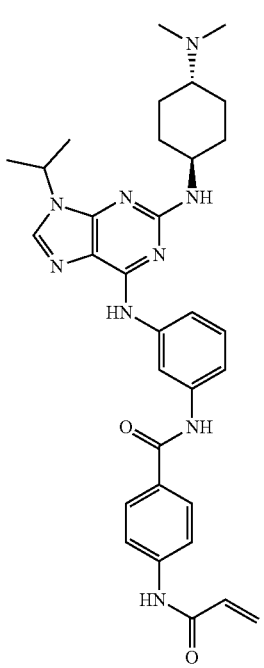

The synthesis of THZ-4-124-1 follows Synthetic Scheme 2. The reagents and conditions used for the synthesis are: (1) pyridine, 80° C. (2) NMP, 135° C. (3) SnCl$_2$, Ethyl acetate and Methanol (4) acryl chloride, acetonitrile, 0° C.

temperature and poured into saturated aqueous NaHCO$_3$. The mixture was stirred for 10 min and the aqueous phase was then extracted with 30 mL of chloroform and 2-propanol (4:1). The combined organic layer was washed with water and brine, dried over MgSO$_4$, filtered through a pad of celite and concentrated under reduced pressure. The resulting crude product was purified by flash column chromatography with CH$_2$Cl$_2$/methanol (10/1) to provide the title compound (126 mg, 65%).

4-Acrylamido-N-(3-((2-((trans-4-(dimethylamino)cyclohexyl)amino)-9-isopropyl-9H-purin-6-yl)amino)phenyl)benzamide

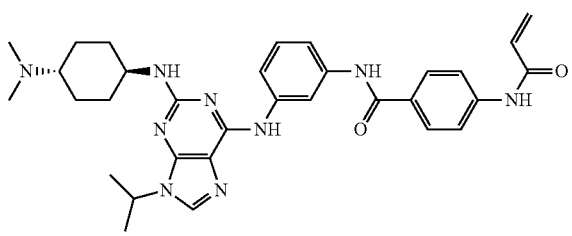 [SMILES: C=CC(=O)Nc1ccc(C(=O)Nc2cccc(Nc3nc(N[C@H]4CC[C@H](N(C)C)CC4)nc4c3ncn4C(C)C)c2)cc1]

To the solution of the aniline (26 mg, 0.05 mmol)) obtained above in 5 mL of acetonitrile was added diisopropylethylamine (13 mg, 2.0 equiv). The reaction mixture was cooled to 0° C. and then treated with 4-chlorobut-2-enoyl chloride (15 mg, 3.0 equiv) in CH$_2$Cl$_2$. After the stirring for 10 min at 0° C., the reaction was then quenched with Sat. NaHCO$_3$ and extracted with 30 mL of chloroform and 2-propanol (4:1). The solvent was removed at reduce pressure and the crude was purified with HPLC to give the final product (17 mg, 60%) MS 582 (M+1), $^1$H NMR (DMSO-d6): 10.45 (s, 1H), 10.17 (s, 1H), 9.63 (br, 1H), 9.43 (br, 1H), 8.26 (br, 1H), 8.25 (s, 1H), 7.98 (d, J=7.2 Hz, 2H), 7.79 (d, J=7.2 Hz, 2H), 7.65 (br, 1H), 7.45 (br, 1H), 7.28 (t, J=7.8 Hz, 1H), 6.48 (m, 1H), 6.28 (d, J=15 Hz, 1H), 5.78 (d, J=9.6 Hz, 1H), 4.62 (m, 1H), 2.75-2.60 (m, 2H), 2.55 (s, 6H), 2.22-1.65 (m, 4H), 1.51 (d, J=6.6 Hz, 6H), 1.55-1.25 (m, 4H).

Example 3. 4-((E)-4-(Dimethylamino)but-2-enamido)-N-(3-((2-(((1r,4r)-4-(dimethylamino)cyclohexyl)amino)-9-isopropyl-9H-purin-6-yl)amino)phenyl)benzamide (THZ-3-49-1)

Synthetic Scheme 3

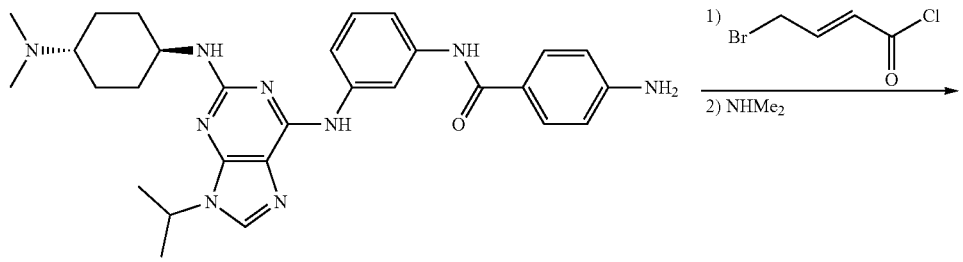

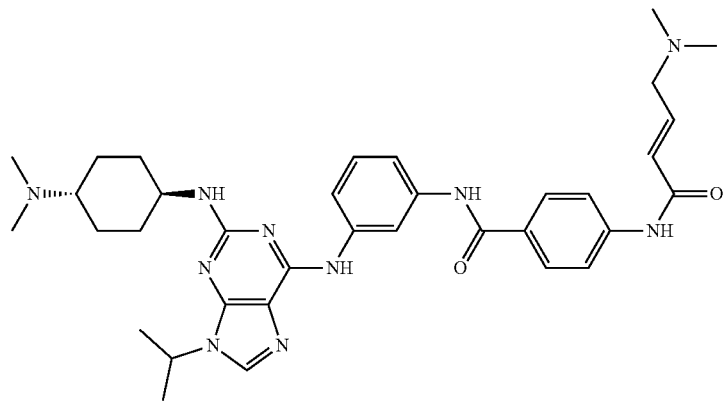

To the solution of the aniline (53 mg) obtained above in 10 mL of acetonitrile was added diisopropylethylamine (26 mg, 2.0 equiv). The reaction mixture was cooled to 0° C. and then treated with 4-chlorobut-2-enoyl chloride (54 mg, 3.0 equiv) in CH$_2$Cl$_2$. The reaction mixture was stirred for 10 min at 0° C. and then treated with a solution of dimethylamine in THF (3 mL, 1M). The reaction mixture was then warmed to room temperature, stirred for 1 h and concentrated under reduced pressure. The resulting crude product was purified by preparative HPLC to give the final product (28.8 mg, 45%). MS 639 (M+1).

Example 4. (E)-N-(3-((2-(3-Aminopiperidin-1-yl)-9-isopropyl-9H-purin-6-yl)amino)phenyl)-4-(4-(dimethylamino)but-2-enamido)benzamide (THZ-4-119-1)

The synthesis of THZ-4-119-1 follows Synthetic Scheme 4. The reagents and conditions used for the synthesis are: (1) NMP, 135° C. (2) SnCl$_2$, Ethyl acetate and Methanol (3) a) 4-bromobut-2-enoyl chloride, CH$_3$CN, NHMe$_2$, 0° C.-RT b) TFA, CHCl$_3$.

Synthetic Scheme 4

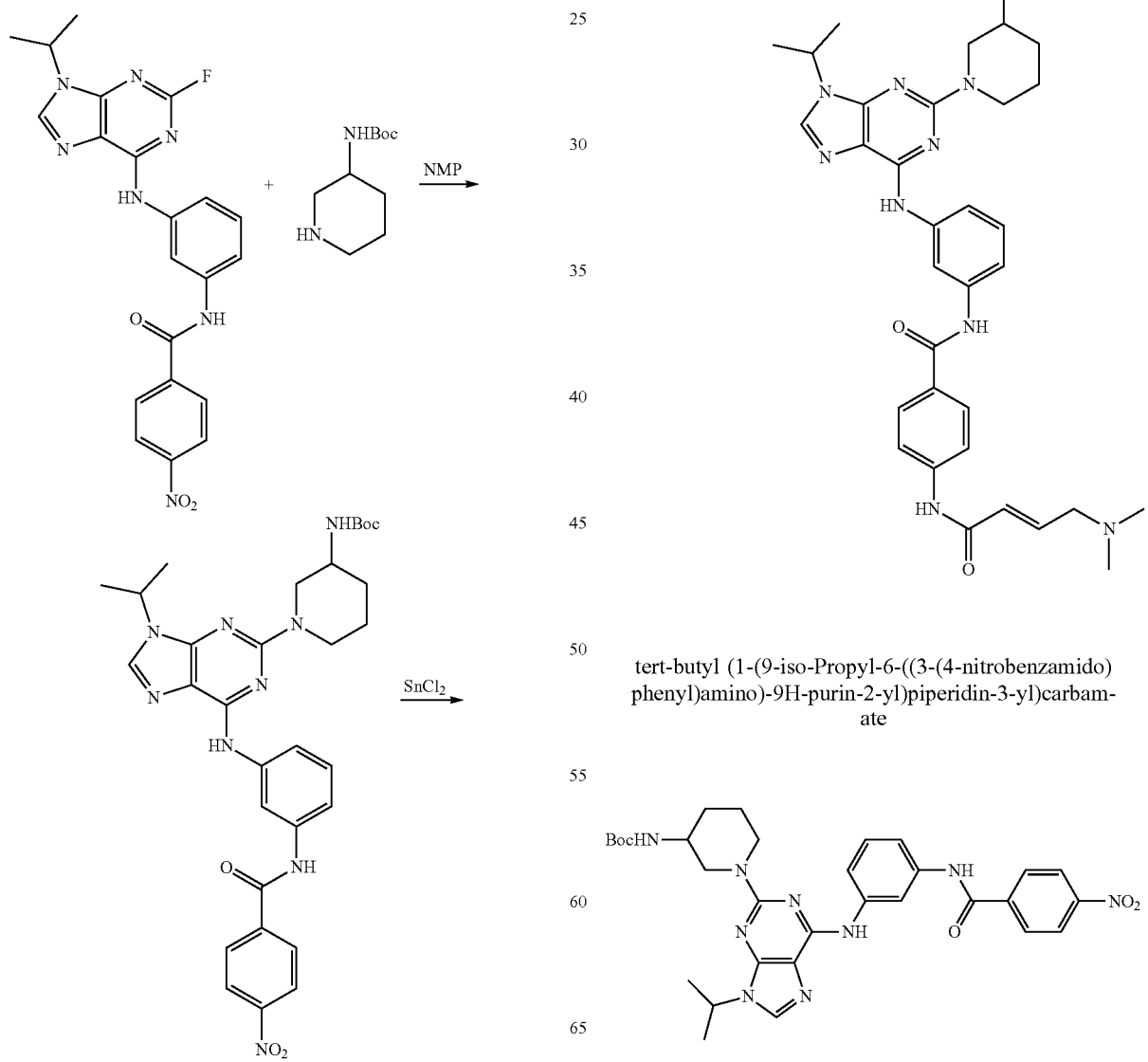

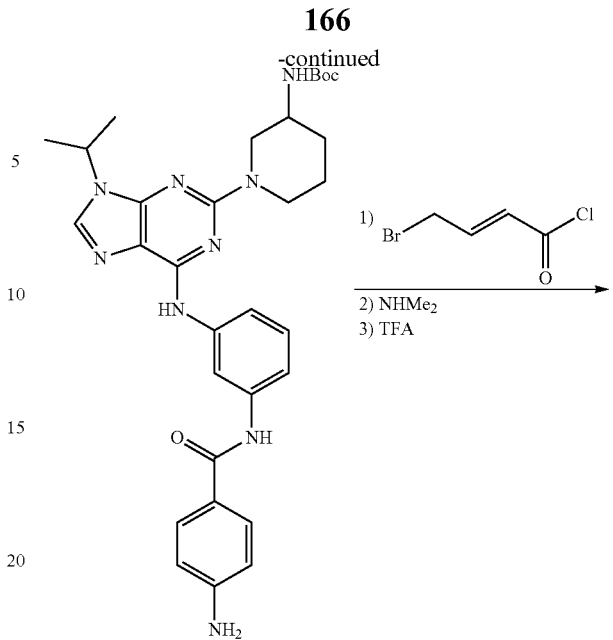

tert-butyl (1-(9-iso-Propyl-6-((3-(4-nitrobenzamido)phenyl)amino)-9H-purin-2-yl)piperidin-3-yl)carbamate To a stirred solution of N-(3-((2-fluoro-9-isopropyl-9H-purin-6-yl)amino)phenyl)-4-nitrobenzamide (435 mg) in NMP (3 mL) was added tert-butyl piperidin-3-ylcarbamate (300 mg, 1.5 equiv) and then the resulting solution was heated to 130° C. for 6 h. After cooling down to RT, the solution was then extracted with ethyl acetate, washed with water and brine and then dried on $Na_2SO_4$. The crude was obtained after removing the solvent and then was used in the next step directly.

tert-butyl (1-(6-((3-(4-Aminobenzamido)phenyl)amino)-9-isopropyl-9H-purin-2-yl)piperidin-3-yl)carbamate

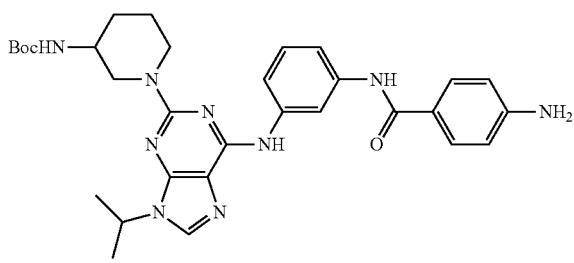 [SMILES: CC(C)n1cnc2c(Nc3cccc(NC(=O)c4ccc(N)cc4)c3)nc(N3CCCC(NC(=O)OC(C)(C)C)C3)nc21]

The crude from step 1 was suspended in 5 mL of ethyl acetate/methanol (5:1) and treated with $SnCl_2$ (562 mg, 2.5 equiv). After stirring for 2 h at 80° C., the reaction mixture was cooled to room temperature and poured into saturated aqueous $NaHCO_3$. The mixture was stirred for 10 min and the aqueous phase was then extracted with 30 mL of chloroform and 2-propanol (4:1). The combined organic layer was washed with water and brine, dried over $MgSO_4$, filtered through a pad of celite and concentrated under reduced pressure. The resulting crude product was purified by flash column chromatography with $CH_2Cl_2$/methanol (10/1) to provide the product (230 mg, 40% from two steps).

(E)-N-(3-((2-(3-Aminopiperidin-1-yl)-9-isopropyl-9H-purin-6-yl)amino)phenyl)-4-(4-(dimethylamino)but-2-enamido)benzamide

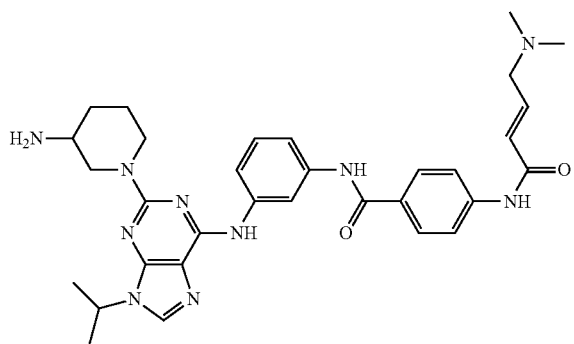 [SMILES: CC(C)n1cnc2c(Nc3cccc(NC(=O)c4ccc(NC(=O)/C=C/CN(C)C)cc4)c3)nc(N3CCCC(N)C3)nc21]

To the solution of the aniline (58 mg) obtained above in 10 mL of acetonitrile was added diisopropylethylamine (26 mg, 2.0 equiv). The reaction mixture was cooled to 0° C. and then treated with 4-chlorobut-2-enoyl chloride (54 mg, 3.0 equiv) in $CH_2Cl_2$. The reaction mixture was stirred for 10 min at 0° C. and then treated with a solution of dimethylamine in THF (3 mL, 1M). The reaction mixture was then warmed up to room temperature, stirred for 1 h and concentrated under reduced pressure. The resulting crude product was then dissolved in CHCl3 (3 mL) and TFA (1 mL). The solution was then allowed for stirring for 2 h. After removing the solvent, the crude was purified by preparative HPLC to give the final product (24.8 mg, 35%). MS 597 (M+1) $^1$H NMR (DMSO-d6): 10.64 (s, 1H), 10.20 (s, 1H), 10.01 (br, 1H), 9.56 (s, 1H), 8.60 (s, 1H), 8.17 (s, 1H), 8.02 (m, 3H), 7.95 (d, J=7.2 Hz, 2H), 7.80 (d, J=7.2 Hz, 2H), 7.45 (d, J=8.4 Hz, 1H), 7.26 (t, J=7.8 Hz, 1H), 7.20 (d, J=8.4 Hz, 1H), 6.78 (m, 1H), 6.50 (d, J=15 Hz, 1H), 4.66 (m, 1H), 4.53 (m, 1H), 4.21 (m, 1H), 3.96 (d, J=7.2 Hz, 2H), 3.37-3.25 (m, 4H), 2.83 (s, 6H), 1.97 (m, 1H), 1.76 (m, 1H), 1.59-1.55 (m, 2H), 1.50 (d, J=6.6 Hz, 6H).

Example 5. (E)-N-(3-((5-(3-Aminopiperidin-1-yl)-3-ethylpyrazolo[1,5-a]pyrimidin-7-yl)amino)phenyl)-4-(4-(dimethylamino)but-2-enamido)benzamide (THZ-4-128-1)

The synthesis of THZ-4-128-1 follows Synthetic Scheme 5. The reagents and conditions used for the synthesis are: (1) a) NMP, DIPEA, 100° C. b) TFA, CHCl$_3$ (2) Pyridine, 80° C. (3) NMP, DIPEA, 135° C. (4) SnCl$_2$, Ethyl acetate and Methanol (5) a) 4-bromobut-2-enoyl chloride, CH$_3$CN, NHMe$_2$, 0° C.-RT b) TFA, CHCl$_3$.

Synthetic Scheme 5

169
-continued

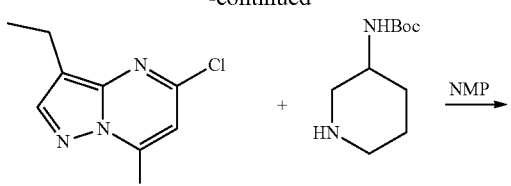

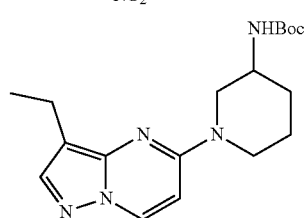

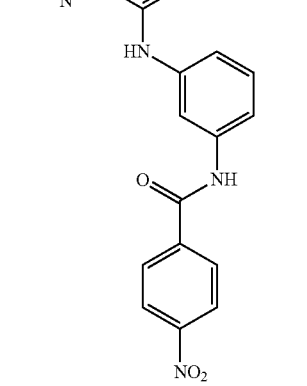

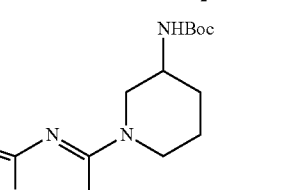

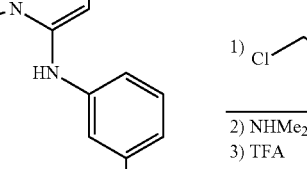

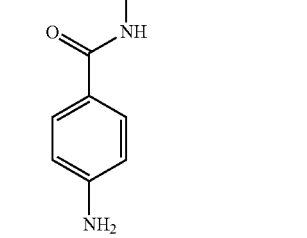

170
-continued

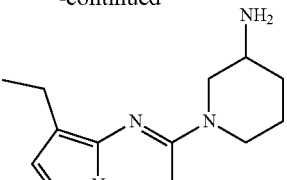

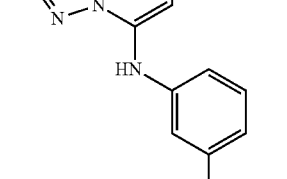

N1-(5-Chloro-3-ethylpyrazolo[1,5-a]pyrimidin-7-yl)
benzene-1,3-diamine

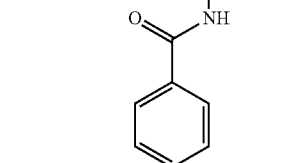

To a solution of 5,7-dichloro-3-ethylpyrazolo[1,5-a]pyrimidine (215 mg) in NMP (N-Methyl-2-pyrrolidone) was added tert-butyl (3-aminophenyl)carbamate (230 mg, 1.1 equiv) and diisopropylethylamine (129 mg, 1.0 equiv). The solution was heated for 2 h at 100° C. The cooled solution was diluted with 100 mL of ethyl acetate and then washed with water. After removing the solvent, the crude was obtained which was dissolved in CHCl$_3$ (3 mL) and TFA (1 mL). The resulting solution was stirred for 1 h and then the solvent was removed in the reduced pressure. The crude was then purified by silica gel with CH$_2$Cl$_2$/methanol (10/1) to give the product (215 mg, 75%).

N-(3-O-Chloro-3-ethylpyrazolo[1,5-a]pyrimidin-7-yl)amino)phenyl)-4-nitrobenzamide

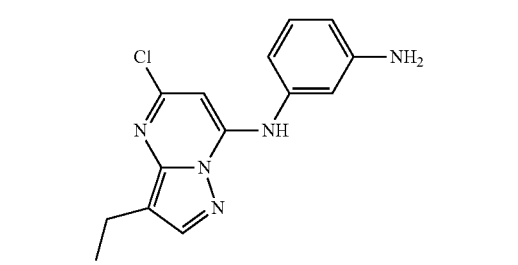 [SMILES: CCc1cnn2c(Nc3cccc(N)c3)cc(Cl)nc12]

To a stirred solution of the above product (215 mg, 0.75 mmol) in 10 mL of pyridine was added 4-nitrobenzoyl chloride (210 mg, 1.5 equiv) and resulting solution was heated to 80° C. The reaction mixture was stirred for 2 h and concentrated under reduced pressure. The crude was purified by silica gel with $CH_2Cl_2$/methanol (10/1) to give the product (212 mg, 65%).

tert-Butyl (1-(3-ethyl-7-O-(4-nitrobenzamido)phenyl)amino)pyrazolo[1,5-a]pyrimidin-5-yl)piperidin-3-yl)carbamate

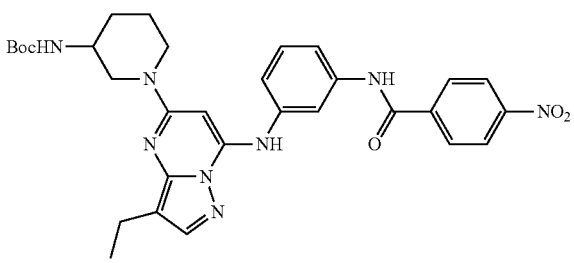 [SMILES: CCc1cnn2c(Nc3cccc(NC(=O)c4ccc([N+](=O)[O-])cc4)c3)cc(N3CCCC(NC(=O)OC(C)(C)C)C3)nc12]

To a stirred solution of the product from step 2 (212 mg) in NMP (3 mL) was added tert-butyl piperidin-3-ylcarbamate (145 mg, 1.5 equiv) and then the resulting solution was heated to 130° C. for 6 h. After cooling down to RT, the solution was then extracted with ethyl acetate washed with water and brine and dried on $Na_2SO_4$. The crude was obtained after removing the solvent and then was used in the next step directly.

tert-butyl (1-(7-((3-(4-Aminobenzamido)phenyl)amino)-3-ethylpyrazolo[1,5-a]pyrimidin-5-yl)piperidin-3-yl)carbamate

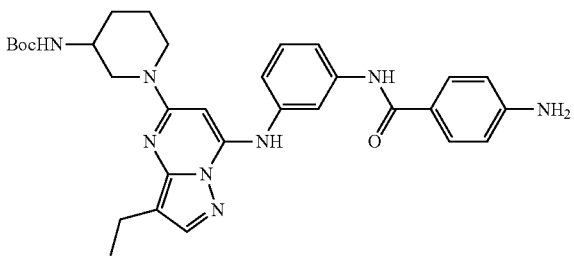 [SMILES: CCc1cnn2c(Nc3cccc(NC(=O)c4ccc(N)cc4)c3)cc(N3CCCC(NC(=O)OC(C)(C)C)C3)nc12]

The crude from step 3 was suspended in 5 mL of ethyl acetate/methanol (5:1) and treated with $SnCl_2$ (281 mg, 2.5 equiv). After stirring for 2 h at 80° C., the reaction mixture was cooled to room temperature and poured into saturated aqueous $NaHCO_3$. The mixture was stirred for 10 min and the aqueous phase was then extracted with 30 mL of chloroform and 2-propanol (4:1). The combined organic layer was washed with water and brine, dried over $MgSO_4$, filtered through a pad of celite and concentrated under reduced pressure. The resulting crude product was purified by flash column chromatography with $CH_2Cl_2$/methanol (10/1) to provide the product (82 mg, 30% from two steps).

(E)-N-(3-((5-(3-Aminopiperidin-1-yl)-3-ethylpyrazolo[1,5-a]pyrimidin-7-yl)amino)phenyl)-4-(4-(dimethylamino)but-2-enamido)benzamide

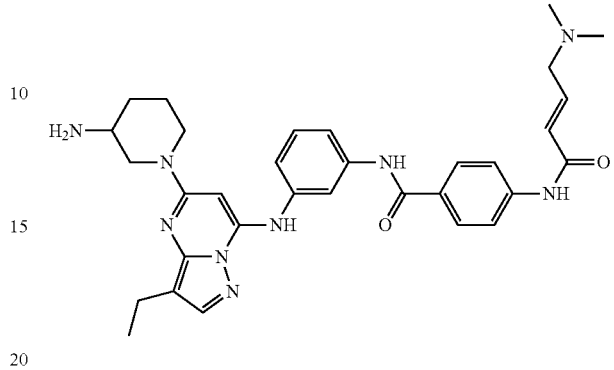

To the solution of the aniline (57 mg) obtained above in 10 mL of acetonitrile was added diisopropylethylamine (26 mg, 2.0 equiv). The reaction mixture was cooled to 0° C. and then treated with 4-chlorobut-2-enoyl chloride (54 mg, 3.0 equiv) in $CH_2Cl_2$. The reaction mixture was stirred for 10 min at 0° C. and then treated with a solution of dimethylamine in THF (3 mL, 1M). The reaction mixture was then warmed to room temperature, stirred for 1 h and concentrated under reduced pressure. The resulting crude product was then dissolved in CHCl3 (3 mL) and TFA (1 mL). The solution was then allowed for stirring for 2 h. After removing the solvent, the crude was purified by preparative HPLC to give the final product (15 mg, 25%). MS 582 (M+1) $^1$H NMR (DMSO-d6): 10.64 (s, 1H), 10.32 (s, 1H), 10.09 (br, 1H), 9.44 (s, 1H), 8.03 (m, 1H), 7.98 (br, 2H), 7.95 (d, J=7.2 Hz, 2H), 7.80 (d, J=7.2 Hz, 2H), 7.43 (d, J=8.4 Hz, 1H), 7.37 (t, J=7.8 Hz, 1H), 7.15 (d, J=8.4 Hz, 1H), 6.78 (m, 1H), 6.50 (d, J=15 Hz, 1H), 6.06 (s, 1H), 4.31 (m, 1H), 3.96 (d, J=7.2 Hz, 2H), 3.86 (m, 1H), 3.20-3.10 (m, 3H), 2.79 (s, 6H), 2.59 (q, J=8.4 Hz, 2H), 1.97 (m, 1H), 1.76 (m, 1H), 1.59 (m, 2H), 1.23 (d, J=7.8 Hz, 3H).

Example 6. 4-Acrylamido-N-(3-(3-ethyl-5-(2-(2-hydroxyethyl)piperidin-1-yl)pyrazolo[1,5-a]pyrimidin-7-ylamino)phenyl)benzamide (SB1-E-24)

Synthetic Scheme 6

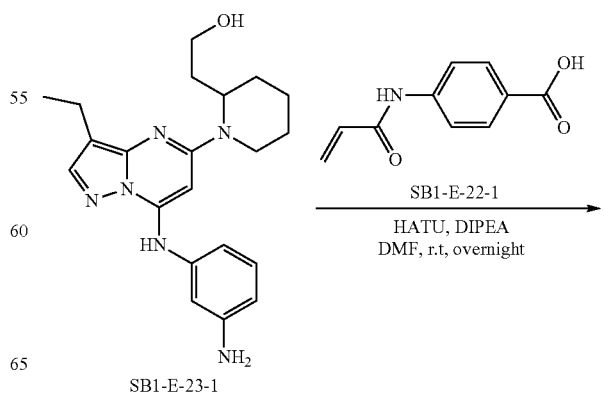

173
-continued

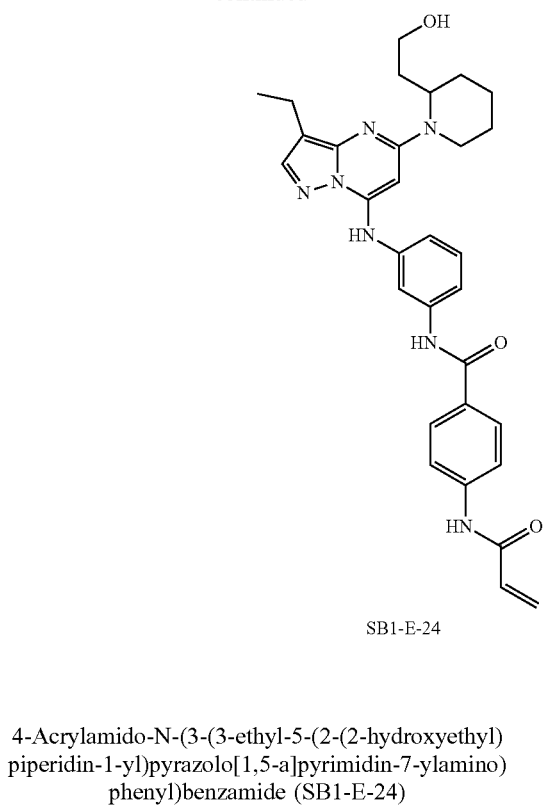

SB1-E-24

4-Acrylamido-N-(3-(3-ethyl-5-(2-(2-hydroxyethyl)
piperidin-1-yl)pyrazolo[1,5-a]pyrimidin-7-ylamino)
phenyl)benzamide (SB1-E-24)

The mixture of SB1-E-23-1 (100 mg, 0.263 mmol), SB1-E-22-1 (100 mg, 0.523 mmol), HATU (200 mg, 0.526 mmol), DIPEA (0.5 mL) and DMF (5 mL) was stirred at r.t overnight. After completion, the mixture was purified by prep-TLC (DCM/MeOH=15/1) and prep-HPLC (C18 column, CH$_3$CN/H$_2$O, containing 0.05% NH$_4$HCO$_3$) to obtain SB1-E-24 (off-white solid, 23 mg, 16%). HPLC: 99% (254 nm); LCMS (m/z): 554 [M+H]$^+$; $^1$H NMR (DMSO-d$_6$, 500 MHz): δ 10.45 (s, 1H), 10.27 (s, 1H), 9.63 (bs, 1H), 8.01 (s, 1H), 7.97 (d, J=9.0 Hz, 2H), 7.83 (m, 3H), 7.49 (d, J=8.5 Hz, 1H), 7.39 (t, J=8.5 Hz, 1H), 7.19 (d, J=7.5 Hz, 1H), 6.48 (dd, J$_1$=16.5 Hz, J$_2$=10.5 Hz, 1H), 6.31 (d, J=16.5 Hz, 1H), 6.03 (s, 1H), 5.81 (d, J=10.5 Hz, 1H), 4.58 (s, 1H), 4.17 (m, 1H), 3.33-3.43 (m, 2H), 2.99 (m, 1H), 2.55-2.60 (m, 2H), 1.18-1.89 (m, 12H).

Example 7. 4-Acrylamido-N-(3-(5-((1r,4r)-4-(dimethylamino)cyclohexylamino)-3-isopropylpyrazolo[1,5-a]pyrimidin-7-ylamino)phenyl)benzamide (SB1-E-25)

Synthetic Scheme 7

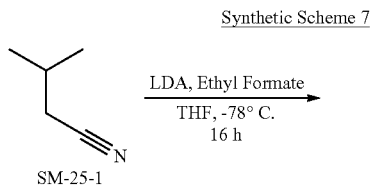

174
-continued

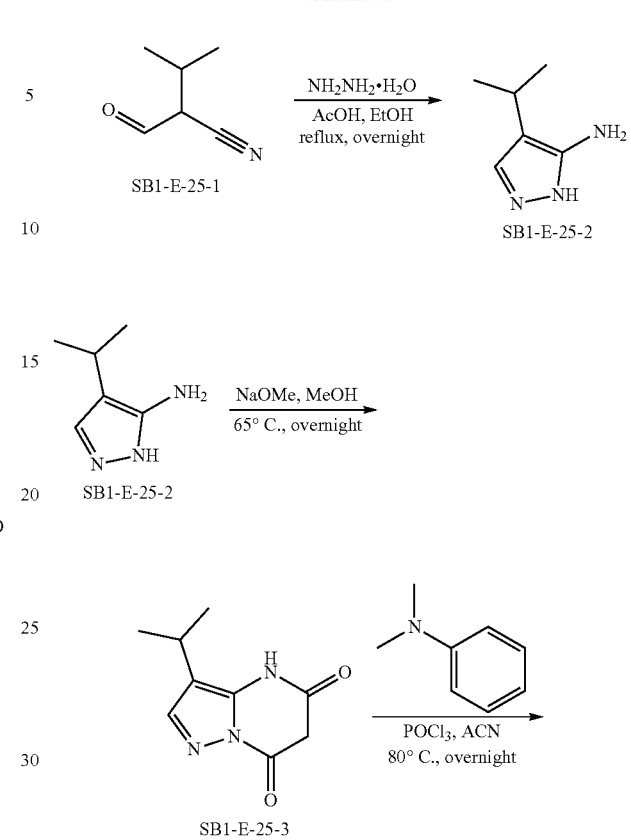

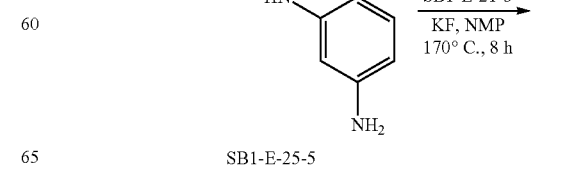

-continued

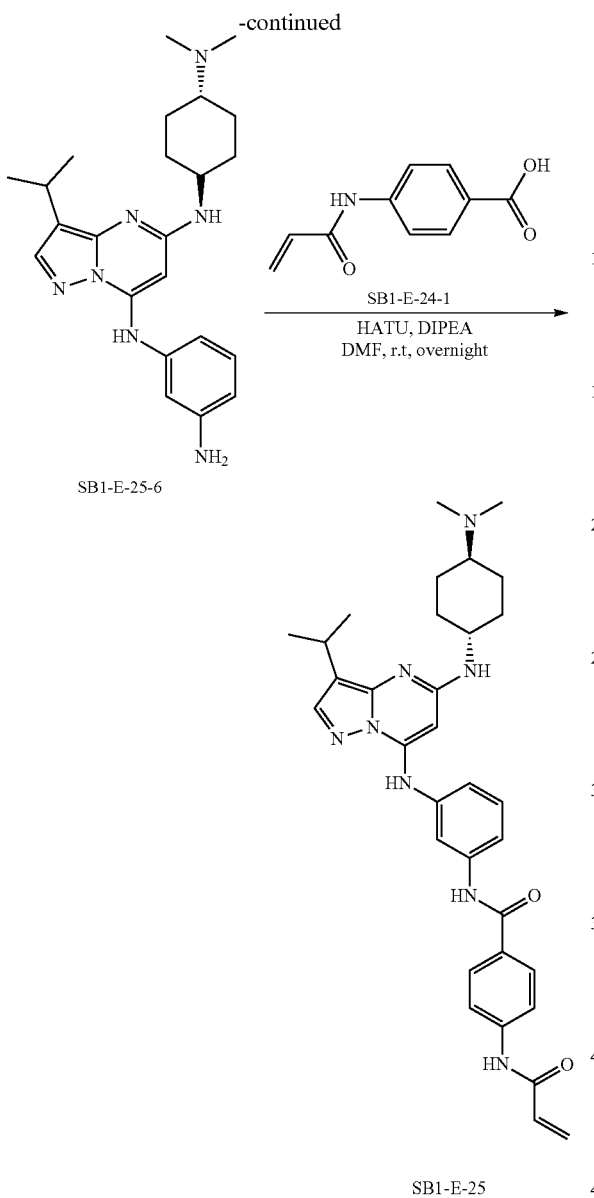

2-Formyl-3-methylbutanenitrile (SB1-E-25-1)

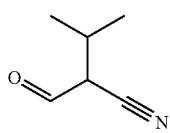

To a solution of SM-25-1 (10.0 g, 120 mmol) in THF (10 mL), LDA (2M, 60 ml, 120 mmol) was added slowly at −78° C. After completion, the mixture was added to a solution of ethyl formate (9.0 g, 121.5 mmol) in THF (40 ml) at −78° C. After completion, the mixture was stirred at 0° C. for 3h. The solvent was removed, then water (100 mL) was added, and the resulting mixture was extracted with Et$_2$O (200 mL×3). The combined organic layer was washed with brine (100 mL×2), dried over sodium sulfate, filtered through Celite, and concentrated under reduced pressure to give the crude SB1-E-25-1 (colorless oil, 12.5 g, 94% yield). The crude product was used directly for the next step without further purification.

4-iso-Propyl-1H-pyrazol-5-amine (SB1-E-25-2)

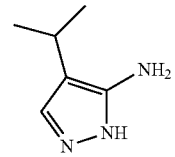

To a solution of SB1-E-25-1 (12.5 g, 112 mmol) in EtOH (200 mL), hydrazine hydrate (28 g, 560 mmol) and AcOH (26.9 g, 448 mmol) was added. The mixture was stirred at 80° C. for 4h. The solvent was removed, then water (200 ml) was added, and the resulting mixture was extracted with DCM (300 mL×3). The combined organic layer was washed with brine (100 mL×2), dried over sodium sulfate, filtered through Celite, and concentrated under reduced pressure. The residue was purified by column chromatography on silica gel (DCM/MeOH=15/1 to 8/1) to afford SB1-E-25-2 (yellow solid, 13.3 g, 95% yield). LCMS (m/z): 126 [M+H]$^+$.

3-iso-Propylpyrazolo[1,5-a]pyrimidine-5,7(4H,6H)-dione (SB1-E-25-3)

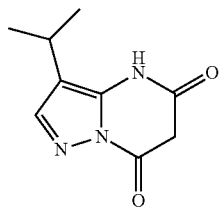

To a solution of SB1-E-25-2 (1.7 g, 13.6 mmol) in CH$_3$OH (20 ml), SM-25-2 (5.4 g, 40.8 mmol) and sodium methoxide (3.7 g, 68 mmol) was added. The mixture was stirred at 70° C. for 4 h. After completion, the solvent was removed, water (200 ml) was added, then 1M HCl aq. (40 mL) was added to adjust the pH to 3. The mixture was filtered and the filter residue was evaporated to dryness under reduced pressure to give the crude SB1-E-25-3 (off-white solid, 2.5 g, 95% yield). LCMS (m/z): 194 [M+H]$^+$.

5,7-Dichloro-3-isopropylpyrazolo[1,5-a]pyrimidine (SB1-E-25-4)

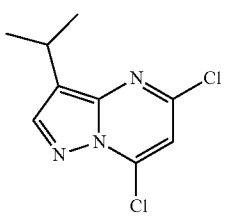

To a solution of SB1-E-25-3 (2.4 g, 12.4 mmol) in CH₃CN (30 ml), POCl₃ (9.4 g, 62 mmol) and N,N-dimethylaniline (4.5 g, 37.2 mmol) was added. The mixture was stirred at 80° C. for 8 h. The mixture was concentrated and water (40 mL) was added. The mixture was filtered and concentrated to remove the solvent. The residue was washed with water (100 ml) and then evaporated to dryness under reduced pressure to give the crude SB1-E-25-4 (brown solid, 2.7 g, 85% yield). LCMS (m/z): 230 [M+H]⁺.

N¹-(5-Chloro-3-isopropylpyrazolo[1,5-a]pyrimidin-7-yl)benzene-1,3-diamine (SB1-E-25-5)

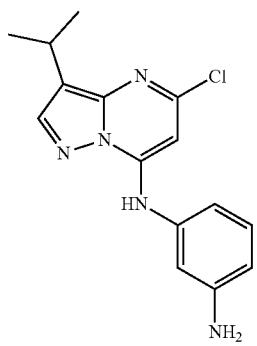 [SMILES: CC(C)c1cnn2c(Nc3cccc(N)c3)cc(Cl)nc12]

To a solution of SB1-E-25-4 (2.6 g, 11.3 mmol), in i-PrOH (20 mL), 1,3-diaminobenzene (1.47 g, 13.6 mmol) and DIPEA (2.92 g, 22.6 mmol) was added. The mixture was stirred at 110° C. for 8 h. The mixture was concentrated, water (20 mL) was added, and the resulting mixture was extracted with DCM (30 mL×3). The combined organic layer was washed with brine (20 mL×2), dried over sodium sulfate, filtered through Celite, and concentrated under reduced pressure. The residue was purified by column chromatography on silica gel (PE/ethyl acetate=8/1 to 4/1) to afford SB1-E-25-5 (off-white solid, 2.2 g, 65% yield). LCMS (m/z): 302 [M+H]⁺.

N7-(3-Aminophenyl)-N5-((1s,4s)-4-(dimethylamino)cyclohexyl)-3-isopropylpyrazolo[1,5-a]pyrimidine-5,7-diamine (SB1-E-25-6)

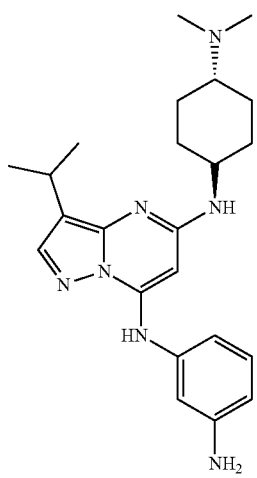

The mixture of SB1-E-25-5 (350 mg, 1.16 mmol), SB1-E-21-3 (200 mg, 1.41 mmol), KF (400 mg, 6.88 mmol) and NMP (2 mL) was stirred at 170° C. for 8 h, after completion, concentrated to remove the solvent, the residue was purified by prep-TLC (DCM/MeOH=10/1) to obtain SB1-E-25-6 (light brown solid, 130 mg, yield 28%). LCMS (m/z): 408 [M+H]⁺.

4-Acrylamido-N-(3-(5-((1r,4r)-4-(dimethylamino)cyclohexylamino)-3-isopropylpyrazolo[1,5-a]pyrimidin-7-ylamino)phenyl)benzamide (SB1-E-25)

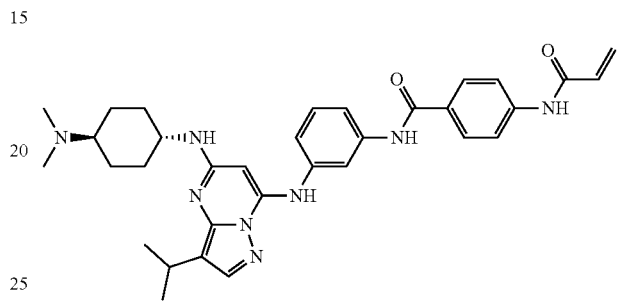

The mixture of SB1-E-25-5 (40 mg, 0.0981 mmol), SB1-E-24-1 (35 mg, 0.183 mmol), HATU (75 mg, 0.197 mmol) and DMF (5 mL) was stirred at r.t overnight. After completion, the mixture was purified by prep-TLC (DCM/MeOH=8/1) and prep-HPLC (C18 column, CH₃CN/H₂O, containing 0.05% NH₄HCO₃) to obtain SB1-E-25 (gray solid, 15 mg, yield 26%). HPLC: 97% (254 nm); LCMS (m/z): 581 [M+H]⁺; ¹H NMR (DMSO-d₆, 500 MHz): δ 10.44 (s, 1H), 10.26 (s, 1H), 9.07 (s, 1H), 7.97 (d, J=8.5 Hz, 2H), 7.85 (s, 1H), 7.82 (d, J=8.5 Hz, 2H), 7.67 (s, 1H), 7.64 (t, J=4.0 Hz, 1H), 7.37 (t, J=8.0 Hz, 1H), 7.10 (d, J=7.5 Hz, 1H), 6.62 (d, J=7.0 Hz, 1H), 6.47 (dd, J₁=17.0 Hz, J₂=10.5 Hz, 1H), 6.31 (d, J=17.0 Hz, 1H), 5.81 (d, J=10.5 Hz, 1H), 3.63 (s, 1H), 3.00 (m, 1H), 1.77-2.17 (m, 11H), 1.09-1.29 (m, 10H).

Example 8. 4-Acrylamido-N-(3-(5-((1r,4r)-4-(dimethylamino)cyclohexylamino)-3-ethylpyrazolo[1,5-a]pyrimidin-7-ylamino)phenyl)benzamide (SB1-E-22)

Synthetic Scheme 8

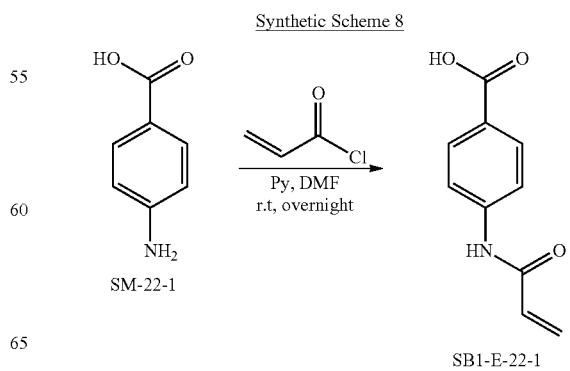

179
-continued

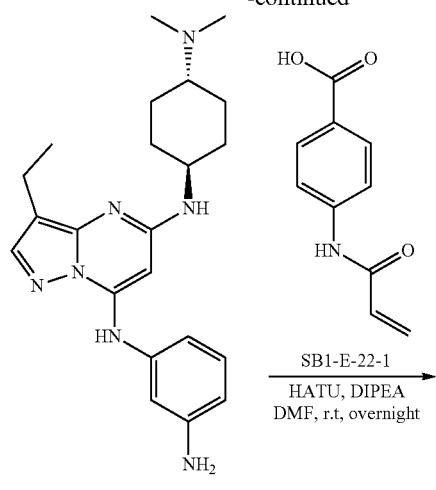

SB1-E-21-7

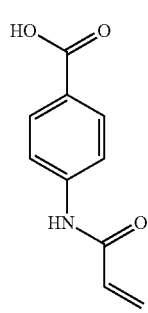

4-Acrylamidobenzoic Acid (SB1-E-22-1)

To the solution of SM-22-1 (500 mg, 3.65 mmol) in pyridine (20 mL) was added acrylyl chloride (500 mg, 5.52 mmol), the mixture was stirred at r.t overnight, after completion, the mixture was poured to a ice-water (20 mL), filtered, the solid was washed with H₂O, dried to obtain SB1-E-22-1 (light yellow solid, 600 mg, yield 86%). LCMS (m/z): 192 [M+H]⁺.

180

4-Acrylamido-N-(3-(5-((1r,4r)-4-(dimethylamino) cyclohexylamino)-3-ethylpyrazolo[1,5-a]pyrimidin-7-ylamino)phenyl)benzamide (SB1-E-22)

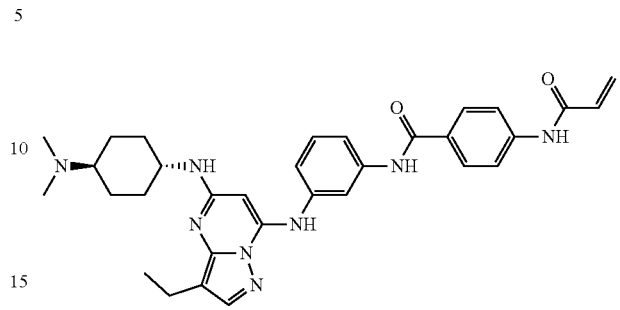

The mixture of SB1-E-21-7 (50 mg, 0.127 mmol), SB1-E-22-1 (45 mg, 0.235 mmol), HATU (88 mg, 0.231 mmol), DIPEA (0.3 mL) and DMF (2 mL) was stirred at r.t overnight, after completion, concentrated to remove the solvent, the residue was purified by prep-TLC (DCM/MeOH=10/) and prep-HPLC (C18 column, CH₃CN/H₂O, containing 0.05% NH₄HCO₃) to obtain SB1-E-22 (light gray solid, 7 mg, yield 10%). HPLC: 95% (214 nm); LCMS (m/z): 567 [M+H]⁺; ¹H NMR (DMSO-d₆, 500 MHz): δ 10.44 (s, 1H), 10.25 (s, 1H), 9.06 (s, 1H), 7.97 (d, J=9.0 Hz, 2H), 7.85 (d, J=5.0 Hz, 1H), 7.82 (d, J=9.0 Hz, 2H), 7.70 (s, 1H), 7.63 (d, J=8.0 Hz, 1H), 7.37 (t, J=8.5 Hz, 1H), 7.10 (d, J=7.0 Hz, 1H), 6.61 (d, J=7.5 Hz, 1H), 6.47 (dd, J₁=16.5 Hz, J₂=9.5 Hz, 1H), 6.31 (d, J=16.5 Hz, 1H), 5.81 (d, J=9.5 Hz, 1H), 5.63 (s, 1H), 3.68 (s, 1H), 2.54 (q, J=7.5 Hz, 2H), 2.15 (s, 6H), 1.77-2.15 (m, 5H), 1.11-1.27 (m, 7H).

Example 9. 4-Acrylamido-N-(3-(8-ethyl-2-(2-(2-hydroxyethyl)piperidin-1-yl)pyrazolo[1,5-a][1,3,5]triazin-4-ylamino)phenyl)benzamide (SB1-E-19)

Synthetic Scheme 9

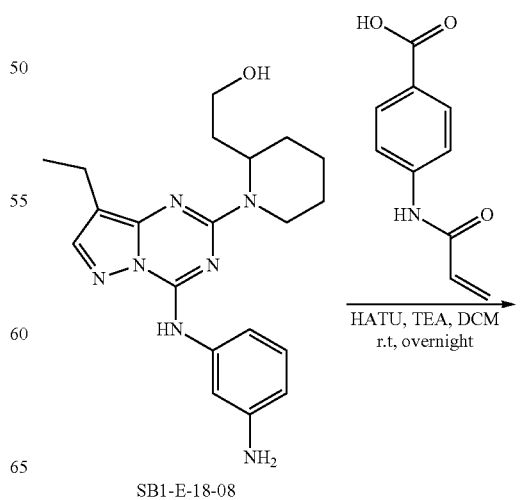

SB1-E-18-08

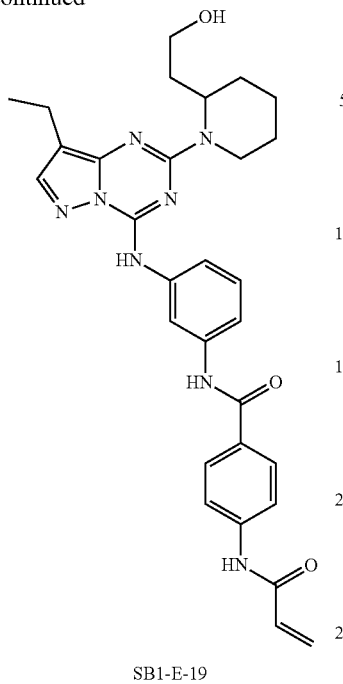

SB1-E-19

4-Acrylamido-N-(3-(8-ethyl-2-(2-(2-hydroxyethyl)piperidin-1-yl)pyrazolo[1,5-a][1,3,5]triazin-4-ylamino)phenyl)benzamide (SB1-E-19)

A mixture of SB1-E-18-08 (70 mg, 0.18 mmol), 4-acrylamidobenzoic acid (52 mg, 0.27 mmol), HATU (68 mg, 0.18 mmol) and triethylamine (54 mg, 0.54 mmol) in DCM (3 mL) was stirred at r.t overnight, diluted with dichloromethane (10 ml), washed with water (10 mL) and saturated sodium bicarbonate solution (10 mL×2), dried over anhydrous sodium sulfate filtered and concentrated in vacuo, purified by prep-HPLC (C18 column, $CH_3CN/H_2O$, containing 0.05% TFA) to get SB1-E-19, also referred to herein as E19 and E-19 (white solid, 25 mg, yield: 25%). HPLC: 100% (254 nm); LCMS (m/z): 555 $[M+H]^+$; $^1H$ NMR (DMSO-$d_6$, 500 MHz): δ: 10.45 (s, 1H), 10.19 (s, 1H), 8.49 (s, 1H), 7.97 (d, J=8.5 Hz, 2H), 7.88 (s, 1H), 7.82 (d, J=8.5 Hz, 1H), 7.45-7.51 (m, 2H), 7.34 (t, J=8.0 Hz, 1H), 6.48 (dd, J=16.5, 10 Hz, 1H), 6.32 (d, J=17.0 Hz, 1H), 5.82 (d, J=10.0 Hz, 1H), 5.00 (s, 1H), 4.66 (d, J=10.0 Hz, 1H), 2.91 (t, J=13.0 Hz, 1H), 2.50-2.54 (m, 2H), 1.56-1.71 (m, 8H), 1.38-1.40 (m, 1H), 1.20-1.23 (m, 4H).

Example 10. N-(3-(2-((1s,4s)-4-(Dimethylamino)cyclohexylamino)-9-isopropyl-9H-purin-6-ylamino)phenyl)acrylamide (SB1-E-14)

Synthetic Scheme 10

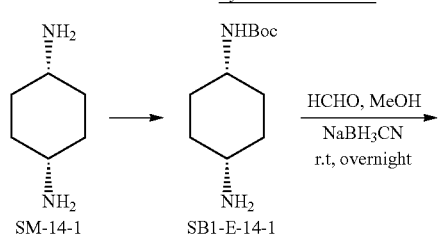

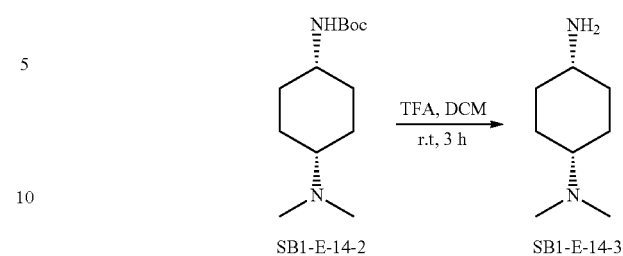

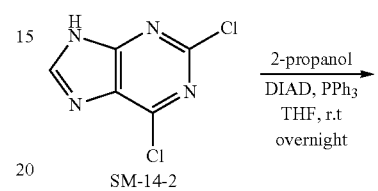

SM-14-2

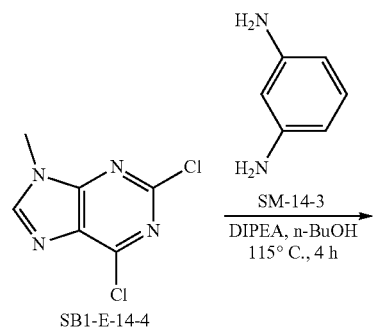

SB1-E-14-4

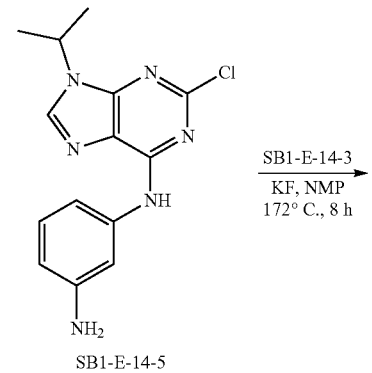

SB1-E-14-5

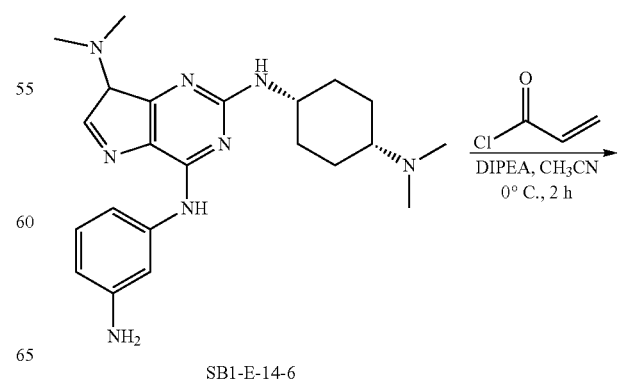

SB1-E-14-6

-continued

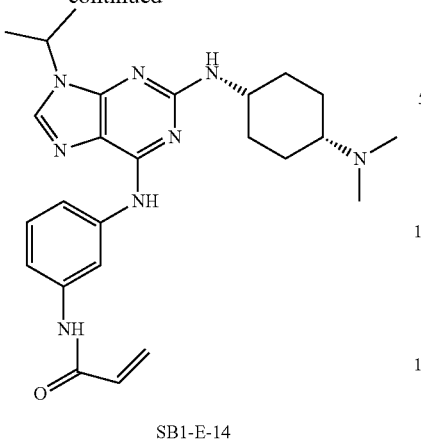

SB1-E-14 tert-Butyl (1s,4s)-4-(dimethylamino)cyclohexylcarbamate (SB1-E-14-2)

To the solution of SB1-E-14-1 (1.0 g, 4.67 mmol), MeOH (30 mL) and HCHO (600 mg, 20.0 mmol) was added NaBH$_3$CN (1.5 g, 23.9 mmol), the mixture was stirred at r.t overnight. After completion, concentrated to remove the solvent, then extracted with ethyl acetate (100 mL×4), the organic phase was washed with H$_2$O (50 mL), brine (50 mL×2), dried with Na$_2$SO$_4$. Filtered, concentrated to remove the solvent, the residue was purified by silica gel (DCM/MeOH=10/1, 4/1) to obtain SB1-E-14-2 (light brown solid, 800 mg, yield 71%). LCMS (m/z): 243 [M+H]$^+$.

(1s,4s)-N1,N1-Dimethylcyclohexane-1,4-diamine (SB1-E-14-3)

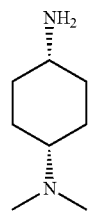

The mixture of SB1-E-14-2 (350 mg, 1.44 mmol), DCM (3 mL) and TFA (3 mL) was stirred at r.t for 3 h. after completion, concentrated to remove the solvent to obtain SB1-E-14-3 (light yellow sticky oil, 200 mg, yield 98%). LCMS (m/z): 143 [M+H]$^+$.

2,6-Dichloro-9-isopropyl-9H-purine (SB1-E-14-4)

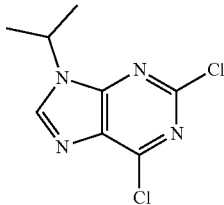

To a solution of SM-14-2 (3.0 g, 15.3 mmol) and 2-propanol (2.75 g, 45.9 mmol) in THF (30 mL), PPh$_3$ (8.02 g, 30.6 mmol) was added. The mixture was stirred at room temperature for 10 min. Then DIEA (6.18 g, 30.6 mmol) was added. The final mixture was stirred at 70° C. for 3h. after completion, concentrated to remove the solvent, water (30 mL) was added, the resulting mixture was extracted with DCM (50 mL×3). The combined organic layer was washed with brine (50 mL×2), dried over sodium sulfate, filtered through Celite, and concentrated under reduced pressure. The residue was purified by column chromatography on silica gel (ethyl acetate/acetone=20/1 to 10/1) to afford SB1-E-14-4 (off-white solid, 2.34 g, 66% yield).

N1-(2-Chloro-9-isopropyl-9H-purin-6-yl)benzene-1,3-diamine (SB1-E-14-5)

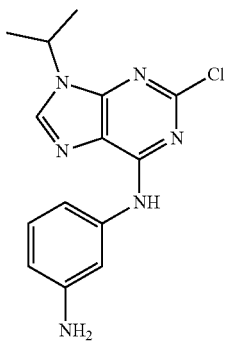 [SMILES: CC(C)n1cnc2c(Nc3cccc(N)c3)nc(Cl)nc21]

The mixture of SB1-E-14-4 (1.2 g, 5.19 mmol), SM-14-3 (850 mg, 7.86 mmol), n-BuOH (30 mL) and DIPEA (2 mL) was stirred at 115° C. for 4 h. after completion, concentrated to remove the solvent, the residue was purified by silica gel (DCM/MeOH=50/1) to obtain SB1-E-14-5 (light brown solid, 1.2 g, yield 76%). LCMS (m/z): 303 [M+H]$^+$.

N6-(3-Aminophenyl)-N2-((1s,4s)-4-(dimethylamino)cyclohexyl)-9-isopropyl-9H-purine-2,6-diamine (SB1-E-14-6)

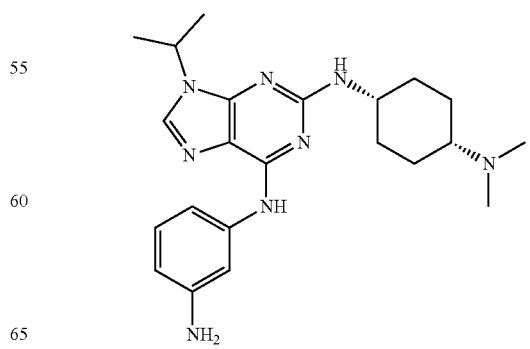

The mixture of SB1-E-14-5 (370 mg, 1.22 mmol), SB1-E-14-3 (200 mg, 1.41 mmol), KF (360 mg, 6.20 mmol) and NMP (2 mL) was stirred at 172° C. for 8 h. after completion, the mixture was purified by silica gel (DCM/MeOH=10/1, 8/1, 6/1) to obtain SB1-E-14-6 (brown solid, 150 mg, yield 30%). LCMS (m/z): 409 [M+H]⁺.

N-(3-(2-((1s,4s)-4-(Dimethylamino)cyclohexylamino)-9-isopropyl-9H-purin-6-ylamino)phenyl)acrylamide (SB1-E-14)

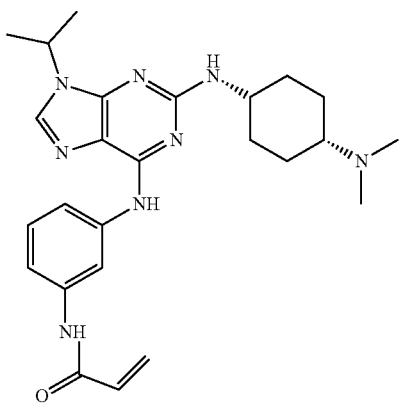

To a solution of SB1-E-14-6 (60 mg, 0.147 mmol), DIPEA (0.5 mL) in CH₃CN (4 mL) was added the solution of acryloyl chloride (20 mg, 0.221 mmol) in CH₃CN (1 mL) dropwise, the mixture was stirred at OC for 2 h. after completion, concentrated to remove the solvent, the residue was purified by prep-TLC (DCM/MeOH=30/1) and prep-HPLC (C18 column, CH₃CN/H₂O, containing 0.05% NH₄HCO₃) to obtain SB1-E-14 (off-white solid, 20 mg, yield 29%). HPLC: 100% (254 nm); LCMS (m/z): 463 [M+H]⁺; ¹H NMR (DMSO-d₆, 400 MHz): δ 10.04 (s, 1H), 9.38 (s, 1H), 8.44 (s, 1H), 7.95 (s, 1H), 7.63 (d, J=7.2 Hz, 1H), 7.25 (s, 1H), 7.20 (t, J=8.0 Hz, 1H), 6.47 (dd, J₁=16.8 Hz, J₂=9.6 Hz, 1H), 6.26 (d, J=16.8 Hz, 1H), 5.75 (d, J=9.6 Hz, 1H), 4.59 (m, 1H), 3.95 (m, 1H), 2.20 (s, 6H), 2.07 (m, 1H), 1.48-1.76 (m, 14H).

Example 11. N-(3-(2-((1r,4r)-4-(Dimethylamino)cyclohexylamino)-9-isopropyl-9H-purin-6-ylamino)cyclohexyl)acrylamide (SB1-E-15)

Synthetic Scheme 11

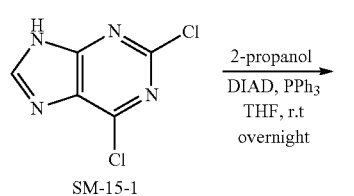

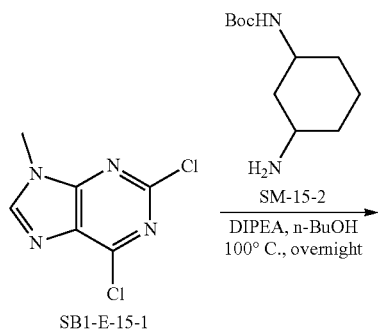

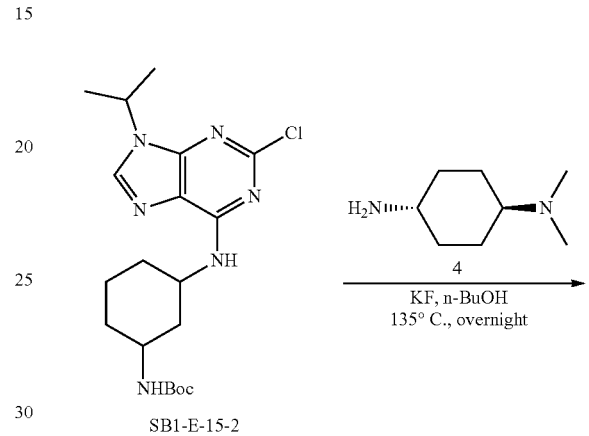

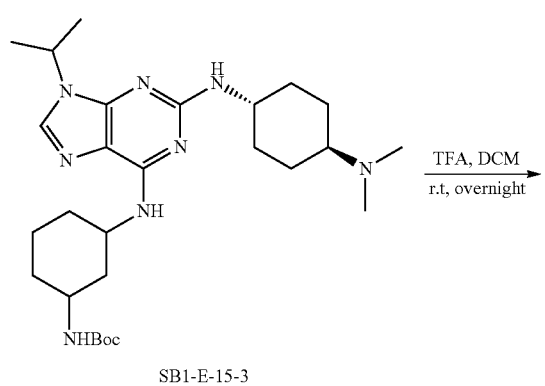

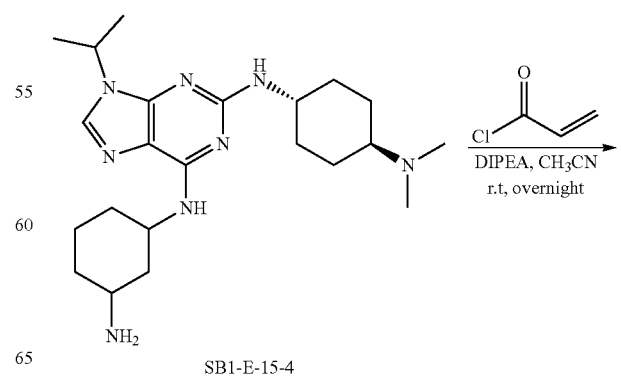

-continued

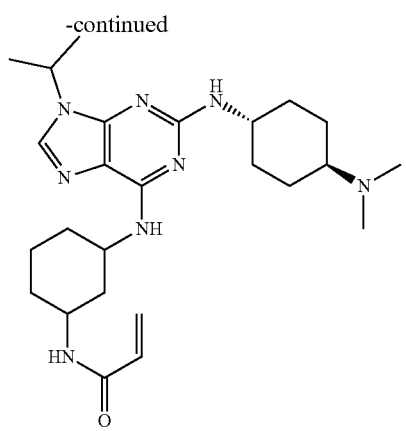

SB1-E-15 tert-butyl 3-(2-Chloro-9-isopropyl-9H-purin-6-ylamino)cyclohexylcarbamate (SB1-E-15-2)

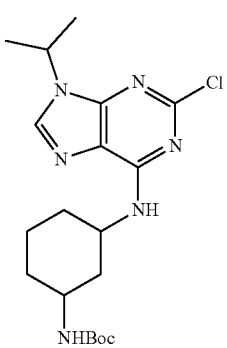 [SMILES: CC(C)n1cnc2c(NC3CCCC(NC(=O)OC(C)(C)C)C3)nc(Cl)nc21]

The mixture of SB1-E-15-1 (520 mg, 2.25 mmol), SM-15-2 (490 mg, 2.29 mmol), n-BuOH (15 mL) and DIPEA (1 mL) was stirred at 100° C. overnight, after completion, concentrated to remove the solvent, the residue was purified by silica gel (PE/ethyl acetate=2/1) to obtain SB1-E-15-2 (light broen solid, 380 mg, yield 41%). LCMS (m/z): 409 [M+H]$^+$.

tert-butyl 3-(2-((1r,4r)-4-(Dimethylamino)cyclohexylamino)-9-isopropyl-9H-purin-6-ylamino)cyclohexylcarbamate (SB1-E-15-3)

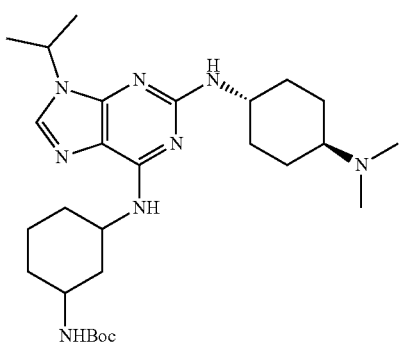 [SMILES: CC(C)n1cnc2c(NC3CCCC(NC(=O)OC(C)(C)C)C3)nc(N[C@H]3CC[C@H](N(C)C)CC3)nc21]

The mixture of SB1-E-15-2 (180 mg, 0.440 mmol), 4 (150 mg, 1.05 mmol), KF (110 mg, 1.89 mmol) and n-BuOH (1.5 mL) was stirred at 135° C. overnight, after completion, concentrated to remove the solvent, the residue was purified by prep-TLC (DCM/MeOH=6/1) to obtain SB1-E-15-3 (light brown solid, 25 mg, yield 11%). LCMS (m/z): 515 [M+H]$^+$.

N6-(3-Aminocyclohexyl)-N2-((1r,4r)-4-(dimethylamino)cyclohexyl)-9-isopropyl-9H-purine-2,6-diamine (SB1-E-15-4)

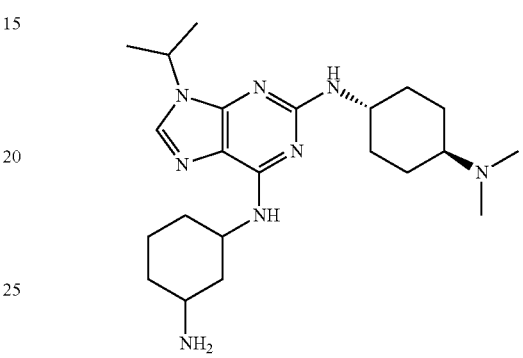

The mixture of SB1-E-15-3 (25 mg, 0.0486 mmol), DCM (3 mL) and TFA (3 mL) was stirred at r.t overnight. after completion, concentrated to remove the solvent to obtain SB1-E-15-4 (light brown sticky oil, 20 mg, yield 95%). LCMS (m/z): 415 [M+H]$^+$.

N-(3-(2-((1r,4r)-4-(Dimethylamino)cyclohexylamino)-9-isopropyl-9H-purin-6-ylamino)cyclohexyl)acrylamide (SB1-E-15)

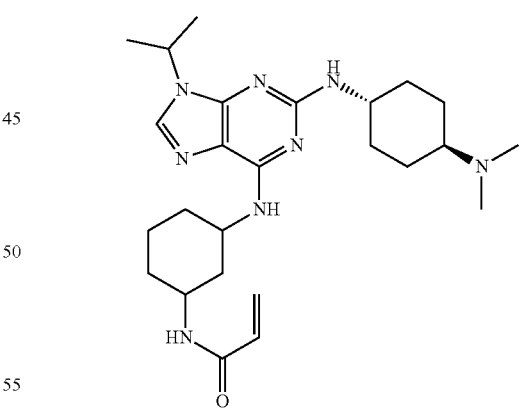

To a solution of SB1-E-15-4 (20 mg, 0.0482 mmol), CH$_3$CN (4 mL) and DIPEA (0.5 mL) was added acryloyl chloride (7 mg, 0.0773 mmol) in CH$_3$CN (1 mL) dropwise, the mixture was stirred at r.t overnight. After completion, the mixture was purified by prep-TLC (DCM/MeOH=8/1) and prep-HPLC (C18 column, CH$_3$CN/H$_2$O, containing 0.05% NH$_4$HCO$_3$) to obtain SB1-E-15 (white solid, 5 mg, yield 24%). HPLC: 100% (254 nm); LCMS (m/z): 469 [M+H]$^+$; $^1$H NMR (DMSO-d$_6$, 500 MHz): δ 8.03 (m, 1H), 7.79 (s, 1H), 6.79 (s, 1H), 6.34 (dd, J$_1$=17.0 Hz, J$_2$=12.0 Hz, 1H), 6.07 (d, J=17.0 Hz, 1H), 5.56 (d, J=12.0 Hz, 1H), 4.51 (m, 1H), 4.07 (s, 1H), 3.61 (s, 1H), 2.22 (s, 7H), 2.00 (s, 2H), 1.81 (m, 5H), 1.19-1.65 (m, 17H).

Example 12. N-(3-(2-((1r,4r)-4-(Dimethylamino)cyclohexylamino)-9-isopropyl-9H-purin-6-ylamino)benzyl)acrylamide (SB1-E-16)

Synthetic Scheme 12

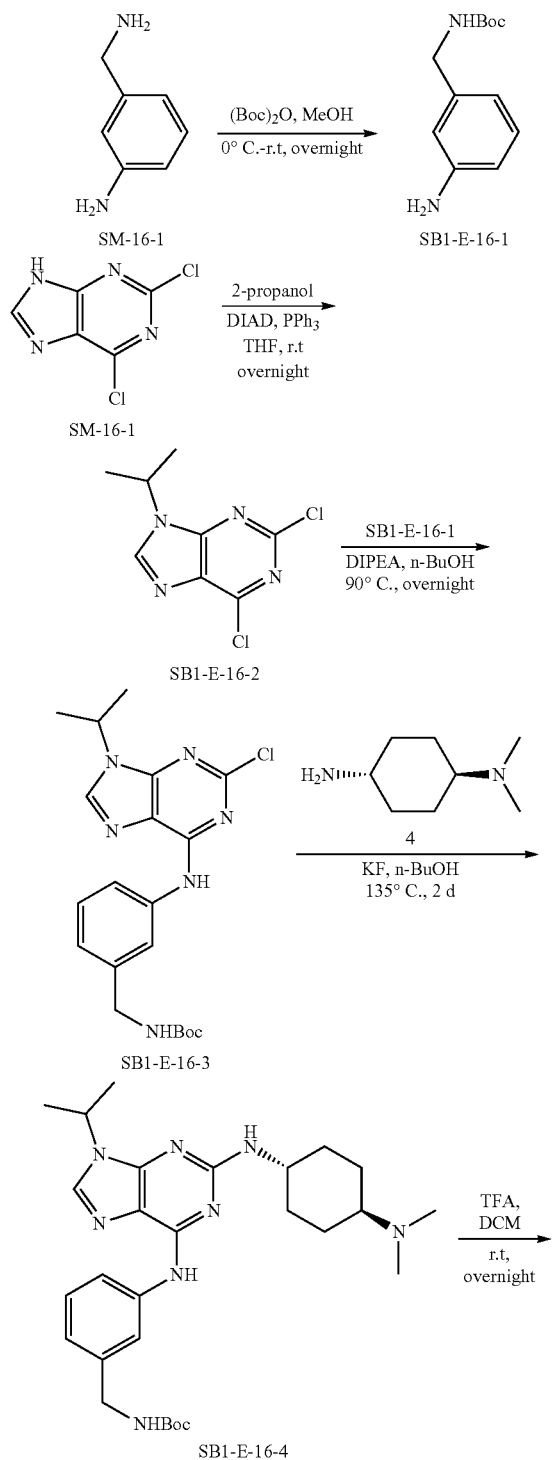

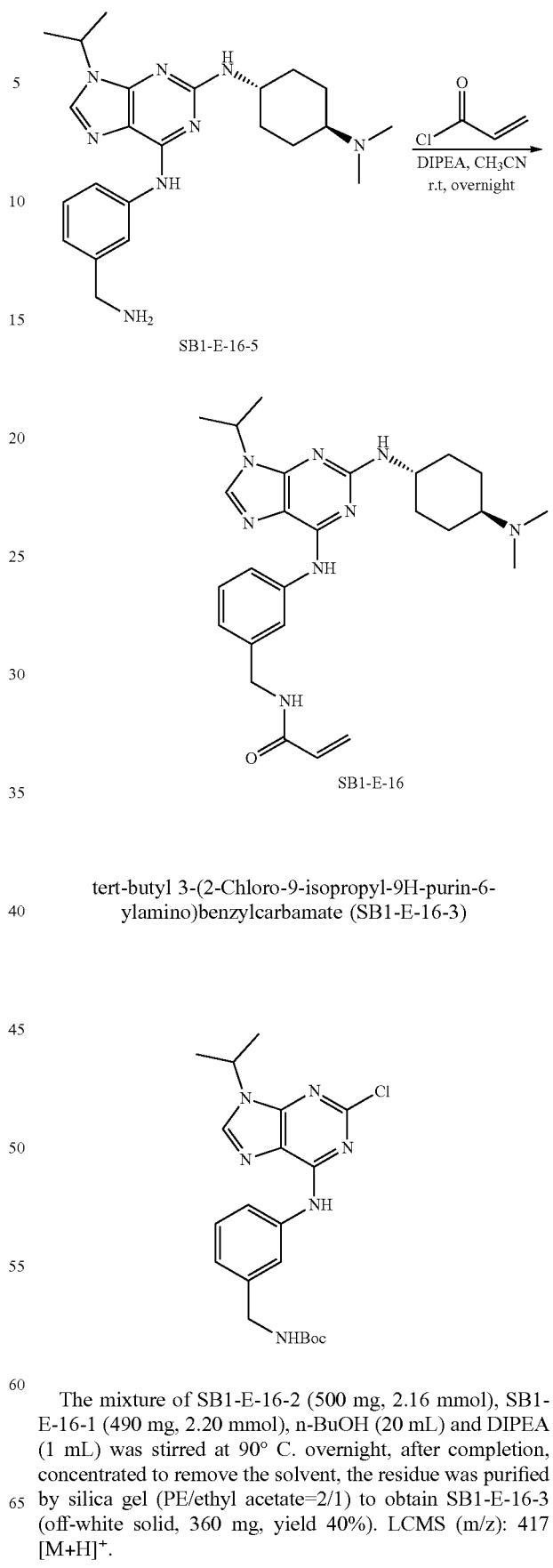

tert-butyl 3-(2-Chloro-9-isopropyl-9H-purin-6-ylamino)benzylcarbamate (SB1-E-16-3)

The mixture of SB1-E-16-2 (500 mg, 2.16 mmol), SB1-E-16-1 (490 mg, 2.20 mmol), n-BuOH (20 mL) and DIPEA (1 mL) was stirred at 90° C. overnight, after completion, concentrated to remove the solvent, the residue was purified by silica gel (PE/ethyl acetate=2/1) to obtain SB1-E-16-3 (off-white solid, 360 mg, yield 40%). LCMS (m/z): 417 [M+H]+.

191 tert-butyl 3-(2-((1r,4r)-4-(Dimethylamino)cyclo-hexylamino)-9-isopropyl-9H-purin-6-ylamino)ben-zylcarbamate (SB1-E-16-4)

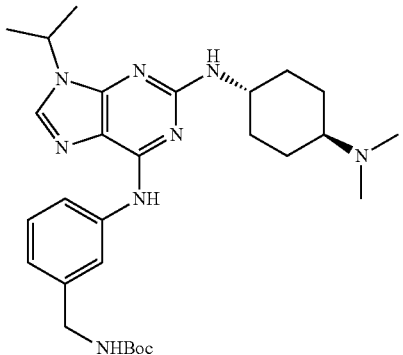 [SMILES: CC(C)n1cnc2c(Nc3cccc(CNC(=O)OC(C)(C)C)c3)nc(N[C@H]3CC[C@H](N(C)C)CC3)nc21]

The mixture of SB1-E-16-3 (210 mg, 0.504 mmol), 4 (150 mg, 1.05 mmol), KF (90 mg, 1.55 mmol) and n-BuOH (2 mL) was stirred at 135° C. for 2 days, after completion, concentrated to remove the solvent, the residue was purified by prep-TLC (DCM/MeOH=10/1) to get SB1-E-16-4 (light yellow solid, 90 mg, yield 34%. LCMS (m/z): 523 [M+H]$^+$.

N6-(3-(Aminomethyl)phenyl)-N2-((1r,4r)-4-(dim-ethylamino)cyclohexyl)-9-isopropyl-9H-purine-2,6-diamine (SB1-E-16-5)

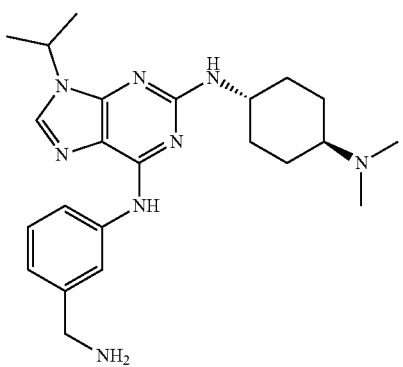 [SMILES: CC(C)n1cnc2c(Nc3cccc(CN)c3)nc(N[C@H]3CC[C@H](N(C)C)CC3)nc21]

The mixture of SB1-E-16-4 (50 mg, 0.0957 mmol), DCM (5 mL) and TFA (3 mL) was stirred at r.t overnight, after completion, concentrated to remove the solvent to get SB1-E-16-5 (light brown solid, 40 mg, 95%). LCMS (m/z): 423 [M+H]$^+$.

192

N-(3-(2-((1r,4r)-4-(Dimethylamino)cyclohexy-lamino)-9-isopropyl-9H-purin-6-ylamino)benzyl) acrylamide (SB1-E-16)

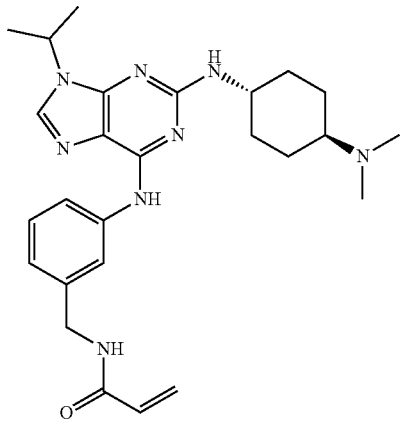 [SMILES: C=CC(=O)NCc1cccc(Nc2nc(N[C@H]3CC[C@H](N(C)C)CC3)nc3c2ncn3C(C)C)c1]

To a solution of SB1-E-16-5 (40 mg, 0.0947 mmol), CH$_3$CN (9 mL) and DIPEA (1 mL) was added acryloyl chloride (13 mg, 0.144 mmol) in CH$_3$CN (1 mL) dropwise, the mixture was stirred at r.t overnight, after completion, concentrated to remove the solvent, the residue was purified by prep-TLC (DCM/MeOH=8/1) and prep-HPLC (C18 column, CH$_3$CN/H$_2$O, containing 0.05% NH$_4$HCO$_3$) to obtain SB1-E-16 (white solid, 4.5 mg, yield 10%). HPLC: 95% (214 nm); LCMS (m/z): 477 [M+H]$^+$; $^1$H NMR (DMSO-d$_6$, 500 MHz): δ 9.40 (s, 1H), 8.60 (d, 1H), 7.94 (s, 1H), 7.88 (d, 1H), 7.22 (t, J=8.0 Hz, 1H), 6.87 (d, J=7.5 Hz, 1H), 6.30 (dd, J$_1$=17.0 Hz, J$_2$=10.0 Hz, 1H), 6.14 (d, J=17.0 Hz, 1H), 5.62 (d, J=10.0 Hz, 1H), 4.57 (m, 1H), 4.36 (d, J=6.0 Hz, 2H), 1.84-2.36 (m, 10H), 1.49 (s, 3H), 1.46 (s, 3H), 1.23-1.34 (m, 5H).

Example 13. N-(3-((2-(2-(2-Hydroxyethyl)piperi-din-1-yl)-9-isopropyl-9H-purin-6-yl)amino)phenyl) acrylamide (THZ-4-134-1)

Synthetic Scheme 13

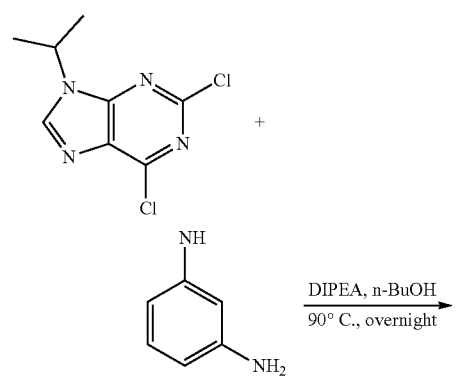

193
-continued 194
2-(1-(6-((3-Aminophenyl)amino)-9-isopropyl-9H-purin-2-yl)piperidin-2-yl)ethan-1-ol

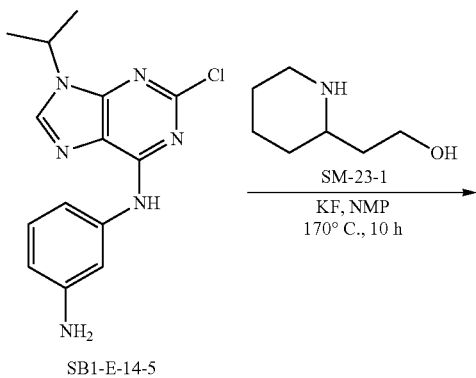

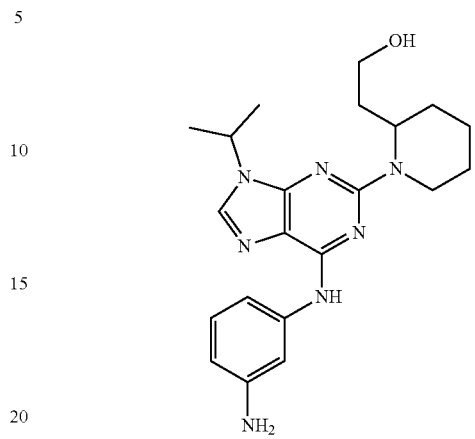

The mixture of SB1-E-14-5 (1.1 g, 3.72 mmol), SM-23-1 (800 mg, 6.19 mmol), KF (1.0 g, 17.2 mmol) and NMP (3 mL) was stirred at 168° C. for 12 h, after completion, concentrated to remove the solvent, the residue was purified by silica gel (PE/ethyl acetate=2/1, 1/1) to obtain desired product (1.2 g, yield 81%). LCMS (m/z): 396 [M+H]⁺.

N-(3-((2-(2-(2-Hydroxyethyl)piperidin-1-yl)-9-isopropyl-9H-purin-6-yl)amino)phenyl)acrylamide (THZ-4-134-1)

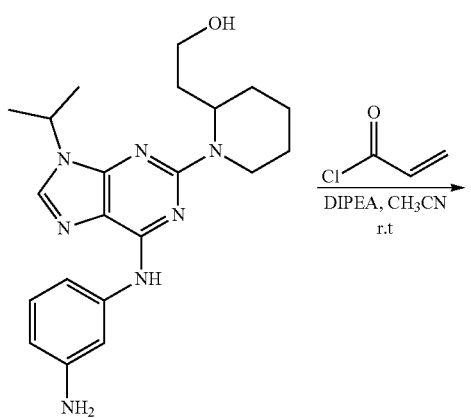

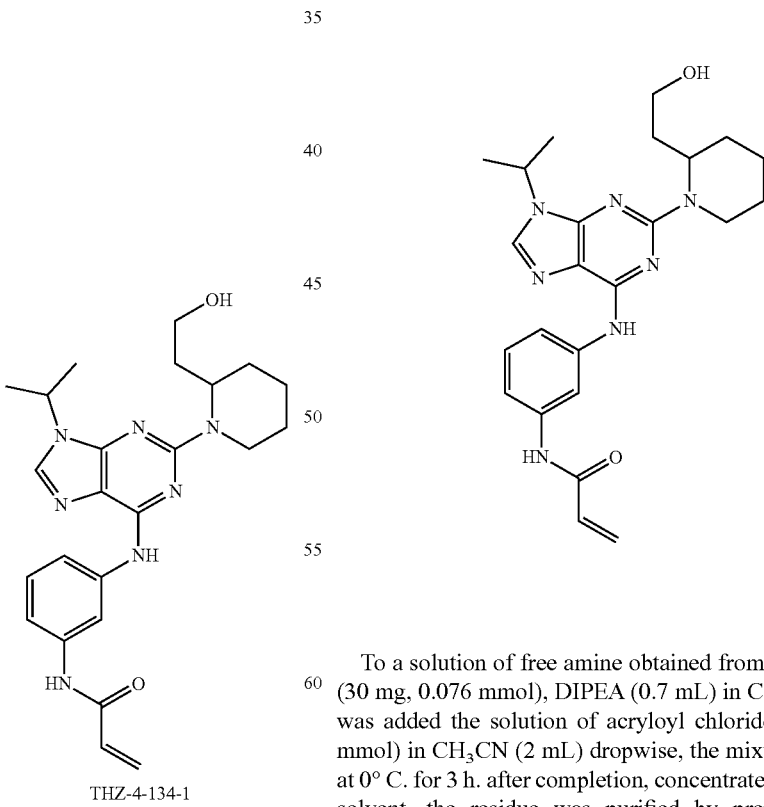

To a solution of free amine obtained from above reaction (30 mg, 0.076 mmol), DIPEA (0.7 mL) in CH3CN (12 mL) was added the solution of acryloyl chloride (11 mg, 0.12 mmol) in CH₃CN (2 mL) dropwise, the mixture was stirred at 0° C. for 3 h. after completion, concentrated to remove the solvent, the residue was purified by prep-TLC (DCM/MeOH=30/1) and prep-HPLC (C18 column, CH₃CN/H₂O, containing 0.05% NH₄HCO₃) to obtain THZ-4-134-1 (off-white solid, 23 mg, yield 70%). HPLC: 98% (254 nm); LCMS (m/z): 450 [M+H]⁺; ¹H NMR (DMSO-d$_6$, 600 MHz): δ 10.42 (s, 1H), 9.50 (s, 1H), 8.34 (s, 1H), 7.25 (s, 1H), 7.52 (d, J=7.8 Hz, 1H), 7.25-7.16 (m, 2H), 6.45 (dd, J$_1$=17.2 Hz, J$_2$=10.0 Hz, 1H), 6.27 (d, J=17.2 Hz, 1H), 5.77 (d, J=10.0 Hz, 1H), 4.97 (br, 1H), 4.61 (m, 1H), 3.34-3.38 (m, 3H), 2.87 (t, J=12 Hz, 1H), 1.83 (m, 1H), 1.74 (m, 1H), 1.69 (m, 3H), 1.60-1.50 (m, 9H), 1.34 (m, 1H).

Example 14. N-(3-(2-((1r,4r)-4-(Dimethylamino)cyclohexylamino)-8-ethylpyrazolo[1,5-a][1,3,5]triazin-4-ylamino)phenyl)acrylamide (compound SB1-E-17)

Synthetic Scheme 14

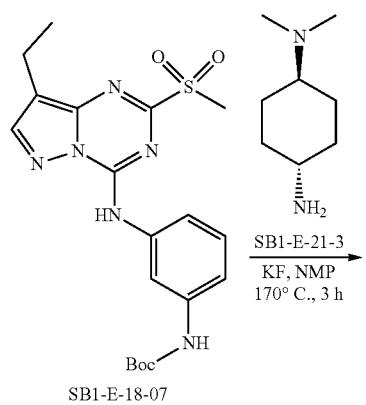

SB1-E-18-07

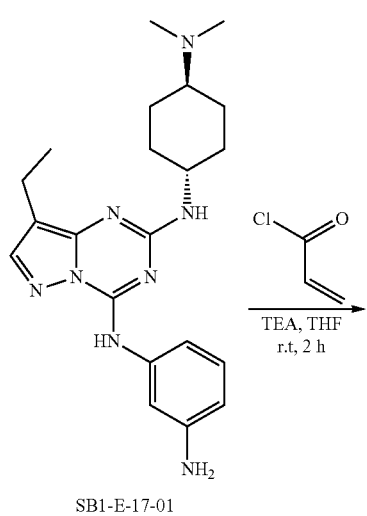

SB1-E-17-01

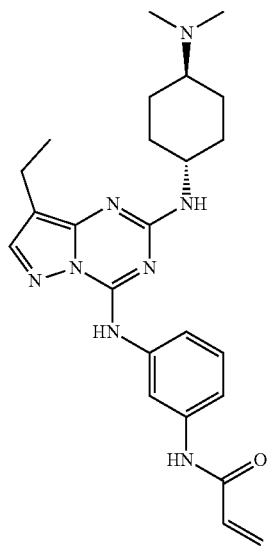

SB1-E-17

N4-(3-Aminophenyl)-N2-((1r,4r)-4-(dimethylamino)cyclohexyl)-8-ethylpyrazolo[1,5-a][1,3,5]triazine-2,4-diamine (SB1-E-17-01)

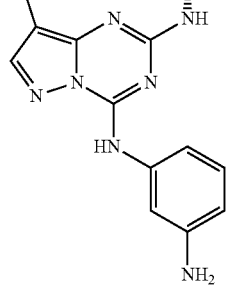

To a stirred mixture of SB1-E-18-07 (60 mg, 0.14 mmol) and SB1-E-21-3 (30 mg, 0.21 mmol) in N-methyl-2-pyrrolidone (1 mL) was added KF (24 mg, 0.42 mmol). This mixture was heated at 170° C. for 3 h, cooled to r.t, filtered, purified by prep-TLC (DCM/MeOH=6/1) to get SB1-E-17-01 (white solid, 40 mg, yield: 73%). MS (ESI): m/z 395 [M+H]⁺.

197

N-(3-(2-((1r,4r)-4-(Dimethylamino)cyclohexylamino)-8-ethylpyrazolo[1,5-a][1,3,5]triazin-4-ylamino)phenyl)acrylamide (compound SB1-E-17)

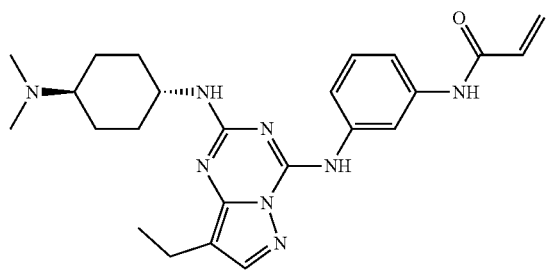 [SMILES: C=CC(=O)Nc1cccc(Nc2nc(N[C@H]3CC[C@H](N(C)C)CC3)nc3c(CC)cnn23)c1]

To a solution of SB1-E-17-01 (40 mg, 0.10 mmol) in THF (1 mL) was added Acryloyl chloride (14 mg, 0.15 mmol) and Triethylamine (30 mg, 0.30 mmol) was stirred at r.t for 2 h. After completion, the reaction mixture was diluted with dichloromethane (10 ml), washed with water (10 mL) and saturated sodium bicarbonate solution (10 mL×2), dried over anhydrous sodium sulfate, concentrated, purified by prep-HPLC (C18 column, $CH_3CN/H_2O$, containing 0.05% $NH_4HCO_3$) to get SB1-E-17, also referred to herein as E17 and E-17 (white solid, 4 mg, yield: 11%). MS (ESI): m/z 449 [M+H]$^+$. $^1$H NMR (300 MHz, DMSO) δ: 9.98 (s, 1H), 9.65 (s, 1H), 8.14 (s, 1H), 7.76 (s, 1H), 7.52 (d, J=8.1 Hz, 1H), 7.45 (d, J=7.8 Hz, 1H), 7.29 (t, J=8.1 Hz, 1H), 6.64 (s, 1H), 6.42-6.51 (m, 1H), 6.23-6.29 (m, 1H), 5.70-5.74 (m, 1H), 3.69-3.72 (m, 1H), 2.51-2.56 (m, 2H), 2.36 (s, 6H), 2.03-2.06 (m, 2H), 1.86-1.90 (m, 2H), 1.18-1.37 (m, 8H).

Example 15. N-(3-(8-Ethyl-2-(2-(2-hydroxyethyl)piperidin-1-yl)pyrazolo[1,5-a][1,3,5]triazin-4-ylamino)phenyl)acrylamide (SB1-E-18)

Synthetic Scheme 15

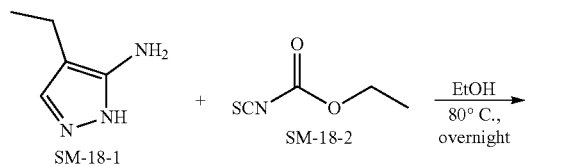

SB1-E-18-01

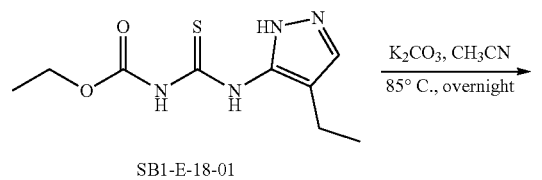

SB1-E-18-02

198

-continued

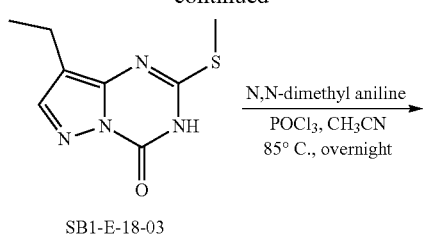

SB1-E-18-03

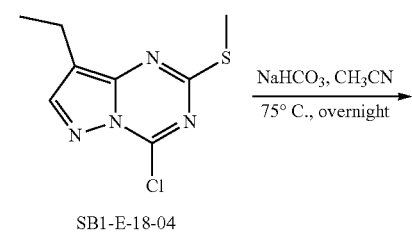

SB1-E-18-04

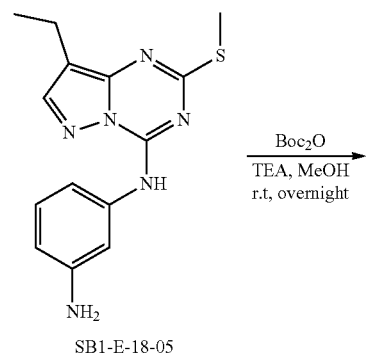

SB1-E-18-05

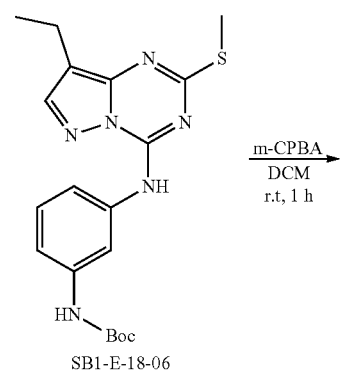

SB1-E-18-06

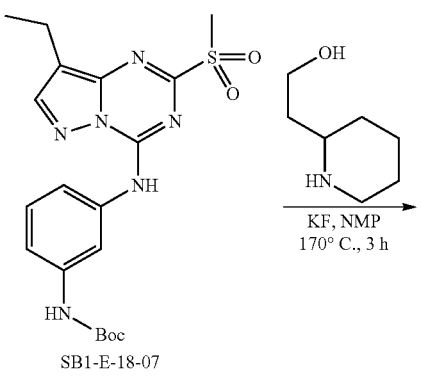

SB1-E-18-07

-continued

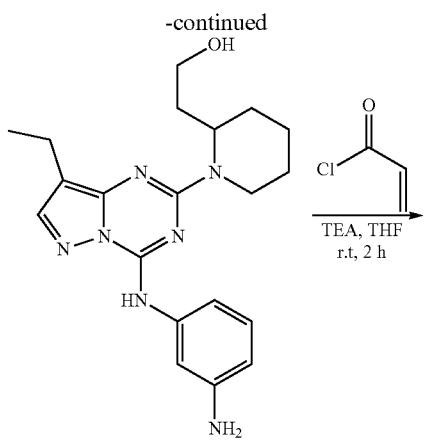

SB1-E-18-08

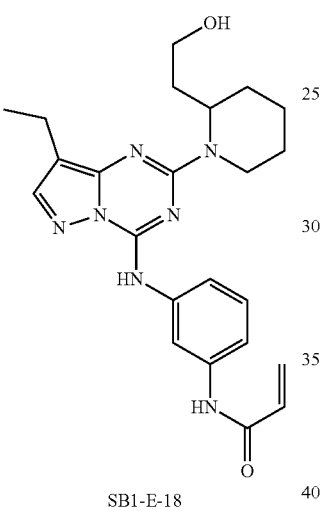

SB1-E-18 ethyl N-[(4-Ethyl-1H-pyrazol-5-yl)carbamothioyl]
carbamate (SB1-E-18-01)

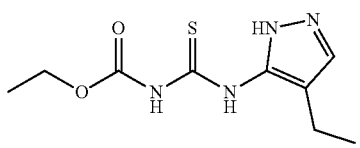 [SMILES: CCOC(=O)NC(=S)Nc1[nH]ncc1CC]

To a solution of SM-18-1 (2.8 g, 25.2 mmol) in ethanol (50.0 mL) was added ethoxycarbonyl isothiocyanate (3.3 g, 25.2 mL) in one portion at r.t. The mixture was stirred at 80° C. overnight. The reaction mixture was concentrated under reduced pressure to afford the residue, purified by flash column chromatography (PE/ethyl acetate=3/1) to get SB1-E-18-01 (white solid, 4 g, yield: 65%). LCMS (m/z): 243 [M+H]$^+$.

8-Ethyl-2-thioxo-2,3-dihydropyrazolo[1,5-a][1,3,5]triazin-4(1H)-one (SB1-E-18-02)

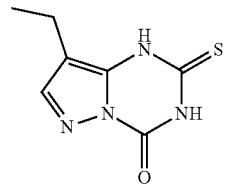

To a solution of SB1-E-18-01 (3.9 g, 16.1 mmol) in acetonitrile (40 mL) was added K$_2$CO$_3$ (6.67 g, 48.3 mmol) in one portion at r.t. The mixture was heated at 85° C. overnight, cooled, acidified with AcOH. The solid was filtered off to get SB1-E-18-02 (yellow solid, 2.1 g, yield: 66%). LCMS (m/z): 197 [M+H]$^+$.

8-Ethyl-2-(methylthio)pyrazolo[1,5-a][1,3,5]triazin-4(3H)-one (SB1-E-18-03)

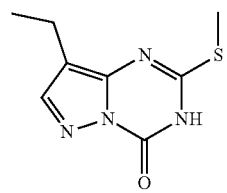

To a stirred mixture of SB1-E-18-02 (2.1 g, 10.7 mmol) and NaOH (0.86 g, 21.4 mmol) in Dioxane/H$_2$O (30/8 mL) was added iodomethane (1.52 g, 10.7 mol). This mixture was stirred at r.t for 1 h, acidified with Hydrochloric acid, concentrated to remove the solvent, the residue was purified by silica gel (DCM/MeOH=30/1) to get SB1-E-18-03 (white solid, 2.0 g, yield: 89%). LCMS (m/z): 211 [M+H]$^+$.

4-Chloro-8-ethyl-2-(methylthio)pyrazolo[1,5-a][1,3,5]triazine (SB1-E-18-04)

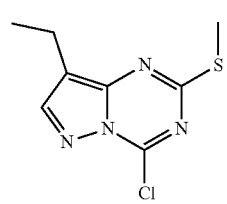

To a stirred mixture SB1-E-18-03 (2.0 g, 9.5 mmol) and N,N-dimethyl aniline (2.3 g, 19.0 mmol) in acetonitrile (10 mL) under argon was added POCl$_3$ (20 ml, 219 mol). This mixture was heated at 85° C. overnight, cooled, the reaction mixture was concentrated under reduced pressure to afford the residue SB1-E-18-04 (white solid, 2.2 g, yield: 100% used next step directly). LCMS (m/z): 229 [M+H]$^+$.

201

N1-(8-Ethyl-2-(methylthio)pyrazolo[1,5-a][1,3,5]triazin-4-yl)benzene-1,3-diamine (SB1-E-18-05)

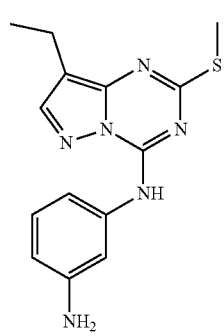 [SMILES: CCc1cnn2c(Nc3cccc(N)c3)nc(SC)nc12]

To a stirred mixture SB1-E-18-04 (2.2 g, 9.5 mmol), benzene-1,3-diamine (1.23 g, 11.4 mmol) and NaHCO$_3$ (130.4 mg, 0.95 mmol) in acetonitrile (25 mL). This mixture was heated at 75° C. overnight, cooled, filtered and concentrated to remove the solvent, the residue was purified by silica gel (PE/ethyl acetate=3/1 to 1/1) to get SB1-E-18-05 (white solid, 1.1 g, yield: 38%). LCMS (m/z): 301 [M+H]$^+$.

tert-Butyl 3-(8-ethyl-2-(methylthio)pyrazolo[1,5-a][1,3,5]triazin-4-ylamino) phenylcarbamate (SB1-E-18-06)

To a solution of SB1-E-18-05 (1.1 g, 3.67 mmol) in MeOH (20.0 mL) was added Di-tert-butyl dicarbonate (1.2 g, 5.5 mmol) and TEA (1.1 g, 11.0 mmol) in one portion at r.t. The reaction was stirred at r.t. overnight. The reaction mixture was concentrated under reduced pressure to afford the residue, purified by flash column chromatography (PE/ethyl acetate=3/1) to get SB1-E-18-06 (white solid, 1.26 g, yield: 86%). LCMS (m/z): 401 [M+H]+.

202 tert-Butyl 3-(8-ethyl-2-(methylsulfonyl)pyrazolo[1,5-a][1,3,5]triazin-4-ylamino) phenylcarbamate (SB1-E-18-07)

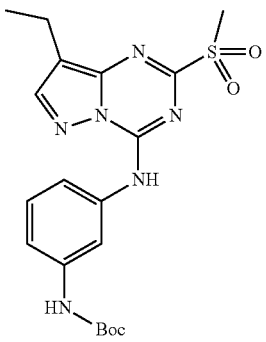 [SMILES: CCc1cnn2c(Nc3cccc(NC(=O)OC(C)(C)C)c3)nc(S(C)(=O)=O)nc12]

To a solution of SB1-E-18-06 (600 mg, 1.5 mmol) in DCM (15 mL) was added 3-Chloroperbenzoic acid (776 mg, 4.5 mmol) in one portion at r.t. The mixture was stirred at r.t for 1 h. The reaction mixture was quenched with sat Na$_2$S$_2$O$_3$ solution (10 mL), diluted with DCM (50 mL) and washed with saturated aqueous NaCl (3×50 mL), dried over anhydrous Na$_2$SO$_4$, filtered and concentrated to give SB1-E-18-07 (yellow solid, 620 mg, yield: 96%), used for next step directly. LCMS (m/z): 433 [M+H]+.

2-(1-(4-(3-Aminophenylamino)-8-ethylpyrazolo[1,5-a][1,3,5]triazin-2-yl) piperidin-2-yl)ethanol (SB1-E-18-08)

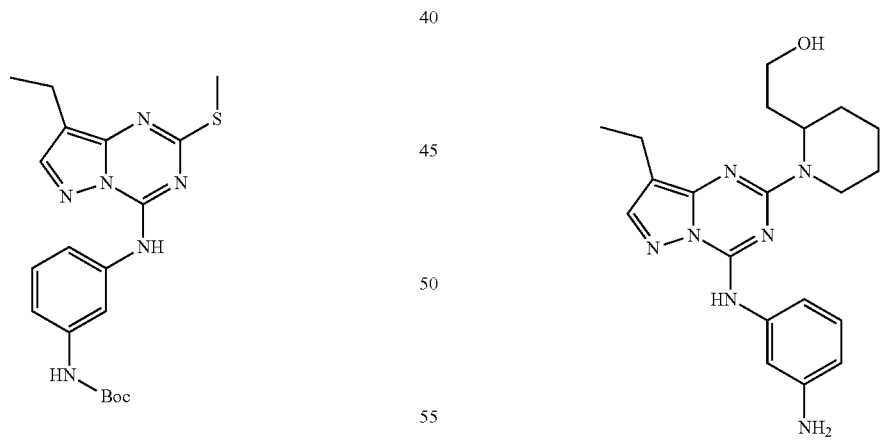

To a stirred mixture SB1-E-18-07 (360 mg, 0.84 mmol) and 2-(piperidin-2-yl)ethanol (215 mg, 1.67 mmol) in N-methyl-2-pyrrolidone (3 mL) was added KF (146 mg, 2.51 mmol). This mixture was heated at 170° C. for 3 h, cooled, filtered, the crude was purified by silica gel (PE/ethyl acetate=2/1) to get SB1-E-18-08 (yellow solid, 150 mg, yield: 47%). LCMS (m/z): 382 [M+H]$^+$.

203

N-(3-(8-Ethyl-2-(2-(2-hydroxyethyl)piperidin-1-yl)pyrazolo[1,5-a][1,3,5] triazin-4-ylamino)phenyl)acrylamide (SB1-E-18)

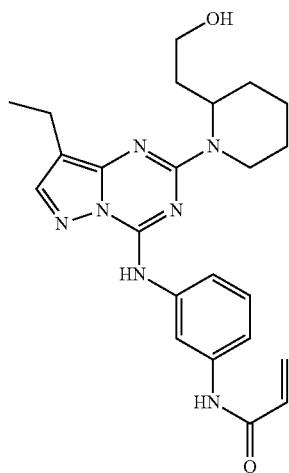 [SMILES: C=CC(=O)Nc1cccc(Nc2nc(N3CCCCC3CCO)nc3c(CC)cnn23)c1]

To a solution of SB1-E-18-08 (70 mg, 0.18 mmol) in THF (2 mL) was added Acryloyl chloride (18 mg, 0.20 mmol) and triethylamine (54 mg, 0.54 mmol) was stirred at r.t for 2 h. After completion, the reaction mixture was diluted with dichloromethane (10 ml), washed with water (10 mL) and saturated sodium bicarbonate solution (10 mL×2), dried over anhydrous sodium sulfate, concentrated, purified by prep-HPLC (C18 column, CH$_3$CN/H$_2$O, containing 0.05% NH$_4$HCO$_3$) to get SB1-E-18, also referred to herein as E-18 and E18 (white solid, 13 mg, yield: 16%). HPLC: 100% (254 nm); LCMS (m/z): 555 [M+H]$^+$; $^1$H NMR (DMSO-d$_6$, 500 MHz): δ: 10.17 (s, 1H), 10.07 (s, 1H), 8.34 (s, 1H), 7.84 (s, 1H), 7.51 (s, 1H), 7.30-7.34 (m, 2H), 6.46 (dd, J=17, 10.0 Hz, 1H), 6.28 (d, J=17 Hz, 1H), 5.77 (d, J=11.5 Hz, 1H), 4.98 (s, 1H), 4.65 (d, J=13 Hz, 1H), 4.56 (s, 1H), 2.88 (t, J=12.5 Hz, 1H), 2.47-2.50 (m, 2H), 1.56-1.88 (m, 8H), 1.36-1.38 (m, 1H), 1.19-1.23 (m, 4H).

Example 16. N-(3-(3-Ethyl-5-(2-(2-hydroxyethyl)piperidin-1-yl)pyrazolo[1,5-a]pyrimidin-7-ylamino)phenyl)acrylamide (SB1-E-23)

Synthetic Scheme 16

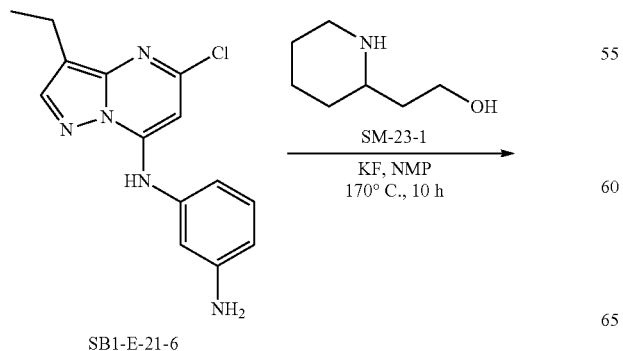

204

-continued

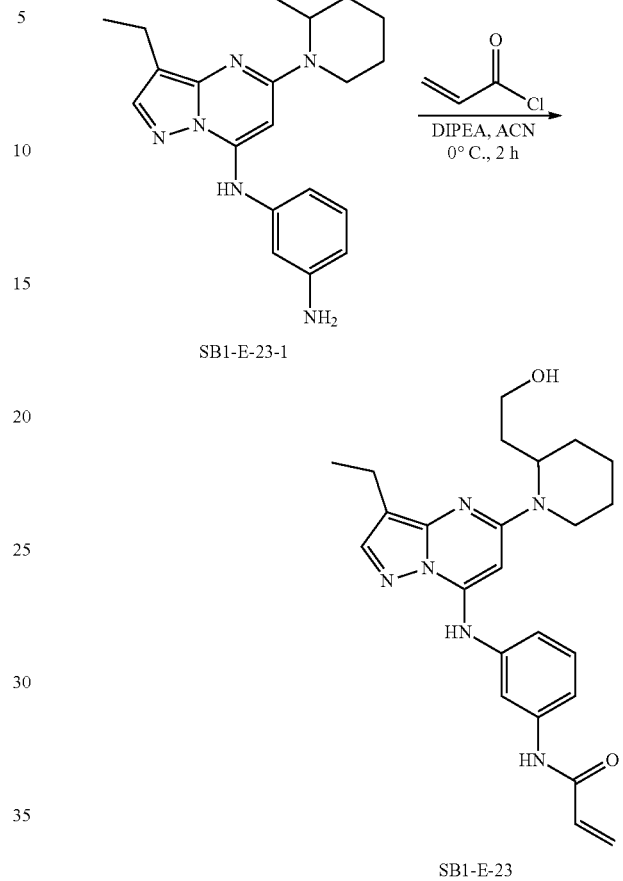

2-(1-(7-(3-Aminophenylamino)-3-ethylpyrazolo[1,5-a]pyrimidin-5-yl)piperidin-2-yl)ethanol (SB1-E-23-1)

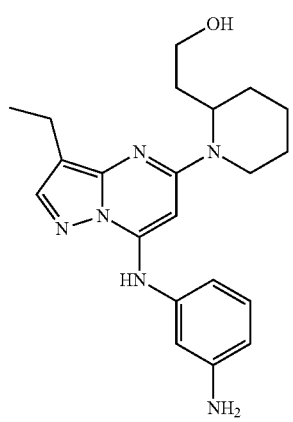 [SMILES: CCc1cnn2c(Nc3cccc(N)c3)cc(N3CCCCC3CCO)nc12]

The mixture of SB1-E-21-6 (1.1 g, 3.82 mmol), SM-23-1 (800 mg, 6.19 mmol), KF (1.0 g, 17.2 mmol) and NMP (3 mL) was stirred at 168° C. for 12 h, after completion, concentrated to remove the solvent, the residue was purified by silica gel (PE/ethyl acetate=2/1, 1/1) to obtain SB1-E-23-1 (light brown solid, 1.0 g, yield 69%). LCMS (m/z): 381 [M+H]$^+$.

N-(3-(3-Ethyl-5-(2-(2-hydroxyethyl)piperidin-1-yl) pyrazolo[1,5-a]pyrimidin-7-ylamino)phenyl)acrylamide (SB1-E-23)

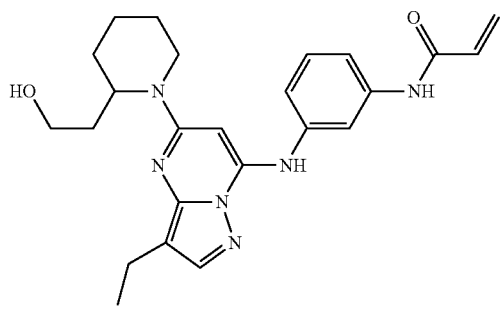 [SMILES: C=CC(=O)Nc1cccc(Nc2cc(N3CCCCC3CCO)nc3c(CC)cnn23)c1]

To a solution of SB1-E-23-1 (150 mg, 0.394 mmol), DIPEA (0.7 mL) in CH3CN (12 mL) was added the solution of acryloyl chloride (54 mg, 0.597 mmol) in CH$_3$CN (2 mL) dropwise, the mixture was stirred at 0° C. for 3 h. after completion, concentrated to remove the solvent, the residue was purified by prep-TLC (DCM/MeOH=30/1) and prep-HPLC (C18 column, CH$_3$CN/H$_2$O, containing 0.05% NH$_4$HCO$_3$) to obtain SB1-E-23, also referred to herein as E-9 and E9 (off-white solid, 15 mg, yield 9%). HPLC: 98% (254 nm); LCMS (m/z): 435 [M+H]$^+$; $^1$H NMR (DMSO-d$_6$, 500 MHz): δ 10.23 (s, 1H), 9.29 (s, 1H), 7.88 (s, 1H), 7.76 (s, 1H), 7.33-7.36 (m, 2H), 7.16-7.19 (m, 1H), 6.45 (dd, J$_1$=17.2 Hz, J$_2$=10.0 Hz, 1H), 6.27 (d, J=17.2 Hz, 1H), 6.01 (s, 1H), 5.77 (d, J=10.0 Hz, 1H), 4.58 (m, 2H), 4.26 (m, 1H), 3.34-3.38 (m, 1H), 2.87 (t, 1H), 2.54 (q, J=7.2 Hz, 2H), 1.28-1.84 (m, 8H), 1.22 (t, J=7.6 Hz, 3H).

Example 17. N-(3-(5-((1r,4r)-4-(Dimethylamino)cyclohexylamino)-3-ethylpyrazolo[1,5-a]pyrimidin-7-ylamino)phenyl)acrylamide (SB1-E-21)

Synthetic Scheme 17

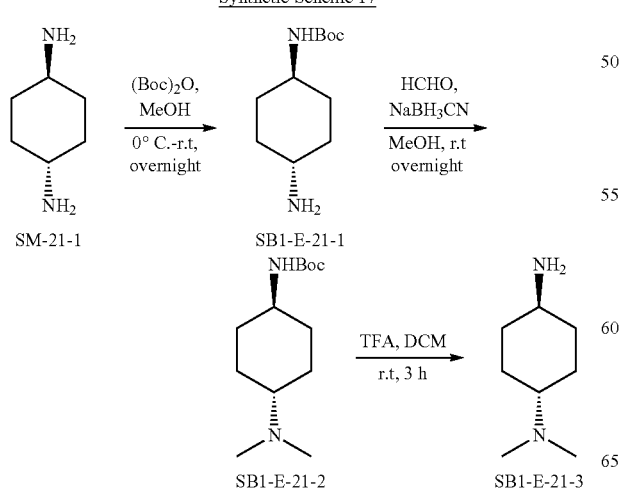

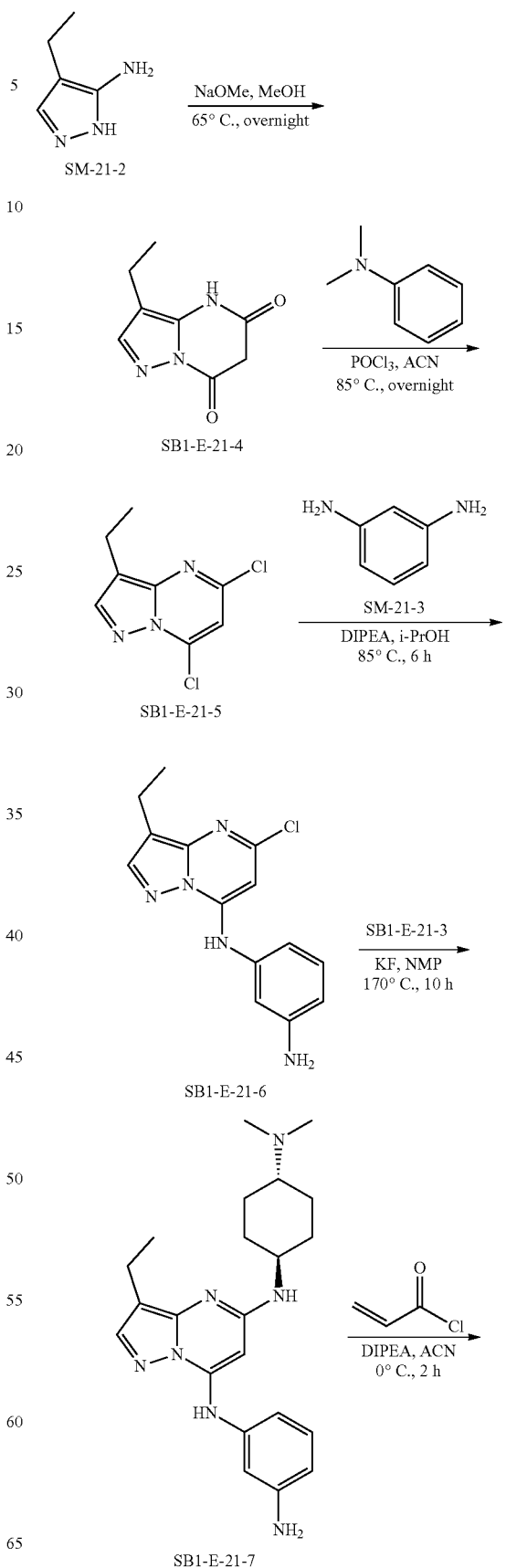

-continued

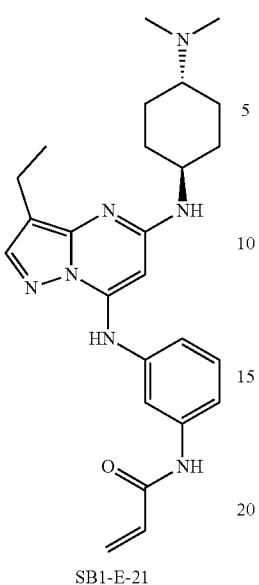

SB1-E-21 tert-Butyl (1r,4r)-4-aminocyclohexylcarbamate
(SB1-E-21-1)

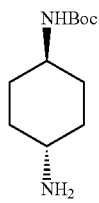

To a solution of SM-21-1 (2.0 g, 17.5 mmol) in MeOH (100 mL) was added the solution of (Boc)₂O (1.1 g, 5.04 mmol) in MeOH (60 mL) dropwise for 30 min, the mixture was stirred at r.t overnight. After completion, concentrated to remove the solvent, the residue was added H₂O (50 mL), further stirred at r.t for 20 min, then filtered, the filtrate was extracted with ethyl acetate (120 mL×2), the organic phase was washed with brine (50 mL×2), dried with Na₂SO₄. Filtered, concentrated to remove the solvent to obtain SB1-E-21-1 (off-white solid, 900 mg, yield 83%).

tert-Butyl (1r,4r)-4-(dimethylamino)cyclohexylcarbamate (SB1-E-21-2)

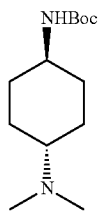 [SMILES: CN(C)[C@H]1CC[C@H](NC(=O)OC(C)(C)C)CC1]

To a solution of SB1-E-21-1 (850 mg, 3.97 mmol) and HCHO (600 mg, 20.0 mmol) in MeOH (30 mL) was added NaBH₃CN (1.1 g, 17.5 mmol), the mixture was stirred at r.t overnight, after completion, concentrated to remove the solvent, the residue was extracted with ethyl acetate (100 mL×4), the organic phase was washed with brine (50 mL×2), dried with Na₂SO₄. Filtered, concentrated to remove the solvent, the residue was purified by silica gel (DCM/MeOH=10/1, 5/1) to obtain SB1-E-21-2 (light brown solid, 800 mg, yield 83%). LCMS (m/z): 243 [M+H]⁺.

(1r,4r)-N1,N1-Dimethylcyclohexane-1,4-diamine (SB1-E-21-3)

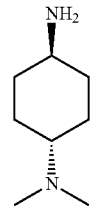

The mixture of SB1-E-21-2 (350 mg, 1.44 mmol), DCM (3 mL) and TFA (3 mL) was stirred at r.t for 3 h, after completion, concentrated to remove the solvent to get SB1-E-21-3 (light yellow sticky oil, 200 mg, yield 98%). LCMS (m/z): 143 [M+H]⁺.

3-Ethylpyrazolo[1,5-a]pyrimidine-5,7(4H,6H)-dione (SB1-E-21-4)

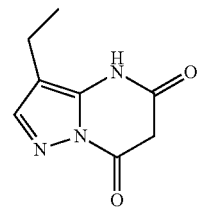

The mixture of SM-21-2 (5.0 g, 24.8 mmol), dimethyl malonate (10 mL, 87.0 mmol), MeOH (80 mL) and NaOMe (7.0 g, 129.6 mmol) was stirred at 65° C. overnight, after completion, concentrated to remove the solvent, the residue was added H₂O (10 mL), 2M HCl to make PH<7, then filtered, the solid was washed with H₂O (50 mL), dried to obtain SB1-E-21-4 (light yellow solid, 2.6 g, yield 58%). LCMS (m/z): 180 [M+H]⁺.

5,7-Dichloro-3-ethylpyrazolo[1,5-a]pyrimidine (SB1-E-21-5)

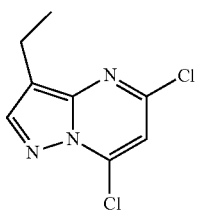

To a suspension of SB1-21-4 (2.6 g, 14.5 mmol) in CH₃CN (20 mL) was added N,N-dimethylaniline (3.6 g, 29.7 mmol), POCl₃ (11.5 g, 75.0 mmol) dropwise, the mixture was stirred at 85° C. overnight. After completion, cooled to 0° C., added H₂O (50 mL) to quench the reaction, filtered, the solid was washed with H₂O (50 mL), dried to obtain SB1-E-21-5 (light brown solid, 2.7 g, 86%). LCMS (m/z): 216 [M+H]⁺

N1-(5-Chloro-3-ethylpyrazolo[1,5-a]pyrimidin-7-yl)benzene-1,3-diamine (SB1-E-21-6)

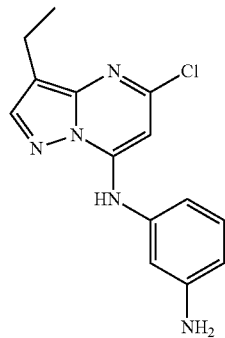 [SMILES: CCc1cnn2c(Nc3cccc(N)c3)cc(Cl)nc12]

The mixture of SB1-E-21-5 (2.6 g, 12.0 mmol), SM-21-3 (1.5 g, 13.9 mmol), DIPEA (5 mL) and i-PrOH (30 mL) was stirred at 85° C. for 6 h, after completion, concentrated to remove the solvent, the residue was purified by silica gel (DCM/MeOH=200/1) to obtain SB1-E-21-6 (brown solid, 2.8 g, yield 81%). LCMS (m/z): 288 [M+H]⁺.

N7-(3-Aminophenyl)-N5-((1r,4r)-4-(dimethylamino)cyclohexyl)-3-ethylpyrazolo[1,5-a]pyrimidine-5,7-diamine (SB1-E-21-7)

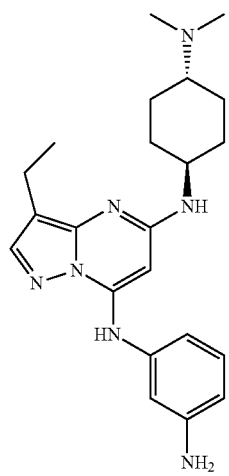 [SMILES: CCc1cnn2c(Nc3cccc(N)c3)cc(N[C@H]3CC[C@H](N(C)C)CC3)nc12]

The mixture of SB1-E-21-6 (400 mg, 1.39 mmol), SB1-E-21-3 (200 mg, 1.41 mmol), KF (400 mg, 6.88 mmol) and NMP (1.5 mL) was stirred at 145° C. for 10 h in a sealed tube. After completion, concentrated to remove the solvent, the residue was purified by prep-TLC (DCM/MeOH=6/1) to obtain SB1-E-21-7 (light brown solid, 160 mg, yield 29%). LCMS (m/z): 394 [M+H]⁺.

N-(3-(5-((1r,4r)-4-(Dimethylamino)cyclohexylamino)-3-ethylpyrazolo[1,5-a]pyrimidin-7-ylamino)phenyl)acrylamide (SB1-E-21)

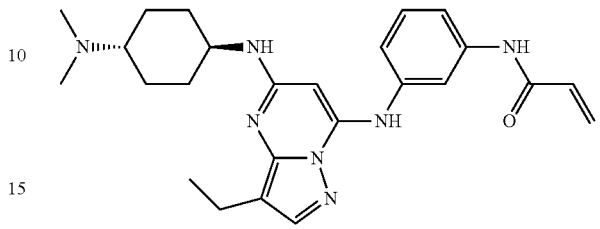

To a solution of SB1-E-21-7 (60 mg, 0.152 mmol) and DIPEA (0.3 mL) in CH₃CN (3 mL) was added acrylyl chloride (25 mg, 0.276 mmol) in CH₃CN (1 mL) dropwise, the mixture was stirred at 0° C. for 3 h. after completion, concentrated to remove the solvent, the residue was purified by prep-TLC (DCM/MeOH=10/1) and prep-HPLC (C18 column, CH₃CN/H₂O, containing 0.05% NH₄HCO₃) to obtain SB1-E-21, also referred to herein as E-21 and E21 (off-white solid, 7 mg, yield 10%). HPLC: 99% (254 nm); LCMS (m/z): 448 [M+H]⁺; ¹H NMR (DMSO-d₆, 500 MHz): δ 10.26 (s, 1H), 9.07 (s, 1H), 7.69 (s, 2H), 7.54 (d, J=9.0 Hz, 1H), 7.36 (t, J=8.5 Hz, 1H), 7.09 (d, J=7.0 Hz, 1H), 6.63 (d, J=7.0 Hz, 1H), 6.46 (dd, J₁=17.5 Hz, J₂=12.0 Hz, 1H), 6.28 (d, J=17.5 Hz, 1H), 5.78 (d, J=12.0 Hz, 1H), 5.62 (s, 1H), 2.55 (m, 4H), 2.17 (s, 6H), 1.78-2.13 (m, 4H), 1.12-1.27 (m, 8H).

Example 18. N-(3-(5-((1r,4r)-4-(Dimethylamino)cyclohexylamino)-3-isopropylpyrazolo[1,5-a]pyrimidin-7-ylamino)phenyl)acrylamide (SB1-E-26)

Synthetic Scheme 18

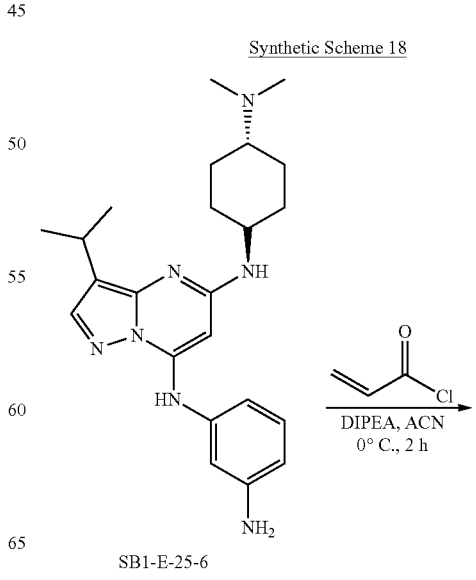

SB1-E-25-6

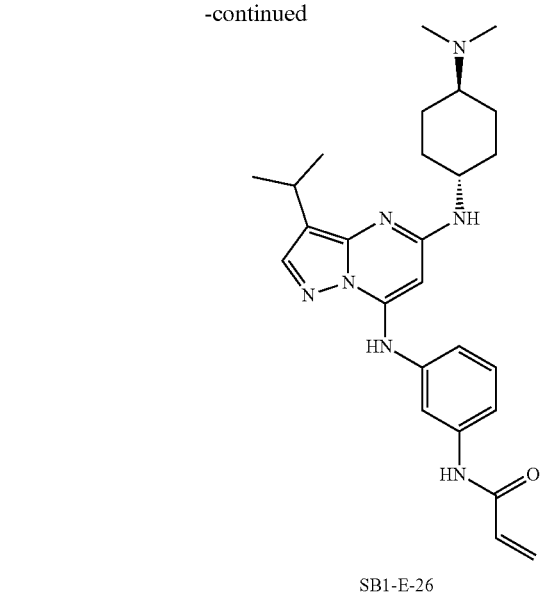

SB1-E-26

N-(3-(5-((1r,4r)-4-(Dimethylamino)cyclohexylamino)-3-isopropylpyrazolo[1,5-a]pyrimidin-7-ylamino)phenyl)acrylamide (SB1-E-26)

To a solution of SB1-E-25-6 (70 mg, 0.172 mmol) and DIPEA (0.5 mL) in CH$_3$CN (5 mL) was added acrylyl chloride (30 mg, 0.331 mmol) in CH$_3$CN (1 mL), the mixture was stirred at r.t for 15 h, after completion, concentrated to remove the solvent, the residue was purified by prep-TLC (DCM/MeOH=10/1) and prep-HPLC (C18 column, CH$_3$CN/H$_2$O, containing 0.05% NH$_4$HCO$_3$) to obtain SB1-E-26, also referred to herein as E-26 and E26 (white solid, 12 mg, yield 15%). HPLC: 100% (254 nm); LCMS (m/z): 462 [M+H]$^+$; $^1$H NMR (DMSO-d$_6$, 500 MHz): δ 10.26 (s, 1H), 9.06 (s, 1H), 7.70 (s, 1H), 7.67 (s, H), 7.54 (d, J=6.5 Hz, 1H), 7.36 (t, J=6.5 Hz, 1H), 7.08 (d, J=1.5 Hz, 1H), 6.62 (d, J=6.0 Hz, 1H), 6.45 (dd, J$_1$=16.0 Hz, J$_2$=9.5 Hz, 1H), 6.28 (d, J=16.0 Hz, 1H), 5.78 (d, J=9.5 Hz, 1H), 5.62 (s, 1H), 3.00 (m, 1H), 2.18 (s, 7H), 2.06 (d, J=10.5 Hz, 1H), 1.80 (d, J=10.5 Hz, 1H), 1.12-1.29 (m, 11H).

Example 19. N-((1R,4s)-4-((3-ethyl-5-((S)-2-(2-hydroxyethyl)piperidin-1-yl)pyrazolo[1,5-a]pyrimidin-7-yl)amino)cyclohexyl)acrylamide (MFH-1-169-1)

MFH-1-169-1

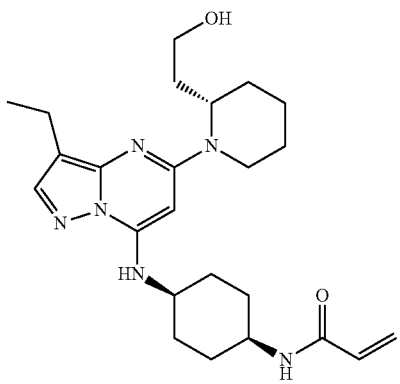

Synthetic Scheme 19

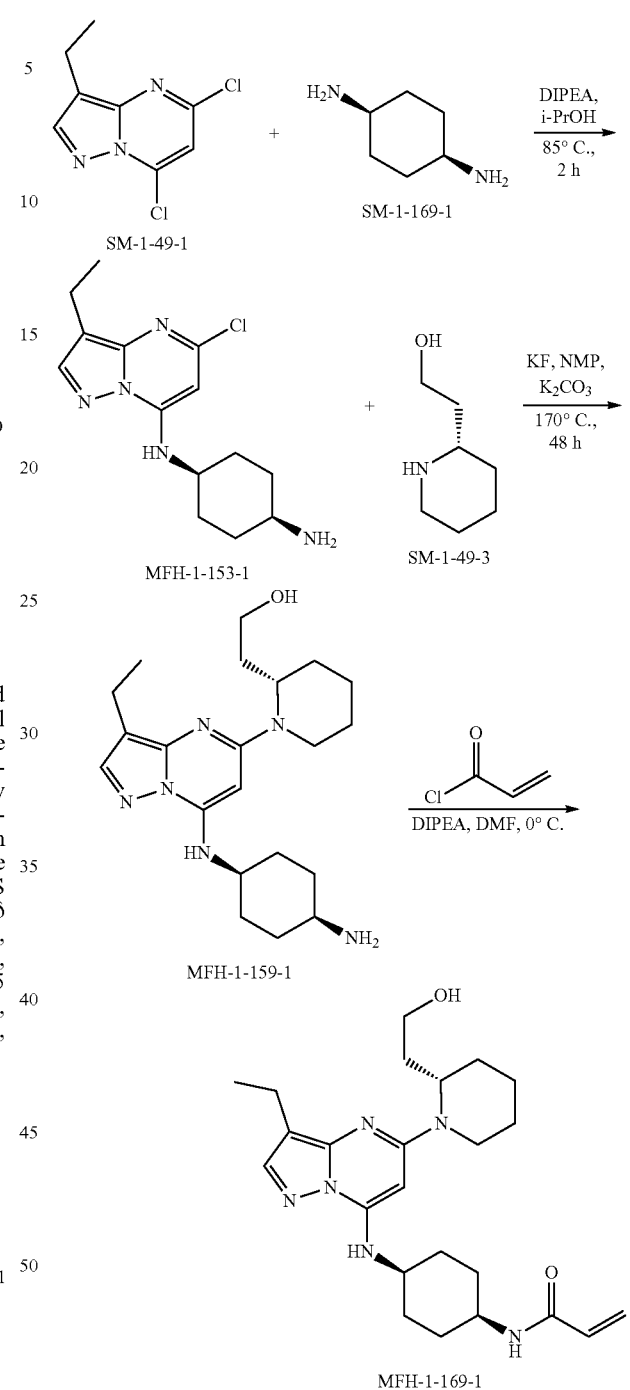

(1s,4s)-N1-(5-chloro-3-ethylpyrazolo[1,5-a]pyrimidin-7-yl)cyclohexane-1,4-diamine (MFH-1-153-1)

The mixture of SM-1-49-1 (300 mg, 1.388 mmol), SM-1-167-1 (182 mg, 1.6 mmol), DIPEA (270 mg) and i-PrOH (8 mL) was stirred at 85° C. for 2 h. After completion, the solvent was removed and the residue was purified by silica gel (NH$_3$/MeOH (1.75N)/DCM=0-20%) to obtain MFH-1-153-1 (240 g, yield 59%). LCMS (m/z): 294 [M+H]$^+$.

2-((S)-1-(7-((1s,4R)-4-aminocyclohexylamino)-3-ethylpyrazolo[1,5-a]pyrimidin-5-yl)piperidin-2-yl)ethanol (MFH-1-159-1)

The mixture of MFH-1-153-1 (230 mg, 0.783 mmol), SM-1-49-3 (182 mg, 1.41 mmol), KF (205 mg, 3.5235 mmol), K$_2$CO$_3$ (194 mg, 1.41 mmol) and NMP (2 mL) was stirred at 170° C. for 48 h. After completion, the residue was extracted with chloroform/i-propanol (4/1) and the organic phase was washed with brine (50 mL×2) and dried with Na$_2$SO$_4$. The residue after removal of the solvent was purified by silica gel (NH$_3$/MeOH (1.75N)/DCM=0-20%) to obtain MFH-1-159-1 (50 mg, yield 16.5%). LCMS (m/z): 387 [M+H]$^+$.

N-((1R,4s)-4-(3-ethyl-5-((S)-2-(2-hydroxyethyl)piperidin-1-yl)pyrazolo[1,5-a]pyrimidin-7-ylamino)cyclohexyl)acrylamide (MFH-1-169-1)

To a solution of MFH-1-159-1 (25 mg, 0.06468 mmol) and DIPEA (0.2 mL) in CH$_3$CN (2 mL) was added acryloyl chloride (8 mg, 0.0841 mmol) in DCM (0.5 mL) dropwise. The mixture was stirred at 0° C. for 1 h. After completion, the solvent was removed and the residue was purified by prep-HPLC (C18 column, MeOH/H$_2$O, containing 0.05% TFA) to obtain MFH-1-169-1 (off-white solid, 4.8 mg, yield 16%). HPLC: 97% (254 nm); LCMS (m/z): 441 [M+H]$^+$; $^1$H NMR (500 MHz, DMSO) δ 7.97 (d, J=7.2 Hz, 1H), 7.87 (s, 1H), 7.44 (s, 1H), 6.30 (dd, J=17.1, 10.2 Hz, 1H), 6.09 (dd, J=17.1, 2.1 Hz, 1H), 5.78 (s, 1H), 5.59 (dd, J=10.2, 2.1 Hz, 1H), 4.49 (s, 1H), 4.15 (d, J=12.3 Hz, 1H), 3.98-3.79 (m, 3H), 3.08 (t, J=12.4 Hz, 2H), 2.61-2.52 (m, 2H), 1.95 (dd, J=18.6, 10.5 Hz, 1H), 1.84 (dt, J=12.9, 7.4 Hz, 2H), 1.79-1.57 (m, 10H), 1.56-1.44 (m, 1H), 1.18 (t, J=7.5 Hz, 3H).

Example 20. N-((1S,4r)-4-((3-ethyl-5-((S)-2-(2-hydroxyethyl)piperidin-1-yl)pyrazolo[1,5-a]pyrimidin-7-yl)amino)cyclohexyl)acrylamide (MFH-1-175-1)

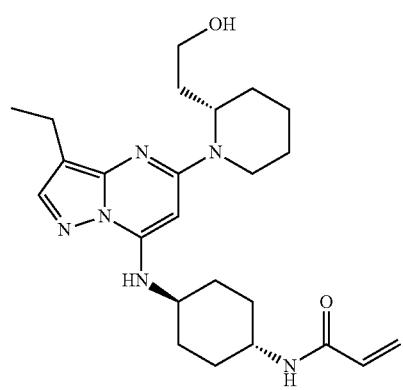

MFH-1-175-1

Synthetic Scheme 20

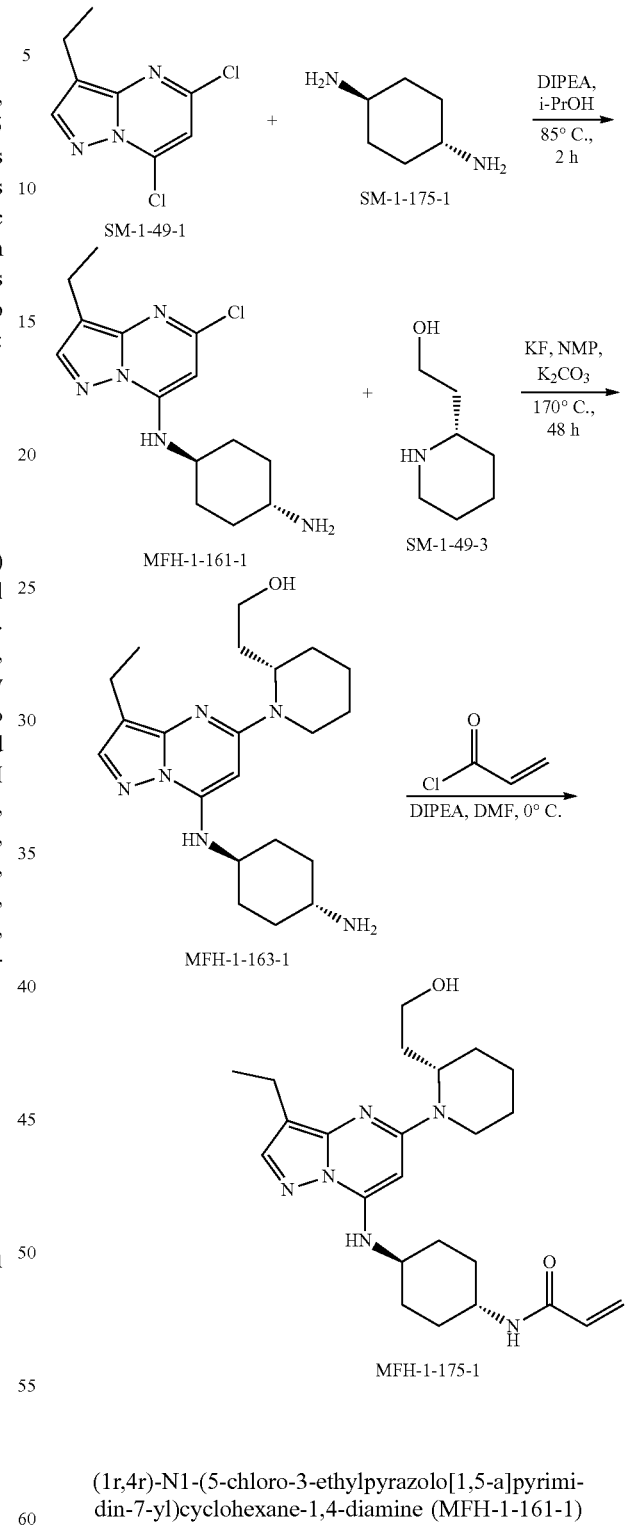

(1r,4r)-N1-(5-chloro-3-ethylpyrazolo[1,5-a]pyrimidin-7-yl)cyclohexane-1,4-diamine (MFH-1-161-1)

The mixture of SM-1-49-1 (300 mg, 1.388 mmol), SM-1-175-1 (250 mg, 2.19 mmol), DIPEA (270 mg) and i-PrOH (8 mL) was stirred at 85° C. for 1 h. After completion, the solvent was removed and the residue was purified by silica gel (NH$_3$/MeOH (1.75N)/DCM=0-20%) to obtain MFH-1-161-1 (230 g, yield 56%). LCMS (m/z): 294 [M+H]$^+$.

2-((S)-1-(7-((1r,4S)-4-aminocyclohexylamino)-3-ethylpyrazolo[1,5-a]pyrimidin-5-yl)piperidin-2-yl)ethanol (MFH-1-163-1)

The mixture of MFH-1-161-1 (230 mg, 0.783 mmol), SM-1-49-3 (182 mg, 1.41 mmol), KF (205 mg, 3.5235 mmol), K₂CO₃ (194 mg, 1.41 mmol) and NMP (2 mL) was stirred at 170° C. for 48 h. After completion, the residue was extracted with chloroform and 2-propanol (4:1) and the organic phase was washed with brine (50 mL×2) and dried with Na₂SO₄. The residue after removal of solvent was purified by silica gel (NH₃/MeOH (1.75N)/DCM=0-20%) to obtain MFH-1-163-1(30 mg, yield 10%). LCMS (m/z): 387 [M+H]⁺.

N-((1S,4r)-4-(3-ethyl-5-((S)-2-(2-hydroxyethyl)piperidin-1-yl)pyrazolo[1,5-a]pyrimidin-7-ylamino)cyclohexyl)acrylamide (MFH-1-175-1)

To a solution of MFH-1-163-1 (30 mg, 0.07762 mmol) and DIPEA (0.2 mL) in CH₃CN (2 mL) was added acryloyl chloride (9 mg, 0.101 mmol) in DCM (0.5 mL) dropwise. The mixture was stirred at 0° C. for 1 h. After completion, the solvent was removed and the residue was purified by prep-HPLC (C18 column, MeOH/H₂O, containing 0.05% TFA) to obtain MFH-1-175-1 (off-white solid, 12.8 mg, yield 37%). HPLC: 97% (254 nm); LCMS (m/z): 441 [M+H]⁺; ¹H NMR (500 MHz, DMSO) δ 8.03 (d, J=7.5 Hz, 1H), 7.90 (s, 1H), 6.24 (dd, J=17.1, 10.1 Hz, 1H), 6.08 (dd, J=17.1, 2.2 Hz, 1H), 5.77 (d, J=10.8 Hz, 1H), 5.58 (dd, J=10.1, 2.3 Hz, 1H), 4.49 (s, 1H), 4.14 (d, J=12.4 Hz, 2H), 3.74 (s, 2H), 3.62-3.49 (m, 2H), 3.43-3.34 (m, 1H), 3.11 (t, J=13.0 Hz, 1H), 2.57 (dt, J=9.8, 4.9 Hz, 2H), 2.07-1.82 (m, 5H), 1.83-1.56 (m, 8H), 1.53 (d, J=11.8 Hz, 1H), 1.39 (td, J=12.9, 3.6 Hz, 2H), 1.25-1.13 (m, 3H).

Example 21. (S)—N-(4-((3-ethyl-5-(2-(2-hydroxyethyl)piperidin-1-yl)pyrazolo[1,5-a]pyrimidin-7-yl)amino)phenyl)acrylamide (MFH-1-187-1)

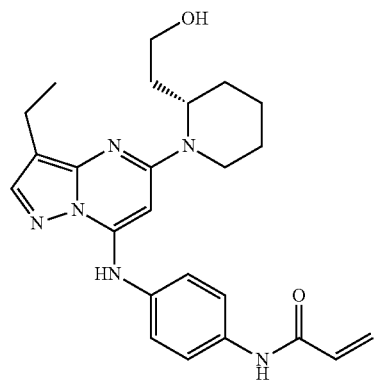

MFH-1-187-1

Synthetic Scheme 21

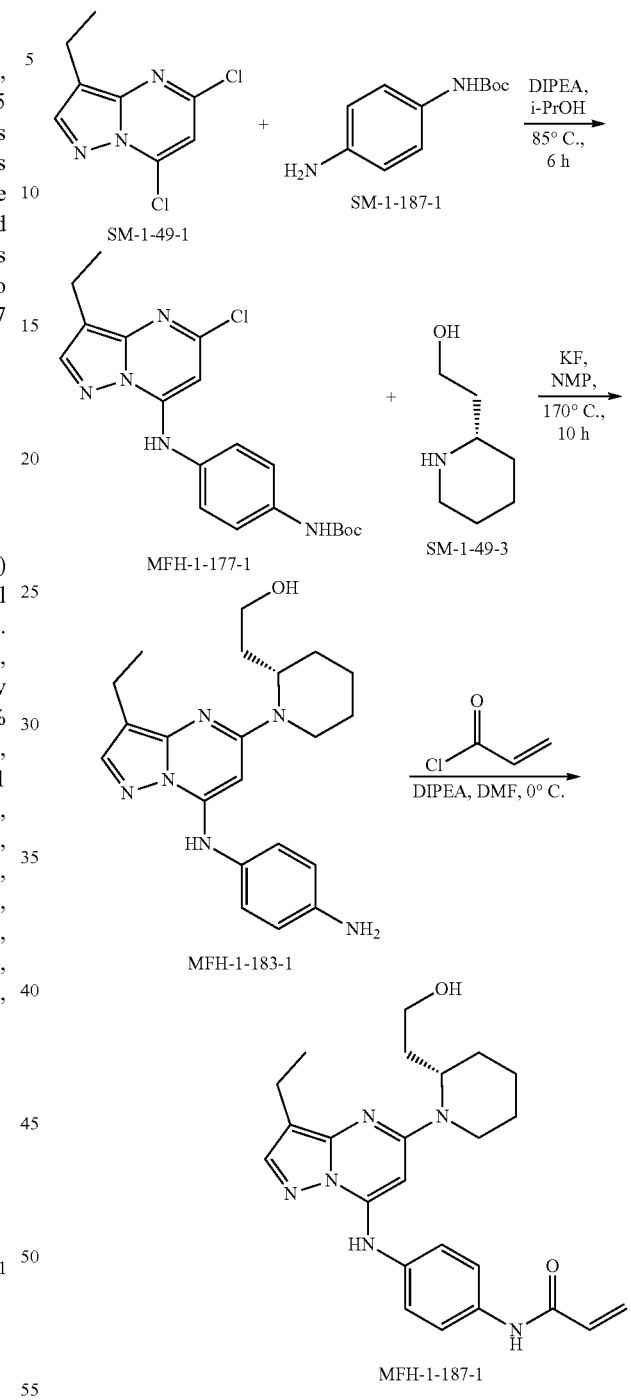

tert-butyl 4-(5-chloro-3-ethylpyrazolo[1,5-a]pyrimidin-7-ylamino)phenylcarbamate (MFH-1-177-1)

The mixture of SM-1-49-1 (500 mg, 2.314 mmol), SM-1-187-1 (520 mg, 2.5 mmol), DIPEA (898 mg) and i-PrOH (8 mL) was stirred at 85° C. for 6 h. After completion, the solvent was removed and the residue was purified by silica gel chromatography (MeOH/DCM=0-20%) to obtain MFH-1-177-1 (898 g, yield 100%). LCMS (m/z): 388 [M+H]⁺.

(S)-2-(1-(7-(4-aminophenylamino)-3-ethylpyrazolo [1,5-a]pyrimidin-5-yl)piperidin-2-yl)ethanol (MFH-1-183-1)

The mixture of MFH-1-177-1 (449 mg, 1.157 mmol), SM-1-49-3 (240 mg, 1.8512 mmol), KF (303 mg, 5.2 mmol) and NMP (2 mL) was stirred at 170° C. for 10 h. After completion, the solution was extracted with chloroform and 2-propanol (4:1) and the organic phase was washed with brine (50 mL×2) and dried with $Na_2SO_4$. The solvent was removed and the residue was purified by silica gel chromatography (MeOH/DCM=0-20%) to obtain MFH-1-183-1 (400 mg, yield 91%). LCMS (m/z): 381 [M+H]$^+$.

(S)—N-(4-(3-ethyl-5-(2-(2-hydroxyethyl)piperidin-1-yl)pyrazolo[1,5-a]pyrimidin-7-ylamino)phenyl) acrylamide (MFH-1-187-1)

To a solution of MFH-1-183-1 (80 mg, 0.21 mmol) and DIPEA (0.2 mL) in $CH_3CN$ (2 mL) was added acryloyl chloride (25 mg, 0.273 mmol) in DCM (0.5 mL) dropwise. The mixture was stirred at 0° C. for 1 h. After completion, the solvent was removed and the residue was purified by prep-HPLC (C18 column, MeOH/$H_2O$, containing 0.05% TFA) to obtain MFH-1-187-1 (off-white solid, 33.6 mg, yield 36.8%). HPLC: 96% (254 nm); LCMS (m/z): 435 [M+H]$^+$; $^1$H NMR (500 MHz, DMSO) δ 10.26 (s, 1H), 9.83 (s, 1H), 7.91 (s, 1H), 7.76 (t, J=13.5 Hz, 2H), 7.42 (d, J=8.9 Hz, 2H), 6.46 (dd, J=17.0, 10.1 Hz, 1H), 6.28 (dd, J=17.0, 1.9 Hz, 1H), 5.84-5.68 (m, 2H), 4.42 (s, 1H), 4.02 (s, 2H), 3.32 (ddd, J=10.9, 8.2, 4.9 Hz, 2H), 3.00 (dd, J=24.6, 11.8 Hz, 1H), 2.64-2.55 (m, 2H), 1.90 (td, J=13.5, 5.1 Hz, 1H), 1.76-1.51 (m, 6H), 1.49-1.33 (m, 1H), 1.27-1.17 (m, 3H).

Example 22. N-(3-(((2-(((1r,4r)-4-(dimethylamino) cyclohexyl)amino)-8-ethylpyrazolo[1,5-a][1,3,5] triazin-4-yl)amino)methyl)phenyl)acrylamide (MFH-2-67-1)

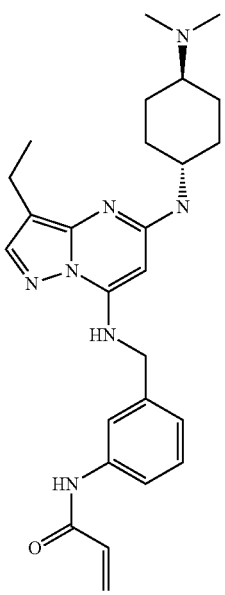

MFH-2-67-1

Synthetic Scheme 22

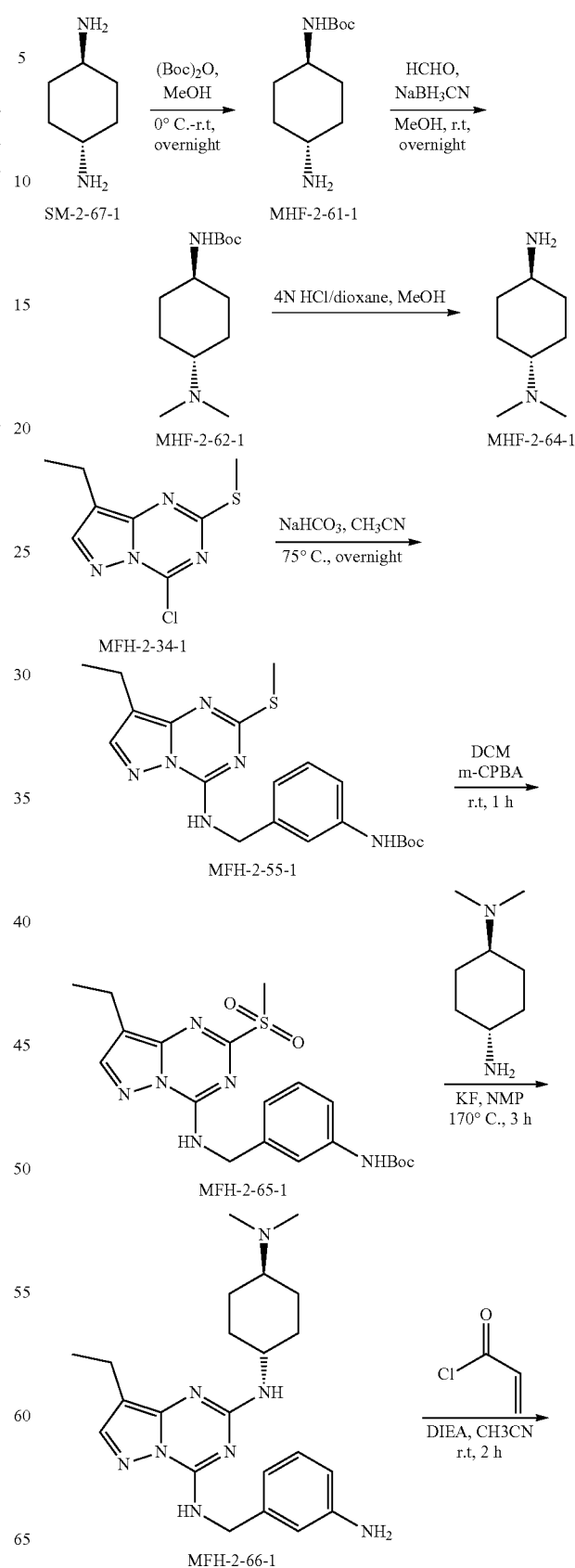

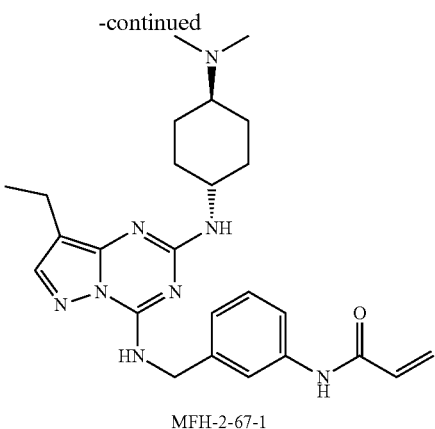

MFH-2-67-1 tert-butyl (1r,4r)-4-aminocyclohexylcarbamate (MFH-2-61-1)

To a solution of SM-2-67-1 (2.0 g, 17.5 mmol) in MeOH (100 mL) was added the solution of (Boc)$_2$O (1.1 g, 5.04 mmol) in MeOH (60 mL) dropwise for 30 min. The mixture was stirred at room temperature overnight. After completion, the solvent was removed and to the residue was added H$_2$O (50 mL) and further stirred at room temperature for 20 min and then filtered. The filtrate was extracted with ethyl acetate (120 mL×2) and the organic phase was washed with brine (50 mL×2) and dried with Na$_2$SO$_4$. The solution was then concentrated under reduced pressure to obtain MFH-2-61-1 (off-white solid, 900 mg, yield 83%).

tert-butyl (1r,4r)-4-(dimethylamino)cyclohexylcarbamate (MFH-2-62-1)

To a solution of MFH-2-61-1 (850 mg, 3.97 mmol) and HCHO (600 mg, 20.0 mmol) in MeOH (30 mL) was added NaBH$_3$CN (1.1 g, 17.5 mmol) and the mixture was stirred at room temperature overnight. After completion, the solvent was removed and the residue was extracted with ethyl acetate (100 mL×4) and the organic phase was washed with brine (50 mL×2) and dried with Na$_2$SO$_4$. The residue after removal of solvent was purified by silica gel chromatography (DCM/MeOH=10/1, 5/1) to obtain MFH-2-62-1 (light brown solid, 800 mg, yield 83%). LCMS (m/z): 243 [M+H]$^+$.

(1r,4r)-N1,N1-dimethylcyclohexane-1,4-diamine (MFH-2-64-1)

To a mixture of compound MFH-2-62-1 (350 mg, 1.44 mmol) in methanol (5 mL) was added 4N HCl/dioxane (10 mL) and stirred for 3h at room temperature. The mixture was concentrated and the crude mixture was directly used in the next step. LCMS (m/z): 143 [M+H]$^+$.

tert-butyl3-((8-ethyl-2-(methylthio)pyrazolo[1,5-a][1,3,5]triazin-4-ylamino)methyl)phenylcarbamate (MFH-2-55-1)

A stirred mixture of MFH-2-34-1 (220 mg, 0.962 mmol), tert-butyl 3-(aminomethyl) phenylcarbamate (214 mg, 0.962 mmol) and NaHCO$_3$ (121 mg, 1.443 mmol) in acetonitrile (5 mL) was heated at 75° C. overnight and then was cooled to room temperature. The solution was filtered and concentrated under reduced pressure. The residue was purified by silica gel chromatography (PE/ethyl acetate=3:1 to 1:1) to afford MFH-2-55-1 (white solid, 210 mg, yield: 52%). LCMS (m/z): 415 [M+H]$^+$.

tert-butyl3-((8-ethyl-2-(methylsulfonyl)pyrazolo[1,5-a][1,3,5]triazin-4-ylamino)methyl)phenylcarbamate (MFH-2-65-1)

To a solution of MFH-2-55-1 (110 mg, 0.2654 mmol) in DCM (3 mL) was added 3-chloroperbenzoic acid (137 mg, 0.7961 mmol) in one portion at room temperature and was stirred at for 1 h. The reaction mixture was quenched with a saturated Na$_2$S$_2$O$_3$ solution (10 mL), diluted with DCM (50 mL), washed with saturated aqueous NaCl (3×50 mL), dried over anhydrous Na$_2$SO$_4$, filtered, and concentrated to give MFH-2-65-1 (yellow solid, 118 mg, yield: 100%), which was used in next step directly. LCMS (m/z): 447 [M+H]$^+$.

N4-(3-aminobenzyl)-N2-((1r,4r)-4-(dimethylamino)cyclohexyl)-8-ethylpyrazolo[1,5-a][1,3,5]triazine-2,4-diamine (MFH-2-66-1)

To a stirred mixture MFH-2-65-1 (118 mg, 0.2654 mmol) and MFH-2-64-1 (98 mg, 0.4554 mmol) in N-methyl-2-pyrrolidone (3 mL) was added KF (46 mg, 0.7962 mmol). This mixture was heated at 170° C. for 3 h and then was cooled and filtered. The crude mixture was purified by silica gel chromatography (MeOH/DCM=0-20%) to afford MFH-2-66-1 (yellow solid, 30 mg, yield: 28%). LCMS (m/z): 409 [M+H]$^+$.

N-(3-((2-((1r,4r)-4-(dimethylamino)cyclohexylamino)-8-ethylpyrazolo[1,5-a][1,3,5]triazin-4-ylamino)methyl)phenyl)acrylamide (MFH-2-67-1)

To a solution of MFH-2-66-1 (30 mg, 0.07343 mmol) in CH$_3$CN (2 mL) were added acryloyl chloride (9 mg, 0.1 mmol) and DIPEA (0.2 mL). The reaction was stirred at room temperature for 2 h. After completion, the reaction mixture was diluted with dichloromethane (10 ml), washed with water (10 mL) and a saturated sodium bicarbonate solution (10 mL×2), and dried over anhydrous sodium sulfate. The residue after removal of the solvent was purified by prep-HPLC (C18 column, MeOH/H$_2$O, containing 0.05% TFA) to obtain MFH-2-67-1 (off-white solid, 11.3 mg, yield 28%). HPLC: 97% (254 nm); LCMS (m/z): 463 [M+H]$^+$; $^1$H NMR (500 MHz, DMSO) δ 10.16 (s, 1H), 9.81 (s, 1H), 9.53 (s, 1H), 8.75 (s, 1H), 7.95 (d, J=40.1 Hz, 1H), 7.77 (s, 1H), 7.64-7.48 (m, 1H), 7.30 (s, 1H), 6.42 (dd, J=16.9, 10.1 Hz, 1H), 6.31-6.14 (m, 1H), 5.75 (d, J=11.4 Hz, 1H), 4.64 (d, J=6.1 Hz, 2H), 3.17 (d, J=8.6 Hz, 2H), 2.94-2.56 (m, 6H), 2.48 (s, 1H), 1.99 (dd, J=87.3, 31.8 Hz, 4H), 1.51 (s, 2H), 1.39-0.96 (m, 6H).

Example 23. N-(3-((2-(((1r,4r)-4-(dimethylamino)cyclohexyl)amino)-8-ethylpyrazolo[1,5-a][1,3,5]triazin-4-yl)amino)cyclohexyl)acrylamide (MFH-2-78-1)
MFH-2-78-1
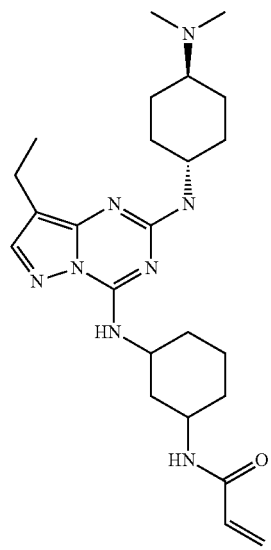
Synthetic Scheme 23
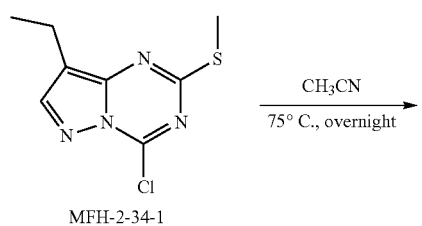
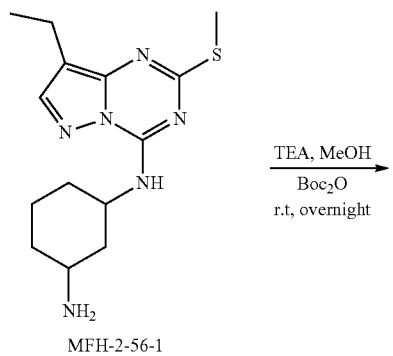
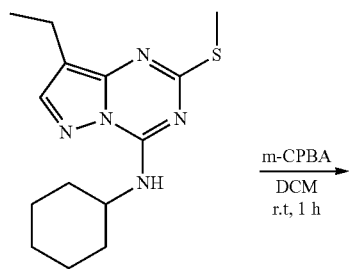
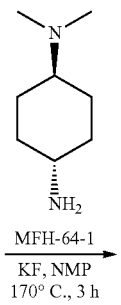
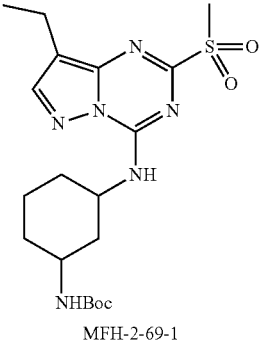
MFH-2-69-1
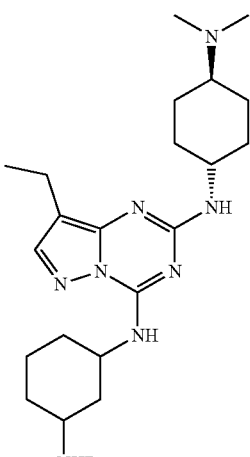
MFH-2-70-1
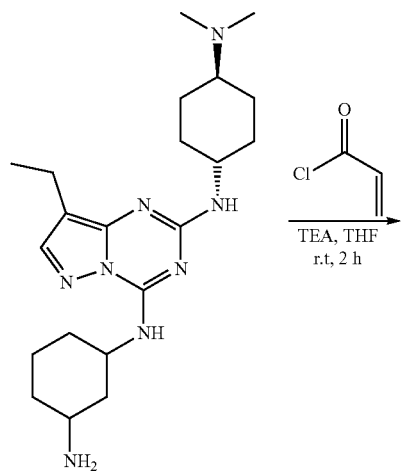
MFH-2-77-1

223

-continued

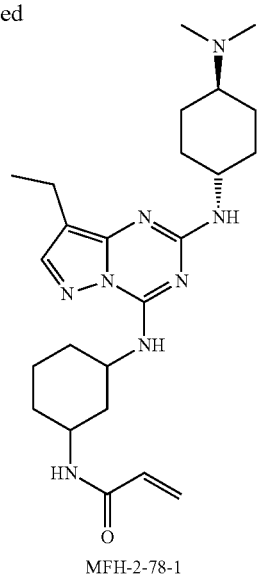

MFH-2-78-1

N1-(8-ethyl-2-(methylthio)pyrazolo[1,5-a][1,3,5]triazin-4-yl)cyclohexane-1,3-diamine (MFH-2-56-1)

MFH-2-34-1 (220 mg, 0.96 mmol) and cyclohexane-1,3-diamine (330 mg, 2.88 mmol) were dissolved in acetonitrile (5 mL). The mixture was heated at 75° C. overnight. The solvent was then removed under reduced pressure. The crude mixture was purified by silica gel chromatography (NH$_3$/MeOH (1.75N)/DCM=0-20%) to obtain MFH-2-56-1 (white solid, 193 mg, yield: 65%). LCMS (m/z): 307 [M+H]$^+$.

tert-butyl3-(8-ethyl-2-(methylthio)pyrazolo[1,3,5]triazin-4-ylamino)cyclohexylcarbamate (MFH-2-58-1)

To a solution of MFH-2-56-1 (193 mg, 0.63 mmol) in MeOH (6 mL) was added di-tert-butyl dicarbonate (206 mg, 0.94 mmol) and TEA (191 mg 1.89 mmol). The reaction mixture was stirred at room temperature overnight. The reaction mixture was concentrated under reduced pressure to afford the residue, which was purified by flash column chromatography (MeOH/DCM=0-20%) to afford MFH-2-58-1 (210 mg, yield: 82%). LCMS (m/z): 407 [M+H]$^+$.

tert-butyl3-(8-ethyl-2-(methylsulfonyl)pyrazolo[1,5-a][1,3,5]triazin-4-ylamino)cyclohexylcarbamate (MFH-2-69-1)

To a solution of MFH-2-58-1 (210 mg, 0.51 mmol) in DCM (5 mL) was added 3-chloroperbenzoic acid (268 mg, 1.55 mmol). The mixture was stirred at room temperature for 1 h and then was quenched with a saturated Na$_2$S$_2$O$_3$ solution (5 mL). The reaction mixture was extracted with DCM (50 mL) and the organic layer was washed with saturated aqueous NaCl (3×50 mL), dried over anhydrous Na$_2$SO$_4$, filtered and concentrated to give MFH-2-69-1 (226.6 mg, yield: 100%) as the crude product, which was used for next step directly. LCMS (m/z): 439 [M+H]$^+$.

tert-butyl3-(2-((1r,4r)-4-(dimethylamino)cyclohexylamino)-8-ethylpyrazolo[1,5-a][1,3,5]triazin-4-ylamino)cyclohexylcarbamate (MFH-2-70-1)

To a stirred mixture MFH-2-69-1 (226.6 mg, 0.51 mmol) and MFH-2-64-1 (118 mg, 0.83 mmol) in N-methyl-2-pyrrolidone (3 mL) was added KF (90 mg, 1.551 mmol). This mixture was heated at 170° C. for 3 h, and then cooled and filtered. The crude mixture was then purified by silica gel chromatography (NH$_3$/MeOH (1.75N)/DCM=0-20%) to afford MFH-2-70-1 (120 mg, yield: 47%). LCMS (m/z): 501 [M+H]$^+$.

N4-(3-aminocyclohexyl)-N2-((1r,4r)-4-(dimethylamino)cyclohexyl)-8-ethylpyrazolo[1,5-a][1,3,5]triazine-2,4-diamine (MFH-2-77-1)

To a mixture of compound MFH-2-70-1 (60 mg, xx mmol) in methanol (5 mL) was added 4N HCl/dioxane (5 mL) and the solution was stirred for 3h at room temperature. The mixture was concentrated under reduced pressure and the crude mixture was directly used in next step. LCMS (m/z): 401 [M+H]$^+$.

N-(3-(2-((1r,4r)-4-(dimethylamino)cyclohexylamino)-8-ethylpyrazolo[1,5-a][1,3,5]triazin-4-ylamino)cyclohexyl)acrylamide (MFH-2-78-1)

To a solution of MFH-2-77-1 (48 mg, 0.12 mmol) in CH$_3$CN (2 mL) was added acryloyl chloride (14 mg, 0.156 mmol) and DIPEA (0.2 ml). The reaction mixture was stirred at room temperature for 2 h. After completion, the reaction mixture was diluted with dichloromethane (10 ml), washed with a saturated NaHCO$_3$ solution (10 mL×2), and washed with water (10 mL). The organic layer was dried over anhydrous sodium sulfate, concentrated under reduced pressure and the residue was purified by prep-HPLC (C18 column, MeOH/H$_2$O, containing 0.05% TFA) to afford MFH-2-78-1 (white solid, 25.2 mg, yield: 46%). HPLC: 97% (254 nm); LCMS (m/z): 455 [M+H]$^+$; $^1$H NMR (500 MHz, DMSO) δ 9.51 (s, 1H), 8.15 (s, 1H), 7.92 (s, 1H), 7.74 (s, 1H), 6.20 (dd, J=16.9, 9.9 Hz, 1H), 6.15-6.03 (m, 1H), 5.58 (d, J=9.8 Hz, 1H), 3.17 (s, 3H), 2.75 (d, J=4.9 Hz, 6H), 2.49 (d, J=2.3 Hz, 1H), 2.47 (dd, J=7.5, 2.1 Hz, 1H), 2.23-1.91 (m, 5H), 1.90-1.71 (m, 3H), 1.45 (ddd, J=45.3, 44.9, 21.3 Hz, 8H), 1.15 (s, 4H).

Example 24. (S)—N-(3-(((3-ethyl-5-(2-(2-hydroxyethyl)piperidin-1-yl)pyrazolo[1,5-a]pyrimidin-7-yl)amino)methyl)phenyl)acrylamide (MFH-1-49-1)

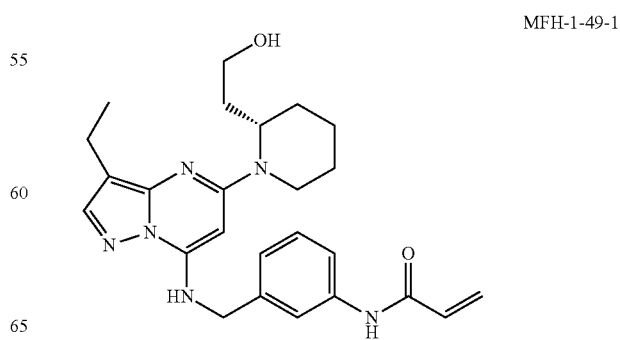

MFH-1-49-1

Synthetic Scheme 24

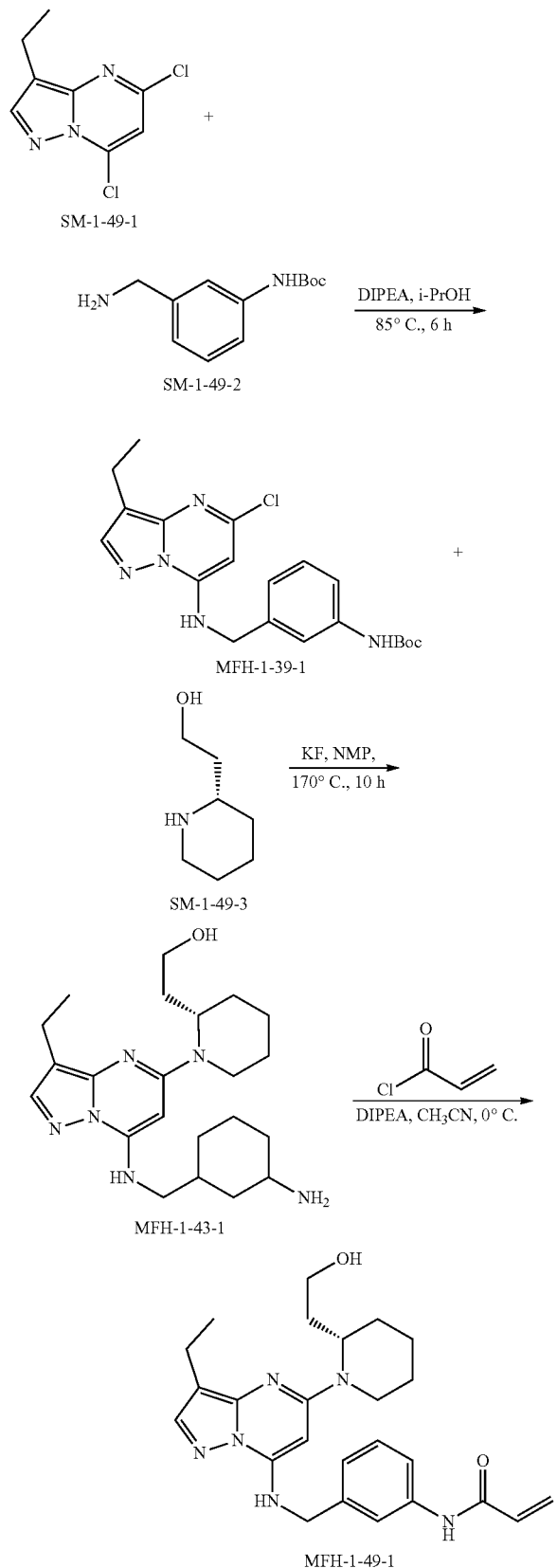

tert-butyl-3-((5-chloro-3-ethylpyrazolo[1,5-a]pyrimidin-7-ylamino)methyl)phenylcarbamate (MFH-1-39-1)

The mixture of SM-1-49-1 (400 mg, 1.85 mmol), SM-1-49-2 (452.6 mg, 2.0364 mmol), DIPEA (718 mg) and i-PrOH (5 mL) was stirred at 85° C. for 6 h. Then the reaction mixture was concentrated under reduced pressure and the residue was purified by silica gel chromatography (PE/EA=0-50%) to obtain MFH-1-39-1 (white solid, 0.66 g, yield 88.7%). LCMS (m/z): 402 [M+H]$^+$.

(S)-2-(1-(7-(3-aminobenzylamino)-3-ethylpyrazolo[1,5-a]pyrimidin-5-yl)piperidin-2-yl)ethanol (MFH-1-43-1)

The mixture of MFH-1-39-1 (660 mg, 1.6422 mmol), SM-1-49-3 (318 mg, 2.4633 mmol), KF (429 mg, 7.4 mmol) and NMP (2 mL) was stirred at 170° C. for 10 h. After completion, the residue was extracted with chloroform and isopropanol (4:1) and the organic phase was washed with brine (50 mL×2) and dried with Na$_2$SO$_4$. The solution was filtered and concentrated under reduced pressure. The residue was purified by silica gel chromatography (MeOH/DCM=0-20%) to obtain MFH-1-43-1 (396.3 mg, yield 61%). LCMS (m/z): 395 [M+H]$^+$.

(S)—N-(3-(((3-ethyl-5-(2-(2-hydroxyethyl)piperidin-1-yl)pyrazolo[1,5-a]pyrimidin-7-ylamino)methyl)phenyl)acrylamide (MFH-1-49-1)

To a solution of MFH-1-43-1 (60 mg, 0.15 mmol) and DIPEA (0.2 mL) in CH$_3$CN (2 mL) was added acryloyl chloride (18 mg, 0.20 mmol) in DCM (0.5 mL) dropwise. The mixture was then stirred at 0° C. for 1 h. After reaction completion, the reaction was concentrated to remove the solvent and the residue was purified by prep-HPLC (C18 column, MeOH/H$_2$O, containing 0.05% TFA) to obtain MFH-1-49-1 (off-white solid, 8.6 mg, yield 12.6%). HPLC: 96% (254 nm); LCMS (m/z): 449 [M+H]$^+$; $^1$H NMR (500 MHz, DMSO) δ 10.14 (s, 1H), 8.94 (s, 1H), 7.91 (s, 1H), 7.72 (s, 1H), 7.53 (d, J=8.1 Hz, 1H), 7.30 (t, J=7.8 Hz, 1H), 7.13 (d, J=7.6 Hz, 1H), 6.41 (dd, J=17.0, 10.1 Hz, 1H), 6.22 (dd, J=17.0, 1.7 Hz, 1H), 5.73 (dd, J=10.1, 1.7 Hz, 1H), 5.66 (s, 1H), 4.62 (d, J=6.3 Hz, 2H), 4.41 (s, 1H), 3.96 (d, J=11.7 Hz, 2H), 3.06 (t, J=12.6 Hz, 1H), 2.60-2.51 (m, 2H), 1.96 (d, J=5.0 Hz, 1H), 1.73-1.58 (m, 5H), 1.53 (s, 1H), 1.43 (d, J=11.6 Hz, 2H), 1.12 (t, J=7.5 Hz, 3H), 1.08 (s, 1H).

Example 25 (R)—N-(3-((3-ethyl-5-(2-(2-hydroxyethyl)piperidin-1-yl)pyrazolo[1,5-a]pyrimidin-7-ylamino)methyl)phenyl)acrylamide (MFH-1-56-1)

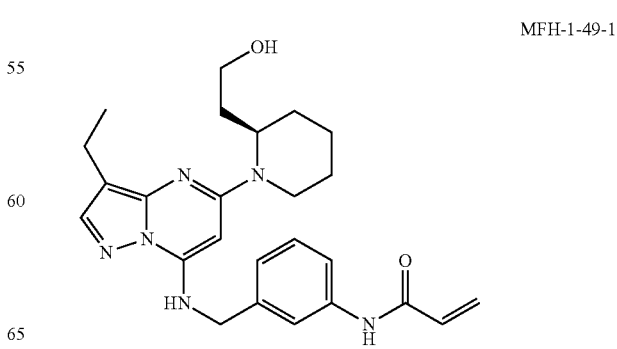

MFH-1-49-1

227

Synthetic Scheme 25

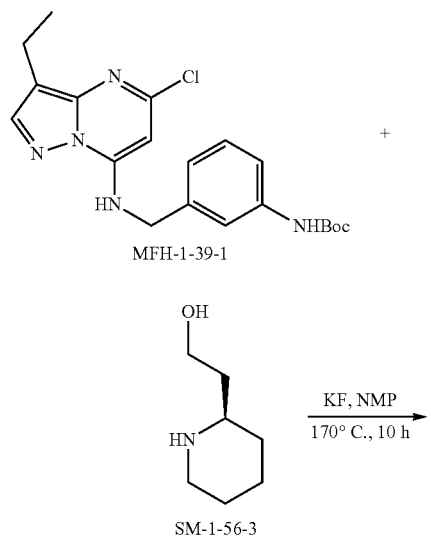

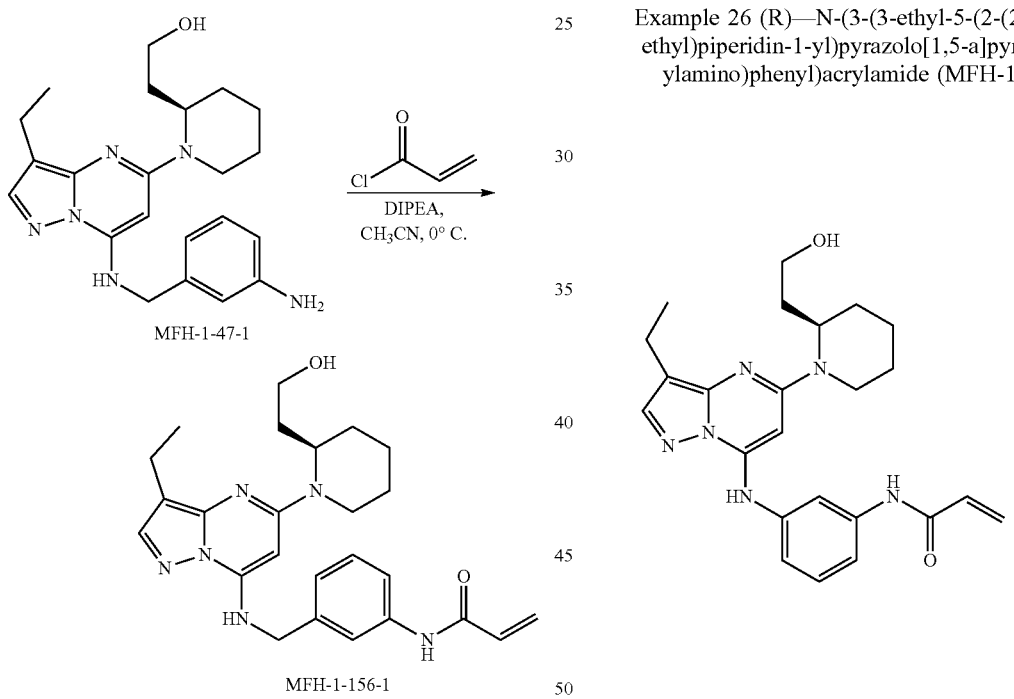

(R)-2-(1-(7-(3-aminobenzylamino)-3-ethylpyrazolo[1,5-a]pyrimidin-5-yl)piperidin-2-yl)ethanol (MFH-1-47-1)

The mixture of MFH-1-39-1 (330 mg, 0.8211 mmol), SM-1-56-1 (248.6 mg, 1.3884 mmol), KF (242 mg, 4.1652 mmol) and NMP (1 mL) was stirred at 170° C. for 10 h. After completion, the residue was extracted with chloroform and 2-propanol (4:1). The organic phase was washed with brine (50 mL×2) and dried with Na₂SO₄. The solvent was removed and the residue was purified by silica gel chromatography (MeOH/DCM=0-20%) to obtain MFH-1-56-1 (259 mg, yield 80%). LCMS (m/z): 395 [M+H]⁺.

228

(R)—N-(3-((3-ethyl-5-(2-(2-hydroxyethyl)piperidin-1-yl)pyrazolo[1,5-a]pyrimidin-7-ylamino)methyl)phenyl)acrylamide (MFH-1-56-1)

To a solution of MFH-1-47-1 (60 mg, 0.152 mmol) and DIPEA (0.2 mL) in CH₃CN (2 mL) was added acryloyl chloride (18 mg, 0.198 mmol) in DCM (0.5 mL) dropwise. The mixture was then stirred at 0° C. for 1 h. After completion, the solution was concentrated and the residue was purified by prep-HPLC (C18 column, MeOH/H₂O, containing 0.05% TFA) to obtain MFH-1-56-1 (off-white solid, 10 mg, yield 14.6%). HPLC: 98% (254 nm); LCMS (m/z): 449 [M+H]⁺; ¹H NMR (500 MHz, DMSO) δ 10.16 (s, 1H), 9.04 (s, 1H), 7.93 (s, 1H), 7.76 (s, 1H), 7.54 (d, J=8.1 Hz, 1H), 7.31 (t, J=7.8 Hz, 1H), 7.14 (d, J=7.6 Hz, 1H), 6.42 (dd, J=17.0, 10.1 Hz, 1H), 6.24 (dd, J=17.0, 1.7 Hz, 1H), 5.75 (dd, J=10.1, 1.7 Hz, 1H), 5.68 (s, 1H), 4.65 (d, J=6.3 Hz, 2H), 4.42 (s, 1H), 3.98 (d, J=11.7 Hz, 2H), 3.09 (t, J=12.6 Hz, 1H), 2.61-2.54 (m, 2H), 1.96 (d, J=5.0 Hz, 1H), 1.76-1.60 (m, 5H), 1.58 (s, 1H), 1.44 (d, J=11.6 Hz, 2H), 1.19 (t, J=7.5 Hz, 3H), 1.10 (s, 1H).

Example 26 (R)—N-(3-(3-ethyl-5-(2-(2-hydroxyethyl)piperidin-1-yl)pyrazolo[1,5-a]pyrimidin-7-ylamino)phenyl)acrylamide (MFH-1-143-1)

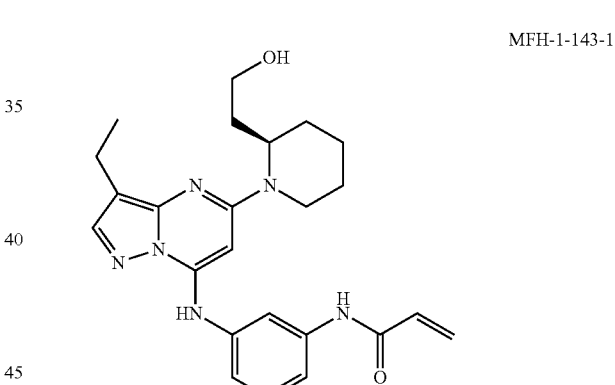

Synthetic Scheme 26

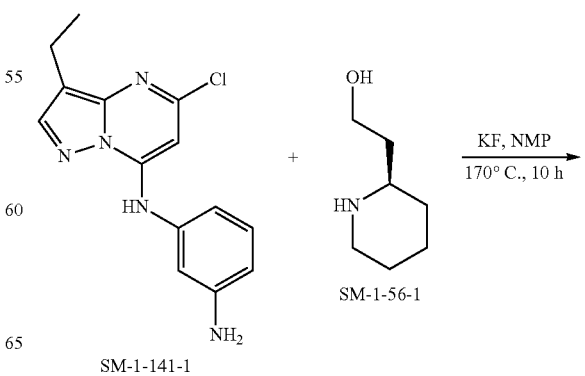

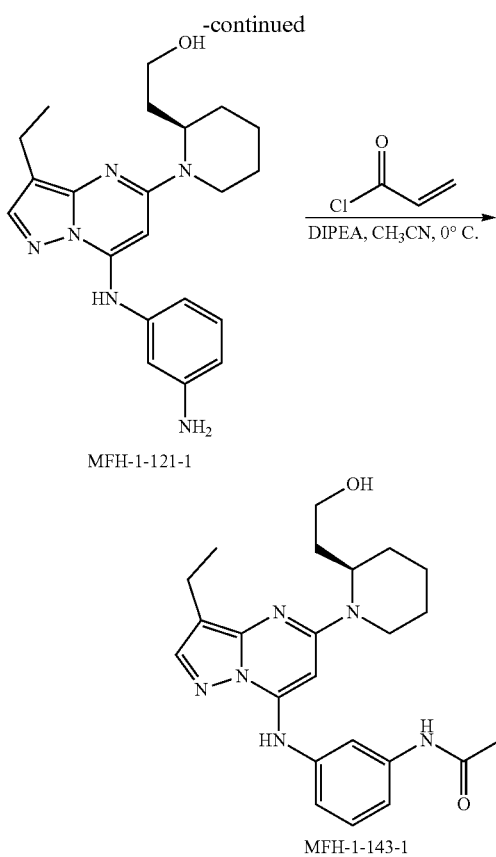

MFH-1-121-1

MFH-1-143-1

(R)-2-(1-(7-(3-aminophenylamino)-3-ethylpyrazolo[1,5-a]pyrimidin-5-yl)piperidin-2-yl)ethanol (MFH-1-121-1)

The mixture of SM-1-141-1 (250 mg, 0.869 mmol), SM-1-56-3 (168 mg, 1.3 mmol), KF (227 mg, 3.9 mmol) and NMP (2 mL) was stirred at 170° C. for 10 h. After completion, the residue was extracted with chloroform and 2-propanol (4:1). The organic phase was washed with brine (50 mL×2) and dried with $Na_2SO_4$. The solvent was removed and the residue was purified by silica gel chromatography (MeOH/DCM=0-20%) to obtain MFH-1-43-1(220 mg, yield 66.5%). LCMS (m/z): 381 [M+H]$^+$.

(R)—N-(3-(3-ethyl-5-(2-(2-hydroxyethyl)piperidin-1-yl)pyrazolo[1,5-a]pyrimidin-7-ylamino)phenyl)acrylamide (MFH-1-143-1)

To a solution of MFH-1-121-1 (50 mg, 0.13141 mmol) and DIPEA (0.2 mL) in $CH_3CN$ (2 mL) was added acryloyl chloride (15 mg, 0.17 mmol) in DCM (0.5 mL) dropwise. The mixture was stirred at 0° C. for 1 h. After completion, the solvent was removed and the residue was purified by prep-HPLC (C18 column, MeOH/$H_2O$, containing 0.05% TFA) to obtain MFH-1-143-1 (off-white solid, 18 mg, yield 31.5%). HPLC: 96% (254 nm); LCMS (m/z): 435 [M+H]$^+$; $^1$H NMR (500 MHz, DMSO) δ 10.29 (s, 1H), 9.89 (s, 1H), 7.92 (d, J=11.7 Hz, 2H), 7.43-7.34 (m, 2H), 7.24-7.15 (m, 1H), 6.46 (dd, J=17.0, 10.1 Hz, 1H), 6.28 (dd, J=17.0, 1.9 Hz, 1H), 5.94 (s, 1H), 5.79 (dd, J=10.1, 1.9 Hz, 1H), 4.51 (s, 1H), 4.07 (s, 1H), 3.48-3.40 (m, 2H), 3.35-3.31 (m, 1H), 3.02 (t, J=12.8 Hz, 1H), 2.63-2.55 (m, 2H), 1.92 (td, J=13.6, 5.2 Hz, 1H), 1.76-1.60 (m, 5H), 1.58 (s, 1H), 1.44 (d, J=11.9 Hz, 1H), 1.28-1.08 (m, 4H).

Example 27 N-(3-(3-ethyl-5-((S)-2-(2-hydroxyethyl)piperidin-1-yl)pyrazolo[1,5-a]pyrimidin-7-ylamino)cyclohexyl)acrylamide (MFH-1-167-1)

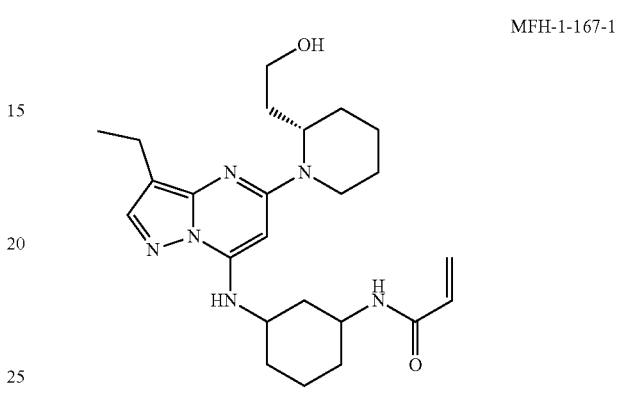

MFH-1-167-1

Synthetic Scheme 27

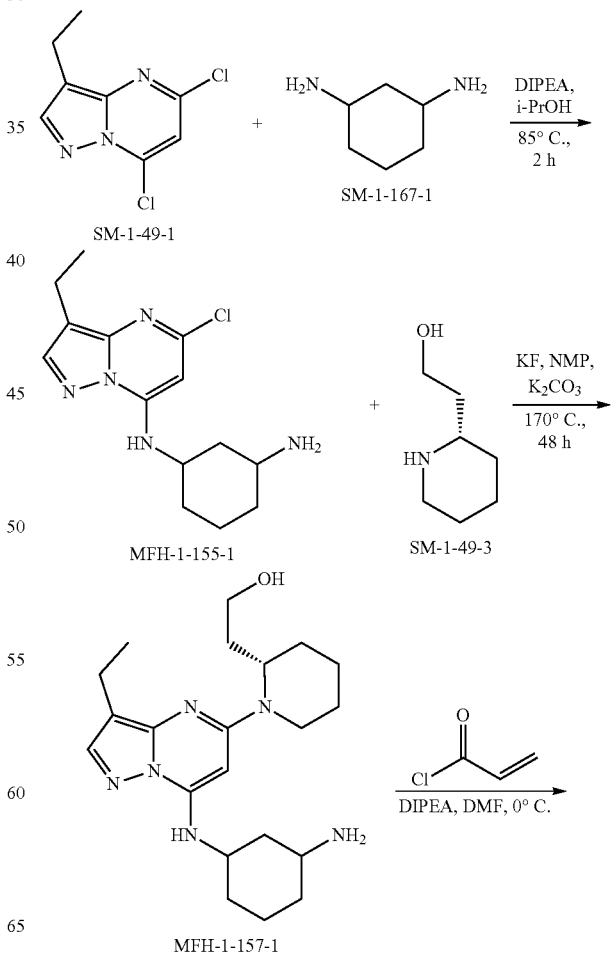

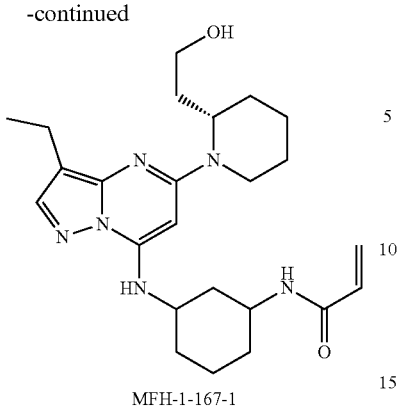

MFH-1-167-1

N1-(5-chloro-3-ethylpyrazolo[1,5-a]pyrimidin-7-yl)cyclohexane-1,3-diamine (MFH-1-151-1)

The mixture of SM-1-49-1 (300 mg, 1.388 mmol), SM-1-167-1 (500 mg, 4.442 mmol), DIPEA (270 mg) and i-PrOH (5 mL) was stirred at 85° C. for 2 h. After completion, the reaction was concentrated to remove the solvent and the residue was purified by silica gel (NH$_3$/MeOH (1.75N)/DCM=0-20%) to obtain MFH-1-155-1 (230 g, yield 56%). LCMS (m/z): 294 [M+H]$^+$.

2-((S)-1-(7-(3-aminocyclohexylamino)-3-ethylpyrazolo[1,5-a]pyrimidin-5-yl)piperidin-2-yl)ethanol (MFH-1-157-1)

The mixture of MFH-1-155-1 (230 mg, 0.783 mmol), SM-1-49-3 (152 mg, 1.1745 mmol), KF (205 mg, 3.5235 mmol) and NMP (2 mL) was stirred at 170° C. for 10 h. After completion, the residue was extracted with chloroform and 2-propanol (4:1), the organic phase was washed with brine (50 mL×2), and dried with Na$_2$SO$_4$. The solution was filtered, concentrated to remove the solvent, and the residue was purified by silica gel chromatography (NH$_3$/MeOH (1.75N)/DCM=0-20%) to obtain MFH-1-157-1 (100 mg, yield 33%). LCMS (m/z): 387 [M+H]$^+$.

N-(3-(3-ethyl-5-((S)-2-(2-hydroxyethyl)piperidin-1-yl)pyrazolo[1,5-a]pyrimidin-7-ylamino)cyclohexyl)acrylamide (MFH-1-167-1)

To a solution of MFH-1-157-1 (30 mg, 0.07762 mmol) and DIPEA (0.2 mL) in CH$_3$CN (2 mL) was added acrylyl chloride (9 mg, 0.101 mmol) in DCM (0.5 mL) dropwise. The mixture was stirred at 0° C. for 1 h. After completion, the reaction was concentrated to remove the solvent and the residue was purified by prep-HPLC (C18 column, MeOH/H$_2$O, containing 0.05% TFA) to obtain MFH-1-167-1 (off-white solid, 13 mg, yield 38%). HPLC: 96% (254 nm); LCMS (m/z): 441 [M+H]$^+$; $^1$H NMR (500 MHz, DMSO) δ 8.26 (s, 1H), 8.14 (dd, J=18.8, 7.9 Hz, 1H), 8.05 (d, J=7.3 Hz, 1H), 7.97-7.83 (m, 2H), 6.41-6.29 (m, 1H), 6.21 (ddd, J=17.1, 10.1, 2.0 Hz, 1H), 6.09 (dddd, J=12.3, 10.2, 3.9, 2.2 Hz, 2H), 5.83 (d, J=9.4 Hz, 1H), 5.69-5.51 (m, 3H), 4.49 (s, 2H), 4.12 (d, J=4.8 Hz, 2H), 3.88-3.81 (m, 2H), 3.11 (dd, J=22.2, 12.4 Hz, 2H), 2.60-2.56 (m, 2H), 2.01-1.96 (m, 2H), 1.69 (d, J=12.3 Hz, 6H), 1.54 (s, 2H), 1.48 (d, J=11.4 Hz, 2H), 1.10 (dd, J=24.9, 12.8 Hz, 1H).

Example 28 (S)—N-(3-(8-ethyl-2-(2-(2-hydroxyethyl)piperidin-1-yl)pyrazolo[1,5-a][1,3,5]triazin-4-ylamino)phenyl)acrylamide (MFH-2-53-1)

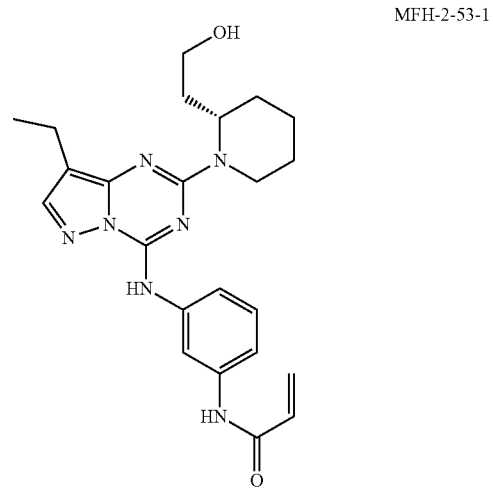 [SMILES: C=CC(=O)Nc1cccc(Nc2nc(N3CCCC[C@H]3CCO)nc3c(CC)cnn23)c1]

MFH-2-53-1

Synthetic Scheme 28

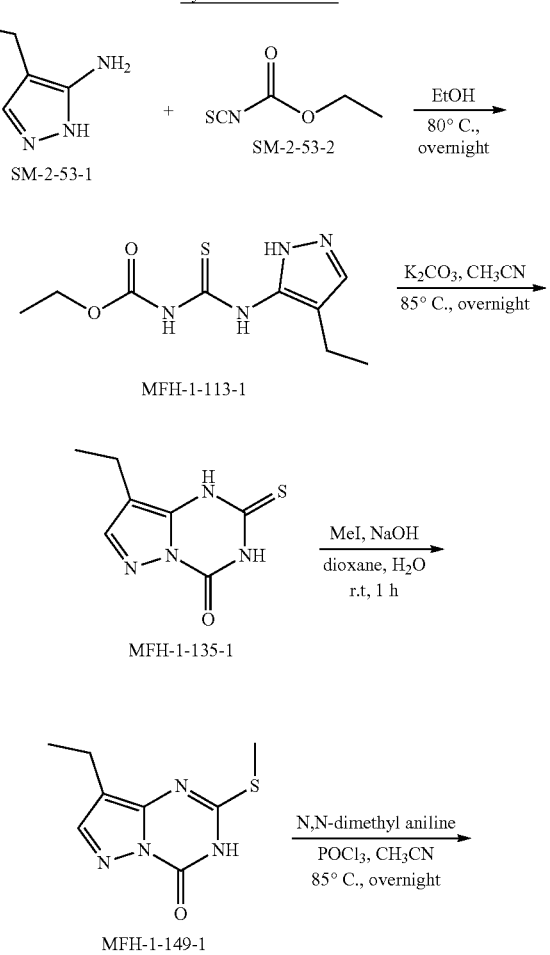

-continued

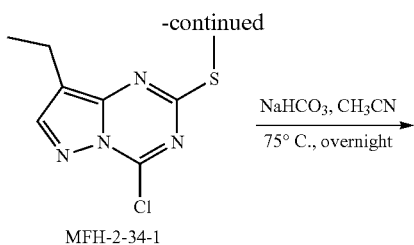

MFH-2-34-1

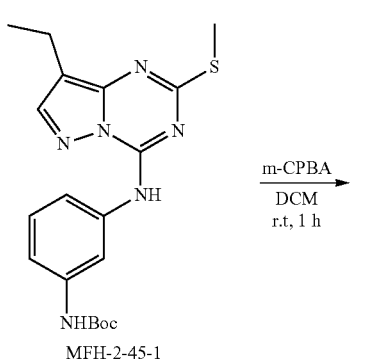

MFH-2-45-1

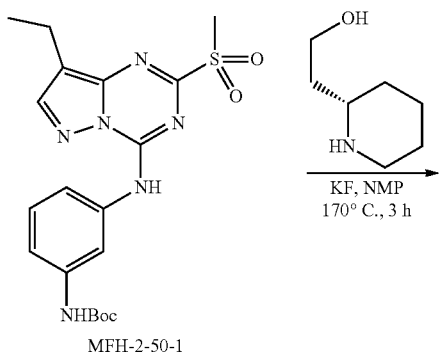

MFH-2-50-1

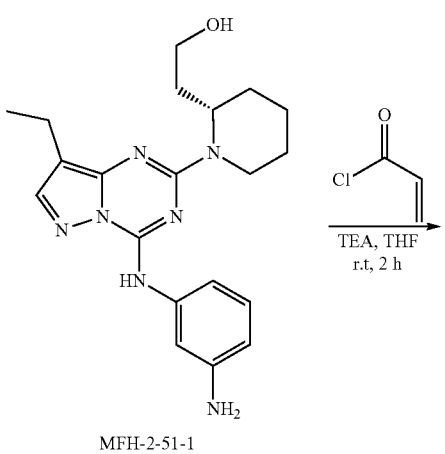

MFH-2-51-1

-continued

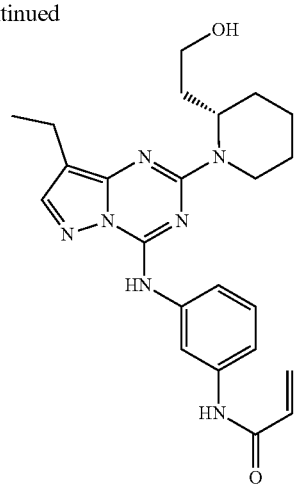

MFH-2-53-1 ethyl N-[(4-ethyl-1H-pyrazol-5-yl)carbamothioyl] carbamate (MFH-1-113-1)

To a solution of SM-2-53-1 (2.8 g, 25.2 mmol) in ethanol (50.0 mL) was added ethoxycarbonyl isothiocyanate (3.3 g, 25.2 mL) in one portion at room temperature. The mixture was stirred at 80° C. overnight. The reaction mixture was concentrated under reduced pressure to afford the residue, which was purified by flash column chromatography (PE/ethyl acetate=3:1) to afford MFH-1-113-1 (white solid, 4 g, yield: 65%). LCMS (m/z): 243 [M+H]$^+$.

8-ethyl-2-thioxo-2,3-dihydropyrazolo[1,5-a][1,3,5] triazin-4(1H)-one (MFH-1-135-1)

To a solution of MFH-1-113-1 (3.9 g, 16.1 mmol) in acetonitrile (40 mL) was added K$_2$CO$_3$ (6.67 g, 48.3 mmol) in one portion at room temperature. The mixture was heated at 85° C. overnight, cooled, and then acidified with AcOH. The resulting solid was filtered off to afford MFH-1-135-1 (yellow solid, 2.1 g, yield: 66%). LCMS (m/z): 197 [M+H]$^+$.

8-ethyl-2-(methylthio)pyrazolo[1,5-a][1,3,5]triazin-4 (3H)-one (MFH-1-149-1)

To a stirred mixture of MFH-1-135-1 (2.1 g, 10.7 mmol) and NaOH (0.86 g, 21.4 mmol) in dioxane/H$_2$O (30/8 mL) was added iodomethane (1.52 g, 10.7 mol). This mixture was stirred at room temperature for 1 h, acidified with hydrochloric acid, concentrated to remove the solvent, and the residue was purified by silica gel chromatography (DCM/MeOH=30:1) to afford MFH-1-149-1 (white solid, 2.0 g, yield: 89%). LCMS (m/z): 211 [M+H]$^+$.

4-chloro-8-ethyl-2-(methylthio)pyrazolo[1,5-a][1,3, 5]triazine (MFH-2-34-1)

To a stirred mixture MFH-1-149-1 (2.0 g, 9.5 mmol) and N,N-dimethyl aniline (2.3 g, 19.0 mmol) in acetonitrile (10 mL) under argon was added POCl$_3$ (20 ml, 219 mol). This mixture was heated at 85° C. overnight. Then the reaction mixture was concentrated under reduced pressure to afford the residue MFH-2-34-1 (white solid, 2.2 g, yield: 100% used next step directly). LCMS (m/z): 229 [M+H]$^+$.

tert-butyl 3-(8-ethyl-2-(methylthio)pyrazolo[1,5-a][1,3,5]triazin-4-ylamino)phenylcarbamate (MFH-2-45-1)

A stirred mixture MFH-2-34-1 (2.2 g, 9.5 mmol), tert-butyl 3-aminophenylcarbamate (2.37 g, 11.4 mmol) and NaHCO$_3$ (130.4 mg, 0.95 mmol) in acetonitrile (25 mL) was heated at 75° C. overnight and then cooled to room temperature. The solvent was removed and the residue was purified by silica gel chromatography (PE/ethyl acetate=3/1 to 1/1) to afford MFH-2-45-1 (white solid, 2.52 g, yield: 67%). LCMS (m/z): 401 [M+H]$^+$.

tert-butyl 3-(8-ethyl-2-(methylsulfonyl)pyrazolo[1,5-a][1,3,5]triazin-4-ylamino) phenylcarbamate (MFH-2-50-1)

To a solution of MFH-2-45-1 (600 mg, 1.5 mmol) in DCM (15 mL) was added 3-chloroperbenzoic acid (776 mg, 4.5 mmol) in one portion at room temperature and stirred for 1 h. The reaction mixture was quenched with a saturated Na$_2$S$_2$O$_3$ solution (10 mL), diluted with DCM (50 mL), washed with saturated aqueous NaCl (3×50 mL), dried over anhydrous Na$_2$SO$_4$, filtered and concentrated to give MFH-2-50-1 (yellow solid, 620 mg, yield: 96%), which was used in the next step directly. LCMS (m/z): 433 [M+H]$^+$.

(S)-2-(1-(4-(3-aminophenylamino)-8-ethylpyrazolo[1,5-a][1,3,5]triazin-2-yl)piperidin-2-yl)ethanol (MFH-2-51-1)

To a stirred mixture of MFH-2-50-1 (360 mg, 0.84 mmol) and (S)-2-(piperidin-2-yl)ethanol (215 mg, 1.67 mmol) in N-methyl-2-pyrrolidone (3 mL) was added KF (146 mg, 2.51 mmol). This mixture was heated at 170° C. for 3 h, cooled, and filtered. The crude mixture was purified by silica gel chromatography (MeOH/DCM=0-20%) to afford MFH-2-51-1 (yellow solid, 150 mg, yield: 47%). LCMS (m/z): 382 [M+H]$^+$.

(S)—N-(3-(8-ethyl-2-(2-(2-hydroxyethyl)piperidin-1-yl)pyrazolo[1,5-a][1,3,5]triazin-4-ylamino)phenyl)acrylamide (MFH-2-53-1)

To a solution of MFH-2-51-1 (70 mg, 0.18 mmol) in THF (2 mL) were added acryloyl chloride (18 mg, 0.20 mmol) and triethylamine (54 mg, 0.54 mmol). The reaction was stirred at room temperature for 2 h. After completion, the reaction mixture was diluted with dichloromethane (10 ml), washed with water (10 mL) and saturated sodium bicarbonate solution (10 mL×2), dried over anhydrous sodium sulfate, concentrated and the crude mixture was purified by prep-HPLC (C18 column, MeOH/H$_2$O, containing 0.05% TFA) to afford MFH-2-53-1 (white solid, 13 mg, yield: 16%). HPLC: 97% (254 nm); LCMS (m/z): 436 [M+H]$^+$; $^1$H NMR (DMSO-d$_6$, 500 MHz): δ: 10.17 (s, 1H), 10.07 (s, 1H), 8.34 (s, $^1$H), 7.84 (s, 1H), 7.51 (s, 1H), 7.30-7.34 (m, 2H), 6.46 (dd, J=17, 10.0 Hz, 1H), 6.28 (d, J=17 Hz, 1H), 5.77 (d, J=11.5 Hz, 1H), 4.98 (s, 1H), 4.65 (d, J=13 Hz, 1H), 4.56 (s, 1H), 2.88 (t, J=12.5 Hz, 1H), 2.47-2.50 (m, 2H), 1.56-1.88 (m, 8H), 1.36-1.38 (m, 1H), 1.19-1.23 (m, 4H).

Example 29 N-(3-(5-(3-aminopiperidin-1-yl)-3-ethylpyrazolo[1,5-a]pyrimidin-7-ylamino)phenyl)acrylamide (MFH-3-140-1)

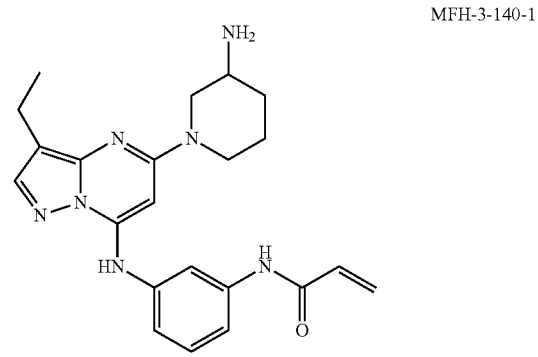 [SMILES: C=CC(=O)Nc1cccc(Nc2cc(N3CCCC(N)C3)nc3c(CC)cnn23)c1]

MFH-3-140-1

Synthetic Scheme 29

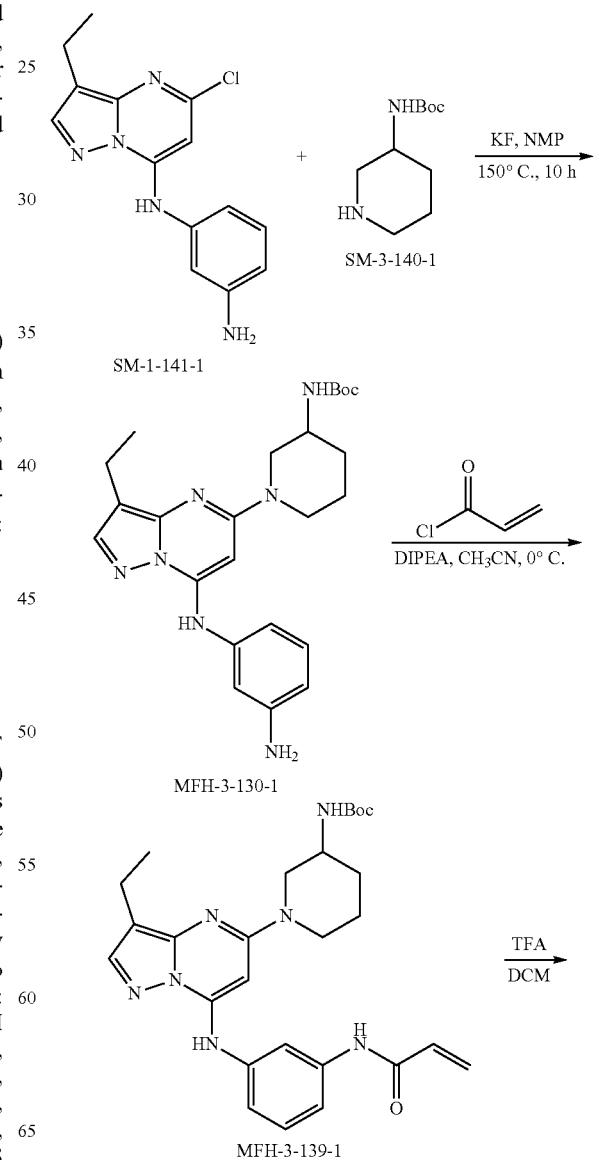

-continued

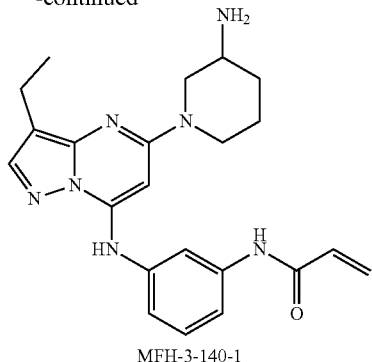

MFH-3-140-1 tert-butyl1-(7-(3-aminophenylamino)-3-ethylpyrazolo[1,5-a]pyrimidin-5-yl)piperidin-3-ylcarbamate (MFH-3-130-1)

To a stirred mixture SM-1-141-1 (150 mg, 0.5213 mmol) and SM-3-140-1 (157 mg, 0.782 mmol) in N-methyl-2-pyrrolidone (1 mL) was added KF (136 mg, 2.3458 mmol). After heating at 150° C. for 10 h, the reaction mixture was cooled and filtered. After removal of the solvent, the crude mixture was purified by silica gel chromatography (MeOH/DCM=0-20%) to afford MFH-3-130-1 (110 mg, yield: 47%). LCMS (m/z): 452 [M+H]$^+$.

tert-butyl1-(7-(3-acrylamidophenylamino)-3-ethyl-pyrazolo[1,5-a]pyrimidin-5-yl)piperidin-3-ylcarbamate (MFH-3-139-1)

To a solution of MFH-3-130-1 (110 mg, 0.24 mmol) in CH$_3$CN (2 mL) was added acryloyl chloride (28 mg, 0.3167 mmol) and DIPEA (0.2 ml). The reaction was stirred at room temperature for 2 h and then was diluted with dichloromethane (10 ml). The solution was washed with saturated NaHCO$_3$ (10 mL×2) and water (10 mL). The organic layer was dried over anhydrous sodium sulfate and then concentrated under reduced pressure. The residue was purified by prep-HPLC (C18 column, MeOH/H$_2$O, containing 0.05% TFA) to afford MFH-3-139-1 (56.6 mg, yield: 46%). LCMS (m/z): 506 [M+H]$^+$.

N-(3-(5-(3-aminopiperidin-1-yl)-3-ethylpyrazolo[1,5-a]pyrimidin-7-ylamino)phenyl)acrylamide (MFH-3-140-1)

To a mixture of compound MFH-3-139-1 (56.6 mg) in DCM (5 mL) was added TFA (2 mL). The reaction mixture was stirred for 1 h at room temperature. The mixture was concentrated under reduced pressure and the residue was purified by prep-HPLC (C18 column, MeOH/H$_2$O, containing 0.05% TFA) to afford MFH-3-140-1 (20 mg, yield: 44%). LCMS (m/z): 406 [M+H]$^+$. $^1$H NMR (500 MHz, DMSO) δ 10.32 (s, 1H), 9.48 (s, 1H), 7.97 (d, J=8.0 Hz, 1H), 7.94 (s, 2H), 7.84 (s, 1H), 7.38 (t, J=8.0 Hz, 1H), 7.32 (d, J=8.2 Hz, 1H), 7.17 (d, J=8.6 Hz, 1H), 6.46 (dd, J=17.0, 10.2 Hz, 1H), 6.28 (dd, J=17.0, 1.8 Hz, 1H), 6.03 (s, 1H), 5.80 (dd, J=10.1, 1.8 Hz, 1H), 4.30 (s, 1H), 3.85 (s, 1H), 3.22 (s, 1H), 3.13 (dd, J=12.6, 9.2 Hz, 2H), 2.66-2.57 (m, 2H), 1.98 (s, 1H), 1.81-1.74 (m, 1H), 1.56 (dd, J=16.8, 9.0 Hz, 2H), 1.25 (t, J=7.5 Hz, 3H).

Example 30 (S)—N-(3-(3-ethyl-5-(2-(2-hydroxy-ethyl)piperidin-1-yl)pyrazolo[1,5-a]pyrimidin-7-ylamino)phenyl)acrylamide (MFH-1-141-1)

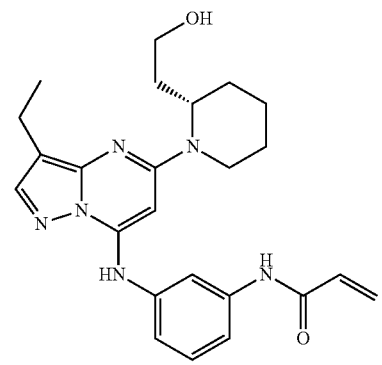

MFH-1-141-1

Synthetic Scheme 30

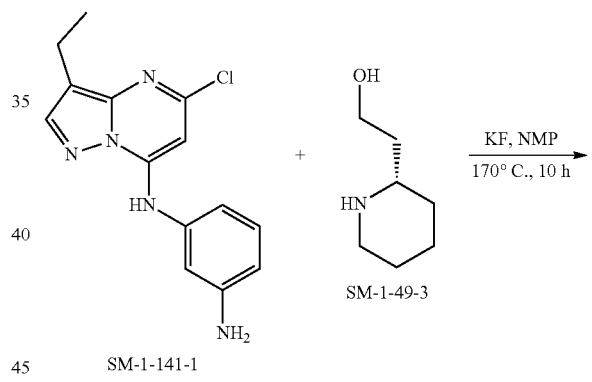

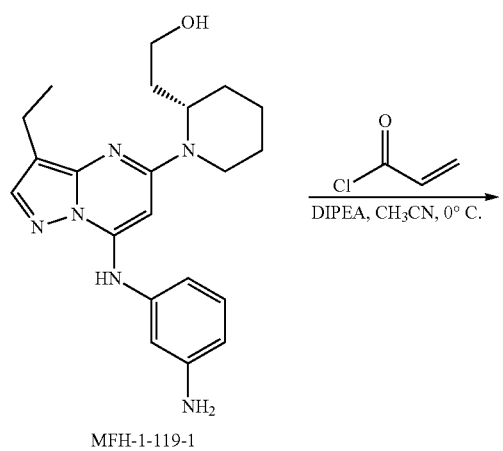

MFH-1-119-1

-continued

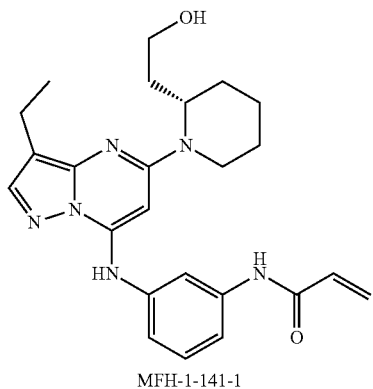

MFH-1-141-1

(S)-2-(1-(7-(3-aminophenylamino)-3-ethylpyrazolo[1,5-a]pyrimidin-5-yl)piperidin-2-yl)ethanol (MFH-1-119-1)

The mixture of SM-1-141-1 (250 mg, 0.87 mmol), SM-1-49-3 (168 mg, 1.3 mmol), KF (227 mg, 3.9 mmol) and NMP (2 mL) was stirred at 170° C. for 10 h. After completion, the residue was extracted with chloroform and isopropanol (4:1). The organic phase was washed with brine (50 mL×2) and dried with $Na_2SO_4$. The mixture was filtered, concentrated to remove the solvent under reduced pressure, and purified by silica gel chromatography (MeOH/DCM=0-20%) to obtain MFH-1-43-1(250 mg, yield 75.6%). LCMS (m/z): 381 [M+H]$^+$.

(S)—N-(3-(3-ethyl-5-(2-(2-hydroxyethyl)piperidin-1-yl)pyrazolo[1,5-a]pyrimidin-7-ylamino)phenyl)acrylamide (MFH-1-141-1)

To a solution of MFH-1-119-1 (50 mg, 0.13 mmol) and DIPEA (0.2 mL) in $CH_3CN$ (2 mL) was added acryloyl chloride (15 mg, 0.17 mmol) in DCM (0.5 mL) dropwise. The mixture was stirred at 0° C. for 1 h. After completion, the reaction was concentrated under reduced pressure, and the residue was purified by prep-HPLC (C18 column, MeOH/$H_2O$, containing 0.05% TFA) to obtain MFH-1-141-1 (off-white solid, 33.7 mg, yield 59%). HPLC: 96% (254 nm); LCMS (m/z): 435 [M+H]$^+$.

Biological Assays of the Compounds
Pulldown Assay

Figure 2:
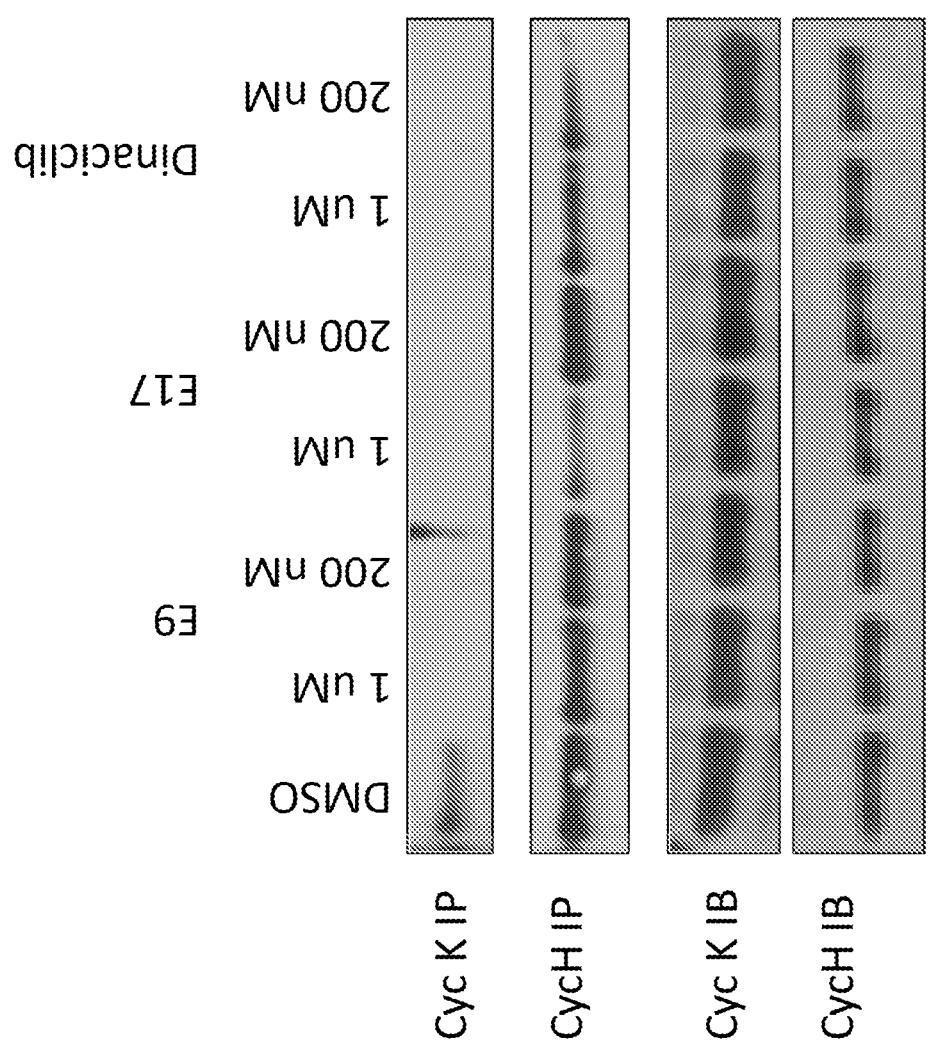
FIG. 2 shows binding of compounds E9 and E17 with CDK12 at two concentrations. Compounds E9 and E17 were able to block pulldown of cyclin K at 1 μM and 200 nM. Specifically, Jurkat cells were treated with DMSO, compounds E9, E17, and dinaciclib at two concentrations for 4 hours. Decreased pulldown of cyclin K with biotin-THZ1 indicated a loss of CDK12 binding. Cyclin H pulldown was not affected, indicating that CDK7 binding is not affected.

Jurkat cells were treated with DMSO, 1 uM or 200 nM of compound E9, E17, or dinaciclib (FIG. 2). 6 hours after treatment, cells were washed and harvested by resuspending in lysis buffer (50 mM Hepes pH 7.4, 150 mM NaCl, 1% NP-40, 5 mM EDTA, protease and phosphatase inhibitors) and lysing on ice 30 minutes. Lysates were cleared by centrifugation at 15,000 rpm 30 minutes. Biotin-labeled THZ1 was added to 1 uM to lysates and rotated at 4° C. overnight. Streptavidin-agarose beads were washed and 30 uL slurry was added to each lysate and rotated for 1 hour at 4° C. Beads were washed 5 times with lysis buffer and 50 uL 2×LDS buffer was added to each sample. Samples were boiled and equal volume of protein was loaded onto gel. Gel was transferred to nitrocellulose and blotted for Cyclin K and Cyclin H.

We conclude that pre-treatment of cells with compound E9, E17 or dinaciclib, but not DMSO, blocks biotin-THZ1 from being able to bind to CDK12, which blocks the pulldown of Cyclin K. This indicates that compound E9 is able to engage CDK12 in cells at 1 uM and 200 nM and block binding of bio-THZ1. We do not see a similar loss of pulldown of Cyclin H, indicating that E9 and E17 are not able to bind to CDK7 and block its association with bio-THZ1.

Jurkat Proliferation Assay

Jurkat cells were seeded at a density of 25,000 cells/well in 96-well plates. Cells were then treated with the indicated compounds in a 10-pt dose escalation format from 1 nM to 10 µM or DMSO control for 72 hrs. After 72 hrs, cells were assayed using CellTiter-Glo Luminescent Cell Viability Assay (Promega) to determine cell viability by measuring the amount of ATP present in each sample cell population, which is an indicator of cell metabolic activity. Results are graphed as fraction of the DMSO control at 72 hrs. All data points were performed in biological triplicate. Error bars are +/−SD.

These results suggest that dinaciclib has the most antiproliferative effect on Jurkat cells with an IC50 below 10 nM. However, the covalent inhibitors E9, E17, and E18 all display potent activity with IC50s in the sub-100 nM range.

Growth Assay

Jurkat cells were treated with 1 uM of compound E9, E17, Dinaciclib or DMSO control. 4 hours after treatment, cells were either not treated or washed three times with RPMI media to remove all compound. Cells were replated and allowed to grow for 68 hours. Cells were assayed using celltiter glo (Promega) to determine cell viability by measuring the amount of ATP present, which is an indicator of cell metabolic activity. Results are graphed as luminescent values (FIG. 1).

We can conclude that the covalent nature of the compounds E9 and E11 allow for a long term effect in cells, even after compound is removed. Conversely, dinaciclib has a strong effect on cell viability when it is maintained in culture, however, once it is removed, cells are able to reinitiate growth. Taken together, this indicates that the covalent nature of E9 and E11 has the advantage of short dosing periods translating into longer term effects.

Washout Expression Assay

Figure 3:
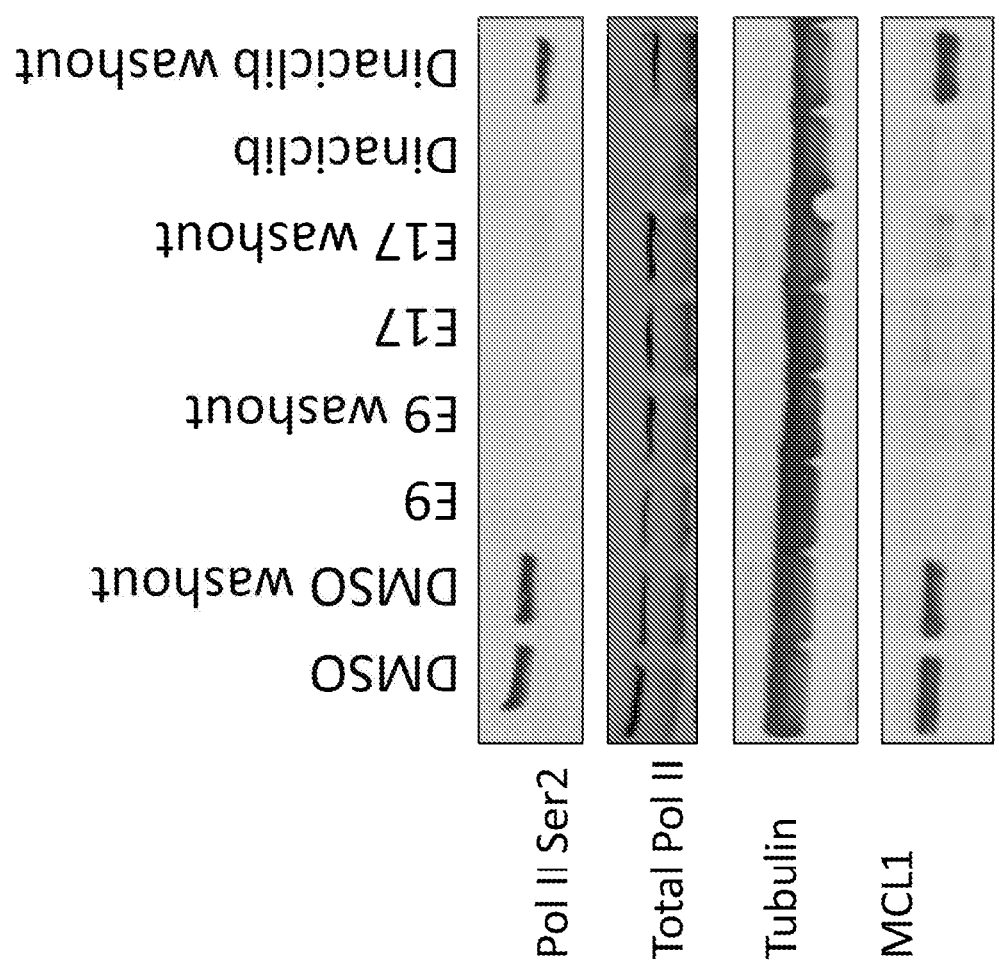
FIG. 3 shows the effect of compounds E9, E17, and Dinaciclib on the downstream protein targets. Specifically, compounds E9 and E17 show an irreversible effect on Polymerase II Serine 2 phosphorylation and MCL1 levels with and without washout. Dinaciclib is only effective when it is present in cells, and its effect is abolished by washout.
Figure 4:
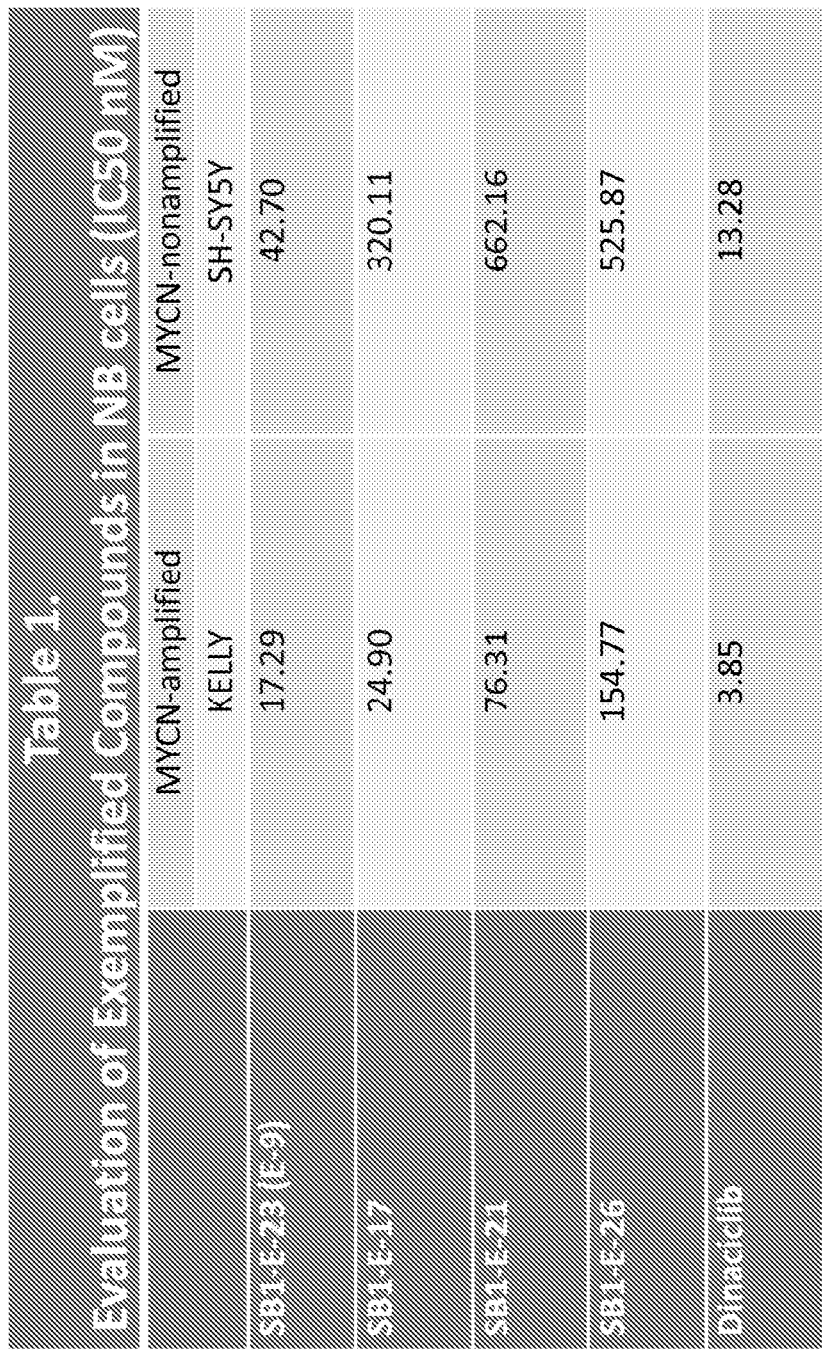
FIG. 4 shows evaluation of the exemplified compounds in neuroblastoma (NB) cells. The IC50 values are shown in nM.
Figure 5:
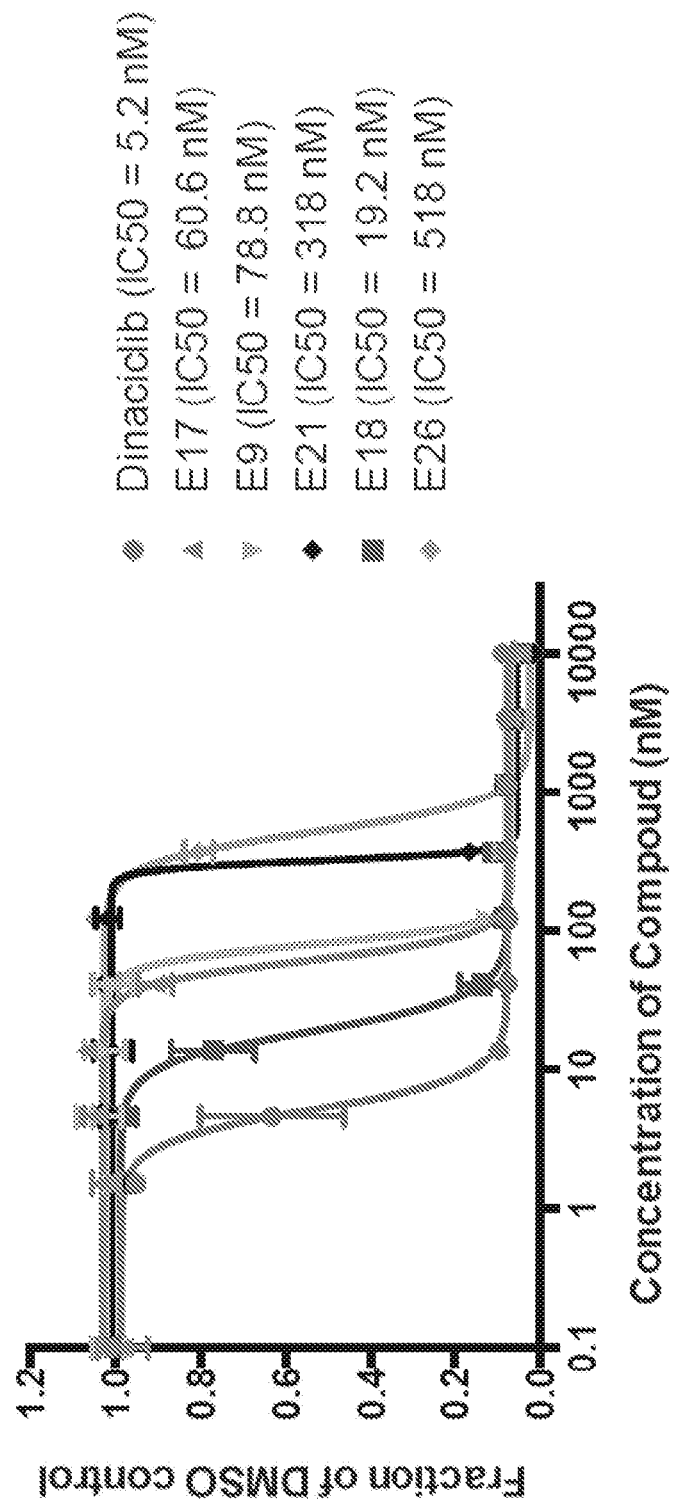
FIG. 5 shows that Dinaciclib and Compounds E9, E17, and E18 inhibit Jurkat T-cell acute lymphoblastic leukemia (T-ALL) cell proliferation. Compounds E9, E17, and E18 irreversibly inhibit T-ALL cell proliferation while Dinaciclib acts as a reversible inhibitor. Jurkat cells were seeded at a density of 25,000 cells/well in 96-well plates. Cells were then treated with the indicated compounds in a 10-pt dose escalation format from 1 nM to 10 μM or DMSO control for 72 hours. After 72 hours, the cells were assayed using CellTiter-Glo Luminescent Cell Viability Assay (Promega) to determine cell viability by measuring the amount of ATP present in each sample cell population, which is an indicator of cell metabolic activity. Results were graphed as fraction of the DMSO control at 72 hours. All data points were performed in biological triplicate. Error bars are +/−SD.

Jurkat cells were treated with 1 uM of compound E9, E17, Dinaciclib or DMSO control (FIG. 3). 4 hours after treatment, cells were either not treated or washed three times with RPMI media to remove all compound. Cells were replated and allowed to grow for 6 hours. Cells were harvested, washed 3 times with PBS and resuspended in RIPA buffer (25 mM Tris-HCl (pH 7.6), 150 mM NaCl, 1% NP-40, 1% sodium deoxycholate, 0.1% SDS). Equal amount of protein was loaded onto gel and blotted for Pol II Ser2 (Millipore 04-1571), total pol II (Santa Cruz 17798), Tubulin (Cell Signaling 11H10) or MCL1 (Cell Signaling 4572S)

We can see that when we treat with any of the compounds that Ser2 phosphorylation and MCL1 levels are decreased. However, when we washout the compounds, only our covalent compounds are able to have an effect after the washout whereas dinaciclib is unable to continue this effect.

TABLE A1
| Compound | Structure | CDK7/CycH | CDK9/CycT | Jurkat | CDK2/CycA |
|---|---|---|---|---|---|
| SB1-E-24 | 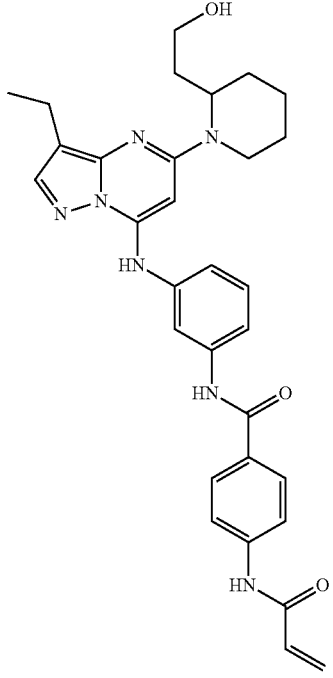 [SMILES: C=CC(=O)Nc1ccc(C(=O)Nc2cccc(Nc3cc(N4CCCCC4CCO)nc4c(CC)cnn34)c2)cc1] | 774 | 140 | — | 1260 |
| SB1-E-19 | 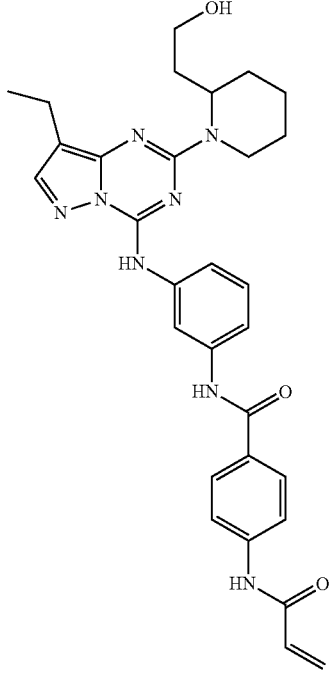 [SMILES: C=CC(=O)Nc1ccc(C(=O)Nc2cccc(Nc3nc(N4CCCCC4CCO)nc4c(CC)cnn34)c2)cc1] | 383 | 123 | — | 295 |

TABLE A1-continued
Biological evaluation of the exemplified compounds (IC50 values/nM)
| Compound | Structure | CDK7/CycH | CDK9/CycT | Jurkat | CDK2/CycA |
|---|---|---|---|---|---|
| THZ-4-124-1 | 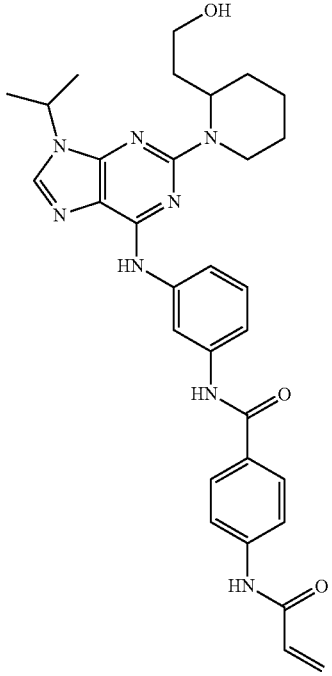 [SMILES: C=CC(=O)Nc1ccc(C(=O)Nc2cccc(Nc3nc(N4CCCCC4CCO)nc4c3ncn4C(C)C)c2)cc1] | 122 | 373 | 117 | 976 |
| SB1-E-22 | 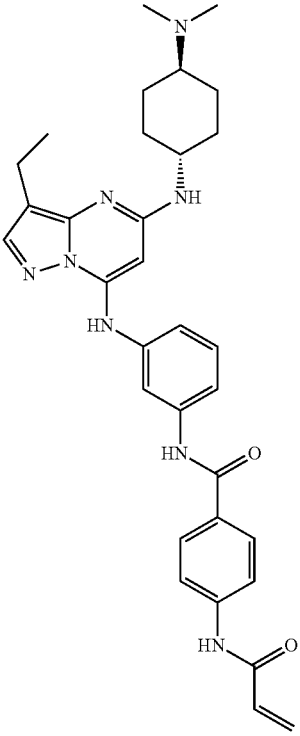 [SMILES: C=CC(=O)Nc1ccc(C(=O)Nc2cccc(Nc3cc(N[C@H]4CC[C@H](N(C)C)CC4)nc4c(CC)cnn34)c2)cc1] | 246 | 88.9 | — | 28300 |

TABLE A1-continued

Biological evaluation of the exemplified compounds (IC50 values/nM)

| Compound | Structure | CDK7/CycH | CDK9/CycT | Jurkat | CDK2/CycA |
|---|---|---|---|---|---|
| SB1-E-25 | 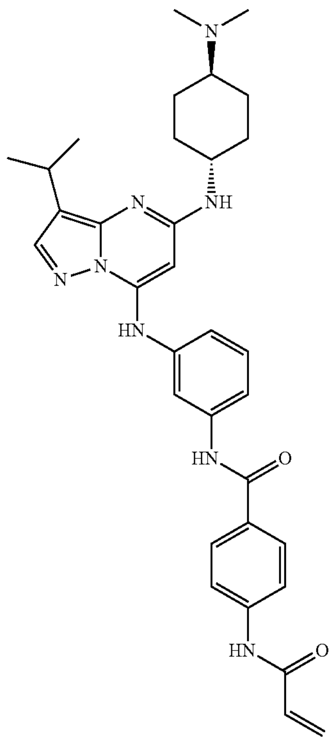 [SMILES: C=CC(=O)Nc1ccc(C(=O)Nc2cccc(Nc3cc(N[C@H]4CC[C@H](N(C)C)CC4)nc4c(C(C)C)cnn34)c2)cc1] | 410 | 387 | — | 33400 |
| THZ-5-38-1 | 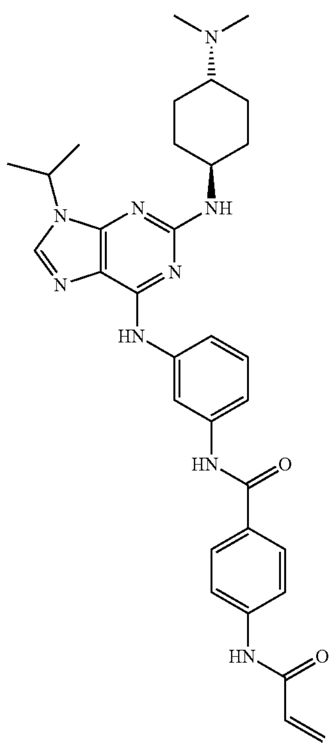 | 25.9 | 220 | — | 563 |

TABLE A1-continued

Biological evaluation of the exemplified compounds (IC50 values/nM)

| Compound | Structure | CDK7/CycH | CDK9/CycT | Jurkat | CDK2/CycA |
|---|---|---|---|---|---|
| THZ-3-49-1 | 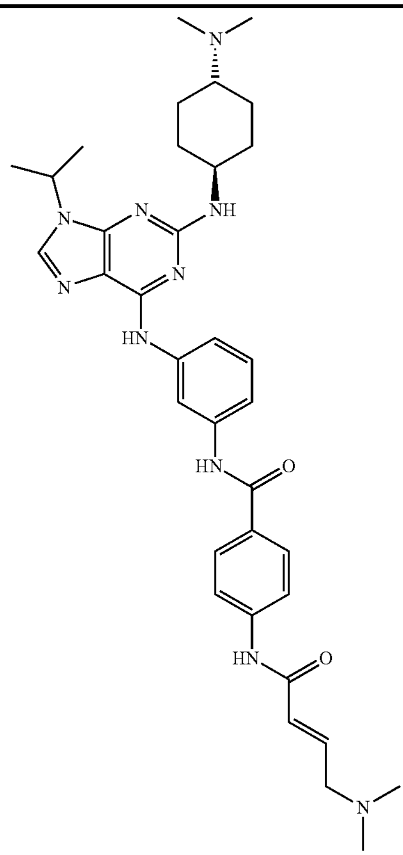 | 9.43 | 445 | 4029 | — |
| THZ-4-119-1 | 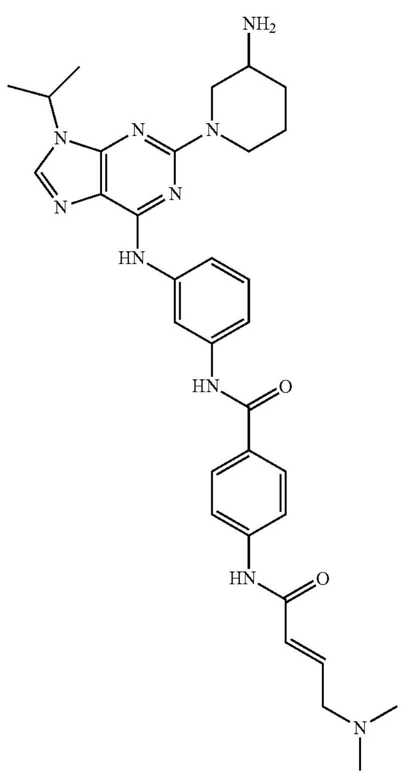 [SMILES: CC(C)n1cnc2c(Nc3cccc(NC(=O)c4ccc(NC(=O)/C=C/CN(C)C)cc4)c3)nc(N3CCCC(N)C3)nc21] | 11.5 | 519 | 1960 | — |

TABLE A1-continued
Biological evaluation of the exemplified compounds (IC50 values/nM)
| Compound | Structure | CDK7/CycH | CDK9/CycT | Jurkat | CDK2/CycA |
|---|---|---|---|---|---|
| THZ-4-128-1 | 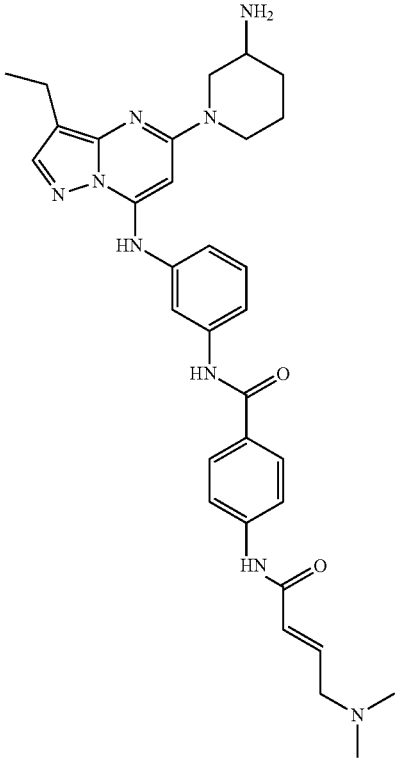 [SMILES: CCc1cnn2c(Nc3cccc(NC(=O)c4ccc(NC(=O)/C=C/CN(C)C)cc4)c3)cc(N3CCCC(N)C3)nc12] | 46.8 | 73.4 | 1037 | 17100 |
| THZ-4-141-1 | 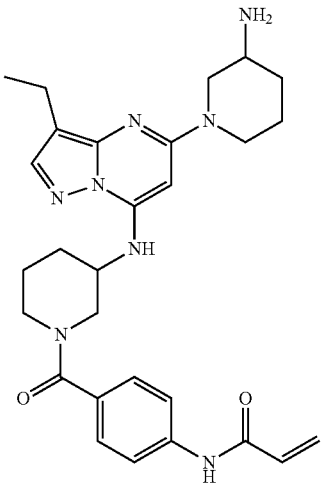 [SMILES: C=CC(=O)Nc1ccc(C(=O)N2CCCC(Nc3cc(N4CCCC(N)C4)nc4c(CC)cnn34)C2)cc1] | 3600 | 3570 | — | >1000 |

TABLE A1-continued
Biological evaluation of the exemplified compounds (IC50 values/nM)
| Compound | Structure | CDK7/CycH | CDK9/CycT | Jurkat | CDK2/CycA |
|---|---|---|---|---|---|
| THZ-4-148-1 | 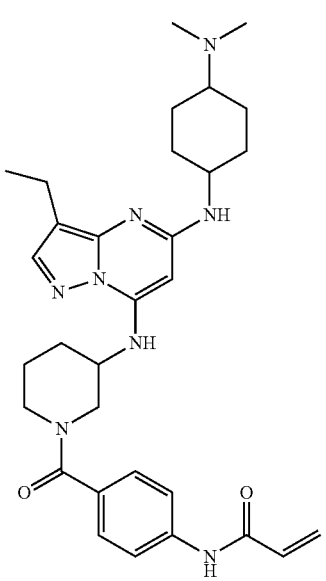 [SMILES: C=CC(=O)Nc1ccc(C(=O)N2CCCC(Nc3cc(NC4CCC(N(C)C)CC4)nc4c(CC)cnn34)C2)cc1] | >10000 | 1710 | — | 7050 |
| THZ-4-149-1 | 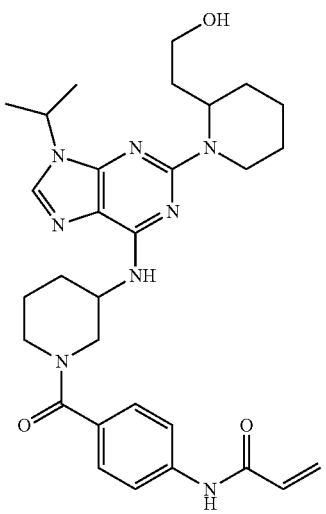 [SMILES: C=CC(=O)Nc1ccc(C(=O)N2CCCC(Nc3nc(N4CCCCC4CCO)nc4c3ncn4C(C)C)C2)cc1] | 4430 | 2290 | — | >1000 |

TABLE A1-continued

Biological evaluation of the exemplified compounds (IC50 values/nM)

| Compound | Structure | CDK7/CycH | CDK9/CycT | Jurkat | CDK2/CycA |
|---|---|---|---|---|---|
| X1 | 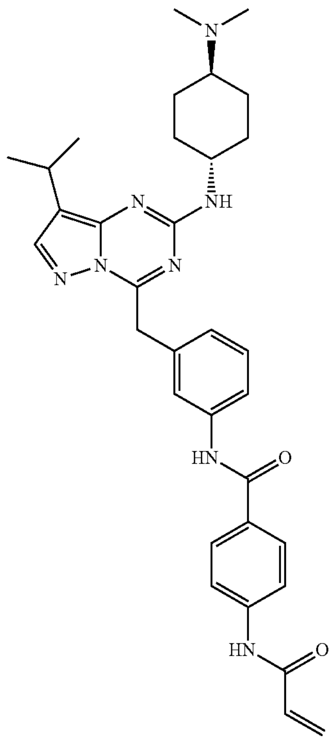 [SMILES: C=CC(=O)Nc1ccc(C(=O)Nc2cccc(Cc3nc(N[C@H]4CC[C@H](N(C)C)CC4)nc4c(C(C)C)cnn34)c2)cc1] | — | — | — | — |
| X2 | 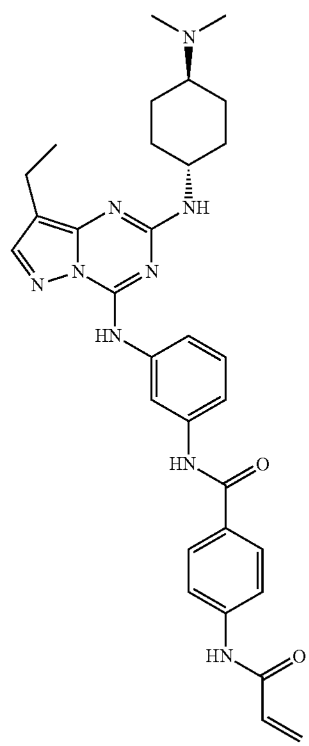 [SMILES: C=CC(=O)Nc1ccc(C(=O)Nc2cccc(Nc3nc(N[C@H]4CC[C@H](N(C)C)CC4)nc4c(CC)cnn34)c2)cc1] | — | — | — | — |

TABLE A1-continued
Biological evaluation of the exemplified compounds (IC50 values/nM)
| Compound | Structure | CDK7/CycH | CDK9/CycT | Jurkat | CDK2/CycA |
|---|---|---|---|---|---|
| X3 | 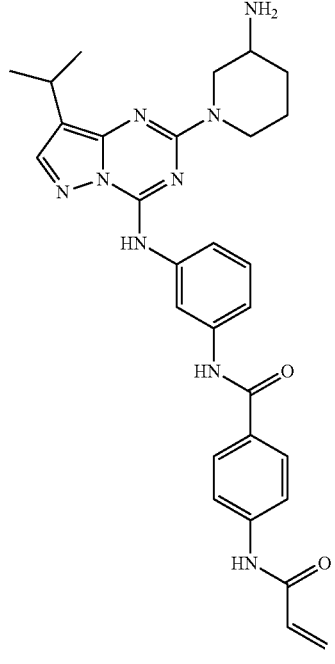 [SMILES: C=CC(=O)Nc1ccc(C(=O)Nc2cccc(Nc3nc(N4CCCC(N)C4)nc4c(C(C)C)cnn34)c2)cc1] | — | — | — | — |
| X4 | 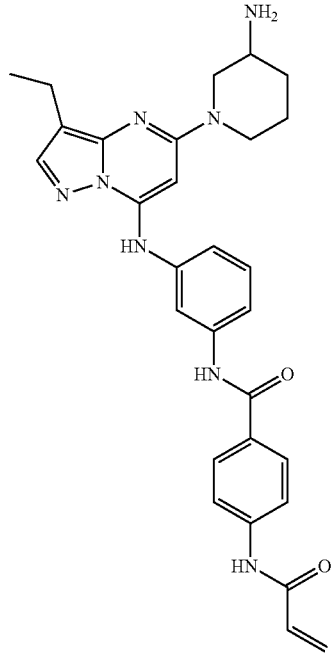 [SMILES: C=CC(=O)Nc1ccc(C(=O)Nc2cccc(Nc3cc(N4CCCC(N)C4)nc4c(CC)cnn34)c2)cc1] | — | — | — | — |

TABLE A2
| Compound | Structure | CDK7/CycH | CDK9/CycT | Jurkat | CDK2/CycA |
|---|---|---|---|---|---|
| THZ-4-134-1 | 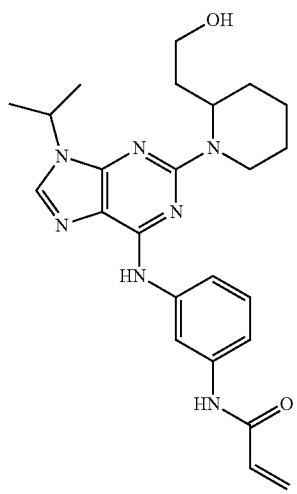 [SMILES: C=CC(=O)Nc1cccc(Nc2nc(N3CCCCC3CCO)nc3c2ncn3C(C)C)c1] | 1180 | 379 | 522 | 163 |
| THZ-5-18-1 | 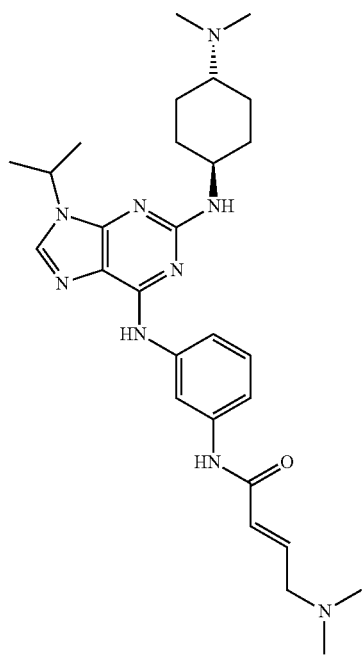 | 121 | 1530 | 1336 | — |

TABLE A2-continued

Biological evaluation of additional exemplified compounds (IC50 values/nM)

| Compound | Structure | CDK7/CycH | CDK9/CycT | Jurkat | CDK2/CycA |
|---|---|---|---|---|---|
| E-9(SB1-E-23) | 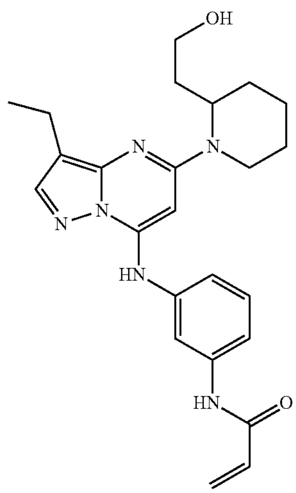 | 1090 | 21.6 | 78.8 | 250 |
| THZ-5-18-1 | 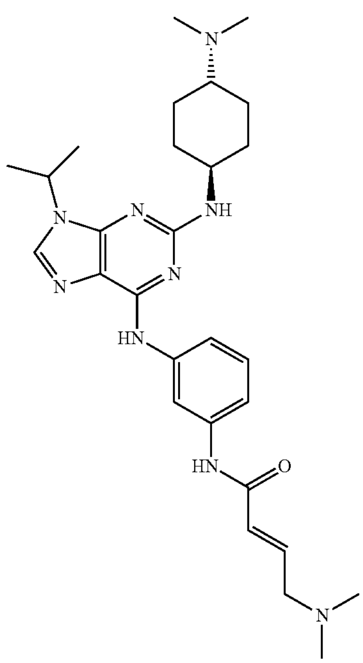 | 121 | 1530 | 1336 | — |

TABLE A2-continued

Biological evaluation of additional exemplified compounds (IC50 values/nM)

| Compound | Structure | CDK7/CycH | CDK9/CycT | Jurkat | CDK2/CycA |
|---|---|---|---|---|---|
| E-1(SB1-E-14) | 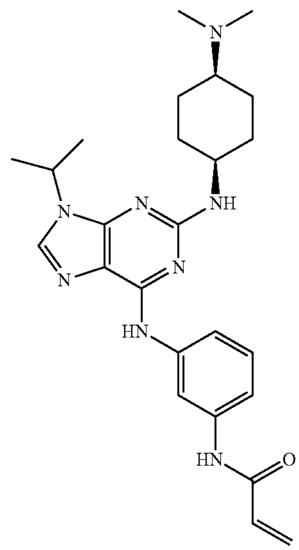 [SMILES: C=CC(=O)Nc1cccc(Nc2nc(N[C@H]3CC[C@@H](N(C)C)CC3)nc3c2ncn3C(C)C)c1] | 254 | 1360 | — | 735 |
| SB1-E-18 | 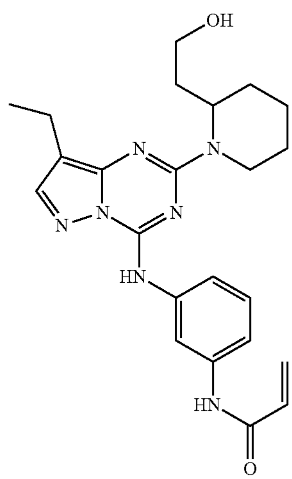 [SMILES: C=CC(=O)Nc1cccc(Nc2nc(N3CCCCC3CCO)nc3c(CC)cnn23)c1] | 461 | 41.8 | 19.2 | 15.0 |
| SB1-E-21 | 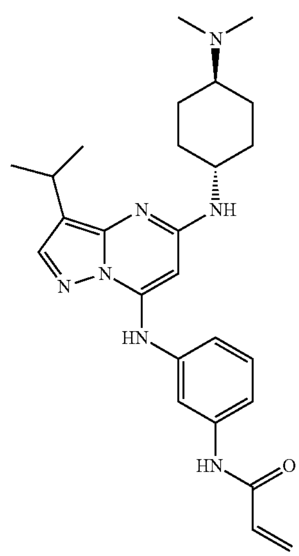 [SMILES: C=CC(=O)Nc1cccc(Nc2cc(N[C@H]3CC[C@H](N(C)C)CC3)nc3c(C(C)C)cnn23)c1] | 1210 | 226 | 318 | 1220 |

TABLE A2-continued

Biological evaluation of additional exemplified compounds (IC50 values/nM)

| Compound | Structure | CDK7/CycH | CDK9/CycT | Jurkat | CDK2/CycA |
|---|---|---|---|---|---|
| SB1-E-26 | 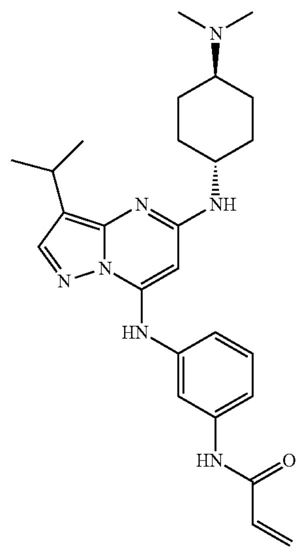 [SMILES: C=CC(=O)Nc1cccc(Nc2cc(N[C@H]3CC[C@H](N(C)C)CC3)nc3c(C(C)C)cnn23)c1] | 1090 | 429 | 518 | 939 |
| SB1-E-15 | 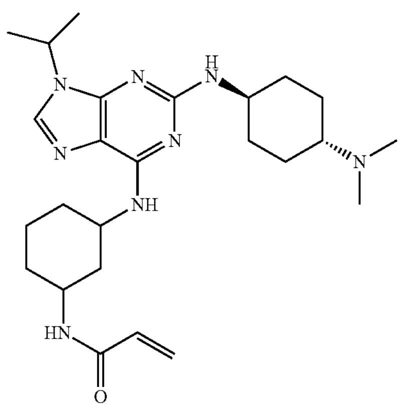 [SMILES: C=CC(=O)NC1CCCC(Nc2nc(N[C@H]3CC[C@H](N(C)C)CC3)nc3c2ncn3C(C)C)C1] | 763 | 58.9 | — | 1480 |
| SB1-E-16 | 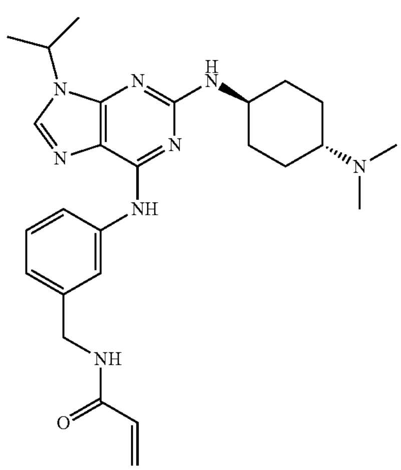 [SMILES: C=CC(=O)NCc1cccc(Nc2nc(N[C@H]3CC[C@H](N(C)C)CC3)nc3c2ncn3C(C)C)c1] | 255 | 116 | — | 30.3 |

TABLE A2-continued

Biological evaluation of additional exemplified compounds (IC50 values/nM)

| Compound | Structure | CDK7/CycH | CDK9/CycT | Jurkat | CDK2/CycA |
|---|---|---|---|---|---|
| SB1-E-17 | 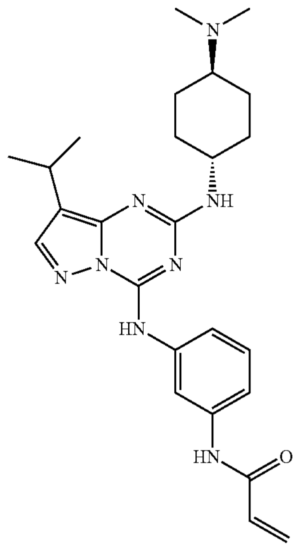 [SMILES: C=CC(=O)Nc1cccc(Nc2nc(N[C@H]3CC[C@H](N(C)C)CC3)nc3c(C(C)C)cnn23)c1] | 1020 | 171 | 60.6 | 247 |
| Y1 | 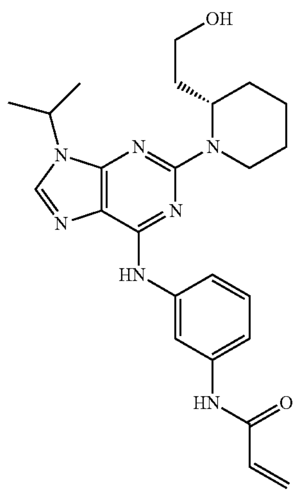 [SMILES: C=CC(=O)Nc1cccc(Nc2nc(N3CCCC[C@H]3CCO)nc3c2ncn3C(C)C)c1] | — | — | — | — |
| Y2 | 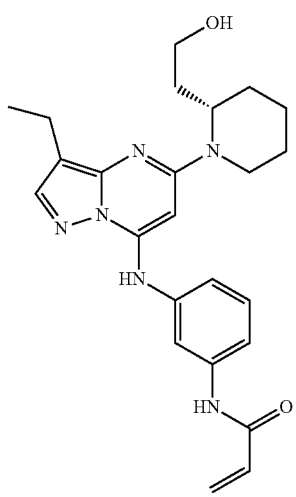 [SMILES: C=CC(=O)Nc1cccc(Nc2cc(N3CCCC[C@H]3CCO)nc3c(CC)cnn23)c1] | — | — | — | — |

TABLE A2-continued

Biological evaluation of additional exemplified compounds (IC50 values/nM)

| Compound | Structure | CDK7/CycH | CDK9/CycT | Jurkat | CDK2/CycA |
|---|---|---|---|---|---|
| Y3 | 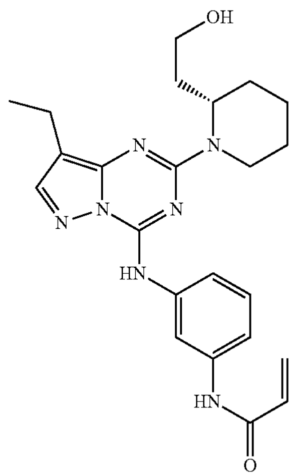 | — | — | — | — |
| Y4 | 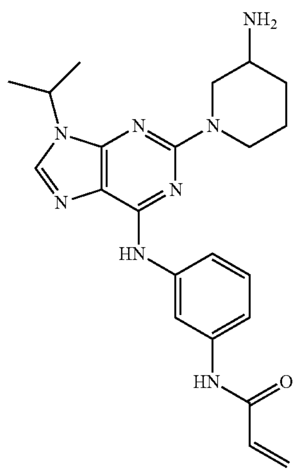 [SMILES: C=CC(=O)Nc1cccc(Nc2nc(N3CCCC(N)C3)nc3c2ncn3C(C)C)c1] | — | — | — | — |
| Y5 | 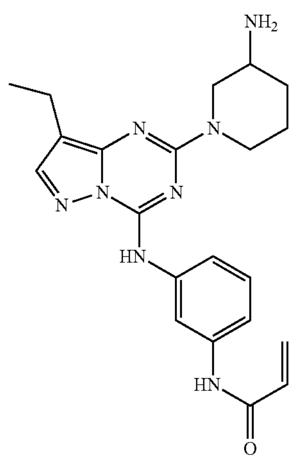 [SMILES: C=CC(=O)Nc1cccc(Nc2nc(N3CCCC(N)C3)nc3c(CC)cnn23)c1] | — | — | — | — |

TABLE A2-continued

Biological evaluation of additional exemplified compounds (IC50 values/nM)

| Compound | Structure | CDK7/CycH | CDK9/CycT | Jurkat | CDK2/CycA |
|---|---|---|---|---|---|
| Y6 | 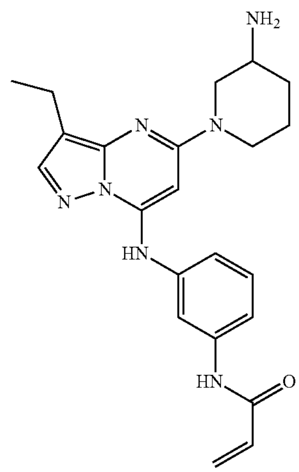 [SMILES: C=CC(=O)Nc1cccc(Nc2cc(N3CCCC(N)C3)nc3c(CC)cnn23)c1] | — | — | — | — |
| Y7 | 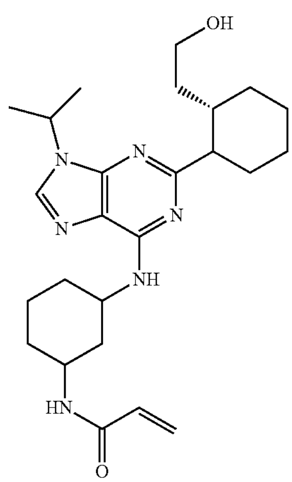 [SMILES: C=CC(=O)NC1CCCC(Nc2nc(C3CCCC[C@H]3CCO)nc3c2ncn3C(C)C)C1] | — | — | — | — |
| Y8 | 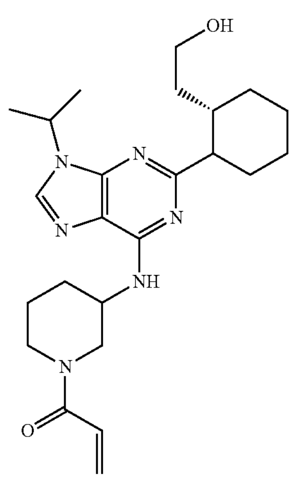 [SMILES: C=CC(=O)N1CCCC(Nc2nc(C3CCCC[C@H]3CCO)nc3c2ncn3C(C)C)C1] | — | — | — | — |

TABLE A2-continued

Biological evaluation of additional exemplified compounds (IC50 values/nM)

| Compound | Structure | CDK7/CycH | CDK9/CycT | Jurkat | CDK2/CycA |
|---|---|---|---|---|---|
| Y9 | 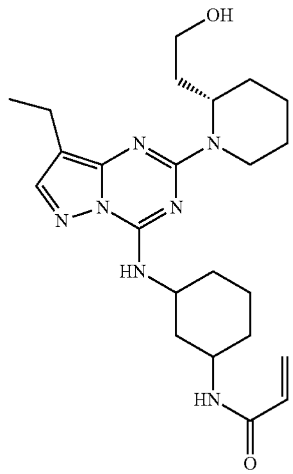 [SMILES: C=CC(=O)NC1CCCC(Nc2nc(N3CCCC[C@H]3CCO)nc3c(CC)cnn23)C1] | — | — | — | — |
| Y10 | 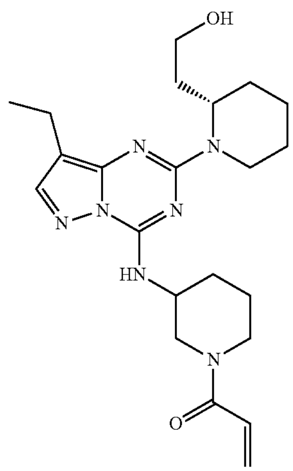 [SMILES: C=CC(=O)N1CCCC(Nc2nc(N3CCCC[C@H]3CCO)nc3c(CC)cnn23)C1] | — | — | — | — |
| Y11 | 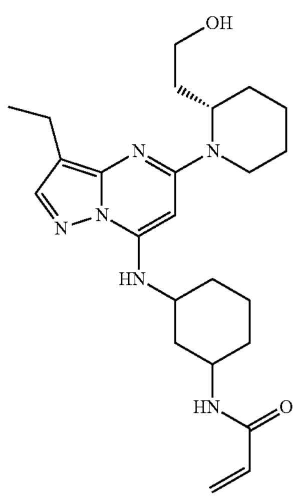 [SMILES: C=CC(=O)NC1CCCC(Nc2cc(N3CCCC[C@H]3CCO)nc3c(CC)cnn23)C1] | — | — | — | — |

TABLE A2-continued

Biological evaluation of additional exemplified compounds (IC50 values/nM)

| Compound | Structure | CDK7/CycH | CDK9/CycT | Jurkat | CDK2/CycA |
|---|---|---|---|---|---|
| Y12 | 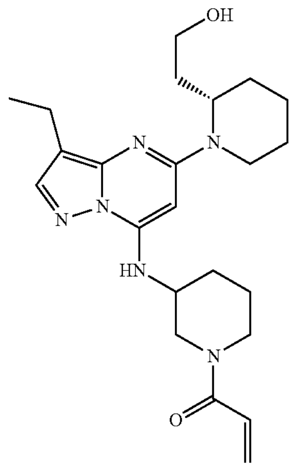 [SMILES: C=CC(=O)N1CCCC(Nc2cc(N3CCCC[C@H]3CCO)nc3c(CC)cnn23)C1] | — | — | — | — |
| Y13 | 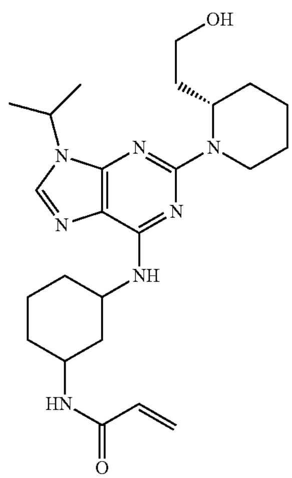 | — | — | — | — |
| Y14 | 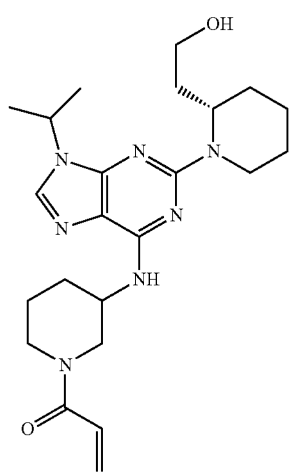 [SMILES: C=CC(=O)N1CCCC(Nc2nc(N3CCCC[C@H]3CCO)nc3c2ncn3C(C)C)C1] | — | — | — | — |

TABLE A2-continued

Biological evaluation of additional exemplified compounds (IC50 values/nM)

| Compound | Structure | CDK7/CycH | CDK9/CycT | Jurkat | CDK2/CycA |
|---|---|---|---|---|---|
| MFH-1-169-1 | 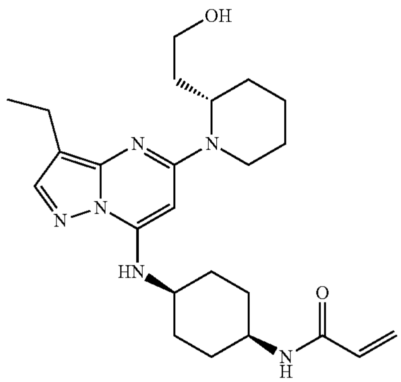 [SMILES: C=CC(=O)N[C@H]1CC[C@@H](Nc2cc(N3CCCC[C@H]3CCO)nc3c(CC)cnn23)CC1] | 7250 | 135 | — | 3880 |
| MFH-1-175-1 | 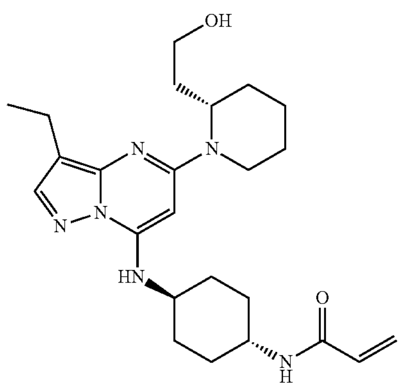 [SMILES: C=CC(=O)N[C@H]1CC[C@H](Nc2cc(N3CCCC[C@H]3CCO)nc3c(CC)cnn23)CC1] | 442 | 48.2 | — | 1080 |
| MFH-1-187-1 | 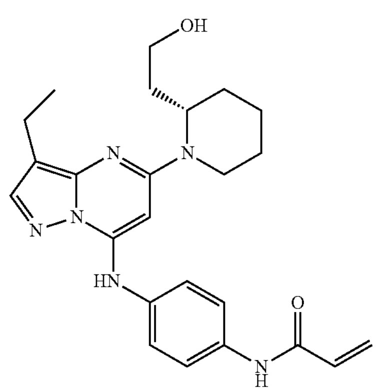 [SMILES: C=CC(=O)Nc1ccc(Nc2cc(N3CCCC[C@H]3CCO)nc3c(CC)cnn23)cc1] | 279 | 23.5 | — | 171 |

TABLE A2-continued

Biological evaluation of additional exemplified compounds (IC50 values/nM)

| Compound | Structure | CDK7/CycH | CDK9/CycT | Jurkat | CDK2/CycA |
|---|---|---|---|---|---|
| MFH-2-67-1 | 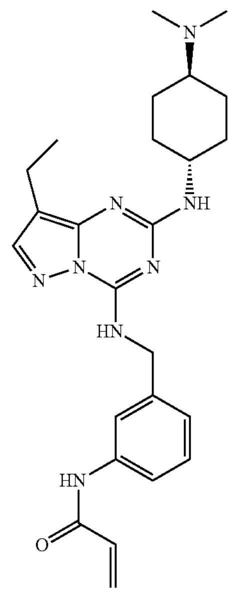 [SMILES: C=CC(=O)Nc1cccc(CNc2nc(N[C@H]3CC[C@H](N(C)C)CC3)nc3c(CC)cnn23)c1] | 23.7 | 103 | — | 1020 |
| MFH-2-78-1 | 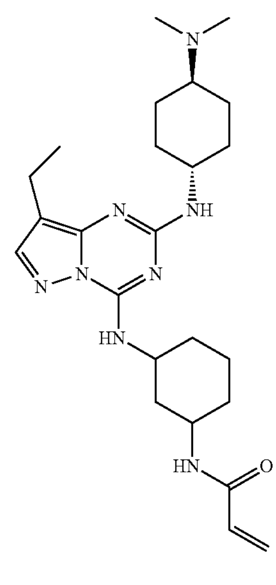 [SMILES: C=CC(=O)NC1CCCC(Nc2nc(N[C@H]3CC[C@H](N(C)C)CC3)nc3c(CC)cnn23)C1] | 842 | 68.7 | — | >1000 |
| MFH-1-49-1 | 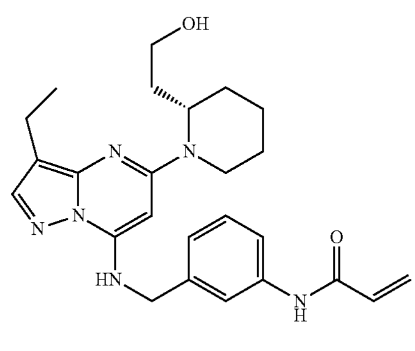 [SMILES: C=CC(=O)Nc1cccc(CNc2cc(N3CCCC[C@H]3CCO)nc3c(CC)cnn23)c1] | 165 | 2.8 | — | 27.6 |

TABLE A2-continued

Biological evaluation of additional exemplified compounds (IC50 values/nM)

| Compound | Structure | CDK7/CycH | CDK9/CycT | Jurkat | CDK2/CycA |
|---|---|---|---|---|---|
| MFH-1-56-1 | 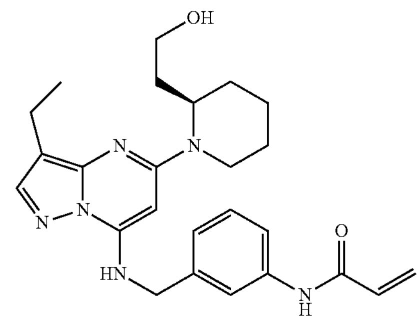 [SMILES: C=CC(=O)Nc1cccc(CNc2cc(N3CCCC[C@@H]3CCO)nc3c(CC)cnn23)c1] | 345 | 300 | | 1530 |
| MFH-1-143-1 | 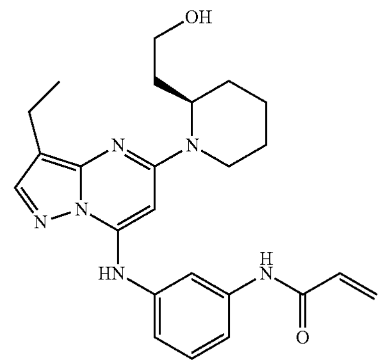 [SMILES: C=CC(=O)Nc1cccc(Nc2cc(N3CCCC[C@@H]3CCO)nc3c(CC)cnn23)c1] | 2510 | 859 | | >10000 |
| MFH-1-167-1 | 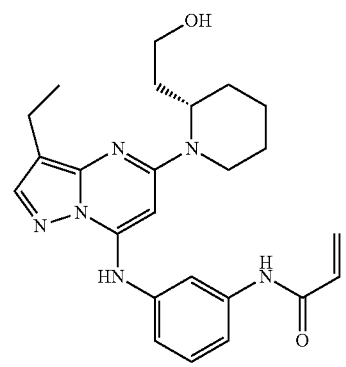 [SMILES: C=CC(=O)Nc1cccc(Nc2cc(N3CCCC[C@H]3CCO)nc3c(CC)cnn23)c1] | 739 | 24.7 | | 328 |
| MFH-2-53-1 | 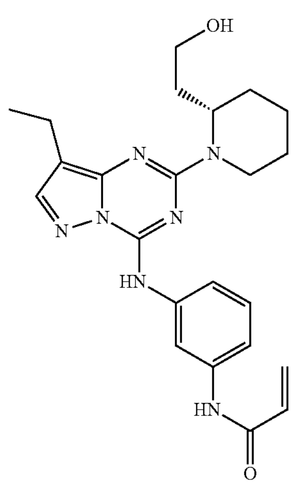 [SMILES: C=CC(=O)Nc1cccc(Nc2nc(N3CCCC[C@H]3CCO)nc3c(CC)cnn23)c1] | 1100 | 61.6 | | 53.5 |

TABLE A2-continued

Biological evaluation of additional exemplified compounds (IC50 values/nM)

| Compound | Structure | CDK7/CycH | CDK9/CycT | Jurkat | CDK2/CycA |
|---|---|---|---|---|---|
| MFH-3-140-1 | 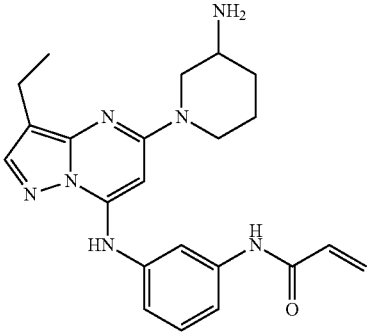 [SMILES: C=CC(=O)Nc1cccc(Nc2cc(N3CCCC(N)C3)nc3c(CC)cnn23)c1] | 356 | 465 | | 4190 |
| MFH-1-141-1 | 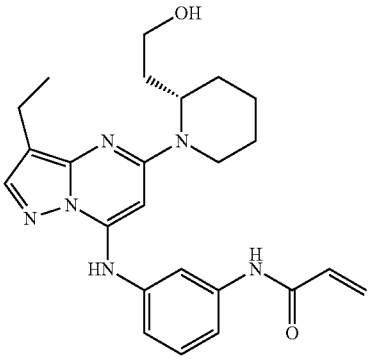 [SMILES: C=CC(=O)Nc1cccc(Nc2cc(N3CCCC[C@H]3CCO)nc3c(CC)cnn23)c1] | 1210 | 23.9 | | 932 |

Example 31. KiNativ™ Kinome Profiling

Jurkat cells were seeded at a density of 100 million cells/50 mL. Cells were treated with E9 (1 µM) or DMSO control for 6 hrs. Cells were washed twice with cold phosphate—buffered saline (PBS). PBS-washed cell pellets were flash frozen and subjected to KiNativ™ kinome profiling at ActivX Biosciences, Inc. according to their specifications using their desthiobiotin-ATP probe. Peptide sequences shown in Table A4 belong to the indicated kinase(s) and were detected by mass spectrometry (MS) under DMSO control conditions following enrichment for biotinylated proteins by streptavidin pulldown and subsequent proteolysis. Kinases labeled by the reactive desthiobiotin-ATP probe indicate that the kinase was accessible to desthiobiotin-ATP probe binding. Results shown are normalized to these paired DMSO controls and numbers represent the percentage (compared to DMSO control) of MS signal lost for sequences of an indicated kinase, eg—numbers approaching 100% indicate that test compound effectively out-competed the desthiobiotin ATP probe for binding to the kinase, resulting in decreased labeling and enrichment for peptides representing this kinase. This result suggests that E9 binds predominantly CDK12 and CDK13 in Jurkat cells (FIG. 10)

Example 32. Jurkat Gene Expression Analysis

Jurkat cells were seeded at a density of 5 million cells/10 mL. Cells were then treated with 200 nM or 1 µM of the indicated compounds or with DMSO control for 6 hrs. Total RNA was extracted from 5 million cells using the RNeasy Plus Mini Kit (Qiagen) with a gDNA eliminator mini column to remove genomic DNA. mRNA was reverse transcribed into cDNA using the SuperScript III First-Strand Synthesis Kit (Life Technologies) using an oligo-dT primer to capture polyadenylated mRNAs. Quantitative PCR (qPCR) using transcript—specific Taqman probes (Applied Biosystems) was used to assess the effect of compound treatment on the expression of the indicated mRNA transcripts. All experiments shown were performed in biological triplicate. Each individual biological sample was qPCR—amplified in technical duplicate. Error bars are +/−SD. Expression data from drug treatments were normalized to GAPDH probe.

Figure 6:
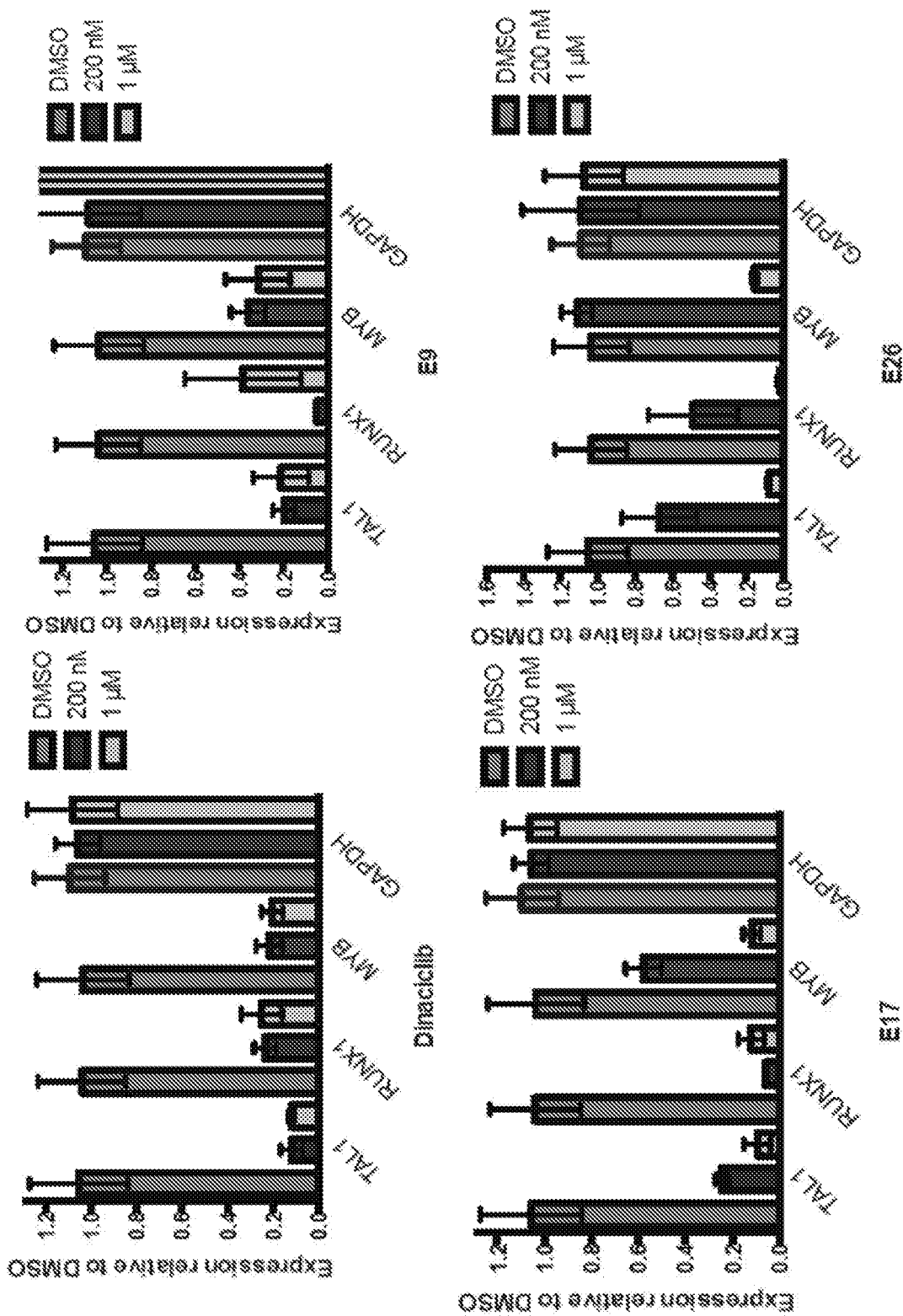
FIG. 6 shows the effect of Dinaciclib and compounds E9, E17, and E18 on the downstream protein targets. Specifically, reversible inhibitor Dinaciclib and covalent inhibitors Compounds E9, E17, and E18 are likely to downregulate mRNA transcripts of TAL1, RUNX1, and MYB in Jurkat T-cell acute lymphoblastic leukemia (T-ALL) cells. Jurkat cells were seeded at a density of 5 million cells/10 mL. Cells were then treated with 200 nM or 1 μM of the indicated compounds or with DMSO control for 6 hours. Total RNA was extracted from 5 million cells using the RNeasy Plus Mini Kit (Qiagen) with a gDNA eliminator mini column to remove genomic DNA. mRNA was reverse transcribed into cDNA using the SuperScript III First-Strand Synthesis Kit (Life Technologies) using an oligo-dT primer to capture polyadenylated mRNAs. Quantitative PCR (qPCR) using transcript—specific Taqman probes (Applied Biosystems) was used to assess the effect of compound treatment on the expression of the indicated mRNA transcripts. All experiments shown were performed in biological triplicate. Each individual biological sample was qPCR—amplified in technical duplicate. Error bars are +/−SD. Expression data from drug treatments were normalized to GAPDH probe.
Figure 7:
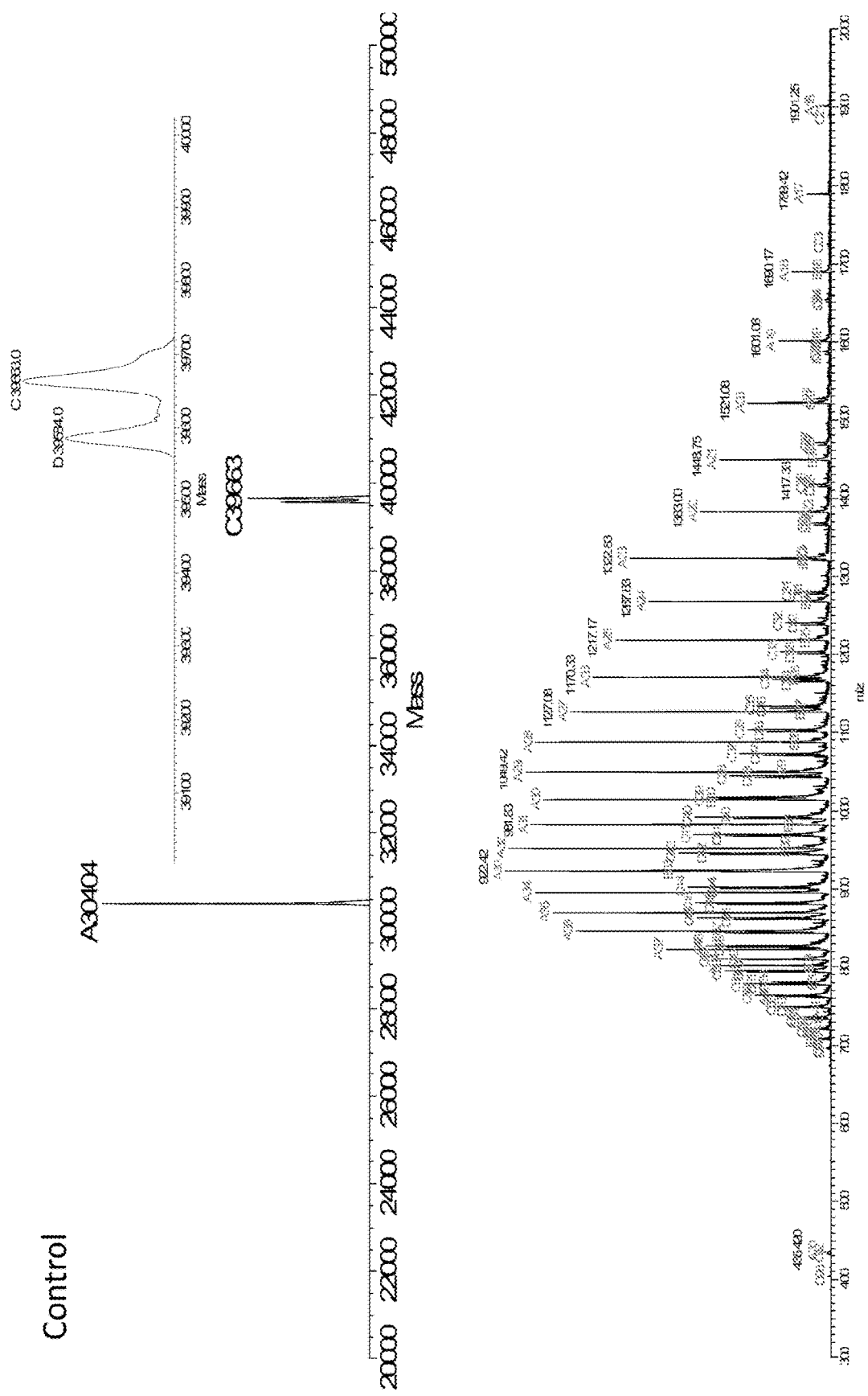
FIG. 7 shows electrospray ionization mass spectra of CDK12/CCNK complex after treatment with DMSO for 1 hr at room temperature. The zero-charge mass spectra in the upper panel and inset is the result of deconvolution of the raw mass spectrum in the lower panel. A, CCNK. C, phosphorylated CDK12. D, CDK12.
Figure 8:
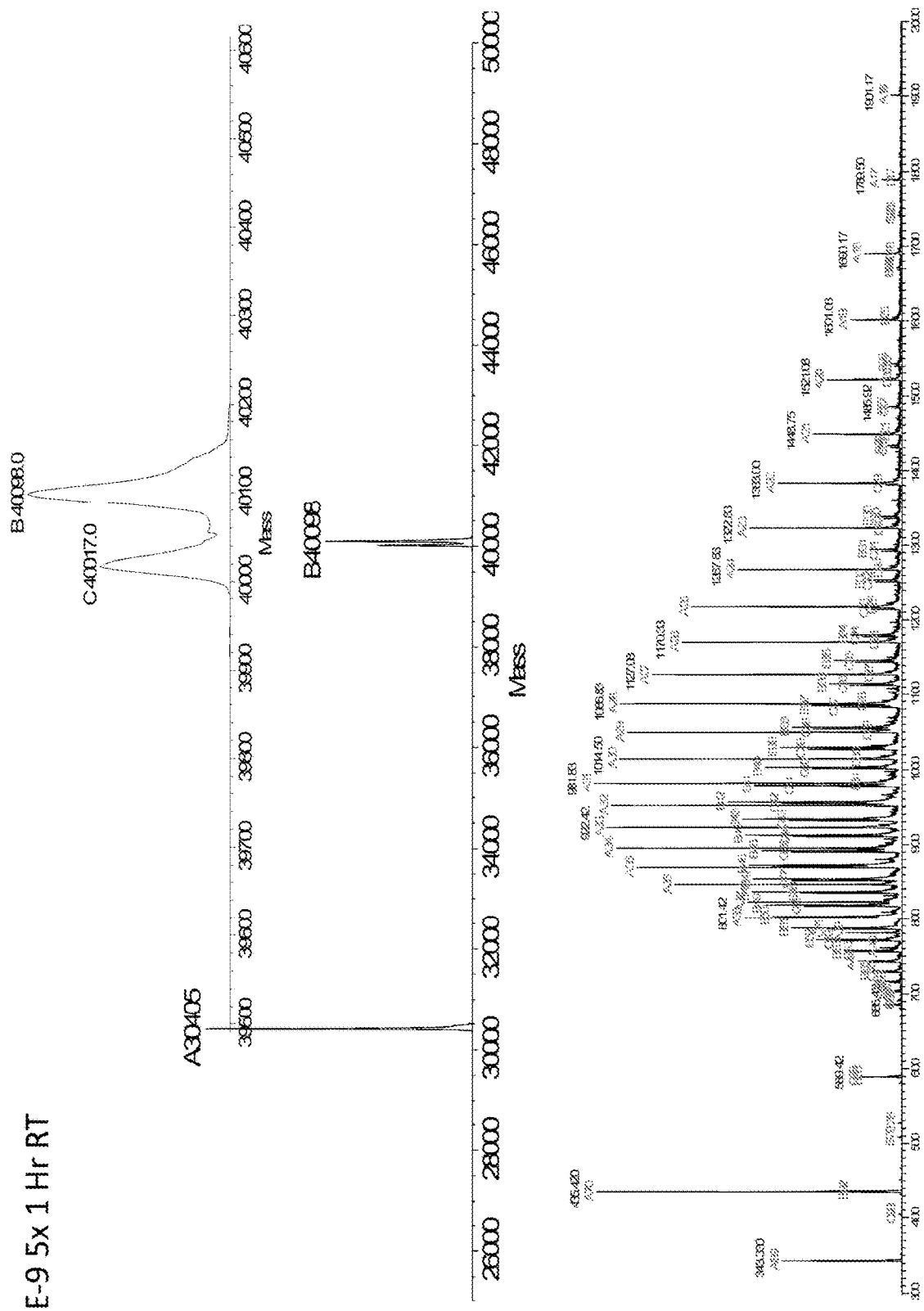
FIG. 8 shows electrospray ionization mass spectra of CDK12/CCNK complex after treatment with E-9 for 1 hr at room temperature. The zero-charge mass spectra in the upper panel and inset is the result of deconvolution of the raw mass spectrum in the lower panel. A, CCNK. B, phosphorylated and E-9 labeled CDK12. C, E-9 labeled CDK12. Only the masses of CDK12 proteins shift after treatment.
Figure 9:
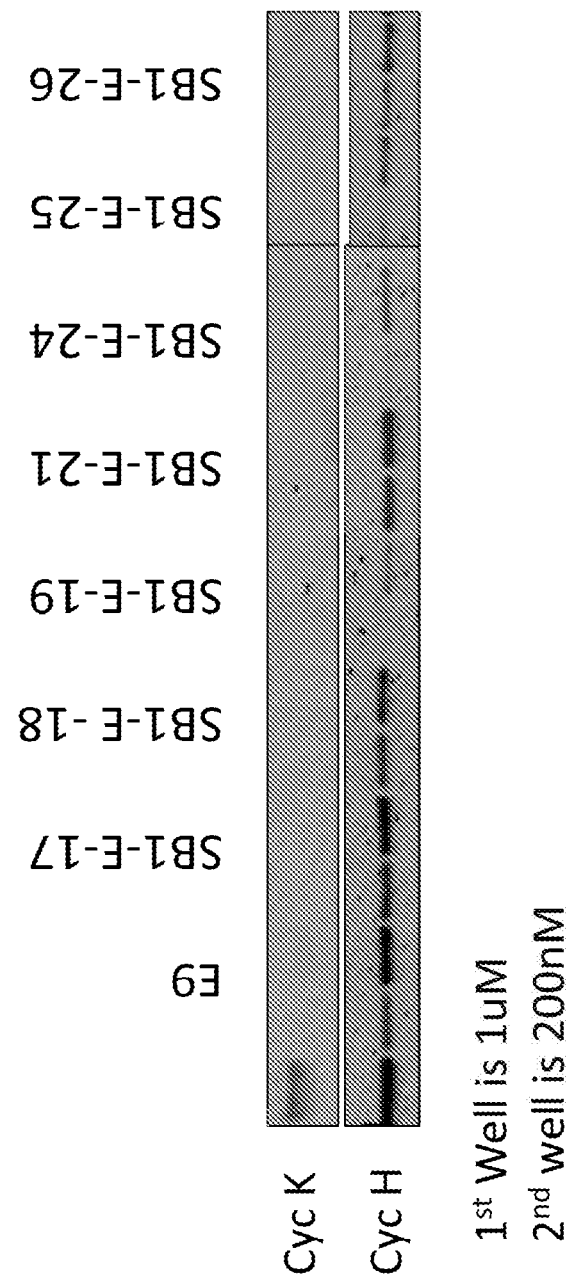
FIG. 9 shows pull down assay with exemplified compounds. The first and second wells are at the concentrations of 1 µM and 200 nM respectively.
Figure 12:
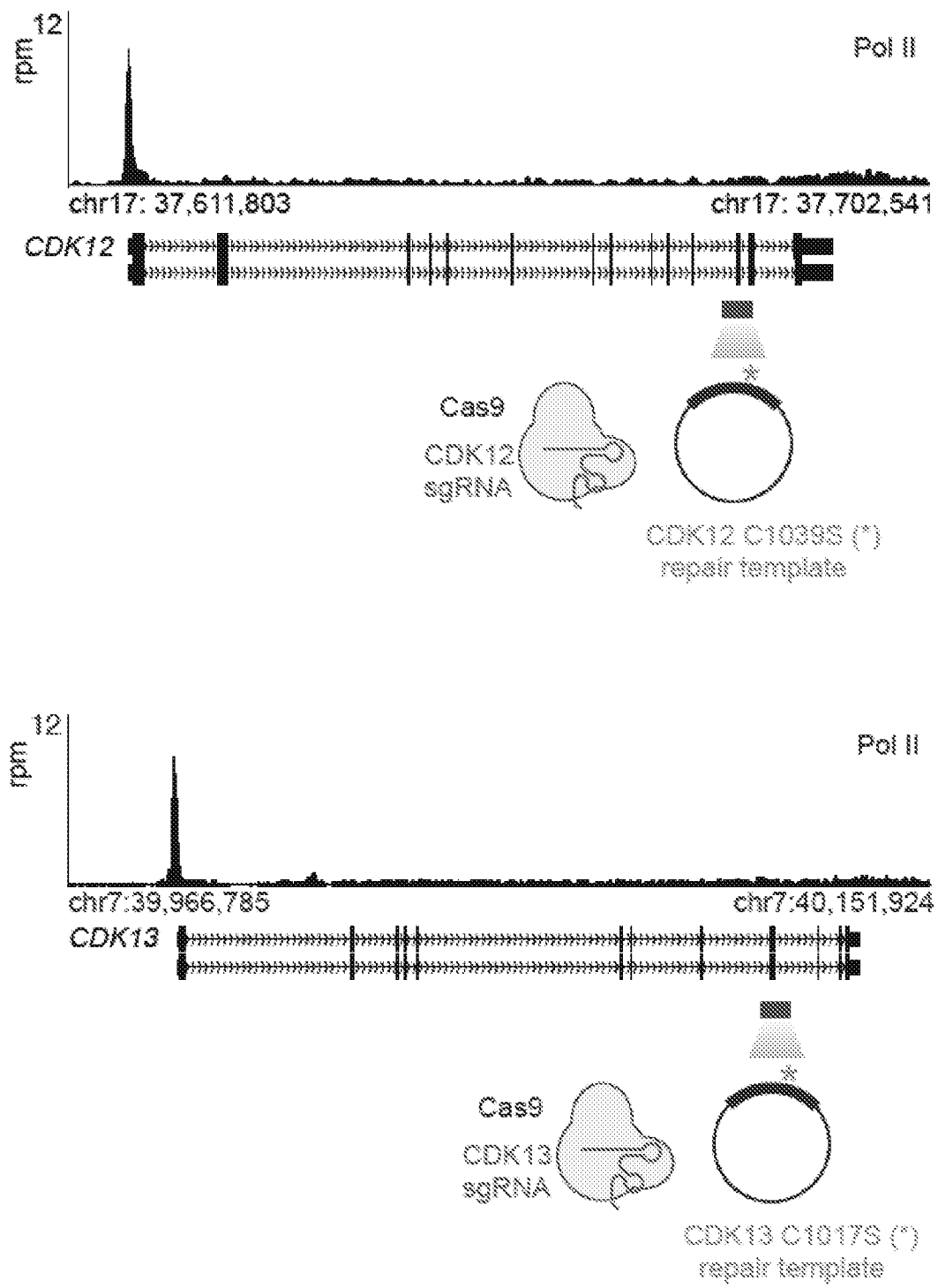
FIG. 12 shows an overview of the CRISPR-mediated strategy to introduce cysteine-to-serine mutations into the genomic loci of CDK12 and CDK13. Shown are gene tracks of RNA polymerase II ChIP-seq signal at CDK12 (left) and CDK13 (left) gene loci in Jurkat cells. Cartoons depict (1) the Cas9/guide RNA construct used to target Cas9-mediated DNA cutting to particular either CDK12 or CDK/13 gene loci and (2) a repair construct that contains DNA sequence encoding for a serine mutation in CDK12 (C1039S) and CDK13 (C1017S), which together introduce the desired cysteine-to-serine coding mutations into these loci.
Figure 13:
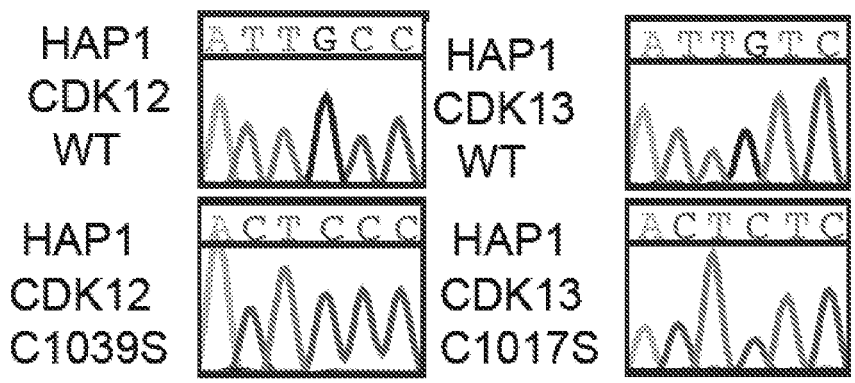
FIG. 13 shows genotype for wild type (top) CDK12 C1039S/CDK13 C1017S double mutant (bottom) cells. The sequencing results for CDK12 (left) and CDK13 (right) loci are depicted. Expression of these putatively inhibitor-refractory mutants is expected to rescue compound-induced proliferation defects that result from CDK12 and CDK13 covalent inhibition. For CDK12 WT loci, TGC codes for cysteine; while for CDK12 C1039S loci, TCC codes for serine. For CDK13 WT loci, TGT codes for cysteine; while for CDK13 C1017S loci, TCT codes for serine.
Figure 14:
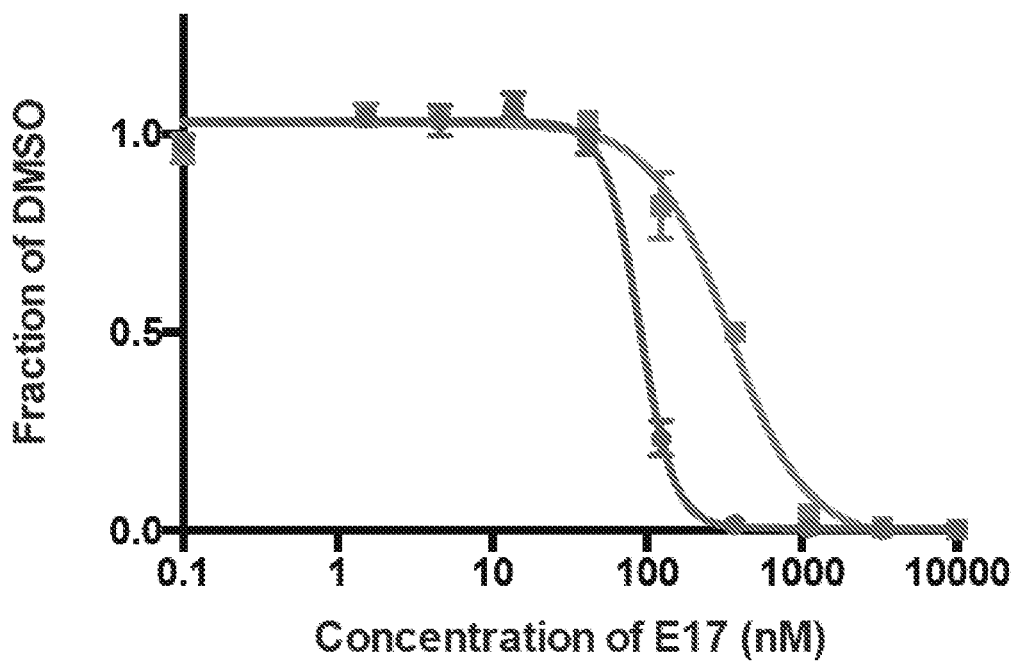
FIG. 14 shows the 72 hour proliferation results from wild type and CDK12 C1039S/CDK13 C1017S HAP1 cells. Double mutant cells are 4-fold less sensitive to E17 compared to wild type cells indicating rescue of CDK12/13 inibition—induced proliferation defects. HAP1 cells were seeded at a density of 12,000 cells/well in 96-well plates. Twenty-four hours later, cells were treated with the indicated compounds in a 10-pt dose escalation format from 1 nM to 10 µM or DMSO control for 72 hours. After 72 hours, the cells were assayed using CellTiter-Glo Luminescent Cell Viability Assay (Promega) to determine cell viability by measuring the amount of ATP present in each sample cell population, which is an indicator of cell metabolic activity.

These results suggest that the covalent inhibitors E9, E17, and E18 as well as Dinaciclib (FIG. 6), a reversible inhibitor, potently downregulate the key T-ALL transcription factors TAL1, RUNX1, and MYB at a dose of 200 nM. Inhibitors E21 and E26 downregulate these factors to a lesser degree at 200 nM and only potently reduce these transcripts at 1 µM. Furthermore, the magnitude with which these inhibitors downregulate the expression of these transcription factors at 200 nM correlates with their effective IC50s on Jurkat T-ALL cell proliferation. For example, Dinaciclib and E18 downregulate these transcription factor genes by at least 80% at 200 nM and have IC50s less than 20 nM. E9 and E17 downregulate these transcription factor genes by at least 40% at 200 nM and have IC50s less than 100 nM. Lastly, E21 and E26 downregulate these genes between 0-60% and have IC50s greater than 300 nM. This suggests that the magnitude of the reduction in expression of these transcription factor genes may serve as an indicator of overall phenotypic response to the inhibitor.

Example 33. Mutagenesis Analysis

Genome Editing: The CRISPR/Cas9 system was used to mutate the endogenous CDK12 and CDK13 loci to encode for CDK12 C1039S and CDK13 C1017S, both of which are putative CDK12/13 inhibitor-refractory mutants. Target-specific oligonucleotides were cloned into pX330, which carries a codon-optimized version of Cas9 and was further modified to express GFP for identifying transfectants. Cells were co-transfected (X-tremeGENE 9 (Roche)) with 1) pX330 expressing Cas9 and CDK12-targeting guide RNAs and 2) a pUC57-AMP construct bearing 1500 bp of modified CDK12 reference genome* that is centered around the CRISPR targeting site in CDK12. Two days after transfection, cells were sorted using GFP as a marker of transfected cells and cells were re-plated for five days. Cells were then re-plated at low density to facilitate the isolation of individual clones. Individual clones were isolated, expanded, and PCR genotyped using mutant specific PCR primers. Following initial PCR screening, individual clones were Sanger sequenced to confirm the presence of the desired mutation. Western blot confirmed the presence of intact CDK12 kinase. The process was sequentially repeated with Cas9/sgRNA constructs to target and replace the CDK13 genetic loci. Subsequent experiments were conducted using a CDK12 C1039S/CDK13 C1017S clone and a wild type control clone that was carried through the entirety of the CRISPR protocol but that was verified by Sanger sequencing to be wild typeT for CDK12 and CDK13. The genomic sequence complementary to the CDK12-directed guide RNA that was cloned into pX330 and used in the genome editing experiments is: GGCAGGATTGCCATGAGTTG. The genomic sequence complementary to the CDK13-directed guide RNA that was cloned into pX330 and used in the genome editing experiments is: GGCAAGAT TGTCATGAGTTA. * The reference genome sequence used as a repair template for CDK12 and CDK13 CRISPR was edited to 1) introduce DNA coding for serine, 2) introduce mutations to either remove the PAM site (NGG) targeted by CRISPR/Cas9 or introduce sufficient wobble mutations such that the guide RNA could not recognize the repair template and thus could not be cut by CRISPR/Cas9, and 3) introduce mutations that could allow for mutant and wild type-specific PCR amplification.

HAP1 cell proliferation assay: HAP1 wild type and double mutants cells were seeded at a density of 12,000 cells/well in 96-well plates. Twenty four hours cells were then treated with the indicated compounds in a 10-pt dose escalation format from 1 nM to 10 µM or DMSO control for 72 hrs. After 72 hrs, cells were assayed using CellTiter-Glo Luminescent Cell Viability Assay (Promega) to determine cell viability by measuring the amount of ATP present in each sample cell population, which is an indicator of cell metabolic activity. Results are graphed as fraction of the DMSO control at 72 hrs. All data points were performed in biological triplicate. Error bars are +/−SD.

HAP1 cells expressing inhibitor-refractory mutations in CDK12 (C1039S) and CDK13 (C1017S) were 4-fold less sensitive to E17 compared to control wild type HAP1 cells. This result indicates that a significant portion of intracellular E17 activity comes from covalent inhibition of CDK12 and/or CDK13. Mutation of these targeted cysteines to a less nucleophilic serine is sufficient to rescue a significant portion of anti-prolierative activity at concentrations less than 350 nM.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (III):

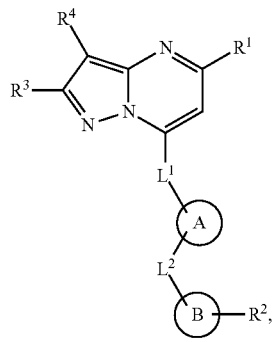

or a pharmaceutically acceptable salt thereof, wherein:
$R^1$ is optionally substituted alkyl, optionally substituted alkenyl, optionally substituted alkynyl, optionally substituted carbocyclyl, optionally substituted aryl, optionally substituted heterocyclyl, optionally substituted heteroaryl, —$NR^aR^b$, —$OR^b$, —$SR^b$, —$C(=O)R^b$, —$C(=O)OR^b$, or —$C(=O)NR^aR^b$, wherein each instance of $R^a$ and $R^b$ is independently hydrogen, optionally substituted alkyl, optionally substituted alkenyl, optionally substituted alkynyl, optionally substituted carbocyclyl, optionally substituted aryl, optionally substituted heterocyclyl, optionally substituted aryl, optionally substituted heteroaryl, a nitrogen protecting group when attached to nitrogen, an oxygen protecting group when attached to oxygen, or a sulfur protecting group when attached to sulfur; or $R^a$ and $R^b$ are joined to form an optionally substituted heterocyclic or optionally substituted heteroaryl ring;

each of $R^3$ and $R^4$ is independently hydrogen, halogen, or optionally substituted $C_1$-$C_6$ alkyl;

$L^1$ is a bond, —$NR^{L1}$—$(CH_2)_t$—, —O—, or —S—;

$R^{L1}$ is hydrogen, optionally substituted $C_1$-$C_6$ alkyl, or a nitrogen protecting group;

t is 0 or an integer between 1 and 5, inclusive;

Ring A is optionally substituted carbocyclyl, optionally substituted heterocyclyl, optionally substituted aryl, or optionally substituted heteroaryl;

$L^2$ is a bond, optionally substituted $C_{1-4}$ alkylene, —C(=O)—, —$NR^{L2}$—, —$C(=O)NR^{L2}$—, —$NR^{L2}C(=O)$—, —O—, or —S—, wherein $R^{L2}$ is hydrogen, optionally substituted $C_1$-$C_6$ alkyl, or a nitrogen protecting group;

Ring B is absent, optionally substituted carbocyclyl, optionally substituted heterocyclyl, optionally substituted aryl, or optionally substituted heteroaryl; and $R^2$ is of the formula:
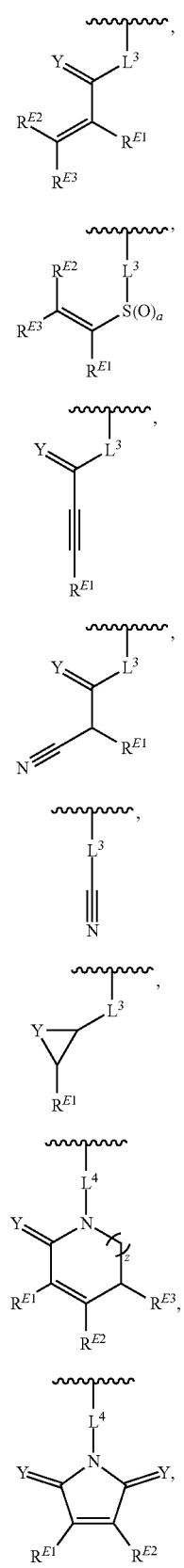
(i-1)
(i-2)
(i-3)
(i-4)
(i-5)
(i-6)
(i-7)
(i-8)
-continued
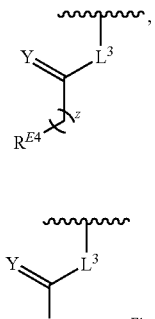 (i-9)
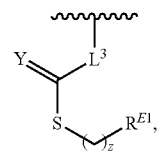 (i-12)
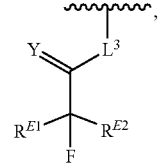 (i-13)
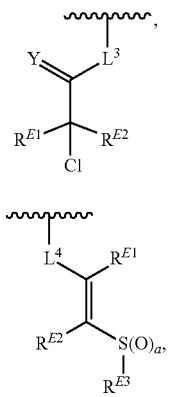 (i-14)
(i-15)
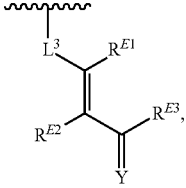 (i-16)
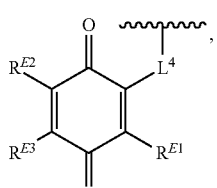 (i-17)
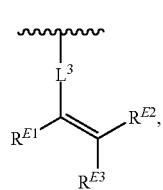 (i-18)

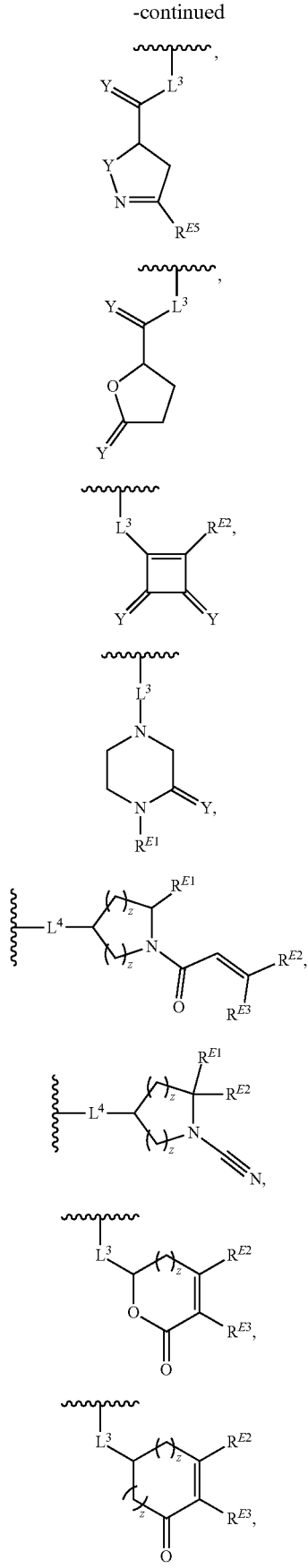
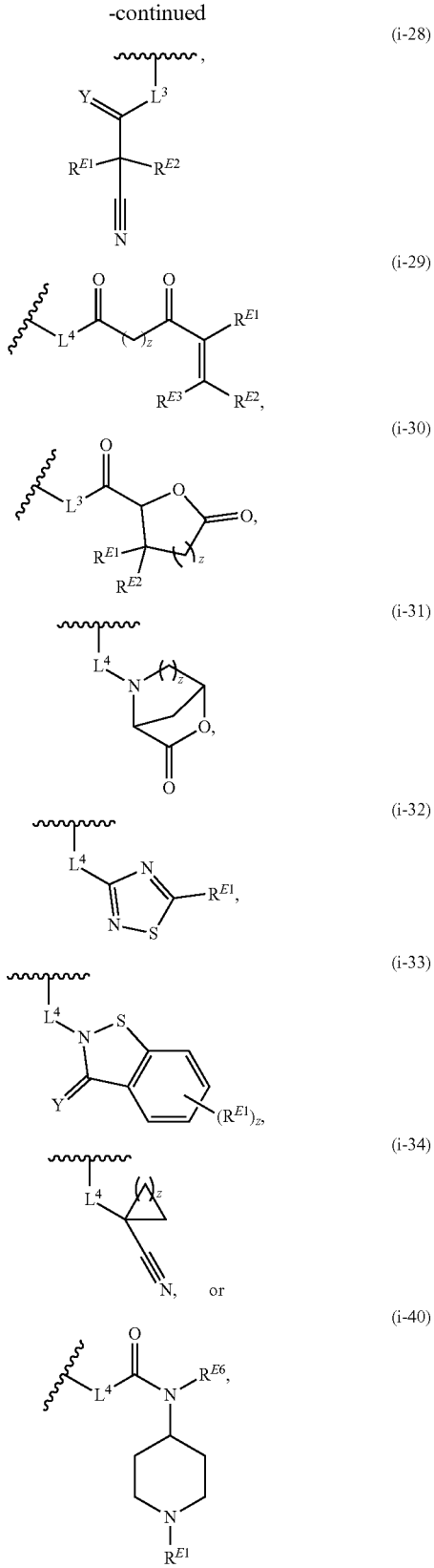
wherein:
L³ is a bond or an optionally substituted C₁₋₄ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted C$_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

L$^4$ is a bond or an optionally substituted, branched or unbranched C$_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$, wherein each occurrence of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring;

or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted C$_{1-6}$ alkyl, or a nitrogen protecting group;

each instance of Y is independently O, S, or NR$^{E7}$, wherein R$^{E7}$ is hydrogen, substituted or unsubstituted C$_{1-6}$ alkyl, or a nitrogen protecting group;

a is 1 or 2; and each instance of z is independently 0, 1, 2, 3, 4, 5, or 6, as valency permits.

2. The compound of claim 1, or a pharmaceutically acceptable salt thereof, wherein L$^2$ is a bond.

3. The compound of claim 1, or a pharmaceutically acceptable salt thereof, wherein R$^1$ is optionally substituted heterocyclyl.

4. The compound of claim 1, or a pharmaceutically acceptable salt thereof, wherein R$^2$ is of the formula:

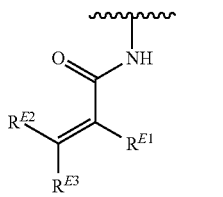 or 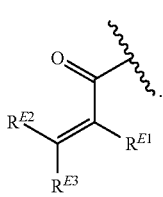

5. The compound of claim 1, or a pharmaceutically acceptable salt thereof, wherein R$^3$ is hydrogen.

6. The compound of claim 1, or a pharmaceutically acceptable salt thereof, wherein R$^4$ is optionally substituted C$_1$-C$_6$ alkyl.

7. The compound of claim 1, wherein the compound is of the formula:

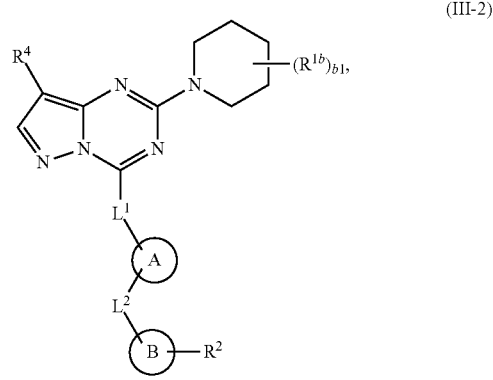

(III-2)

or a pharmaceutically acceptable salt thereof.

8. The compound of claim 1, wherein the compound is of the formula:

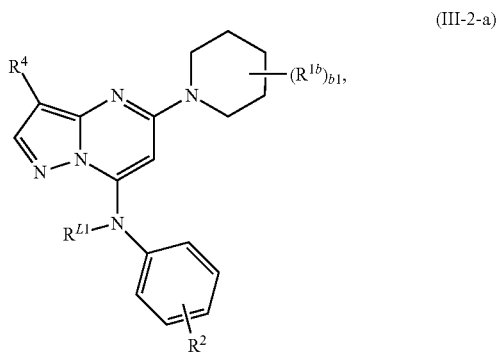

(III-2-a)

or a pharmaceutically acceptable salt thereof.

9. The compound of claim 1, wherein the compound is of the formula:

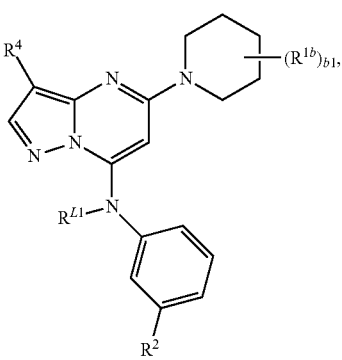

(III-2-a-i)

or a pharmaceutically acceptable salt thereof.

10. The compound of claim 1, wherein the compound is of the formula:
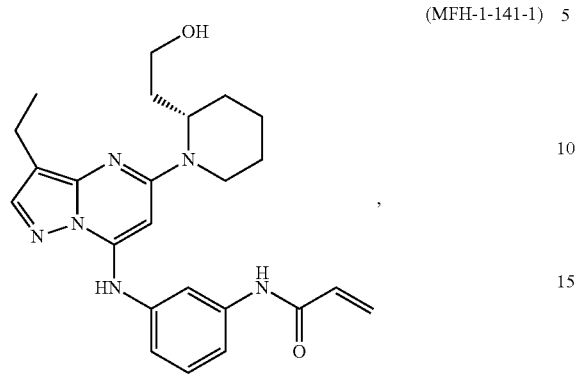
(MFH-1-141-1)
or a pharmaceutically acceptable salt thereof.
* * * * *

UNITED STATES PATENT AND TRADEMARK OFFICE
CERTIFICATE OF CORRECTION

PATENT NO. : 10,550,121 B2
APPLICATION NO. : 15/561729
DATED : February 4, 2020
INVENTOR(S) : Nathanael S. Gray et al.

Page 1 of 5

It is certified that error appears in the above-identified patent and that said Letters Patent is hereby corrected as shown below:

On the Title Page

Under abstract "10 Claims, 25 Drawing Sheets" should read -21 Claims, 25 Drawing Sheets-.

In the Claims

In Claim 1, at Column 405, Line 6, please add the text: -- -C≡C-,-- immediately before the text "-S(=O)-,".

In Claim 7, at Column 406, the formula: 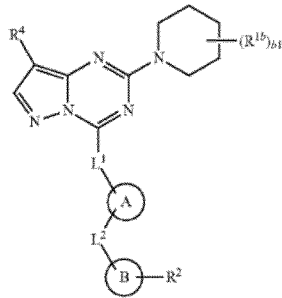 should be replaced with the formula: 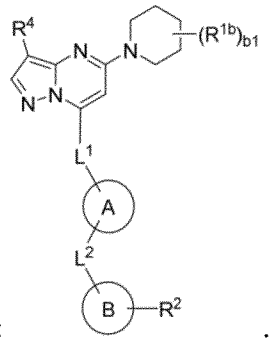 .

Signed and Sealed this
Sixteenth Day of June, 2020

Andrei Iancu
*Director of the United States Patent and Trademark Office*

Column 408 Line 1:
Please add Claim 11 as shown immediately below:
--11. The compound of claim 1, or a pharmaceutically acceptable salt thereof, wherein Ring A is optionally substituted phenyl.--.

Please add Claim 12 as shown immediately below:
--12. The compound of claim 1, or a pharmaceutically acceptable salt thereof, wherein Ring A is optionally substituted cyclohexyl.--.

Please add Claim 13 as shown immediately below:
--13. The compound of claim 1, or a pharmaceutically acceptable salt thereof, wherein $L^1$ is -$NR^{L1}$-.--.

Please add Claim 14 as shown immediately below:
--14. The compound of claim 1, or a pharmaceutically acceptable salt thereof, wherein $L^2$ is -$NR^{L2}(C=O)$-.--.

Please add Claim 15 as shown immediately below:
--15. The compound of claim 1, or a pharmaceutically acceptable salt thereof, wherein Ring B is absent.--.

Please add Claim 16 as shown immediately below:
--16. The compound of claim 1, or a pharmaceutically acceptable salt thereof, wherein Ring B is optionally substituted phenyl.--.

Please add Claim 17 as shown immediately below:
--17. The compound of claim 1, or a pharmaceutically acceptable salt thereof, wherein $R^1$ is of Formula (n-1):

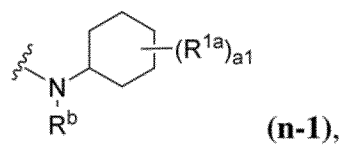

(n-1), wherein:
each instance of $R^{1a}$ is independently hydrogen, halogen, optionally substituted $C_1$-$C_6$ alkyl, -$N(R^{N1})_2$, or -$OR^{O1}$;
each instance of $R^{N1}$ is independently hydrogen, optionally substituted $C_1$-$C_6$ alkyl, or a nitrogen protecting group;
$R^{O1}$ is independently hydrogen, optionally substituted $C_1$-$C_6$ alkyl, or an oxygen protecting group; and
a1 is 0 or an integer between 1 and 6, inclusive.--.

Please add Claim 18 as shown immediately below:
--18. The compound of claim 1, or a pharmaceutically acceptable salt thereof, wherein $R^1$ is of Formula (n-2):

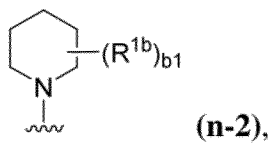 (n-2), wherein:

each instance of $R^{1b}$ is independently hydrogen, halogen, optionally substituted $C_1$-$C_6$ alkyl, $-N(R^{N1})_2$, or $-OR^{O1}$;

each instance of $R^{N1}$ is independently hydrogen, optionally substituted $C_1$-$C_6$ alkyl, or a nitrogen protecting group;

$R^{O1}$ is independently hydrogen, optionally substituted $C_1$-$C_6$ alkyl, or an oxygen protecting group; and b1 is 0 or an integer between 1 and 6, inclusive.--.

Please add Claim 19 as shown immediately below:
--19. The compound of claim 1, or a pharmaceutically acceptable salt thereof, wherein $R^2$ is of Formula (i-1):

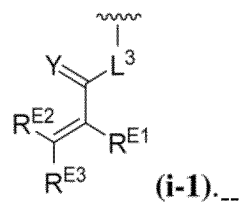 (i-1).--.

Please add Claim 20 as shown immediately below:
--20. The compound of claim 1, wherein the compound is of the formula:

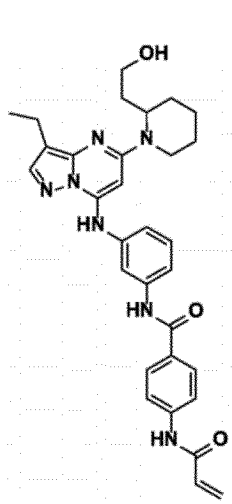 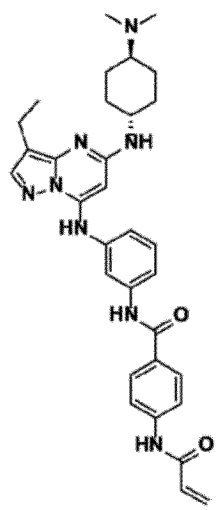 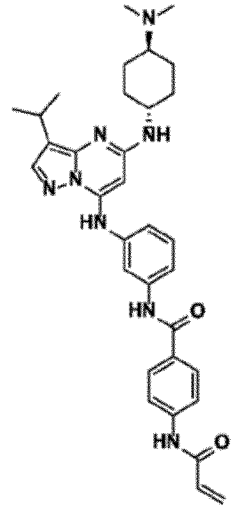

(SB1-E-24), (SB1-E-22), (SB1-E-25),

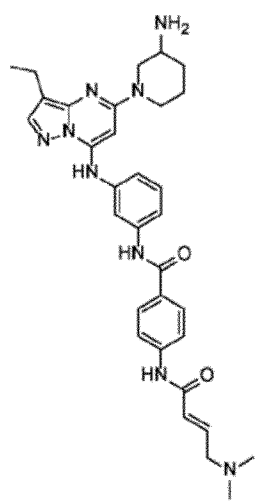
(THZ-4-128-1),
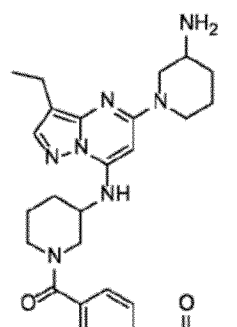
(THZ-4-141-1),
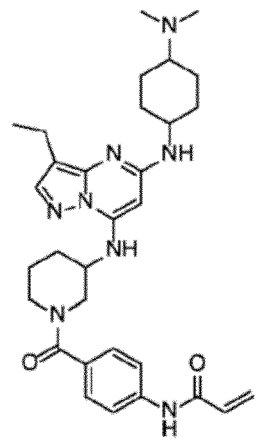
(THZ-4-148-1),
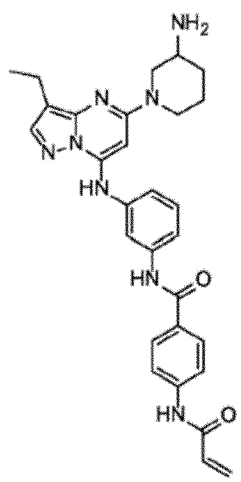
(X4),
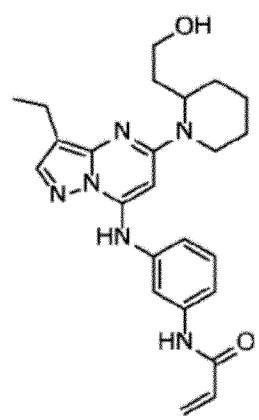
(E-9),
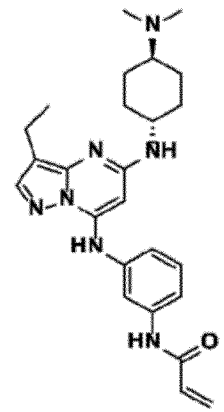
(SB1-E-21),
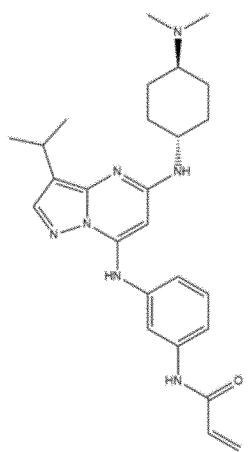
(SB1-E-26),
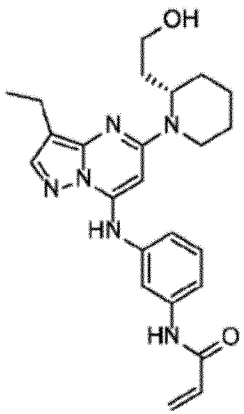
(Y2),
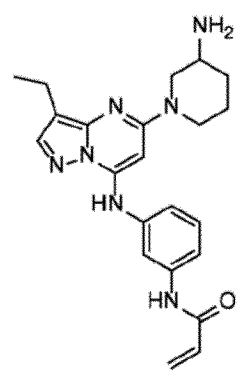
(Y6),

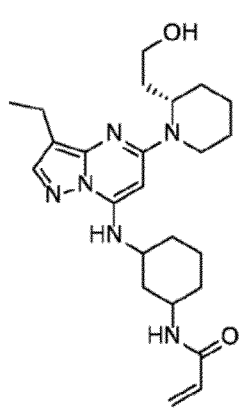 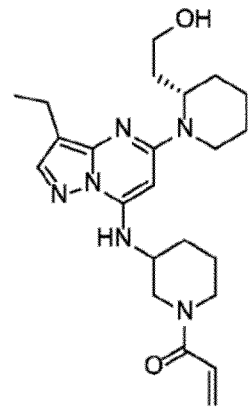 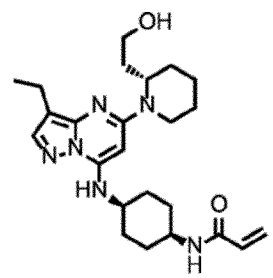
(Y11), (Y12), (MFH-1-169-1),
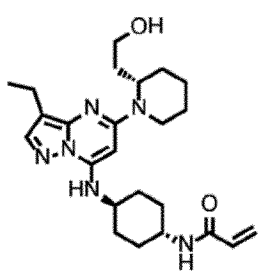 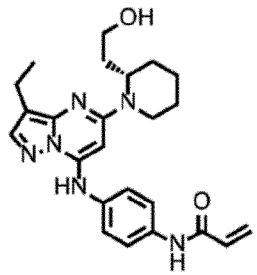 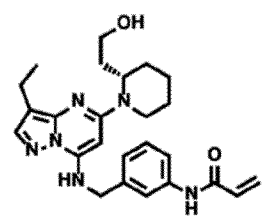
(MFH-1-175-1), (MFH-1-187-1), (MFH-1-49-1),
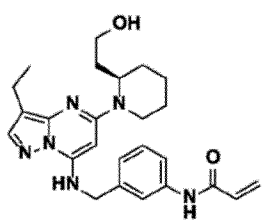 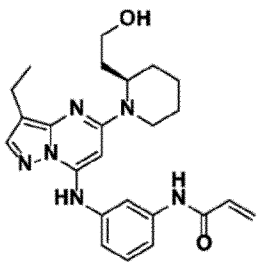 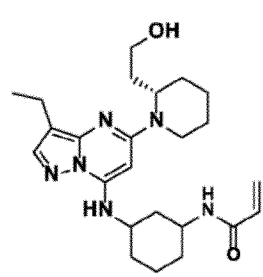
(MFH-1-56-1), (MFH-1-143-1), (MFH-1-167-1),
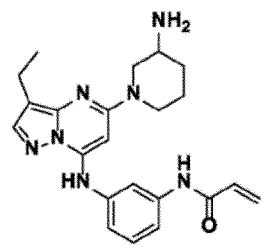 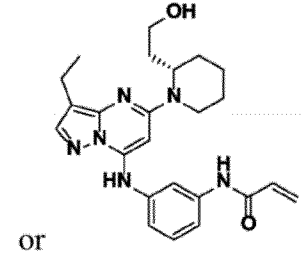
(MFH-3-140-1), or (MFH-1-141-1),
or a pharmaceutically acceptable salt thereof.--.
Please add Claim 21 as shown immediately below:
--21. A pharmaceutical composition comprising a compound of claim 1, or a pharmaceutically acceptable salt thereof, and optionally a pharmaceutically acceptable excipient.--.

SEQUENCE LISTING

<160> NUMBER OF SEQ ID NOS: 279

<210> SEQ ID NO 1
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1

Leu Met Thr Gly Asp Thr Tyr Thr Ala His Ala Gly Ala Lys Phe Pro
1               5                   10                  15

Ile Lys

<210> SEQ ID NO 2
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 2

Tyr Ser Leu Thr Val Ala Val Lys Thr Leu Lys Glu Asp Thr Met Glu
1               5                   10                  15

Val Glu Glu Phe Leu Lys
            20

<210> SEQ ID NO 3
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 3

Thr Val Ser Val Ala Val Lys Cys Leu Lys Pro Asp Val Leu Ser Gln
1               5                   10                  15

Pro Glu Ala Met Asp Asp Phe Ile Arg
            20                  25

<210> SEQ ID NO 4
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 4

Gly Thr Phe Gly Lys Val Ile Leu Val Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 5

Gly Thr Phe Gly Lys Val Ile Leu Val Arg
1               5                   10

<210> SEQ ID NO 6
<211> LENGTH: 19
<212> TYPE: PRT

```
<213> ORGANISM: Artificial Sequence
<220> FEATURE:
<223> OTHER INFORMATION: Synthetic Polypeptide

<400> SEQUENCE: 6

Ile Gly His Tyr Ile Leu Gly Asp Thr Leu Gly Val Gly Thr Phe Gly
1               5                   10                  15

Lys Val Lys

<210> SEQ ID NO 7
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 7

Val Gly Lys His Glu Leu Thr Gly His Lys Val Ala Val Lys Ile Leu
1               5                   10                  15

Asn Arg

<210> SEQ ID NO 8
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 8

Val Ala Val Lys Ile Leu Asn Arg
1               5

<210> SEQ ID NO 9
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 9

Asp Leu Lys Pro Glu Asn Val Leu Leu Asp Ala His Met Asn Ala Lys
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 10

Asp Leu Lys Ser Asn Asn Ile Phe Leu His Glu Gly Leu Thr Val Lys
1               5                   10                  15

<210> SEQ ID NO 11
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 11

Phe Tyr Ile Met Met Cys Lys Pro Lys
1               5
```

```
<210> SEQ ID NO 12
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 12

Phe Ile Leu Ala Leu Lys Val Leu Phe Lys
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 13

Asp Ile Lys Pro Glu Asn Leu Leu Gly Ser Ala Gly Glu Leu Lys
1               5                   10                  15

<210> SEQ ID NO 14
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 14

Gly Lys Phe Gly Asn Val Tyr Leu Ala Arg
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 15

Ser His Phe Ile Val Ala Leu Lys Val Leu Phe Lys
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 16

Asp Leu Lys Pro Ala Asn Ile Leu Leu Asp Glu His Gly His Val Arg
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 17

Asp Leu Lys Ser Asn Asn Ile Phe Leu His Glu Asp Leu Thr Val Lys
1               5                   10                  15

<210> SEQ ID NO 18
```

```
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 18

Leu Phe Ala Val Lys Cys Ile Pro Lys
1               5

<210> SEQ ID NO 19
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 19

Asp Leu Lys Pro Glu Asn Leu Leu Tyr Tyr Ser Gln Asp Glu Glu Ser
1               5                  10                  15

Lys

<210> SEQ ID NO 20
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 20

Asp Leu Lys Pro Glu Asn Leu Leu Leu Ala Ser Lys
1               5                  10

<210> SEQ ID NO 21
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 21

Ile Pro Thr Gly Gln Glu Tyr Ala Ala Lys Ile Ile Asn Thr Lys Lys
1               5                  10                  15

<210> SEQ ID NO 22
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 22

Thr Ser Thr Gln Glu Tyr Ala Ala Lys Ile Ile Asn Thr Lys
1               5                  10

<210> SEQ ID NO 23
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 23

Ile Val Glu His Gln Val Leu Met Lys Thr Val Cys Gly Thr Pro Gly
1               5                  10                  15

Tyr Cys Ala Pro Glu Ile Leu Arg
```

```
<210> SEQ ID NO 24
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 24

Gly Thr Gln Lys Pro Tyr Ala Leu Lys Val Leu Lys
1               5                   10

<210> SEQ ID NO 25
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 25

Asp Leu Lys Pro Glu Asn Leu Leu Tyr Ala Thr Pro Ala Pro Asp Ala
1               5                   10                  15

Pro Leu Lys

<210> SEQ ID NO 26
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 26

Leu Ala Tyr Asn Glu Asn Asp Asn Thr Tyr Tyr Ala Met Lys Val Leu
1               5                   10                  15

Ser Lys

<210> SEQ ID NO 27
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 27

Asp Ile Lys Pro Ser Asn Leu Leu Val Gly Glu Asp Gly His Ile Lys
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 28

Asp Leu Lys Pro Ala Asn Leu Leu Ile Ser Ala Ser Gly Gln Leu Lys
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Synthetic Polypeptide
```

```
<400> SEQUENCE: 29

Asp Leu Lys Pro Gln Asn Leu Leu Ile Asp Asp Lys Gly Thr Ile Lys
1               5                   10                  15

<210> SEQ ID NO 30
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 30

Asp Leu Lys Pro Gln Asn Leu Leu Ile Asp Asp Lys
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 31

Asp Leu Lys Val Ser Asn Leu Leu Met Thr Asp Lys
1               5                   10

<210> SEQ ID NO 32
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 32

Asp Leu Lys Pro Ala Asn Ile Leu Val Met Gly Glu Gly Pro Glu Arg
1               5                   10                  15

<210> SEQ ID NO 33
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 33

Leu Thr Gly Glu Val Val Ala Leu Lys Lys
1               5                   10

<210> SEQ ID NO 34
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 34

Asp Leu Lys Pro Gln Asn Leu Leu Ile Asn Thr Glu Gly Ala Ile Lys
1               5                   10                  15

<210> SEQ ID NO 35
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 35
```

Asn Arg Glu Thr His Glu Ile Val Ala Leu Lys Arg
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 36

Asp Leu Lys Pro Gln Asn Leu Leu Ile Asn Arg
1               5                   10

<210> SEQ ID NO 37
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 37

Asp Leu Lys Pro Gln Asn Ile Leu Val Thr Ser Ser Gly Gln Ile Lys
1               5                   10                  15

<210> SEQ ID NO 38
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 38

Asp Lys Asn Thr Asn Gln Ile Val Ala Ile Lys Lys
1               5                   10

<210> SEQ ID NO 39
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 39

Asp Leu Lys Pro Asn Asn Leu Leu Leu Asp Glu Asn Gly Val Leu Lys
1               5                   10                  15

<210> SEQ ID NO 40
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 40

Asp Met Lys Ala Ala Asn Val Leu Ile Thr Arg
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 41

```
Asp Ile Lys Cys Ser Asn Ile Leu Leu Asn Asn Arg
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 42

Asp Ile Lys Pro Glu Asn Leu Leu Leu Asp Glu Arg
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 43

Leu Ser Lys Gly Asp Gly Leu Glu Phe Lys
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 44

Val Ala Ile Lys Ile Ile Ser Lys
1               5

<210> SEQ ID NO 45
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 45

Asp Leu Lys Pro Glu Asn Val Leu Leu Ser Ser Gln Glu Glu Asp Cys
1               5                   10                  15

Leu Ile Lys

<210> SEQ ID NO 46
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 46

Asp Ile Lys Pro Asp Asn Phe Leu Met Gly Ile Gly Arg
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 47
```

```
Asp Val Lys Pro Asp Asn Phe Leu Met Gly Leu Gly Lys Lys
1               5                   10
```

<210> SEQ ID NO 48
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 48

```
Asp Val Lys Pro Glu Asn Phe Leu Val Gly Arg Pro Gly Thr Lys
1               5                   10                  15
```

<210> SEQ ID NO 49
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 49

```
Gly Gly Pro Asn Ile Ile Thr Leu Ala Asp Ile Val Lys Asp Pro Val
1               5                   10                  15

Ser Arg
```

<210> SEQ ID NO 50
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 50

```
Asp Val Lys Pro His Asn Val Met Ile Asp His Gln Gln Lys
1               5                   10
```

<210> SEQ ID NO 51
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 51

```
Leu Thr His Thr Asp Leu Lys Pro Glu Asn Ile Leu Phe Val Gln Ser
1               5                   10                  15

Asp Tyr Thr Glu Ala Tyr Asn Pro Lys
            20                  25
```

<210> SEQ ID NO 52
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 52

```
Tyr Glu Ile Val Gly Asn Leu Gly Glu Gly Thr Phe Gly Lys Val Val
1               5                   10                  15

Glu Cys Leu Asp His Ala Arg
            20
```

<210> SEQ ID NO 53

<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 53

Asp Ile Lys Cys Ser Asn Ile Leu Leu Asn Asn Ser Gly Gln Ile Lys
1               5                   10                  15

<210> SEQ ID NO 54
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 54

Val Ser Asp Phe Gly Leu Thr Lys Glu Ala Ser Ser Thr Gln Asp Thr
1               5                   10                  15

Gly Lys Leu Pro Val Lys
            20

<210> SEQ ID NO 55
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 55

Val Ala Val Lys Cys Ile Lys
1               5

<210> SEQ ID NO 56
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 56

Ile Asp Pro Val Pro Asn Thr His Pro Leu Leu Val Phe Val Asn Pro
1               5                   10                  15

Lys Ser Gly Gly Lys
            20

<210> SEQ ID NO 57
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 57

Ala Thr Phe Ser Phe Cys Val Ser Pro Leu Leu Val Phe Val Asn Ser
1               5                   10                  15

Lys Ser Gly Asp Asn Gln Gly Val Lys
            20                  25

<210> SEQ ID NO 58
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 58

Lys Gly Gly Ser Trp Ile Gln Glu Ile Asn Val Ala Glu Lys
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 59

Glu His Pro Phe Leu Val Lys Gly Gly Glu Asp Leu Arg
1               5                   10

<210> SEQ ID NO 60
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 60

Asp Val Val His Leu Asp Leu Lys Pro Gln Asn Ile Leu Leu Thr Ser
1               5                   10                  15

Glu Ser Pro Leu Gly Asp Ile Lys
            20

<210> SEQ ID NO 61
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 61

Tyr Ile Lys Tyr Asn Ser Asn Ser Gly Phe Val Arg
1               5                   10

<210> SEQ ID NO 62
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 62

Phe Leu Glu Asp Asp Thr Ser Asp Pro Thr Tyr Thr Ser Ala Leu Gly
1               5                   10                  15

Gly Lys Ile Pro Ile Arg
            20

<210> SEQ ID NO 63
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 63

Asp Leu Lys Pro Ser Asn Leu Leu Ile Asn Thr Thr Cys Asp Leu Lys
1               5                   10                  15

<210> SEQ ID NO 64

```
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 64

Asp Leu Lys Pro Ser Asn Leu Leu Leu Asn Thr Thr Cys Asp Leu Lys
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 65

Asp Leu Lys Pro Ser Asn Leu Leu Val Asn Glu Asn Cys Glu Leu Lys
1               5                   10                  15

<210> SEQ ID NO 66
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 66

Cys Ile Gly Glu Gly Gln Phe Gly Asp Val His Gln Gly Ile Tyr Met
1               5                   10                  15

Ser Pro Glu Asn Pro Ala Leu Ala Val Ala Ile Lys Thr Cys Lys
            20                  25                  30

<210> SEQ ID NO 67
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 67

Gln Glu Asp Gly Gly Val Tyr Ser Ser Ser Gly Leu Lys Gln Ile Pro
1               5                   10                  15

Ile Lys

<210> SEQ ID NO 68
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 68

Thr Ser Val Ala Val Lys Thr Cys Lys Glu Asp Leu Pro Gln Glu Leu
1               5                   10                  15

Lys

<210> SEQ ID NO 69
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 69
```

```
Leu Ile Lys Asp Asp Glu Tyr Asn Pro Cys Gln Gly Ser Lys Phe Pro
1               5                   10                  15

Ile Lys

<210> SEQ ID NO 70
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 70

Ile Gln Ser Ile Ala Pro Ser Leu Gln Val Ile Thr Ser Lys Gln Arg
1               5                   10                  15

Pro Arg

<210> SEQ ID NO 71
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 71

Val Ala Ile Lys Thr Leu Lys Pro Gly Thr Met Ser Pro Glu Ser Phe
1               5                   10                  15

Leu Glu Glu Ala Gln Ile Met Lys
            20

<210> SEQ ID NO 72
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 72

Gln Gly Ala Lys Phe Pro Ile Lys Trp Thr Ala Pro Glu Ala Ala Leu
1               5                   10                  15

Tyr Gly Arg

<210> SEQ ID NO 73
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 73

Asp Thr Val Thr Ser Glu Leu Ala Ala Val Lys Ile Val Lys
1               5                   10

<210> SEQ ID NO 74
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 74

Asp Ile Lys Gly Ala Asn Leu Leu Leu Thr Leu Gln Gly Asp Val Lys
1               5                   10                  15
```

```
<210> SEQ ID NO 75
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 75

Leu Asp Gly Cys Cys Tyr Ala Val Lys Arg
1               5                   10

<210> SEQ ID NO 76
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 76

Asp Leu Lys Pro Val Asn Ile Phe Leu Asp Ser Asp Asp His Val Lys
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 77

Asp Leu Lys Pro Glu Asn Ile Leu Leu Asp Asp Tyr Gly His Ile Arg
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 78

Asp Leu Lys Pro Glu Asn Ile Leu Leu Asp Asp His Gly His Ile Arg
1               5                   10                  15

<210> SEQ ID NO 79
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 79

Asp Ile Lys Pro Gln Asn Leu Leu Val Asp Pro Asp Thr Ala Val Leu
1               5                   10                  15

Lys

<210> SEQ ID NO 80
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 80

Asp Ile Lys Pro Gln Asn Leu Leu Leu Asp Pro Asp Thr Ala Val Leu
1               5                   10                  15
```

Lys

<210> SEQ ID NO 81
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 81

Asp Lys Val Ser Gly Asp Leu Val Ala Leu Lys Met Val Lys
1               5                   10

<210> SEQ ID NO 82
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 82

Asp Ile Lys Gly Ala Asn Ile Leu Ile Asn Asp Ala Gly Glu Val Arg
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 83

Asp Leu Lys Pro Glu Asn Ile Val Leu Gln Asp Val Gly Gly Lys
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 84

Trp His Asn Gln Glu Thr Gly Glu Gln Ile Ala Ile Lys Gln Cys Arg
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 85

Asp Leu Lys Pro Glu Asn Ile Val Leu Gln Gln Gly Glu Gln Arg
1               5                   10                  15

<210> SEQ ID NO 86
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 86

Ser Gly Glu Leu Val Ala Val Lys Val Phe Asn Thr Thr Ser Tyr Leu
1               5                   10                  15

Arg Pro Arg

<210> SEQ ID NO 87
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 87

Asp Ile Lys Pro Gly Asn Ile Met Arg
1               5

<210> SEQ ID NO 88
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 88

Trp Gln Gly Asn Asp Ile Val Val Lys Val Leu Lys
1               5                   10

<210> SEQ ID NO 89
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 89

Ile Ser Met Ala Asp Val Lys Phe Ser Phe Gln Cys Pro Gly Arg
1               5                   10                  15

<210> SEQ ID NO 90
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 90

Ala Ile Gln Phe Leu His Gln Asp Ser Pro Ser Leu Ile His Gly Asp
1               5                   10                  15

Ile Lys Ser Ser Asn Val Leu Leu Asp Glu Arg
            20                  25

<210> SEQ ID NO 91
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 91

Gly Tyr Val Asn Asn Thr Thr Val Ala Val Lys Lys
1               5                   10

<210> SEQ ID NO 92
<211> LENGTH: 16
<212> TYPE: PRT
<213> ORGANISM: Artificial Sequence
<220> FEATURE:
<223> OTHER INFORMATION: Synthetic Polypeptide -continued

```
<400> SEQUENCE: 92

Asp Ile Lys Ser Ala Asn Ile Leu Leu Asp Glu Ala Phe Thr Ala Lys
1               5                   10                  15

<210> SEQ ID NO 93
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 93

Asp Leu Lys Pro His Asn Ile Leu Ile Ser Met Pro Asn Ala His Gly
1               5                   10                  15

Lys

<210> SEQ ID NO 94
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 94

Phe Val Leu Asp Asp Gln Tyr Thr Ser Ser Thr Gly Thr Lys Phe Pro
1               5                   10                  15

Val Lys

<210> SEQ ID NO 95
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 95

Val Ala Ile Lys Thr Ile Arg
1               5

<210> SEQ ID NO 96
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 96

Glu Ser Ile Phe Phe Asn Ser His Asn Val Ser Lys Pro Glu Ser Ser
1               5                   10                  15

Ser Val Leu Thr Glu Leu Asp Lys Ile Glu Gly Val Phe Glu Arg Pro
            20                  25                  30

Ser Asp Glu Val Ile Arg
        35

<210> SEQ ID NO 97
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 97

Gln Leu Ala Ser Ala Leu Ser Tyr Leu Glu Asp Lys Asp Leu Val His
1               5                   10                  15
```

```
Gly Asn Val Cys Thr Lys Asn Leu Leu Leu Ala Arg
            20                  25
```

<210> SEQ ID NO 98
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 98

```
Ile Gly Asp Phe Gly Leu Thr Lys Ala Ile Glu Thr Asp Lys Glu Tyr
1               5                   10                  15

Tyr Thr Val Lys
            20
```

<210> SEQ ID NO 99
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 99

```
Tyr Asp Pro Glu Gly Asp Asn Thr Gly Glu Gln Val Ala Val Lys Ser
1               5                   10                  15

Leu Lys Pro Glu Ser Gly Gly Asn His Ile Ala Asp Leu Lys Lys
            20                  25                  30
```

<210> SEQ ID NO 100
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 100

```
Asp Leu Lys Pro Ser Asn Ile Val Val Lys
1               5                   10
```

<210> SEQ ID NO 101
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 101

```
Tyr Gln Gln Leu Lys Pro Ile Gly Ser Gly Ala Gln Gly Ile Val Cys
1               5                   10                  15

Ala Ala Phe Asp Thr Val Leu Gly Ile Asn Val Ala Val Lys Lys
            20                  25                  30
```

<210> SEQ ID NO 102
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 102

```
Asn Val His Thr Gly Glu Leu Ala Ala Val Lys Ile Ile Lys
1               5                   10
```

```
<210> SEQ ID NO 103
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 103

Asp Ile Lys Gly Ala Asn Ile Leu Leu Thr Asp His Gly Asp Val Lys
1               5                   10                  15

<210> SEQ ID NO 104
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 104

Asn Val Asn Thr Gly Glu Leu Ala Ala Ile Lys Val Ile Lys
1               5                   10

<210> SEQ ID NO 105
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 105

Ala Leu Tyr Ala Thr Lys Thr Leu Arg
1               5

<210> SEQ ID NO 106
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 106

Asp Ile Lys Pro Asp Asn Ile Leu Ile Asp Arg
1               5                   10

<210> SEQ ID NO 107
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 107

Asp Ile Lys Pro Asp Asn Ile Leu Ile Asp Leu Asp Gly His Ile Lys
1               5                   10                  15

<210> SEQ ID NO 108
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 108

Glu Gly Ala Lys Phe Pro Ile Lys Trp Thr Ala Pro Glu Ala Ile Asn
1               5                   10                  15

Tyr Gly Thr Phe Thr Ile Lys
            20
```

<210> SEQ ID NO 109
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 109

Asp Ile Lys Pro Gly Asn Leu Leu Leu Thr Thr Gly Gly Thr Leu Lys
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 110

Asn Lys Glu Thr Gly Ala Leu Ala Ala Ala Lys Val Ile Glu Thr Lys
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 111

Asp Leu Lys Ala Gly Asn Val Leu Met Thr Leu Glu Gly Asp Ile Arg
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 112

Ile Met His Arg Asp Val Lys Pro Ser Asn Ile Leu Val Asn Ser Arg
1               5                   10                  15

<210> SEQ ID NO 113
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 113

Asp Val Lys Pro Ser Asn Ile Leu Val Asn Ser Arg
1               5                   10

<210> SEQ ID NO 114
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 114

His Gln Ile Met His Arg Asp Val Lys Pro Ser Asn Ile Leu Val Asn
1               5                   10                  15

Ser Arg

<210> SEQ ID NO 115
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 115

His Ala Gln Ser Gly Thr Ile Met Ala Val Lys Arg
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 116

Asp Val Lys Pro Ser Asn Val Leu Ile Asn Lys
1               5                   10

<210> SEQ ID NO 117
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 117

Met Val His Lys Pro Ser Gly Gln Ile Met Ala Val Lys Arg
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 118

Asp Ile Lys Pro Ser Asn Ile Leu Leu Asp Arg
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 119

Asp Val Lys Pro Ser Asn Met Leu Val Asn Thr Arg
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 120

His Val Pro Ser Gly Gln Ile Met Ala Val Lys Arg
1               5                   10

<210> SEQ ID NO 121
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 121

Asp Val Lys Pro Ser Asn Val Leu Ile Asn Ala Leu Gly Gln Val Lys
1               5                   10                  15

<210> SEQ ID NO 122
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 122

Asp Val Lys Pro Ser Asn Ile Leu Leu Asp Glu Arg
1               5                   10

<210> SEQ ID NO 123
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 123

Asp Val Lys Gly Ala Asn Leu Leu Ile Asp Ser Thr Gly Gln Arg
1               5                   10                  15

<210> SEQ ID NO 124
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 124

Ile Ala Ile Lys Glu Ile Pro Glu Arg
1               5

<210> SEQ ID NO 125
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 125

Glu Leu Ala Val Lys Gln Val Gln Phe Asp Pro Asp Ser Pro Glu Thr
1               5                   10                  15

Ser Lys Glu Val Asn Ala Leu Glu Cys Glu Ile Gln Leu Leu Lys
            20                  25                  30

<210> SEQ ID NO 126
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 126

```
Asp Ile Lys Gly Ala Asn Ile Leu Arg
1               5
```

```
<210> SEQ ID NO 127
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 127

Glu Leu Ala Ser Lys Gln Val Gln Phe Asp Pro Asp Ser Pro Glu Thr
1               5                   10                  15

Ser Lys Glu Val Ser Ala Leu Glu Cys Glu Ile Gln Leu Leu Lys
            20                  25                  30
```

```
<210> SEQ ID NO 128
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 128

Asp Ile Lys Gly Ala Asn Ile Phe Leu Thr Ser Ser Gly Leu Ile Lys
1               5                   10                  15
```

```
<210> SEQ ID NO 129
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 129

Asp Ile Lys Gly Asp Asn Val Leu Ile Asn Thr Tyr Ser Gly Val Leu
1               5                   10                  15

Lys
```

```
<210> SEQ ID NO 130
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 130

Gln Val Leu Gly Leu Gly Val Asn Gly Lys Val Leu Glu Cys Phe His
1               5                   10                  15

Arg
```

```
<210> SEQ ID NO 131
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 131

Cys Ala Leu Lys Leu Leu Tyr Asp Ser Pro Lys
1               5                   10
```

```
<210> SEQ ID NO 132
<211> LENGTH: 9
<212> TYPE: PRT
```

```
<213> ORGANISM: Artificial Sequence
<220> FEATURE:
<223> OTHER INFORMATION: Synthetic Polypeptide

<400> SEQUENCE: 132

Glu Val Ala Val Lys Ile Ile Asp Lys
1               5

<210> SEQ ID NO 133
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 133

Glu Val Ala Val Lys Ile Ile Asp Lys Thr Gln Leu Asn Ser Ser Ser
1               5                   10                  15

Leu Gln Lys

<210> SEQ ID NO 134
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 134

Phe Ile Val His Arg Asp Leu Lys Ala Glu Asn Leu Leu Leu Asp Ala
1               5                   10                  15

Asp Met Asn Ile Lys
            20

<210> SEQ ID NO 135
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 135

Asp Leu Lys Ala Glu Asn Leu Leu Leu Asp Ala Asp Met Asn Ile Lys
1               5                   10                  15

<210> SEQ ID NO 136
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 136

Glu Val Ala Ile Lys Ile Ile Asp Lys Thr Gln Leu Asn Pro Thr Ser
1               5                   10                  15

Leu Gln Lys

<210> SEQ ID NO 137
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 137

Glu Val Ala Ile Lys Ile Ile Asp Lys
```

```
1               5

<210> SEQ ID NO 138
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 138

Glu Val Ala Ile Lys Ile Ile Asp Lys Thr Gln Leu Asn Pro Ser Ser
1               5                   10                  15

Leu Gln Lys

<210> SEQ ID NO 139
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 139

Asp Leu Lys Ala Glu Asn Leu Leu Leu Asp Ala Glu Ala Asn Ile Lys
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 140

Asp Leu Lys Pro Asp Asn Leu Leu Ile Thr Ser Leu Gly His Ile Lys
1               5                   10                  15

<210> SEQ ID NO 141
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 141

Gly Ala Phe Gly Lys Val Tyr Leu Gly Gln Lys
1               5                   10

<210> SEQ ID NO 142
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 142

Leu Tyr Ala Val Lys Val Val Lys
1               5

<210> SEQ ID NO 143
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 143
```

```
Asp Leu Lys Ser Ser Asn Ile Leu Ile Leu Gln Lys
1               5                   10
```

<210> SEQ ID NO 144
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 144

```
Asp Leu Lys Ser Ile Asn Ile Leu Ile Leu Glu Ala Ile Glu Asn His
1               5                   10                  15

Asn Leu Ala Asp Thr Val Leu Lys
            20
```

<210> SEQ ID NO 145
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 145

```
Gly Glu Leu Val Ala Val Lys Ala Ala Arg
1               5                   10
```

<210> SEQ ID NO 146
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 146

```
Asp Leu Lys Ser Asn Asn Ile Leu Leu Leu Gln Pro Ile Glu Ser Asp
1               5                   10                  15

Asp Met Glu His Lys
            20
```

<210> SEQ ID NO 147
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 147

```
Ala Pro Val Ala Ile Lys Val Phe Lys
1               5
```

<210> SEQ ID NO 148
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 148

```
Leu Gly Glu Gly Gly Phe Ser Tyr Val Asp Leu Val Glu Gly Leu His
1               5                   10                  15

Asp Gly His Phe Tyr Ala Leu Lys Arg
            20                  25
```

<210> SEQ ID NO 149

```
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 149

Asp Leu Lys Pro Thr Asn Ile Leu Leu Gly Asp Glu Gly Gln Pro Val
1               5                   10                  15

Leu Met Asp Leu Gly Ser Met Asn Gln Ala Cys Ile His Val Glu Gly
            20                  25                  30

Ser Arg

<210> SEQ ID NO 150
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 150

Asp Ile Lys Leu Glu Asn Ile Leu Leu Asp Ser Asn Gly His Val Val
1               5                   10                  15

Leu Thr Asp Phe Gly Leu Ser Lys
            20

<210> SEQ ID NO 151
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 151

Asp Leu Lys Leu Glu Asn Val Leu Leu Asp Ser Glu Gly His Ile Val
1               5                   10                  15

Leu Thr Asp Phe Gly Leu Ser Lys
            20

<210> SEQ ID NO 152
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 152

Glu Thr Gly Gln Ile Val Ala Ile Lys Gln Val Pro Val Glu Ser Asp
1               5                   10                  15

Leu Gln Glu Ile Ile Lys
            20

<210> SEQ ID NO 153
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 153

Asp Ile Lys Ala Gly Asn Ile Leu Leu Asn Thr Glu Gly His Ala Lys
1               5                   10                  15

<210> SEQ ID NO 154
```

```
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 154

Glu Ser Gly Gln Val Val Ala Ile Lys Gln Val Pro Val Glu Ser Asp
1               5                   10                  15

Leu Gln Glu Ile Ile Lys
            20

<210> SEQ ID NO 155
<211> LENGTH: 36
<212> TYPE: PRT
<213> ORGANISM: Artificial Sequence
<220> FEATURE:
<223> OTHER INFORMATION: Synthetic Polypeptide

<400> SEQUENCE: 155

Val Val Ala Ile Lys Ile Ile Asp Leu Glu Glu Ala Glu Asp Glu Ile
1               5                   10                  15

Glu Asp Ile Gln Gln Glu Ile Thr Val Leu Ser Gln Cys Asp Ser Pro
            20                  25                  30

Tyr Val Thr Lys
        35

<210> SEQ ID NO 156
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 156

Asp Ile Lys Ala Ala Asn Val Leu Leu Ser Glu His Gly Glu Val Lys
1               5                   10                  15

<210> SEQ ID NO 157
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 157

Thr Gln Gln Val Val Ala Ile Lys Ile Ile Asp Leu Glu Glu Ala Glu
1               5                   10                  15

Asp Glu Ile Glu Asp Ile Gln Gln Glu Ile Thr Val Leu Ser Gln Cys
            20                  25                  30

Asp Ser Ser Tyr Val Thr Lys
        35

<210> SEQ ID NO 158
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 158

Asp Ile Lys Ala Ala Asn Val Leu Leu Ser Glu Gln Gly Asp Val Lys
1               5                   10                  15
```

```
<210> SEQ ID NO 159
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 159

Asp Thr Gly His Val Tyr Ala Met Lys Ile Leu Arg
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 160

Asp Ile Lys Pro Asp Asn Leu Leu Leu Asp Ser Lys
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 161

Asp Thr Gly His Ile Tyr Ala Met Lys Ile Leu Arg
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 162

Asp Ile Lys Pro Asp Asn Leu Leu Leu Asp Ala Lys
1               5                   10

<210> SEQ ID NO 163
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 163

Asp Ile Lys Ser Gln Asn Ile Phe Leu Thr Lys
1               5                   10

<210> SEQ ID NO 164
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 164

Ser Lys Asn Ile Phe Leu Thr Gln Asn Gly Lys
1               5                   10

<210> SEQ ID NO 165
```

```
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 165

Asp Leu Lys Thr Gln Asn Val Phe Leu Thr Arg
1               5                   10

<210> SEQ ID NO 166
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 166

Asp Ile Lys Pro Ala Asn Val Phe Ile Thr Ala Thr Gly Val Val Lys
1               5                   10                  15

<210> SEQ ID NO 167
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 167

Ala Ala Cys Leu Leu Asp Gly Val Pro Val Ala Leu Lys Lys
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 168

Asp Leu Lys Thr Gln Asn Ile Leu Leu Asp Lys
1               5                   10

<210> SEQ ID NO 169
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 169

Arg Thr Glu Asp Asp Ser Leu Val Val Trp Lys Glu Val Asp Leu Thr
1               5                   10                  15

Arg

<210> SEQ ID NO 170
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 170

Asp Ile Lys Thr Leu Asn Ile Phe Leu Thr Lys
1               5                   10
```

```
<210> SEQ ID NO 171
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 171

Asp Ile Lys Pro Gly Asn Leu Leu Val Asn Ser Asn Cys Val Leu Lys
1               5                   10                  15

<210> SEQ ID NO 172
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 172

Asp Val Lys Ala Gly Asn Ile Leu Leu Gly Glu Asp Gly Ser Val Gln
1               5                   10                  15

Ile Ala Asp Phe Gly Val Ser Ala Phe Leu Ala Thr Gly Gly Asp Ile
            20                  25                  30

Thr Arg

<210> SEQ ID NO 173
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 173

Asp Leu Lys Pro Ser Asn Leu Ala Val Asn Glu Asp Cys Glu Leu Lys
1               5                   10                  15

<210> SEQ ID NO 174
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 174

Gln Glu Leu Asn Lys Thr Ile Trp Glu Val Pro Glu Arg
1               5                   10

<210> SEQ ID NO 175
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 175

Gln Glu Leu Asn Lys Thr Val Trp Glu Val Pro Gln Arg
1               5                   10

<210> SEQ ID NO 176
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 176
```

```
Asp Leu Lys Pro Gly Asn Leu Ala Val Asn Glu Asp Cys Glu Leu Lys
1               5                   10                  15
```

<210> SEQ ID NO 177
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 177

```
Asp Leu Lys Pro Glu Asn Ile Met Leu Asn His Gln Gly His Val Lys
1               5                   10                  15
```

<210> SEQ ID NO 178
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 178

```
Gly Gly Tyr Gly Lys Val Phe Gln Val Arg
1               5                   10
```

<210> SEQ ID NO 179
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 179

```
Asp Leu Lys Pro Glu Asn Ile Met Leu Ser Ser Gln Gly His Ile Lys
1               5                   10                  15
```

<210> SEQ ID NO 180
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 180

```
Ile Gly Gln Gly Ala Ser Gly Thr Val Phe Thr Ala Thr Asp Val Ala
1               5                   10                  15

Leu Gly Gln Glu Val Ala Ile Lys Gln Ile Asn Leu Gln Lys
            20                  25                  30
```

<210> SEQ ID NO 181
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 181

```
Val Met Asp Pro Thr Lys Ile Leu Ile Thr Gly Lys
1               5                   10
```

<210> SEQ ID NO 182
<211> LENGTH: 14
<212> TYPE: PRT
<213> ORGANISM: Artificial Sequence
<220> FEATURE:
<223> OTHER INFORMATION: Synthetic Polypeptide

```
<400> SEQUENCE: 182

Ser Lys Leu Thr Asp Asn Leu Val Ala Leu Lys Glu Ile Arg
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 183

Asp Leu Lys Pro Gln Asn Leu Leu Ile Asn Glu Arg
1               5                   10

<210> SEQ ID NO 184
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 184

Asp Leu Lys Pro Gln Asn Leu Leu Ile Asn Glu Lys
1               5                   10

<210> SEQ ID NO 185
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 185

Ser Lys Leu Thr Glu Asn Leu Val Ala Leu Lys Glu Ile Arg
1               5                   10

<210> SEQ ID NO 186
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 186

Glu Tyr Ala Ile Lys Ile Leu Glu Lys
1               5

<210> SEQ ID NO 187
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 187

Asp Leu Lys Pro Ser Asn Ile Phe Phe Thr Met Asp Asp Val Val Lys
1               5                   10                  15

<210> SEQ ID NO 188
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 188
```

```
Ala Thr Gly His Glu Phe Ala Val Lys Ile Met Glu Val Thr Ala Glu
1               5                  10                 15
Arg

<210> SEQ ID NO 189
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 189

Ser Gly Thr Pro Met Gln Ser Ala Ala Lys Ala Pro Tyr Leu Ala Lys
1               5                  10                 15

<210> SEQ ID NO 190
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 190

Val Pro His Thr Gln Ala Val Val Leu Asn Ser Lys Asp Lys
1               5                  10

<210> SEQ ID NO 191
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 191

Leu Leu Ser Val Ile Val Lys Cys Gly Asp Asp Leu Arg Gln Glu Leu
1               5                  10                 15

Leu Ala Phe Gln Val Leu Lys
                20

<210> SEQ ID NO 192
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 192

Val Ile Phe Lys Cys Gly Asp Asp Leu Arg Gln Asp Met Leu Thr Leu
1               5                  10                 15

Gln Met Ile Arg
                20

<210> SEQ ID NO 193
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 193

Thr Glu Asp Gly Gly Lys Tyr Pro Val Ile Phe Lys His Gly Asp Asp
1               5                  10                 15

Leu Arg Gln Asp Gln Leu Ile Leu Gln Ile Ile Ser Leu Met Asp Lys
                20                 25                 30
```

<210> SEQ ID NO 194
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 194

Thr Glu Asp Gly Gly Lys Tyr Pro Val Ile Phe Lys His Gly Asp Asp
1               5                   10                  15

Leu Arg

<210> SEQ ID NO 195
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 195

Arg Pro Leu Trp Leu Asn Trp Glu Asn Pro Asp Ile Met Ser Glu Leu
1               5                   10                  15

Leu Phe Gln Asn Asn Glu Ile Ile Phe Lys Asn Gly Asp Asp Leu Arg
            20                  25                  30

Gln Asp Met Leu Thr Leu Gln Ile Ile Arg
        35                  40

<210> SEQ ID NO 196
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 196

Val Phe Gly Glu Asp Ser Val Gly Val Ile Phe Lys Asn Gly Asp Asp
1               5                   10                  15

Leu Arg Gln Asp Met Leu Thr Leu Gln Met Leu Arg
            20                  25

<210> SEQ ID NO 197
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 197

Thr Lys Val Asn Trp Leu Ala His Asn Val Ser Lys Asp Asn Arg Gln
1               5                   10                  15

<210> SEQ ID NO 198
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 198

Val Asn Trp Leu Ala His Asn Val Ser Lys Asp Asn Arg Gln
1               5                   10

<210> SEQ ID NO 199

```
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 199

Lys Lys Pro Leu Trp Leu Glu Phe Lys
1               5

<210> SEQ ID NO 200
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 200

Ala Lys Glu Leu Pro Thr Leu Lys Asp Asn Asp Phe Ile Asn Glu Gly
1               5                   10                  15

Gln Lys

<210> SEQ ID NO 201
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 201

Ala Lys Asp Leu Pro Thr Phe Lys Asp Asn Asp Phe Leu Asn Glu Gly
1               5                   10                  15

Gln Lys

<210> SEQ ID NO 202
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 202

Val Lys Glu Leu Pro Thr Leu Lys Asp Met Asp Phe Leu Asn Lys
1               5                   10                  15

<210> SEQ ID NO 203
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 203

Thr Leu Val Ile Lys Glu Val Ser Ser Glu Asp Ile Ala Asp Met His
1               5                   10                  15

Ser Asn Leu Ser Asn Tyr His Gln Tyr Ile Val Lys
            20                  25

<210> SEQ ID NO 204
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 204
```

```
Gly Gly Lys Ser Gly Ala Ala Phe Tyr Ala Thr Glu Asp Asp Arg Phe
1               5                   10                  15

Ile Leu Lys

<210> SEQ ID NO 205
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 205

Asp Leu Lys Thr Ser Asn Leu Leu Leu Ser His Ala Gly Ile Leu Lys
1               5                   10                  15

<210> SEQ ID NO 206
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 206

Lys Gly Thr Glu Glu Leu Tyr Ala Ile Lys Ile Leu Lys
1               5                   10

<210> SEQ ID NO 207
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 207

Asp Leu Lys Leu Asp Asn Val Met Leu Asp Ser Glu Gly His Ile Lys
1               5                   10                  15

<210> SEQ ID NO 208
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 208

Val Lys Glu Thr Gly Asp Leu Tyr Ala Val Lys Val Leu Lys
1               5                   10

<210> SEQ ID NO 209
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 209

Ile Tyr Ala Met Lys Val Val Lys
1               5

<210> SEQ ID NO 210
<211> LENGTH: 16
<212> TYPE: PRT
<213> ORGANISM: Artificial Sequence
<220> FEATURE:
<223> OTHER INFORMATION: Synthetic Polypeptide
```

```
<400> SEQUENCE: 210

Asp Leu Lys Leu Asp Asn Val Leu Leu Asp Ser Glu Gly His Ile Lys
1               5                   10                  15

<210> SEQ ID NO 211
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 211

Asn Ile Val His Cys Asp Leu Lys Pro Glu Asn Val Leu Leu Ala Ser
1               5                   10                  15

Ala Asp Pro Phe Pro Gln Val Lys
            20

<210> SEQ ID NO 212
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 212

Asp Val Ala Val Lys Val Ile Asp Lys
1               5

<210> SEQ ID NO 213
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 213

Asp Val Ala Ile Lys Val Ile Asp Lys
1               5

<210> SEQ ID NO 214
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 214

Asn Ile Val His Cys Asp Leu Lys Pro Glu Asn Val Leu Leu Ala Ser
1               5                   10                  15

Ala Glu Pro Phe Pro Gln Val Lys
            20

<210> SEQ ID NO 215
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 215

Val Leu Leu Ser Glu Phe Arg Pro Ser Gly Glu Leu Phe Ala Ile Lys
1               5                   10                  15

Ala Leu Lys
```

```
<210> SEQ ID NO 216
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 216

Asp Leu Lys Leu Asp Asn Leu Leu Asp Thr Glu Gly Tyr Val Lys
1               5                   10                  15

<210> SEQ ID NO 217
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 217

Asp Leu Lys Leu Asp Asn Leu Leu Asp Thr Glu Gly Phe Val Lys
1               5                   10                  15

<210> SEQ ID NO 218
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 218

Ile Gly Asp Phe Gly Leu Val Thr Ser Leu Lys Asn Asp Gly Lys Arg
1               5                   10                  15

<210> SEQ ID NO 219
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 219

Asp Leu Lys Pro Ser Asn Ile Phe Leu Val Asp Thr Lys
1               5                   10

<210> SEQ ID NO 220
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 220

Cys Phe Glu Ile Ser Asp Ala Asp Thr Lys Glu Val Phe Ala Gly Lys
1               5                   10                  15

Ile Val Pro Lys
            20

<210> SEQ ID NO 221
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 221

Asp Leu Lys Leu Gly Asn Leu Phe Leu Asn Glu Asp Leu Glu Val Lys
1               5                   10                  15
```

<210> SEQ ID NO 222
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 222

Cys Asn Ile Leu His Ala Asp Ile Lys Pro Asp Asn Ile Leu Val Asn
1               5                   10                  15

Glu Ser Lys

<210> SEQ ID NO 223
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 223

Ala Ala Gly Ile Gly Lys Asp Phe Lys Glu Asn Pro Asn Leu Arg
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 224

Phe Leu Ser Gly Leu Glu Leu Val Lys Gln Gly Ala Glu Ala Arg
1               5                   10                  15

<210> SEQ ID NO 225
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 225

Tyr Ile Glu Asp Glu Asp Tyr Tyr Lys Ala Ser Val Thr Arg
1               5                   10

<210> SEQ ID NO 226
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 226

Val Ala Ile Lys Ile Ile Asp Lys Thr Gln Leu Asp Glu Glu Asn Leu
1               5                   10                  15

Lys Lys

<210> SEQ ID NO 227
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 227

```
Asp Met Lys Ser Asn Asn Ile Phe Leu His Glu Gly Leu Thr Val Lys
1               5                   10                  15

<210> SEQ ID NO 228
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 228

Asp Val Lys Pro Asp Asn Met Leu Leu Asp Lys
1               5                   10

<210> SEQ ID NO 229
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 229

Leu Thr Asp Phe Gly Leu Ser Lys Glu Ala Ile Asp His Glu Lys Lys
1               5                   10                  15

<210> SEQ ID NO 230
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 230

Lys Val Thr Arg Pro Asp Ser Gly His Leu Tyr Ala Met Lys Val Leu
1               5                   10                  15

Lys

<210> SEQ ID NO 231
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 231

Asp Leu Lys Pro Glu Asn Ile Leu Leu Asp Glu Glu Gly His Ile Lys
1               5                   10                  15

<210> SEQ ID NO 232
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 232

Asp Leu Lys Pro Ser Asn Ile Leu Tyr Val Asp Glu Ser Gly Asn Pro
1               5                   10                  15

Glu Cys Leu Arg
            20

<210> SEQ ID NO 233
<211> LENGTH: 14
<212> TYPE: PRT
<213> ORGANISM: Artificial Sequence
```

```
<220> FEATURE:
<223> OTHER INFORMATION: Synthetic Polypeptide

<400> SEQUENCE: 233

Val Leu Gly Gln Gly Ser Phe Gly Lys Val Phe Leu Val Lys
1               5                   10

<210> SEQ ID NO 234
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 234

Leu Thr Asp Phe Gly Leu Ser Lys Glu Ser Ile Asp His Glu Lys Lys
1               5                   10                  15

<210> SEQ ID NO 235
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 235

Asp Leu Lys Pro Ser Asn Ile Leu Tyr Val Asp Glu Ser Gly Asn Pro
1               5                   10                  15

Glu Ser Ile Arg
            20

<210> SEQ ID NO 236
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 236

Val Leu Gly Val Ile Asp Lys Val Leu Leu Val Met Asp Thr Arg
1               5                   10                  15

<210> SEQ ID NO 237
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 237

Phe Tyr Ala Val Lys Val Leu Gln Lys
1               5

<210> SEQ ID NO 238
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 238

Ile Val Tyr Arg Asp Leu Lys Pro Glu Asn Ile Leu Leu Asp Ser Val
1               5                   10                  15

Gly His Val Val Leu Thr Asp Phe Gly Leu Cys Lys
            20                  25
```

<210> SEQ ID NO 239
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 239

Ala Gln Asn Lys Glu Thr Ser Val Leu Ala Ala Ala Lys Val Ile Asp
1               5                   10                  15

Thr Lys

<210> SEQ ID NO 240
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 240

Asp Leu Lys Ala Gly Asn Ile Leu Phe Thr Leu Asp Gly Asp Ile Lys
1               5                   10                  15

<210> SEQ ID NO 241
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 241

Asp Thr Val Thr Ile His Ser Val Gly Gly Thr Ile Thr Ile Leu Pro
1               5                   10                  15

Thr Lys Thr Lys Pro Lys
            20

<210> SEQ ID NO 242
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 242

Ser Tyr Pro Tyr Leu Phe Lys Gly Leu Glu Asp Leu His Leu Asp Glu
1               5                   10                  15

Arg

<210> SEQ ID NO 243
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 243

Val Ala Val Lys Val Ile Asp Lys
1               5

<210> SEQ ID NO 244
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 244

Asp Leu Lys Pro Glu Asn Val Val Phe Phe Glu Lys
1               5                   10

<210> SEQ ID NO 245
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 245

Ile Ile His Thr Asp Ile Lys Pro Glu Asn Ile Leu Leu Ser Val Asn
1               5                   10                  15

Glu Gln Tyr Ile Arg
            20

<210> SEQ ID NO 246
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 246

Phe Val Ala Met Lys Val Val Lys
1               5

<210> SEQ ID NO 247
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 247

Asp Leu Lys Ala Gly Asn Ile Leu Leu Gly Glu Asp Gly Ser Val Gln
1               5                   10                  15

Ile Ala Asp Phe Gly Val Ser Ala Phe Leu Ala Thr Gly Gly Asp Val
            20                  25                  30

Thr Arg

<210> SEQ ID NO 248
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 248

Tyr Ser Val Lys Val Leu Pro Trp Leu Ser Pro Glu Val Leu Gln Gln
1               5                   10                  15

Asn Leu Gln Gly Tyr Asp Ala Lys
            20

<210> SEQ ID NO 249
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 249

Ser Val Lys Ala Ser His Ile Leu Ile Ser Val Asp Gly Lys
1               5                   10

<210> SEQ ID NO 250
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 250

His Thr Pro Thr Gly Thr Leu Val Thr Ile Lys Ile Thr Asn Leu Glu
1               5                   10                  15

Asn Cys Asn Glu Glu Arg
            20

<210> SEQ ID NO 251
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 251

Ser Ile Lys Ala Ser His Ile Leu Ile Ser Gly Asp Gly Leu Val Thr
1               5                   10                  15

Leu Ser Gly Leu Ser His Leu His Ser Leu Val Lys
            20                  25

<210> SEQ ID NO 252
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 252

Asp Leu Lys Pro Pro Asn Leu Leu Leu Val Ala Gly Gly Thr Val Leu
1               5                   10                  15

Lys

<210> SEQ ID NO 253
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 253

Asp Ile Lys Ala Gly Asn Ile Leu Leu Thr Glu Pro Gly Gln Val Lys
1               5                   10                  15

<210> SEQ ID NO 254
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 254

Asp Val Lys Ala Gly Asn Ile Leu Leu Ser Glu Pro Gly Leu Val Lys
1               5                   10                  15

<210> SEQ ID NO 255
<211> LENGTH: 24

```
<212> TYPE: PRT
<213> ORGANISM: Artificial Sequence
<220> FEATURE:
<223> OTHER INFORMATION: Synthetic Polypeptide

<400> SEQUENCE: 255

Thr Gly Asp Leu Phe Ala Ile Lys Val Phe Asn Asn Ile Ser Phe Leu
1               5                   10                  15

Arg Pro Val Asp Val Gln Met Arg
            20

<210> SEQ ID NO 256
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 256

Tyr Ala Ala Val Lys Ile His Gln Leu Asn Lys
1               5                   10

<210> SEQ ID NO 257
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 257

Tyr Leu Asn Glu Ile Lys Pro Pro Ile Ile His Tyr Asp Leu Lys Pro
1               5                   10                  15

Gly Asn Ile Leu Leu Val Asp Gly Thr Ala Cys Gly Glu Ile Lys
            20                  25                  30

<210> SEQ ID NO 258
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 258

Tyr Val Ala Val Lys Ile His Gln Leu Asn Lys
1               5                   10

<210> SEQ ID NO 259
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 259

Tyr Leu Asn Glu Ile Lys Pro Pro Ile Ile His Tyr Asp Leu Lys Pro
1               5                   10                  15

Gly Asn Ile Leu Leu Val Asn Gly Thr Ala Cys Gly Glu Ile Lys
            20                  25                  30

<210> SEQ ID NO 260
<211> LENGTH: 18
<212> TYPE: PRT
<213> ORGANISM: Artificial Sequence
<220> FEATURE:
<223> OTHER INFORMATION: Synthetic Polypeptide
```

<400> SEQUENCE: 260

Ile Gly Asp Phe Gly Leu Ala Lys Ala Val Pro Glu Gly His Glu Tyr
1               5                   10                  15

Tyr Arg

<210> SEQ ID NO 261
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 261

Asp Leu Lys Pro Gln Asn Ile Leu Leu Ser Asn Pro Ala Gly Arg
1               5                   10                  15

<210> SEQ ID NO 262
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 262

Glu Val Val Ala Ile Lys Cys Val Ala Lys
1               5                   10

<210> SEQ ID NO 263
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 263

Asn Ile Ser His Leu Asp Leu Lys Pro Gln Asn Ile Leu Leu Ser Ser
1               5                   10                  15

Leu Glu Lys Pro His Leu Lys
            20

<210> SEQ ID NO 264
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 264

Gly Ser Phe Lys Thr Val Tyr Lys
1               5

<210> SEQ ID NO 265
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 265

Asp Leu Lys Cys Asp Asn Ile Phe Ile Thr Gly Pro Thr Gly Ser Val
1               5                   10                  15

Lys

<210> SEQ ID NO 266

```
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 266

Ile Gly Asp Leu Gly Leu Ala Thr Leu Lys Arg
1               5                   10

<210> SEQ ID NO 267
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 267

Glu Val Val Ala Ile Lys Ile Ile Asp Leu Glu Glu Ala Glu Asp Glu
1               5                   10                  15

Ile Glu Asp Ile Gln Gln Glu Ile Thr Val Leu Ser Gln Cys Asp Ser
            20                  25                  30

Pro Tyr Ile Thr Arg
        35

<210> SEQ ID NO 268
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 268

Trp Ile Ser Gln Asp Lys Glu Val Ala Val Lys Lys
1               5                   10

<210> SEQ ID NO 269
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 269

Ile Ser Asp Phe Gly Leu Ser Lys Ala Leu Gly Ala Asp Asp Ser Tyr
1               5                   10                  15

Tyr Thr Ala Arg
            20

<210> SEQ ID NO 270
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 270

Gln Ile Asp Val Ala Ile Lys Val Leu Lys
1               5                   10

<210> SEQ ID NO 271
<211> LENGTH: 29
<212> TYPE: PRT
<213> ORGANISM: Artificial Sequence
<220> FEATURE:
<223> OTHER INFORMATION: Synthetic Polypeptide
```

<400> SEQUENCE: 271

Thr Gly Gln Leu Ala Ala Ile Lys Val Met Asp Val Thr Glu Asp Glu
1               5                   10                  15

Glu Glu Glu Ile Lys Leu Glu Ile Asn Met Leu Lys Lys
            20                  25

<210> SEQ ID NO 272
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 272

Asp Ile Lys Gly Gln Asn Val Leu Leu Thr Glu Asn Ala Glu Val Lys
1               5                   10                  15

<210> SEQ ID NO 273
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 273

Thr Gly Gln Leu Ala Ala Ile Lys Val Met Asp Val Thr Gly Asp Glu
1               5                   10                  15

Glu Glu Glu Ile Lys Gln Glu Ile Asn Met Leu Lys Lys
            20                  25

<210> SEQ ID NO 274
<211> LENGTH: 346
<212> TYPE: PRT
<213> ORGANISM: Homo sapiens

<400> SEQUENCE: 274

Met Ala Leu Asp Val Lys Ser Arg Ala Lys Arg Tyr Glu Lys Leu Asp
1               5                   10                  15

Phe Leu Gly Glu Gly Gln Phe Ala Thr Val Tyr Lys Ala Arg Asp Lys
            20                  25                  30

Asn Thr Asn Gln Ile Val Ala Ile Lys Lys Ile Lys Leu Gly His Arg
        35                  40                  45

Ser Glu Ala Lys Asp Gly Ile Asn Arg Thr Ala Leu Arg Glu Ile Lys
    50                  55                  60

Leu Leu Gln Glu Leu Ser His Pro Asn Ile Ile Gly Leu Leu Asp Ala
65                  70                  75                  80

Phe Gly His Lys Ser Asn Ile Ser Leu Val Phe Asp Phe Met Glu Thr
                85                  90                  95

Asp Leu Glu Val Ile Ile Lys Asp Asn Ser Leu Val Leu Thr Pro Ser
            100                 105                 110

His Ile Lys Ala Tyr Met Leu Met Thr Leu Gln Gly Leu Glu Tyr Leu
        115                 120                 125

His Gln His Trp Ile Leu His Arg Asp Leu Lys Pro Asn Asn Leu Leu
    130                 135                 140

Leu Asp Glu Asn Gly Val Leu Lys Leu Ala Asp Phe Gly Leu Ala Lys
145                 150                 155                 160

Ser Phe Gly Ser Pro Asn Arg Ala Tyr Thr His Gln Val Val Thr Arg
                165                 170                 175

```
Trp Tyr Arg Ala Pro Glu Leu Leu Phe Gly Ala Arg Met Tyr Gly Val
            180                 185                 190

Gly Val Asp Met Trp Ala Val Gly Cys Ile Leu Ala Glu Leu Leu Leu
        195                 200                 205

Arg Val Pro Phe Leu Pro Gly Asp Ser Asp Leu Asp Gln Leu Thr Arg
    210                 215                 220

Ile Phe Glu Thr Leu Gly Thr Pro Thr Glu Glu Gln Trp Pro Asp Met
225                 230                 235                 240

Cys Ser Leu Pro Asp Tyr Val Thr Phe Lys Ser Phe Pro Gly Ile Pro
                245                 250                 255

Leu His His Ile Phe Ser Ala Ala Gly Asp Asp Leu Leu Asp Leu Ile
            260                 265                 270

Gln Gly Leu Phe Leu Phe Asn Pro Cys Ala Arg Ile Thr Ala Thr Gln
        275                 280                 285

Ala Leu Lys Met Lys Tyr Phe Ser Asn Arg Pro Gly Pro Thr Pro Gly
    290                 295                 300

Cys Gln Leu Pro Arg Pro Asn Cys Pro Val Glu Thr Leu Lys Glu Gln
305                 310                 315                 320

Ser Asn Pro Ala Leu Ala Ile Lys Arg Lys Arg Thr Glu Ala Leu Glu
                325                 330                 335

Gln Gly Gly Leu Pro Lys Lys Leu Ile Phe
            340                 345

<210> SEQ ID NO 275
<211> LENGTH: 1490
<212> TYPE: PRT
<213> ORGANISM: Homo sapiens

<400> SEQUENCE: 275

Met Pro Asn Ser Glu Arg His Gly Gly Lys Lys Asp Gly Ser Gly Gly
1               5                   10                  15

Ala Ser Gly Thr Leu Gln Pro Ser Ser Gly Gly Gly Ser Ser Asn Ser
            20                  25                  30

Arg Glu Arg His Arg Leu Val Ser Lys His Leu Arg His Lys Ser Lys
        35                  40                  45

His Ser Lys Asp Met Gly Leu Val Thr Pro Glu Ala Ala Ser Leu Gly
    50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
    130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Ser Lys Glu Ser Arg Ser
                165                 170                 175

Ser Lys Leu His Lys Glu Lys Thr Arg Lys Glu Arg Glu Leu Lys Ser
            180                 185                 190

Gly His Lys Asp Arg Ser Lys Ser His Arg Lys Arg Glu Thr Pro Lys
        195                 200                 205
```

-continued

```
Ser Tyr Lys Thr Val Asp Ser Pro Lys Arg Arg Ser Arg Ser Pro His
    210                 215                 220
Arg Lys Trp Ser Asp Ser Ser Lys Gln Asp Asp Ser Pro Ser Gly Ala
225                 230                 235                 240
Ser Tyr Gly Gln Asp Tyr Asp Leu Ser Pro Ser Arg Ser His Thr Ser
                245                 250                 255
Ser Asn Tyr Asp Ser Tyr Lys Lys Ser Pro Gly Ser Thr Ser Arg Arg
            260                 265                 270
Gln Ser Val Ser Pro Pro Tyr Lys Glu Pro Ser Ala Tyr Gln Ser Ser
        275                 280                 285
Thr Arg Ser Pro Ser Pro Tyr Ser Arg Arg Gln Arg Ser Val Ser Pro
290                 295                 300
Tyr Ser Arg Arg Arg Ser Ser Ser Tyr Glu Arg Ser Gly Ser Tyr Ser
305                 310                 315                 320
Gly Arg Ser Pro Ser Pro Tyr Gly Arg Arg Ser Ser Ser Pro Phe
                325                 330                 335
Leu Ser Lys Arg Ser Leu Ser Arg Ser Pro Leu Pro Ser Arg Lys Ser
                340                 345                 350
Met Lys Ser Arg Ser Arg Ser Pro Ala Tyr Ser Arg His Ser Ser Ser
            355                 360                 365
His Ser Lys Lys Lys Arg Ser Ser Arg Ser Arg His Ser Ser Ile
    370                 375                 380
Ser Pro Val Arg Leu Pro Leu Asn Ser Ser Leu Gly Ala Glu Leu Ser
385                 390                 395                 400
Arg Lys Lys Lys Glu Arg Ala Ala Ala Ala Ala Ala Lys Met Asp
                405                 410                 415
Gly Lys Glu Ser Lys Gly Ser Pro Val Phe Leu Pro Arg Lys Glu Asn
                420                 425                 430
Ser Ser Val Glu Ala Lys Asp Ser Gly Leu Glu Ser Lys Lys Leu Pro
            435                 440                 445
Arg Ser Val Lys Leu Glu Lys Ser Ala Pro Asp Thr Glu Leu Val Asn
    450                 455                 460
Val Thr His Leu Asn Thr Glu Val Lys Asn Ser Ser Asp Thr Gly Lys
465                 470                 475                 480
Val Lys Leu Asp Glu Asn Ser Glu Lys His Leu Val Lys Asp Leu Lys
                485                 490                 495
Ala Gln Gly Thr Arg Asp Ser Lys Pro Ile Ala Leu Lys Glu Glu Ile
                500                 505                 510
Val Thr Pro Lys Glu Thr Glu Thr Ser Glu Lys Glu Thr Pro Pro Pro
            515                 520                 525
Leu Pro Thr Ile Ala Ser Pro Pro Leu Pro Thr Thr Pro
    530                 535                 540
Pro Pro Gln Thr Pro Pro Leu Pro Pro Leu Pro Ile Pro Ala Leu
545                 550                 555                 560
Pro Gln Gln Pro Pro Leu Pro Ser Gln Pro Ala Phe Ser Gln Val
                565                 570                 575
Pro Ala Ser Ser Thr Ser Thr Leu Pro Pro Ser Thr His Ser Lys Thr
            580                 585                 590
Ser Ala Val Ser Ser Gln Ala Asn Ser Gln Pro Pro Val Gln Val Ser
        595                 600                 605
Val Lys Thr Gln Val Ser Val Thr Ala Ala Ile Pro His Leu Lys Thr
610                 615                 620
```

```
Ser Thr Leu Pro Pro Leu Pro Leu Pro Pro Leu Leu Pro Gly Asp Asp
625                 630                 635                 640

Asp Met Asp Ser Pro Lys Glu Thr Leu Pro Ser Lys Pro Val Lys Lys
            645                 650                 655

Glu Lys Glu Gln Arg Thr Arg His Leu Leu Thr Asp Leu Pro Leu Pro
                660                 665                 670

Pro Glu Leu Pro Gly Gly Asp Leu Ser Pro Pro Asp Ser Pro Glu Pro
            675                 680                 685

Lys Ala Ile Thr Pro Pro Gln Pro Tyr Lys Lys Arg Pro Lys Ile
        690                 695                 700

Cys Cys Pro Arg Tyr Gly Glu Arg Arg Gln Thr Glu Ser Asp Trp Gly
705                 710                 715                 720

Lys Arg Cys Val Asp Lys Phe Asp Ile Ile Gly Ile Ile Gly Glu Gly
                725                 730                 735

Thr Tyr Gly Gln Val Tyr Lys Ala Lys Asp Lys Asp Thr Gly Glu Leu
            740                 745                 750

Val Ala Leu Lys Lys Val Arg Leu Asp Asn Glu Lys Glu Gly Phe Pro
                755                 760                 765

Ile Thr Ala Ile Arg Glu Ile Lys Ile Leu Arg Gln Leu Ile His Arg
        770                 775                 780

Ser Val Val Asn Met Lys Glu Ile Val Thr Asp Lys Gln Asp Ala Leu
785                 790                 795                 800

Asp Phe Lys Lys Asp Lys Gly Ala Phe Tyr Leu Val Phe Glu Tyr Met
                805                 810                 815

Asp His Asp Leu Met Gly Leu Leu Glu Ser Gly Leu Val His Phe Ser
            820                 825                 830

Glu Asp His Ile Lys Ser Phe Met Lys Gln Leu Met Glu Gly Leu Glu
        835                 840                 845

Tyr Cys His Lys Lys Asn Phe Leu His Arg Asp Ile Lys Cys Ser Asn
        850                 855                 860

Ile Leu Leu Asn Asn Ser Gly Gln Ile Lys Leu Ala Asp Phe Gly Leu
865                 870                 875                 880

Ala Arg Leu Tyr Asn Ser Glu Glu Ser Arg Pro Tyr Thr Asn Lys Val
                885                 890                 895

Ile Thr Leu Trp Tyr Arg Pro Pro Glu Leu Leu Gly Glu Glu Arg
        900                 905                 910

Tyr Thr Pro Ala Ile Asp Val Trp Ser Cys Gly Cys Ile Leu Gly Glu
        915                 920                 925

Leu Phe Thr Lys Pro Ile Phe Gln Ala Asn Leu Glu Leu Ala Gln
930                 935                 940

Leu Glu Leu Ile Ser Arg Leu Cys Gly Ser Pro Cys Pro Ala Val Trp
945                 950                 955                 960

Pro Asp Val Ile Lys Leu Pro Tyr Phe Asn Thr Met Lys Pro Lys Lys
            965                 970                 975

Gln Tyr Arg Arg Arg Leu Arg Glu Phe Ser Phe Ile Pro Ser Ala
        980                 985                 990

Ala Leu Asp Leu Leu Asp His Met Leu Thr Leu Asp Pro Ser Lys Arg
        995                 1000                1005

Cys Thr Ala Glu Gln Thr Leu Gln Ser Asp Phe Leu Lys Asp Val
        1010                1015                1020

Glu Leu Ser Lys Met Ala Pro Pro Asp Leu Pro His Trp Gln Asp
        1025                1030                1035

Cys His Glu Leu Trp Ser Lys Lys Arg Arg Arg Gln Arg Gln Ser
```

-continued

```
            1040                1045                1050
Gly Val Val Glu Glu Pro Pro Ser Lys Thr Ser Arg Lys
    1055                1060                1065
Glu Thr Thr Ser Gly Thr Ser Thr Glu Pro Val Lys Asn Ser Ser
    1070                1075                1080
Pro Ala Pro Pro Gln Pro Ala Pro Gly Lys Val Glu Ser Gly Ala
    1085                1090                1095
Gly Asp Ala Ile Gly Leu Ala Asp Ile Thr Gln Gln Leu Asn Gln
    1100                1105                1110
Ser Glu Leu Ala Val Leu Leu Asn Leu Leu Gln Ser Gln Thr Asp
    1115                1120                1125
Leu Ser Ile Pro Gln Met Ala Gln Leu Leu Asn Ile His Ser Asn
    1130                1135                1140
Pro Glu Met Gln Gln Leu Glu Ala Leu Asn Gln Ser Ile Ser
    1145                1150                1155
Ala Leu Thr Glu Ala Thr Ser Gln Gln Gln Asp Ser Glu Thr Met
    1160                1165                1170
Ala Pro Glu Glu Ser Leu Lys Glu Ala Pro Ser Ala Pro Val Ile
    1175                1180                1185
Leu Pro Ser Ala Glu Gln Thr Thr Leu Glu Ala Ser Ser Thr Pro
    1190                1195                1200
Ala Asp Met Gln Asn Ile Leu Ala Val Leu Leu Ser Gln Leu Met
    1205                1210                1215
Lys Thr Gln Glu Pro Ala Gly Ser Leu Glu Glu Asn Asn Ser Asp
    1220                1225                1230
Lys Asn Ser Gly Pro Gln Gly Pro Arg Arg Thr Pro Thr Met Pro
    1235                1240                1245
Gln Glu Glu Ala Ala Ala Cys Pro Pro His Ile Leu Pro Pro Glu
    1250                1255                1260
Lys Arg Pro Pro Glu Pro Pro Gly Pro Pro Pro Pro Pro Pro Pro
    1265                1270                1275
Pro Pro Leu Val Glu Gly Asp Leu Ser Ser Ala Pro Gln Glu Leu
    1280                1285                1290
Asn Pro Ala Val Thr Ala Ala Leu Leu Gln Leu Leu Ser Gln Pro
    1295                1300                1305
Glu Ala Glu Pro Pro Gly His Leu Pro His Glu His Gln Ala Leu
    1310                1315                1320
Arg Pro Met Glu Tyr Ser Thr Arg Pro Arg Pro Asn Arg Thr Tyr
    1325                1330                1335
Gly Asn Thr Asp Gly Pro Glu Thr Gly Phe Ser Ala Ile Asp Thr
    1340                1345                1350
Asp Glu Arg Asn Ser Gly Pro Ala Leu Thr Glu Ser Leu Val Gln
    1355                1360                1365
Thr Leu Val Lys Asn Arg Thr Phe Ser Gly Ser Leu Ser His Leu
    1370                1375                1380
Gly Glu Ser Ser Ser Tyr Gln Gly Thr Gly Ser Val Gln Phe Pro
    1385                1390                1395
Gly Asp Gln Asp Leu Arg Phe Ala Arg Val Pro Leu Ala Leu His
    1400                1405                1410
Pro Val Val Gly Gln Pro Phe Leu Lys Ala Glu Gly Ser Ser Asn
    1415                1420                1425
Ser Val Val His Ala Glu Thr Lys Leu Gln Asn Tyr Gly Glu Leu
    1430                1435                1440
```

Gly Pro Gly Thr Thr Gly Ala Ser Ser Ser Ala Gly Leu His
    1445                1450                1455

Trp Gly Gly Pro Thr Gln Ser Ser Ala Tyr Gly Lys Leu Tyr Arg
    1460                1465                1470

Gly Pro Thr Arg Val Pro Pro Arg Gly Gly Arg Gly Arg Gly Val
    1475                1480                1485

Pro Tyr
    1490

<210> SEQ ID NO 276
<211> LENGTH: 1512
<212> TYPE: PRT
<213> ORGANISM: Homo sapiens

<400> SEQUENCE: 276

Met Pro Ser Ser Ser Asp Thr Ala Leu Gly Gly Gly Gly Leu Ser
1               5                   10                  15

Trp Ala Glu Lys Lys Leu Glu Glu Arg Arg Lys Arg Arg Phe Leu
            20                  25                  30

Ser Pro Gln Gln Pro Pro Leu Leu Leu Pro Leu Leu Gln Pro Gln Leu
        35                  40                  45

Leu Gln Pro Pro Pro Pro Pro Pro Leu Leu Phe Leu Ala Ala Pro
    50                  55                  60

Gly Thr Ala Ala Ala Ala Ala Ala Ala Ala Ser Ser Ser Cys
65                  70                  75                  80

Phe Ser Pro Gly Pro Leu Glu Val Lys Arg Leu Ala Arg Gly Lys
                85                  90                  95

Arg Arg Ala Gly Gly Arg Gln Lys Arg Arg Gly Pro Arg Ala Gly
            100                 105                 110

Gln Glu Ala Glu Lys Arg Arg Val Phe Ser Leu Pro Gln Pro Gln Gln
        115                 120                 125

Asp Gly Gly Gly Ala Ser Ser Gly Gly Val Thr Pro Leu Val
    130                 135                 140

Glu Tyr Glu Asp Val Ser Ser Gln Ser Glu Gln Gly Leu Leu Leu Gly
145                 150                 155                 160

Gly Ala Ser Ala Ala Thr Ala Ala Thr Ala Ala Gly Gly Thr Gly Gly
                165                 170                 175

Ser Gly Gly Ser Pro Ala Ser Ser Ser Gly Thr Gln Arg Arg Gly Glu
            180                 185                 190

Gly Ser Glu Arg Arg Pro Arg Arg Asp Arg Arg Ser Ser Gly Arg
        195                 200                 205

Ser Lys Glu Arg His Arg Glu His Arg Arg Asp Gly Gln Arg Gly
    210                 215                 220

Gly Ser Glu Ala Ser Lys Ser Arg Ser Arg His Ser His Ser Gly Glu
225                 230                 235                 240

Glu Arg Ala Glu Val Ala Lys Ser Gly Ser Ser Ser Ser Gly Gly
                245                 250                 255

Arg Arg Lys Ser Ala Ser Ala Thr Ser Ser Ser Ser Ser Arg Lys
            260                 265                 270

Asp Arg Asp Ser Lys Ala His Arg Ser Arg Thr Lys Ser Ser Lys Glu
        275                 280                 285

Pro Pro Ser Ala Tyr Lys Glu Pro Pro Lys Ala Tyr Arg Glu Asp Lys
    290                 295                 300

Thr Glu Pro Lys Ala Tyr Arg Arg Arg Arg Ser Leu Ser Pro Leu Gly

```
                305                 310                 315                 320
Gly Arg Asp Asp Ser Pro Val Ser His Arg Ala Ser Gln Ser Leu Arg
                325                 330                 335
Ser Arg Lys Ser Pro Ser Pro Ala Gly Gly Ser Ser Pro Tyr Ser
                340                 345                 350
Arg Arg Leu Pro Arg Ser Pro Ser Pro Tyr Ser Arg Arg Ser Pro
                355                 360                 365
Ser Tyr Ser Arg His Ser Ser Tyr Glu Arg Gly Gly Asp Val Ser Pro
                370                 375                 380
Ser Pro Tyr Ser Ser Ser Trp Arg Arg Ser Arg Ser Pro Tyr Ser
385                 390                 395                 400
Pro Val Leu Arg Arg Ser Gly Lys Ser Arg Ser Arg Ser Pro Tyr Ser
                405                 410                 415
Ser Arg His Ser Arg Ser Arg Ser His Arg Leu Ser Arg Ser Arg
                420                 425                 430
Ser Arg His Ser Ser Ile Ser Pro Ser Thr Leu Thr Leu Lys Ser Ser
                435                 440                 445
Leu Ala Ala Glu Leu Asn Lys Asn Lys Lys Ala Arg Ala Ala Glu Ala
    450                 455                 460
Ala Arg Ala Ala Glu Ala Ala Lys Ala Ala Glu Ala Thr Lys Ala Ala
465                 470                 475                 480
Glu Ala Ala Ala Lys Ala Ala Lys Ala Ser Asn Thr Ser Thr Pro Thr
                485                 490                 495
Lys Gly Asn Thr Glu Thr Ser Ala Ser Ala Ser Gln Thr Asn His Val
                500                 505                 510
Lys Asp Val Lys Lys Ile Lys Ile Glu His Ala Pro Ser Pro Ser Ser
                515                 520                 525
Gly Gly Thr Leu Lys Asn Asp Lys Ala Lys Thr Lys Pro Pro Leu Gln
                530                 535                 540
Val Thr Lys Val Glu Asn Asn Leu Ile Val Asp Lys Ala Thr Lys Lys
545                 550                 555                 560
Ala Val Ile Val Gly Lys Glu Ser Lys Ser Ala Ala Thr Lys Glu Glu
                565                 570                 575
Ser Val Ser Leu Lys Glu Lys Thr Lys Pro Leu Thr Pro Ser Ile Gly
                580                 585                 590
Ala Lys Glu Lys Glu Gln His Val Ala Leu Val Thr Ser Thr Leu Pro
                595                 600                 605
Pro Leu Pro Leu Pro Pro Met Leu Pro Glu Asp Lys Glu Ala Asp Ser
    610                 615                 620
Leu Arg Gly Asn Ile Ser Val Lys Ala Val Lys Lys Glu Val Glu Lys
625                 630                 635                 640
Lys Leu Arg Cys Leu Leu Ala Asp Leu Pro Leu Pro Glu Leu Pro
                645                 650                 655
Gly Gly Asp Asp Leu Ser Lys Ser Pro Glu Glu Lys Lys Thr Ala Thr
                660                 665                 670
Gln Leu His Ser Lys Arg Arg Pro Lys Ile Cys Gly Pro Arg Tyr Gly
                675                 680                 685
Glu Thr Lys Glu Lys Asp Ile Asp Trp Gly Lys Arg Cys Val Asp Lys
                690                 695                 700
Phe Asp Ile Ile Gly Ile Ile Glu Gly Thr Tyr Gly Gln Val Tyr
705                 710                 715                 720
Lys Ala Arg Asp Lys Asp Thr Gly Glu Met Val Ala Leu Lys Lys Val
                725                 730                 735
```

-continued

Arg Leu Asp Asn Glu Lys Glu Gly Phe Pro Ile Thr Ala Ile Arg Glu
                740                 745                 750

Ile Lys Ile Leu Arg Gln Leu Thr His Gln Ser Ile Asn Met Lys
            755                 760                 765

Glu Ile Val Thr Asp Lys Glu Asp Ala Leu Asp Phe Lys Lys Asp Lys
770                 775                 780

Gly Ala Phe Tyr Leu Val Phe Glu Tyr Met Asp His Asp Leu Met Gly
785                 790                 795                 800

Leu Leu Glu Ser Gly Leu Val His Phe Asn Glu Asn His Ile Lys Ser
                805                 810                 815

Phe Met Arg Gln Leu Met Glu Gly Leu Asp Tyr Cys His Lys Lys Asn
            820                 825                 830

Phe Leu His Arg Asp Ile Lys Cys Ser Asn Ile Leu Leu Asn Asn Arg
            835                 840                 845

Gly Gln Ile Lys Leu Ala Asp Phe Gly Leu Ala Arg Leu Tyr Ser Ser
850                 855                 860

Glu Glu Ser Arg Pro Tyr Thr Asn Lys Val Ile Thr Leu Trp Tyr Arg
865                 870                 875                 880

Pro Pro Glu Leu Leu Leu Gly Glu Glu Arg Tyr Thr Pro Ala Ile Asp
                885                 890                 895

Val Trp Ser Cys Gly Cys Ile Leu Gly Glu Leu Phe Thr Lys Lys Pro
            900                 905                 910

Ile Phe Gln Ala Asn Gln Glu Leu Ala Gln Leu Glu Leu Ile Ser Arg
            915                 920                 925

Ile Cys Gly Ser Pro Cys Pro Ala Val Trp Pro Asp Val Ile Lys Leu
930                 935                 940

Pro Tyr Phe Asn Thr Met Lys Pro Lys Lys Gln Tyr Arg Arg Lys Leu
945                 950                 955                 960

Arg Glu Glu Phe Val Phe Ile Pro Ala Ala Ala Leu Asp Leu Phe Asp
                965                 970                 975

Tyr Met Leu Ala Leu Asp Pro Ser Lys Arg Cys Thr Ala Glu Gln Ala
            980                 985                 990

Leu Gln Cys Glu Phe Leu Arg Asp Val Glu Pro Ser Lys Met Pro Pro
            995                 1000                1005

Pro Asp Leu Pro Leu Trp Gln Asp Cys His Glu Leu Trp Ser Lys
    1010                1015                1020

Lys Arg Arg Arg Gln Lys Gln Met Gly Met Thr Asp Asp Val Ser
    1025                1030                1035

Thr Ile Lys Ala Pro Arg Lys Asp Leu Ser Leu Gly Leu Asp Asp
    1040                1045                1050

Ser Arg Thr Asn Thr Pro Gln Gly Val Leu Pro Ser Ser Gln Leu
    1055                1060                1065

Lys Ser Gln Gly Ser Ser Asn Val Ala Pro Val Lys Thr Gly Pro
    1070                1075                1080

Gly Gln His Leu Asn His Ser Glu Leu Ala Ile Leu Leu Asn Leu
    1085                1090                1095

Leu Gln Ser Lys Thr Ser Val Asn Met Ala Asp Phe Val Gln Val
    1100                1105                1110

Leu Asn Ile Lys Val Asn Ser Glu Thr Gln Gln Gln Leu Asn Lys
    1115                1120                1125

Ile Asn Leu Pro Ala Gly Ile Leu Ala Thr Gly Glu Lys Gln Thr
    1130                1135                1140

```
Asp Pro Ser Thr Pro Gln Gln Glu Ser Ser Lys Pro Leu Gly Gly
    1145                1150                1155

Ile Gln Pro Ser Ser Gln Thr Ile Gln Pro Lys Val Glu Thr Asp
    1160                1165                1170

Ala Ala Gln Ala Ala Val Gln Ser Ala Phe Ala Val Leu Leu Thr
    1175                1180                1185

Gln Leu Ile Lys Ala Gln Ser Lys Gln Lys Asp Val Leu Leu
    1190                1195                1200

Glu Glu Arg Glu Asn Gly Ser Gly His Glu Ala Ser Leu Gln Leu
    1205                1210                1215

Arg Pro Pro Glu Pro Ser Thr Pro Val Ser Gly Gln Asp Asp
    1220                1225                1230

Leu Ile Gln His Gln Asp Met Arg Ile Leu Glu Leu Thr Pro Glu
    1235                1240                1245

Pro Asp Arg Pro Arg Ile Leu Pro Pro Asp Gln Arg Pro Pro Glu
    1250                1255                1260

Pro Pro Glu Pro Pro Val Thr Glu Glu Asp Leu Asp Tyr Arg
    1265                1270                1275

Thr Glu Asn Gln His Val Pro Thr Thr Ser Ser Leu Thr Asp
    1280                1285                1290

Pro His Ala Gly Val Lys Ala Ala Leu Leu Gln Leu Leu Ala Gln
    1295                1300                1305

His Gln Pro Gln Asp Asp Pro Lys Arg Glu Gly Gly Ile Asp Tyr
    1310                1315                1320

Gln Ala Gly Asp Thr Tyr Val Ser Thr Ser Asp Tyr Lys Asp Asn
    1325                1330                1335

Phe Gly Ser Ser Ser Phe Ser Ala Pro Tyr Val Ser Asn Asp
    1340                1345                1350

Gly Leu Gly Ser Ser Ala Pro Pro Leu Glu Arg Arg Ser Phe
    1355                1360                1365

Ile Gly Asn Ser Asp Ile Gln Ser Leu Asp Asn Tyr Ser Thr Ala
    1370                1375                1380

Ser Ser His Ser Gly Gly Pro Pro Gln Pro Ser Ala Phe Ser Glu
    1385                1390                1395

Ser Phe Pro Ser Ser Val Ala Gly Tyr Gly Asp Ile Tyr Leu Asn
    1400                1405                1410

Ala Gly Pro Met Leu Phe Ser Gly Asp Lys Asp His Arg Phe Glu
    1415                1420                1425

Tyr Ser His Gly Pro Ile Ala Val Leu Ala Asn Ser Ser Asp Pro
    1430                1435                1440

Ser Thr Gly Pro Glu Ser Thr His Pro Leu Pro Ala Lys Met His
    1445                1450                1455

Asn Tyr Asn Tyr Gly Gly Asn Leu Gln Glu Asn Pro Ser Gly Pro
    1460                1465                1470

Ser Leu Met His Gly Gln Thr Trp Thr Ser Pro Ala Gln Gly Pro
    1475                1480                1485

Gly Tyr Ser Gln Gly Tyr Arg Gly His Ile Ser Thr Ser Thr Gly
    1490                1495                1500

Arg Gly Arg Gly Arg Gly Leu Pro Tyr
    1505                1510
```

<210> SEQ ID NO 277
<211> LENGTH: 20
<212> TYPE: DNA

```
<213> ORGANISM: Artificial Sequence
<220> FEATURE:
<223> OTHER INFORMATION: Synthetic Polynucleotide

<400> SEQUENCE: 277
ggcaggattg ccatgagttg                                                    20

<210> SEQ ID NO 278
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 278
ggcaagattg tcatgagtta                                                    20

<210> SEQ ID NO 279
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be phosphorylated serine or
      phosphorylated threonine
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be lysine or arginine

<400> SEQUENCE: 279

Xaa Pro Xaa Xaa
1
```